US012258353B2

(12) United States Patent
La et al.

(10) Patent No.: US 12,258,353 B2
(45) Date of Patent: Mar. 25, 2025

(54) HETEROCYCLIC COMPOUND AND ORGANIC LIGHT-EMITTING ELEMENT INCLUDING SAME

(71) Applicant: LT MATERIALS CO., LTD., Yongin-Si (KR)

(72) Inventors: Hyun-Ju La, Osan-si (KR); Hye-Su Ji, Hwaseong-si (KR); Won-Jang Jeong, Hwaseong-si (KR)

(73) Assignee: LT MATERIALS CO., LTD., Yongin-si (KR)

( * ) Notice: Subject to any disclaimer, the term of this patent is extended or adjusted under 35 U.S.C. 154(b) by 966 days.

(21) Appl. No.: 17/299,376

(22) PCT Filed: Dec. 6, 2019

(86) PCT No.: PCT/KR2019/017203
§ 371 (c)(1),
(2) Date: Jun. 3, 2021

(87) PCT Pub. No.: WO2020/116995
PCT Pub. Date: Jun. 11, 2020

(65) Prior Publication Data

US 2022/0033415 A1 Feb. 3, 2022

(30) Foreign Application Priority Data

Dec. 6, 2018 (KR) ........................ 10-2018-0156184

(51) Int. Cl.
*C07D 498/04* (2006.01)
*C07D 471/04* (2006.01)
(Continued)

(52) U.S. Cl.
CPC ......... *C07D 498/04* (2013.01); *C07D 471/04* (2013.01); *C07D 519/00* (2013.01); *C07F 9/5325* (2013.01); *H10K 85/622* (2023.02); *H10K 85/654* (2023.02); *H10K 85/6572* (2023.02); *H10K 50/11* (2023.02);
(Continued)

(58) Field of Classification Search
None
See application file for complete search history.

(56) References Cited

U.S. PATENT DOCUMENTS

2008/0278072 A1 11/2008 Noh et al.
2012/0313091 A1 12/2012 Kang et al.
(Continued)

FOREIGN PATENT DOCUMENTS

CN 107428769 A 12/2017
CN 197848399 A 1/2018
(Continued)

OTHER PUBLICATIONS

1 Page brochure for Benzoquinoline, CAS Reg. No. 230-27-3, by NIST Chemistry Webbook, SRD 69, Downloaded on Nov. 7, 2024.*
(Continued)

*Primary Examiner* — Tae H Yoon
(74) *Attorney, Agent, or Firm* — Birch, Stewart, Kolasch & Birch, LLP

(57) ABSTRACT

The present specification relates to a heterocyclic compound represented by Chemical Formula 1, and an organic light emitting device including the same.

12 Claims, 2 Drawing Sheets

(51) Int. Cl.

| | |
|---|---|
| ***C07D 519/00*** | (2006.01) |
| ***C07F 9/53*** | (2006.01) |
| ***H01L 51/00*** | (2006.01) |
| ***H10K 85/60*** | (2023.01) |
| *H10K 50/11* | (2023.01) |
| *H10K 50/13* | (2023.01) |
| *H10K 50/18* | (2023.01) |
| *H10K 101/30* | (2023.01) |
| *H10K 101/40* | (2023.01) |

(52) U.S. Cl.

CPC ............ *H10K 50/13* (2023.02); *H10K 50/18* (2023.02); *H10K 2101/30* (2023.02); *H10K 2101/40* (2023.02)

(56) References Cited

U.S. PATENT DOCUMENTS

| | | | |
|---|---|---|---|
| 2018/0047914 | A1 | 2/2018 | Cha et al. |
| 2018/0208837 | A1 | 7/2018 | Ahn |
| 2018/0323379 | A1 | 11/2018 | Kim et al. |
| 2018/0323397 | A1 | 11/2018 | Ahn et al. |
| 2020/0066996 | A1 | 2/2020 | La et al. |

FOREIGN PATENT DOCUMENTS

| | | | |
|---|---|---|---|
| CN | 108884090 | A | 11/2018 |
| JP | 2005-255992 | A | 9/2005 |
| JP | 2005-259687 | A | 9/2005 |
| KR | 10-2008-0097153 | A | 11/2008 |
| KR | 10-2011-0096453 | A | 8/2011 |
| KR | 10-2017-0022865 | A | 3/2017 |
| KR | 10-2017-0051198 | A | 5/2017 |
| KR | 10-2018-0075398 | A | 7/2018 |

OTHER PUBLICATIONS

International Search Report (PCT/ISA/210) issued in PCT/KR2019/017203 mailed on Mar. 16, 2020.

* cited by examiner

【FIG. 1】
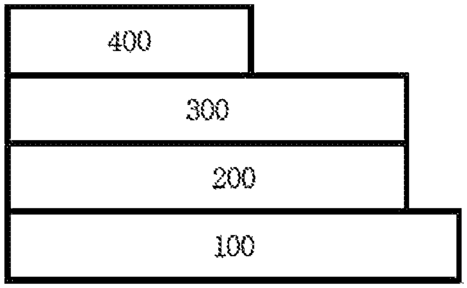
【FIG. 2】
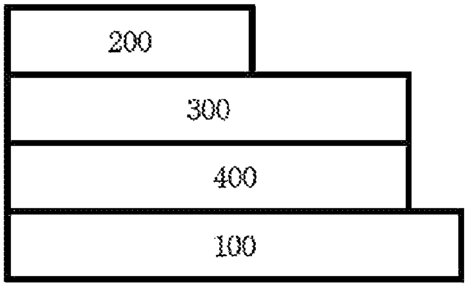
【FIG. 3】
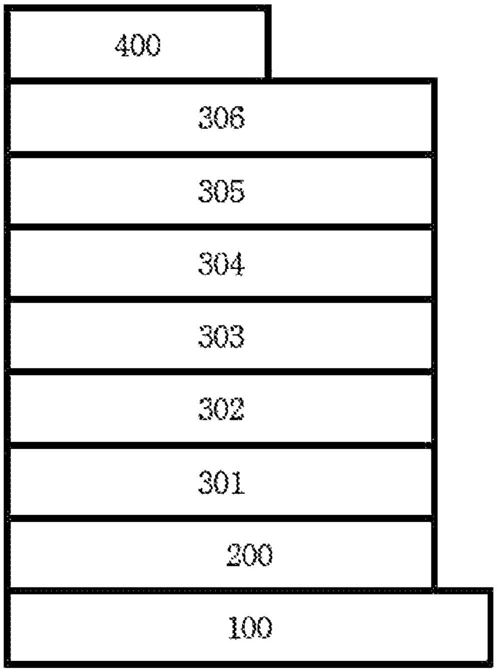

【FIG. 4】
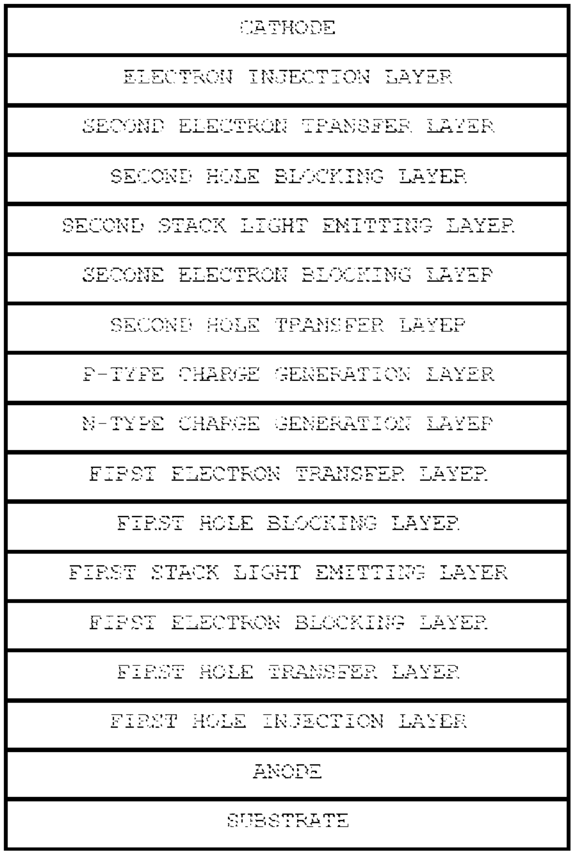

HETEROCYCLIC COMPOUND AND ORGANIC LIGHT-EMITTING ELEMENT INCLUDING SAME

TECHNICAL FIELD

The present specification claims priority to and the benefits of Korean Patent Application No. 10-2018-0156184, filed with the Korean Intellectual Property Office on Dec. 6, 2018, the entire contents of which are incorporated herein by reference.

The present specification relates to a heterocyclic compound, and an organic light emitting device including the same.

BACKGROUND ART

An electroluminescent device is one type of self-emissive display devices, and has an advantage of having a wide viewing angle, and a high response speed as well as having an excellent contrast.

An organic light emitting device has a structure disposing an organic thin film between two electrodes. When a voltage is applied to an organic light emitting device having such a structure, electrons and holes injected from the two electrodes bind and pair in the organic thin film, and light emits as these annihilate. The organic thin film may be formed in a single layer or a multilayer as necessary.

A material of the organic thin film may have a light emitting function as necessary. For example, as a material of the organic thin film, compounds capable of forming a light emitting layer themselves alone may be used, or compounds capable of performing a role of a host or a dopant of a host-dopant-based light emitting layer may also be used. In addition thereto, compounds capable of performing roles of hole injection, hole transfer, electron blocking, hole blocking, electron transfer, electron injection and the like may also be used as a material of the organic thin film.

Development of an organic thin film material has been continuously required for enhancing performance, lifetime or efficiency of an organic light emitting device.

DISCLOSURE

Technical Problem

The present specification is directed to providing a heterocyclic compound, and an organic light emitting device including the same.

Technical Solution

One embodiment of the present specification provides a heterocyclic compound represented by the following Chemical Formula 1.

[Chemical Formula 1]

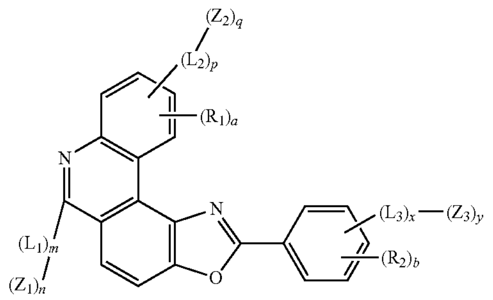

wherein, in Chemical Formula 1, $L_1$ to $L_3$ are the same as or different from each other, and each independently a direct bond; a substituted or unsubstituted arylene group; or a substituted or unsubstituted heteroarylene group, $Z_1$ to $Z_3$ are the same as or different from each other, and each independently selected from the group consisting of hydrogen; deuterium; a halogen group; a cyano group; a substituted or unsubstituted alkyl group; a substituted or unsubstituted alkenyl group; a substituted or unsubstituted alkynyl group; a substituted or unsubstituted alkoxy group; a substituted or unsubstituted cycloalkyl group; a substituted or unsubstituted heterocycloalkyl group; a substituted or unsubstituted aryl group; a substituted or unsubstituted heteroaryl group; a substituted or unsubstituted phosphine oxide group; and a substituted or unsubstituted amine group, $R_1$ and $R_2$ are the same as or different from each other, and each independently selected from the group consisting of hydrogen; deuterium; a halogen group; a cyano group; a substituted or unsubstituted alkyl group; a substituted or unsubstituted alkenyl group; a substituted or unsubstituted alkynyl group; a substituted or unsubstituted alkoxy group; a substituted or unsubstituted cycloalkyl group; a substituted or unsubstituted heterocycloalkyl group; a substituted or unsubstituted aryl group; a substituted or unsubstituted heteroaryl group; a substituted or unsubstituted phosphine oxide group; and a substituted or unsubstituted amine group, or two or more groups adjacent to each other bond to each other to form a substituted or unsubstituted aliphatic or aromatic hydrocarbon ring or heteroring, m, p, x, n, q and y are each an integer of 1 to 5, a is an integer of 1 to 3, b is an integer of 1 to 4, and when m, p, x, n, q, y, a and b are an integer of 2 or greater, substituents in the parentheses are the same as or different from each other.

Another embodiment of the present specification provides an organic light emitting device including a first electrode; a second electrode; and one or more organic material layers provided between the first electrode and the second electrode, wherein one or more layers of the organic material layers include the heterocyclic compound represented by Chemical Formula 1.

Advantageous Effects

A compound described in the present specification can be used as a material of an organic material layer of an organic light emitting device. The compound is capable of performing a role of a hole injection material, a hole transfer material, a light emitting material, an electron transfer material, an electron injection material and the like. Particularly, the compound can be used as an electron transfer layer material, a hole blocking layer material or a charge generation layer material of an organic light emitting device.

Specifically, when using the compound represented by Chemical Formula 1 in an organic material layer, a device driving voltage can be lowered, light efficiency can be enhanced, and device lifetime properties can be enhanced.

DESCRIPTION OF DRAWINGS

FIG. 1 to FIG. 4 are diagrams each illustrating a lamination structure of an organic light emitting device according to one embodiment of the present specification.

REFERENCE NUMERAL

100: Substrate
200: Anode
300: Organic Material Layer
301: Hole Injection Layer
302: Hole Transfer Layer
303: Light Emitting Layer
304: Hole Blocking Layer
305: Electron Transfer Layer
306: Electron Injection Layer
400: Cathode

MODE FOR DISCLOSURE

Hereinafter, the present specification will be described in more detail.

In the present specification, a certain part "including" certain constituents means capable of further including other constituents, and does not exclude other constituents unless particularly stated on the contrary.

A term "substitution" means a hydrogen atom bonding to a carbon atom of a compound being changed to another substituent, and the position of substitution is not limited as long as it is a position at which the hydrogen atom is substituted, that is, a position at which a substituent can substitute, and when two or more substituents substitute, the two or more substituents may be the same as or different from each other.

In the present specification, the halogen may be fluorine, chlorine, bromine or iodine.

In the present specification, the alkyl group includes linear or branched having 1 to 60 carbon atoms, and may be further substituted with other substituents. The number of carbon atoms of the alkyl group may be from 1 to 60, specifically from 1 to 40 and more specifically from 1 to 20. Specific examples thereof may include a methyl group, an ethyl group, a propyl group, an n-propyl group, an isopropyl group, a butyl group, an n-butyl group, an isobutyl group, a tert-butyl group, a sec-butyl group, a 1-methyl-butyl group, a 1-ethyl-butyl group, a pentyl group, an n-pentyl group, an isopentyl group, a neopentyl group, a tert-pentyl group, a hexyl group, an n-hexyl group, a 1-methylpentyl group, a 2-methylpentyl group, a 4-methyl-2-pentyl group, a 3,3-dimethylbutyl group, a 2-ethylbutyl group, a heptyl group, an n-heptyl group, a 1-methylhexyl group, a cyclopentylmethyl group, a cyclohexylmethyl group, an octyl group, an n-octyl group, a tert-octyl group, a 1-methylheptyl group, a 2-ethylhexyl group, a 2-propylpentyl group, an n-nonyl group, a 2,2-dimethylheptyl group, a 1-ethyl-propyl group, a 1,1-dimethyl-propyl group, an isohexyl group, a 2-methylpentyl group, a 4-methylhexyl group, a 5-methylhexyl group and the like, but are not limited thereto.

In the present specification, the alkenyl group includes linear or branched having 2 to 60 carbon atoms, and may be further substituted with other substituents. The number of carbon atoms of the alkenyl group may be from 2 to 60, specifically from 2 to 40 and more specifically from 2 to 20. Specific examples thereof may include a vinyl group, a 1-propenyl group, an isopropenyl group, a 1-butenyl group, a 2-butenyl group, a 3-butenyl group, a 1-pentenyl group, a 2-pentenyl group, a 3-pentenyl group, a 3-methyl-1-butenyl group, a 1,3-butadienyl group, an allyl group, a 1-phenylvinyl-1-yl group, a 2-phenylvinyl-1-yl group, a 2,2-diphenylvinyl-1-yl group, a 2-phenyl-2-(naphthyl-1-yl)vinyl-1-yl group, a 2,2-bis(diphenyl-1-yl)vinyl-1-yl group, a stilbenyl group, a styrenyl group and the like, but are not limited thereto.

In the present specification, the alkynyl group includes linear or branched having 2 to 60 carbon atoms, and may be further substituted with other substituents. The number of carbon atoms of the alkynyl group may be from 2 to 60, specifically from 2 to 40 and more specifically from 2 to 20.

In the present specification, the alkoxy group may be linear, branched or cyclic. The number of carbon atoms of the alkoxy group is not particularly limited, but is preferably from 1 to 20. Specific examples thereof may include methoxy, ethoxy, n-propoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy and the like, but are not limited thereto.

In the present specification, the cycloalkyl group includes monocyclic or polycyclic having 3 to 60 carbon atoms, and may be further substituted with other substituents. Herein, the polycyclic means a group in which the cycloalkyl group is directly linked to or fused with other cyclic groups. Herein, the other cyclic groups may be a cycloalkyl group, but may also be different types of cyclic groups such as a heterocycloalkyl group, an aryl group and a heteroaryl group. The number of carbon groups of the cycloalkyl group may be from 3 to 60, specifically from 3 to 40 and more specifically from 5 to 20. Specific examples thereof may include a cyclopropyl group, a cyclobutyl group, a cyclopentyl group, a 3-methylcyclopentyl group, a 2,3-dimethylcyclopentyl group, a cyclohexyl group, a 3-methylcyclohexyl group, a 4-methylcyclohexyl group, a 2,3-dimethylcyclohexyl group, a 3,4,5-trimethylcyclohexyl group, a 4-tert-butylcyclohexyl group, a cycloheptyl group, a cyclooctyl group and the like, but are not limited thereto.

In the present specification, the heterocycloalkyl group includes O, S, Se, N or Si as a heteroatom, includes monocyclic or polycyclic having 2 to 60 carbon atoms, and may be further substituted with other substituents. Herein, the polycyclic means a group in which the heterocycloalkyl group is directly linked to or fused with other cyclic groups. Herein, the other cyclic groups may be a heterocycloalkyl group, but may also be different types of cyclic groups such as a cycloalkyl group, an aryl group and a heteroaryl group. The number of carbon atoms of the heterocycloalkyl group may be from 2 to 60, specifically from 2 to 40 and more specifically from 3 to 20.

In the present specification, the aryl group includes monocyclic or polycyclic having 6 to 60 carbon atoms, and may be further substituted with other substituents. Herein, the polycyclic means a group in which the aryl group is directly linked to or fused with other cyclic groups. Herein, the other cyclic groups may be an aryl group, but may also be different types of cyclic groups such as a cycloalkyl group, a heterocycloalkyl group and a heteroaryl group. The aryl group includes a spiro group. The number of carbon atoms of the aryl group may be from 6 to 60, specifically from 6 to 40 and more specifically from 6 to 25. Specific examples of the aryl group may include a phenyl group, a biphenyl group, a triphenyl group, a naphthyl group, an anthryl group, a chrysenyl group, a phenanthrenyl group, a perylenyl group, a fluoranthenyl group, a triphenylenyl group, a phenalenyl group, a pyrenyl group, a tetracenyl group, a pentacenyl group, a fluorenyl group, an indenyl group, an acenaphthylenyl group, a benzofluorenyl group, a spirobifluorenyl group, a 2,3-dihydro-1H-indenyl group, a fused ring thereof, and the like, but are not limited thereto.

In the present specification, the fluorenyl group may be substituted, and adjacent substituents may bond to each other to form a ring.

When the fluorenyl group is substituted,

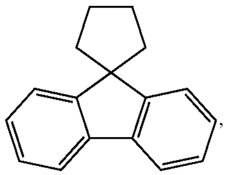
,
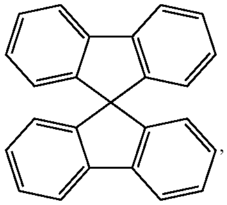
,
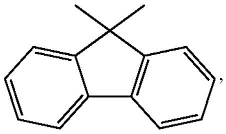
,
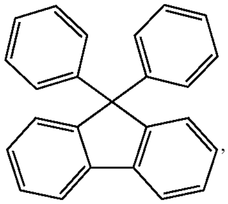
,
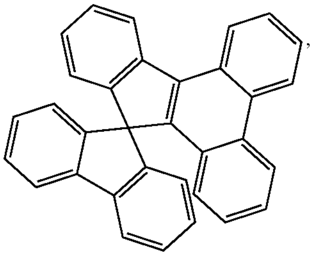
,
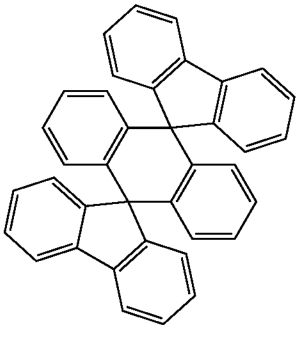

and the like may be included, however, the structure is not limited thereto.

In the present specification, the heteroaryl group includes O, S, Se, N or Si as a heteroatom, includes monocyclic or polycyclic having 2 to 60 carbon atoms, and may be further substituted with other substituents. Herein, the polycyclic means a group in which the heteroaryl group is directly linked to or fused with other cyclic groups. Herein, the other cyclic groups may be a heteroaryl group, but may also be different types of cyclic groups such as a cycloalkyl group, a heterocycloalkyl group and an aryl group. The number of carbon atoms of the heteroaryl group may be from 2 to 60, specifically from 2 to 40 and more specifically from 3 to 25. Specific examples of the heteroaryl group may include a pyridyl group, a pyrrolyl group, a pyrimidyl group, a pyridazinyl group, a furanyl group, a thiophene group, an imidazolyl group, a pyrazolyl group, an oxazolyl group, an isoxazolyl group, a thiazolyl group, an isothiazolyl group, a triazolyl group, a furazanyl group, an oxadiazolyl group, a thiadiazolyl group, a dithiazolyl group, a tetrazolyl group, a pyranyl group, a thiopyranyl group, a diazinyl group, an oxazinyl group, a thiazinyl group, a dioxynyl group, a triazinyl group, a tetrazinyl group, a quinolyl group, an isoquinolyl group, a quinazolinyl group, an isoquinazolinyl group, a quinazolinyl group, a naphthyridyl group, an acridinyl group, a phenanthridinyl group, an imidazopyridinyl group, a diazanaphthalenyl group, a triazaindene group, an indolyl group, an indolizinyl group, a benzothiazolyl group, a benzoxazolyl group, a benzimidazolyl group, a benzothiophene group, a benzofuran group, a dibenzothiophene group, a dibenzofuran group, a carbazolyl group, a benzocarbazolyl group, a dibenzocarbazolyl group, a phenazinyl group, a dibenzosilole group, spirobi(dibenzosilole), a dihydrophenazinyl group, a phenoxazinyl group, a phenanthridyl group, an imidazopyridinyl group, a thienyl group, an indolo[2,3-a]carbazolyl group, an indolo[2,3-b]carbazolyl group, an indolinyl group, a 10,11-dihydro-dibenzo[b,f]azepine group, a 9,10-dihydroacridinyl group, a phenanthrazinyl group, a phenothiathiazinyl group, a phthalazinyl group, a naphthylidinyl group, a phenanthrolinyl group, a benzo[c][1,2,5]thiadiazolyl group, a 5,10-dihydrobenzo[b,e][1,4]azasilinyl, a pyrazolo[1,5-c]quinazolinyl group, a pyrido[1,2-b]indazolyl group, a pyrido[1,2-a]imidazo[1,2-e]indolinyl group, a 5,11-dihydroindeno[1,2-b]carbazolyl group and the like, but are not limited thereto.

In the present specification, the phosphine oxide group may be specifically substituted with an aryl group, and as the aryl group, examples described above may be used. Examples of the phosphine oxide group may include a diphenylphosphine oxide group, a dinaphthylphosphine oxide group and the like, but are not limited thereto.

In the present specification, the amine group may be selected from the group consisting of a monoalkylamine group; a monoarylamine group; a monoheteroarylamine group; —$NH_2$; a dialkylamine group; a diarylamine group; a diheteroarylamine group; an alkylarylamine group; an alkylheteroarylamine group; and an arylheteroarylamine group, and although not particularly limited thereto, the number of carbon atoms is preferably from 1 to 30. Specific examples of the amine group may include a methylamine group, a dimethylamine group, an ethylamine group, a diethylamine group, a phenylamine group, a naphthylamine group, a biphenylamine group, a dibiphenylamine group, an anthracenylamine group, a 9-methyl-anthracenylamine group, a diphenylamine group, a phenylnaphthylamine group, a ditolylamine group, a phenyltolylamine group, a triphenylamine group, a biphenylnaphthylamine group, a phenylbiphenylamine group, a biphenylfluorenylamine group, a phenyltriphenylenylamine group, a biphenyltriphenylenylamine group and the like, but are not limited thereto.

In the present specification, the structures illustrated above as the aryl group and the heteroaryl group may be applied to the arylene group and the heteroarylene group except that these are divalent.

In the present specification, an "adjacent" group may mean a substituent substituting an atom directly linked to an atom substituted by the corresponding substituent, a substituent sterically most closely positioned to the corresponding substituent, or another substituent substituting an atom substituted by the corresponding substituent. For example, two substituents substituting ortho positions in a benzene ring, and two substituents substituting the same carbon in an aliphatic ring may be interpreted as groups "adjacent" to each other.

As the aliphatic or aromatic hydrocarbon ring or heteroring that the adjacent groups may form, the structures illustrated as the cycloalkyl group, the cycloheteroalkyl group, the aryl group and the heteroaryl group may be used except for those that are not monovalent.

In the present specification, "substituted or unsubstituted" means being substituted with one or more substituents selected from the group consisting of C1 to C60 linear or branched alkyl; C2 to C60 linear or branched alkenyl; C2 to C60 linear or branched alkynyl; C3 to C60 monocyclic or polycyclic cycloalkyl; C2 to C60 monocyclic or polycyclic heterocycloalkyl; C6 to C60 monocyclic or polycyclic aryl; C2 to C60 monocyclic or polycyclic heteroaryl; —SiRR'R"; P(═O)RR'; C1 to C20 alkylamine; C6 to C60 monocyclic or polycyclic arylamine; and C2 to C60 monocyclic or polycyclic heteroarylamine, or being unsubstituted, or being substituted with a substituent linking two or more substituents selected from among the substituents illustrated above, or being unsubstituted. R, R' and R" are the same as or different from each other, and each independently hydrogen; deuterium; a cyano group; a substituted or unsubstituted alkyl group; a substituted or unsubstituted cycloalkyl group; a substituted or unsubstituted aryl group; or a substituted or unsubstituted heteroaryl group.

One embodiment of the present specification provides a compound represented by Chemical Formula 1. Electron distribution of HOMO and LUMO is discontinued by the fused structure of quinoline and benzoxazole of Chemical Formula 1 resulting in a wide band gap and a high T1 value, and efficiency of an organic light emitting device may increase through increasing intermolecular interactions by unshared electron pairs of nitrogen and oxygen.

In one embodiment of the present specification, $L_1$ to $L_3$ are the same as or different from each other, and may be each independently a direct bond; a substituted or unsubstituted arylene group; or a substituted or unsubstituted heteroarylene group.

In another embodiment, $L_1$ to $L_3$ are the same as or different from each other, and may be each independently a direct bond; a substituted or unsubstituted C6 to C60 arylene group; or a substituted or unsubstituted C2 to C60 heteroarylene group.

In another embodiment, $L_1$ to $L_3$ are the same as or different from each other, and may be each independently a direct bond; a substituted or unsubstituted C6 to C40 arylene group; or a substituted or unsubstituted C2 to C40 heteroarylene group.

In another embodiment, $L_1$ to $L_3$ are the same as or different from each other, and may be each independently a direct bond; a substituted or unsubstituted C6 to C20 arylene group; or a substituted or unsubstituted C2 to C20 heteroarylene group.

In another embodiment, $L_1$ to $L_3$ are the same as or different from each other, and may be each independently a direct bond; a C6 to C20 arylene group; or a C2 to C20 heteroarylene group.

In another embodiment, $L_1$ to $L_3$ are the same as or different from each other, and may be each independently a direct bond; a phenylene group; a biphenylene group; a naphthalene group; an anthracene group; a pyrene group; a phenanthrene group; a quinoline group; a quinazoline group; a pyridine group unsubstituted or substituted with one or more substituents selected from the group consisting of a phenyl group and a pyridine group; a pyrimidine group unsubstituted or substituted with one or more substituents selected from the group consisting of a phenyl group and a naphthalene group; or a triazine group unsubstituted or substituted with one or more substituents selected from the group consisting of a phenyl group and a naphthalene group, and the substituents are a divalent group.

In one embodiment of the present specification, $Z_1$ to $Z_3$ are the same as or different from each other, and may be each independently selected from the group consisting of hydrogen; deuterium; a halogen group; a cyano group; a substituted or unsubstituted alkyl group; a substituted or unsubstituted alkenyl group; a substituted or unsubstituted alkynyl group; a substituted or unsubstituted alkoxy group; a substituted or unsubstituted cycloalkyl group; a substituted or unsubstituted heterocycloalkyl group; a substituted or unsubstituted aryl group; a substituted or unsubstituted heteroaryl group; a substituted or unsubstituted phosphine oxide group; and a substituted or unsubstituted amine group.

In another embodiment, $Z_1$ to $Z_3$ are the same as or different from each other, and may be each independently hydrogen; deuterium; a cyano group; a substituted or unsubstituted aryl group; a substituted or unsubstituted heteroaryl group; or a substituted or unsubstituted phosphine oxide group.

In another embodiment, $Z_1$ to $Z_3$ are the same as or different from each other, and may be each independently hydrogen; deuterium; a cyano group; a substituted or unsubstituted C6 to C60 aryl group; a substituted or unsubstituted C2 to C60 heteroaryl group; or a substituted or unsubstituted phosphine oxide group.

In another embodiment, $Z_1$ to $Z_3$ are the same as or different from each other, and may be each independently hydrogen; deuterium; a cyano group; a substituted or unsubstituted C6 to C40 aryl group; a substituted or unsubstituted C2 to C40 heteroaryl group; or a substituted or unsubstituted phosphine oxide group.

In another embodiment, $Z_1$ to $Z_3$ are the same as or different from each other, and may be each independently hydrogen; deuterium; a cyano group; a C6 to C40 aryl group unsubstituted or substituted with one or more substituents selected from the group consisting of a C6 to C40 aryl group, a C2 to C40 heteroaryl group and a C1 to C40 alkyl group; a C2 to C40 heteroaryl group unsubstituted or substituted with one or more substituents selected from the group consisting of a C6 to C40 aryl group, a C2 to C40 heteroaryl group and a C1 to C40 alkyl group; or a phosphine oxide group unsubstituted or substituted with one or more substituents selected from the group consisting of a C6 to C40 aryl group and a C1 to C40 alkyl group.

In another embodiment, $Z_1$ to $Z_3$ are the same as or different from each other, and may be each independently hydrogen; deuterium; a cyano group; a phenyl group unsubstituted or substituted with one or more substituents selected from the group consisting of a carbazole group and a pyridine group; a biphenyl group; a naphthyl group; an anthracene group; a triphenyl group; a pyrene group; a phenanthrenyl group; a phenanthroline group; a carbazole group; a dibenzofuran group; a dibenzothiophene group; a quinoline group; a pyridine group unsubstituted or substituted with one or more substituents selected from the group consisting of a phenyl group and a pyridine group; a pyrimidine group unsubstituted or substituted with one or more more substituents selected from the group consisting of a phenyl group and a naphthyl group; a triazine group unsubstituted or substituted with one or more substituents selected from the group consisting of a phenyl group and a naphthyl group; a quinazoline group unsubstituted or substituted with a phenyl group; a benzimidazole group unsubstituted or substituted with one or more substituents selected from the group consisting of a phenyl group and an ethyl group; a benzothiazole group unsubstituted or substituted with a phenyl group; an imidazo[1,2-a]pyridine group; a pyrido[1,2-b]indazole group; a 1,3,4-oxadiazole group; or a phosphine oxide group unsubstituted or substituted with one or more substituents selected from the group consisting of a phenyl group and a methyl group.

In one embodiment of the present specification, $R_1$ and $R_2$ are the same as or different from each other, and each independently selected from the group consisting of hydrogen; deuterium; a halogen group; a cyano group; a substituted or unsubstituted alkyl group; a substituted or unsubstituted alkenyl group; a substituted or unsubstituted alkynyl group; a substituted or unsubstituted alkoxy group; a substituted or unsubstituted cycloalkyl group; a substituted or unsubstituted heterocycloalkyl group; a substituted or unsubstituted aryl group; a substituted or unsubstituted heteroaryl group; a substituted or unsubstituted phosphine oxide group; and a substituted or unsubstituted amine group, or two or more groups adjacent to each other may bond to each other to form a substituted or unsubstituted aliphatic or aromatic hydrocarbon ring or heteroring.

In one embodiment of the present specification, $R_1$ and $R_2$ may be hydrogen.

In the heterocyclic compound provided in one embodiment of the present specification, Chemical Formula 1 is represented by any one of the following Chemical Formula 2 to Chemical Formula 4.

[Chemical Formula 2]

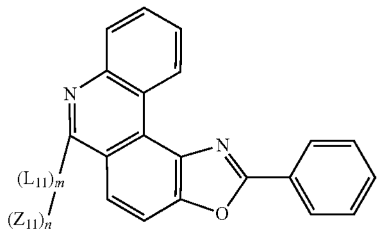

[Chemical Formula 3]

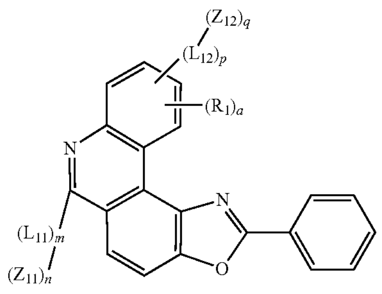

-continued

[Chemical Formula 4]

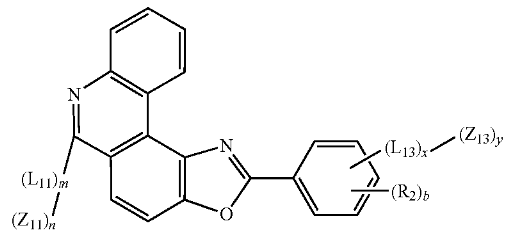

In Chemical Formula 2 to Chemical Formula 4, $R_1$, $R_2$, m, p, x, n, q, y, a and b have the same definitions as in Chemical Formula 1, $L_{11}$ to $L_{13}$ are the same as or different from each other, and each independently a direct bond; a substituted or unsubstituted arylene group; or a substituted or unsubstituted heteroarylene group, and $Z_{11}$ to $Z_{13}$ are the same as or different from each other, and each independently selected from the group consisting of a cyano group; a substituted or unsubstituted aryl group; a substituted or unsubstituted heteroaryl group; and a substituted or unsubstituted phosphine oxide group.

The heterocyclic compound represented by Chemical Formula 2 leads to low driving voltage and high efficiency by increasing electron mobility through increasing intermolecular interactions by unshared electron pairs of oxygen and nitrogen in the skeleton, and the heterocyclic compound represented by Chemical Formula 3 leads to long lifetime properties by introducing both an electrophilic substituent and a stabilizing group to the skeleton and thereby dispersing injected electrons. In addition, the heterocyclic compound represented by Chemical Formula 4 may enhance efficiency of an organic light emitting device by having a wide band gap and a high T1 value by discontinuing electron distribution of HOMO and LUMO due to the fused structure of quinoline and benzoxazole.

In one embodiment of the present specification, $L_{11}$ to $L_{13}$ are the same as or different from each other, and may be each independently a direct bond; a substituted or unsubstituted arylene group; or a substituted or unsubstituted heteroarylene group.

In another embodiment, $L_{11}$ to $L_{13}$ are the same as or different from each other, and may be each independently a direct bond; a substituted or unsubstituted C6 to C60 arylene group; or a substituted or unsubstituted C2 to C60 heteroarylene group.

In another embodiment, $L_{11}$ to $L_{13}$ are the same as or different from each other, and may be each independently a direct bond; a substituted or unsubstituted C6 to C40 arylene group; or a substituted or unsubstituted C2 to C40 heteroarylene group.

In another embodiment, $L_{11}$ to $L_{13}$ are the same as or different from each other, and may be each independently a direct bond; a substituted or unsubstituted C6 to C20 arylene group; or a substituted or unsubstituted C2 to C20 heteroarylene group.

In another embodiment, $L_{11}$ to $L_{13}$ are the same as or different from each other, and may be each independently a direct bond; a C6 to C20 arylene group; or a C2 to C20 heteroarylene group.

In another embodiment, $L_{11}$ to $L_{13}$ are the same as or different from each other, and may be each independently a direct bond; a phenylene group; a biphenylene group; a naphthalene group; an anthracene group; a pyrene group; a phenanthrene group; a quinoline group; a quinazoline group; a pyridine group unsubstituted or substituted with one or more substituents selected from the group consisting of a phenyl group and a pyridine group; a pyrimidine group unsubstituted or substituted with one or more substituents selected from the group consisting of a phenyl group and a naphthyl group; or a triazine group unsubstituted or substituted with one or more substituents selected from the group consisting of a phenyl group and a naphthyl group.

In one embodiment of the present specification, $Z_{11}$ to $Z_{13}$ are the same as or different from each other, and may be each independently selected from the group consisting of a cyano group; a substituted or unsubstituted aryl group; a substituted or unsubstituted heteroaryl group; and a substituted or unsubstituted phosphine oxide group.

In another embodiment, $Z_{11}$ to $Z_{13}$ are the same as or different from each other, and may be each independently a cyano group; a substituted or unsubstituted C6 to C60 aryl group; a substituted or unsubstituted C2 to C60 heteroaryl group; or a substituted or unsubstituted phosphine oxide group.

In another embodiment, $Z_{11}$ to $Z_{13}$ are the same as or different from each other, and may be each independently a cyano group; a substituted or unsubstituted C6 to C40 aryl group; a substituted or unsubstituted C2 to C40 heteroaryl group; or a substituted or unsubstituted phosphine oxide group.

In another embodiment, $Z_{11}$ to $Z_{13}$ are the same as or different from each other, and may be each independently a cyano group; a C6 to C40 aryl group unsubstituted or substituted with one or more substituents selected from the group consisting of a C6 to C40 aryl group, a C2 to C40 heteroaryl group and a C1 to C40 alkyl group; a C2 to C40 heteroaryl group unsubstituted or substituted with one or more substituents selected from the group consisting of a C6 to C40 aryl group, a C2 to C40 heteroaryl group and a C1 to C40 alkyl group; or a phosphine oxide group unsubstituted or substituted with one or more substituents selected from the group consisting of a C6 to C40 aryl group and a C1 to C40 alkyl group.

In another embodiment, $Z_{11}$ to $Z_{13}$ are the same as or different from each other, and may be each independently a cyano group; a phenyl group unsubstituted or substituted with one or more substituents selected from the group consisting of a carbazole group and a pyridine group; a biphenyl group; a naphthyl group; an anthracene group; a triphenyl group; a pyrene group; a phenanthrenyl group; a phenanthroline group; a carbazole group; a dibenzofuran group; a dibenzothiophene group; a quinoline group; a pyridine group unsubstituted or substituted with one or more substituents selected from the group consisting of a phenyl group and a pyridine group; a pyrimidine group unsubstituted or substituted with one or more substituents selected from the group consisting of a phenyl group and a naphthyl group; a triazine group unsubstituted or substituted with one or more substituents selected from the group consisting of a phenyl group and a naphthyl group; a quinazoline group unsubstituted or substituted with a phenyl group; a benzimidazole group unsubstituted or substituted with one or more substituents selected from the group consisting of a phenyl group and an ethyl group; a benzothiazole group unsubstituted or substituted with a phenyl group; an imidazo[1,2-a]pyridine group; a pyrido[1,2-b]indazole group; a 1,3,4-oxadiazole group; or a phosphine oxide group unsubstituted or substituted with one or more substituents selected from the group consisting of a phenyl group and a methyl group.

In one embodiment of the present specification, Chemical Formula 1 may be represented by any one of the following compounds, but is not limited thereto.

1

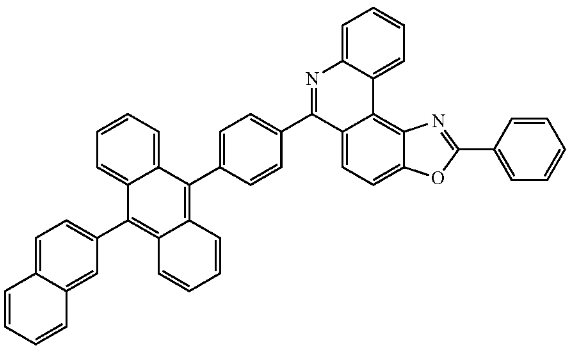

2

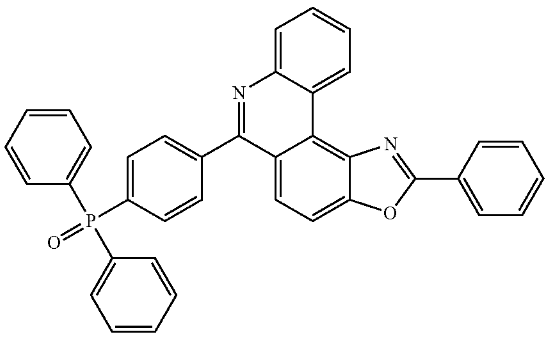

-continued
3
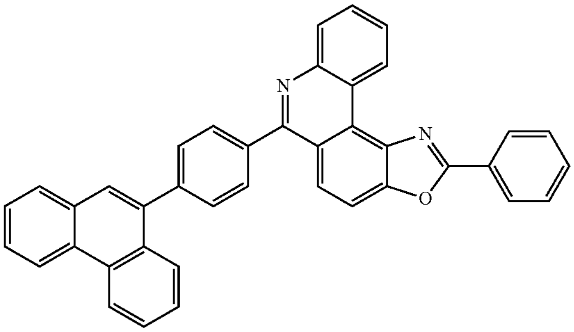
4
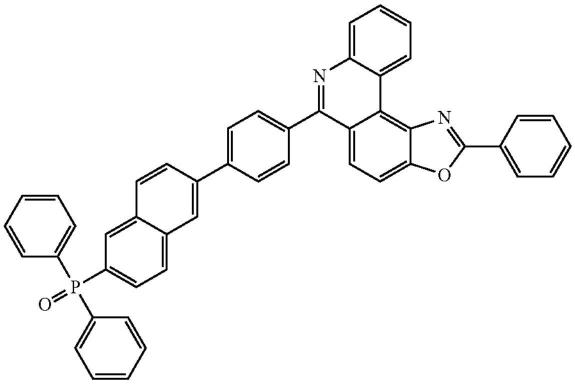
5
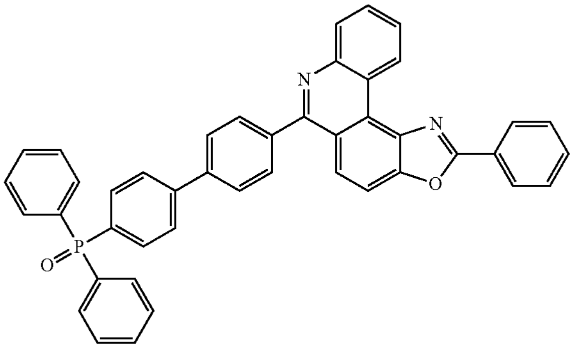
6
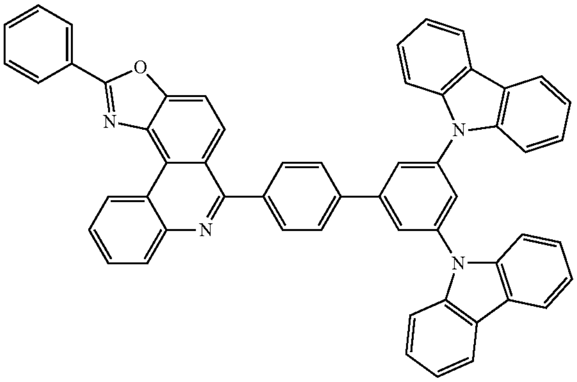
7
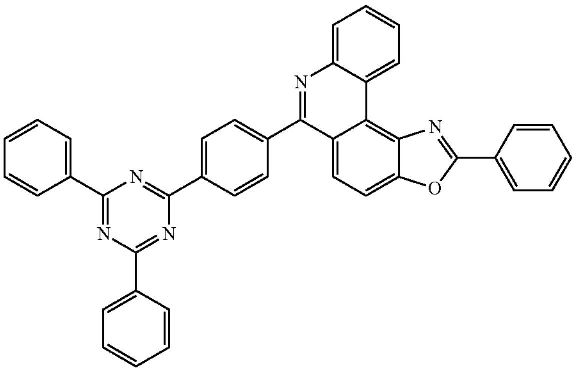
8
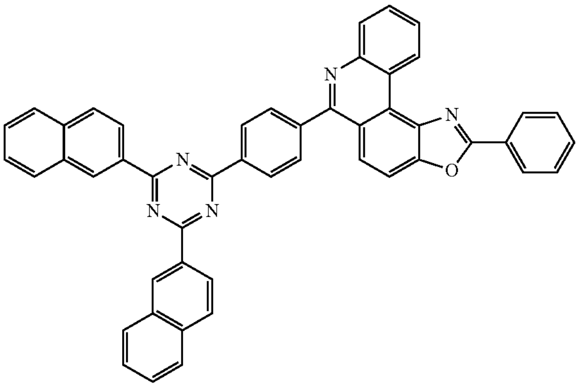

-continued
9
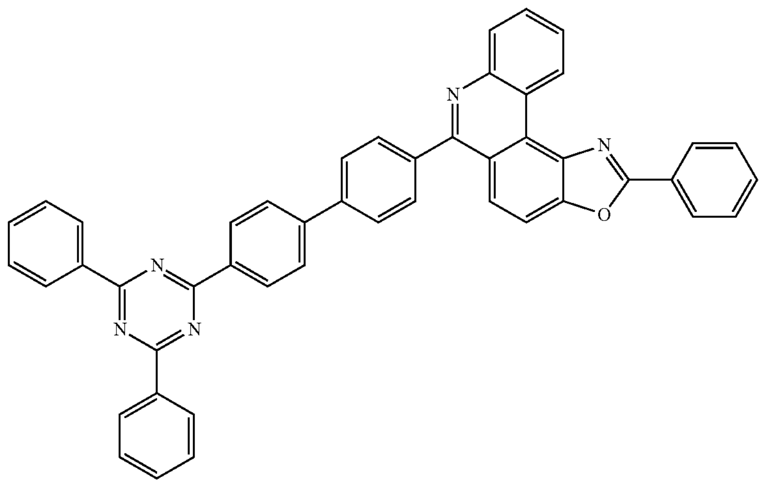
10
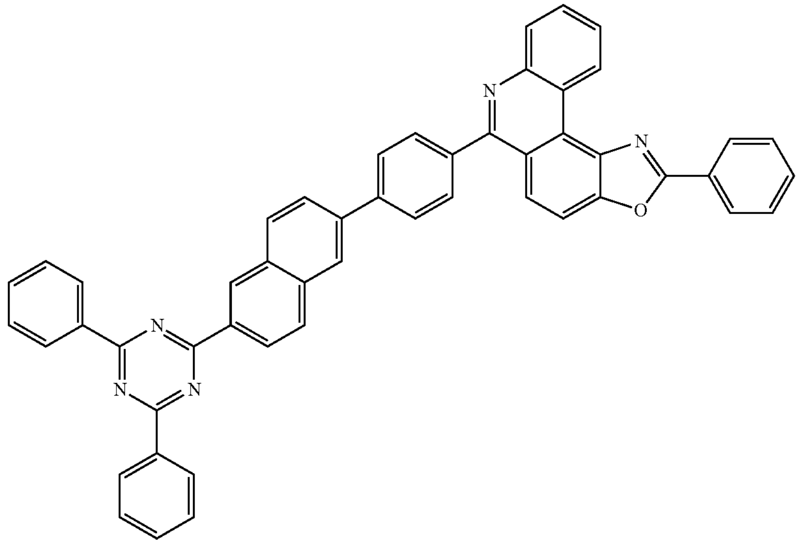
11
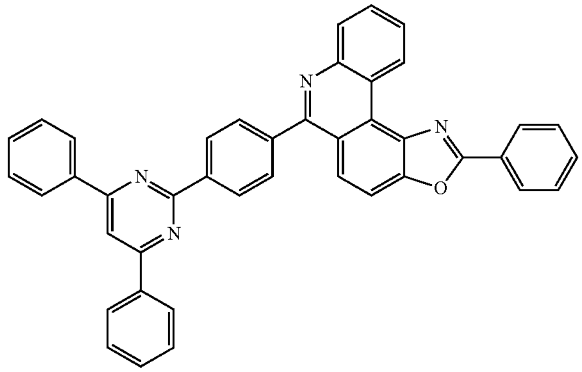
12
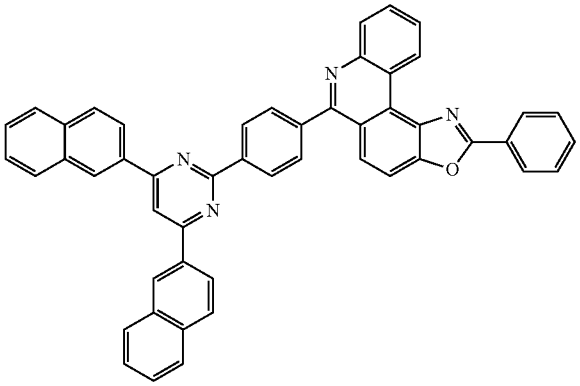

-continued
13
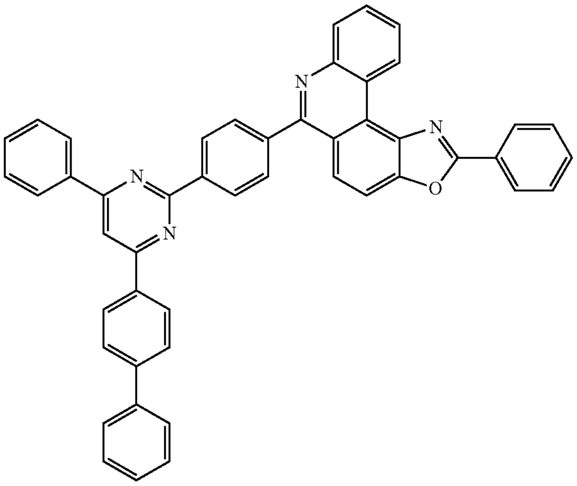
14
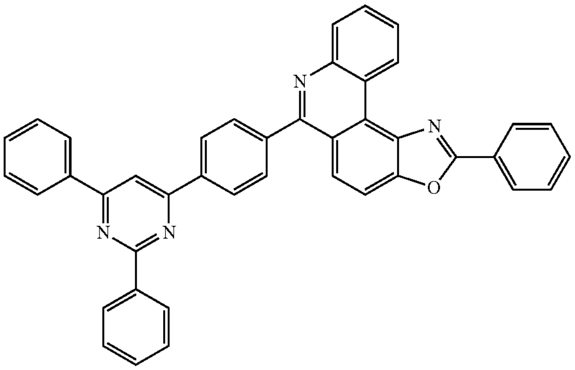
15
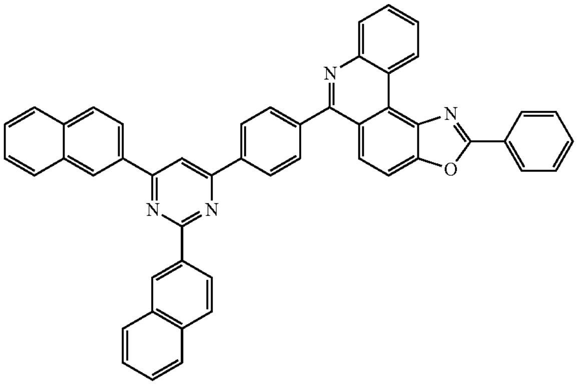
16
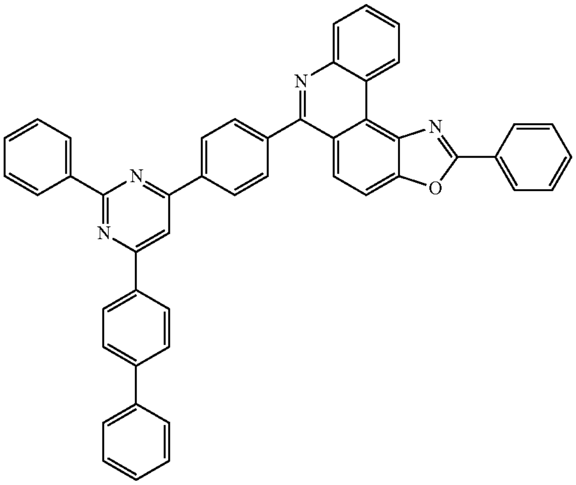
17
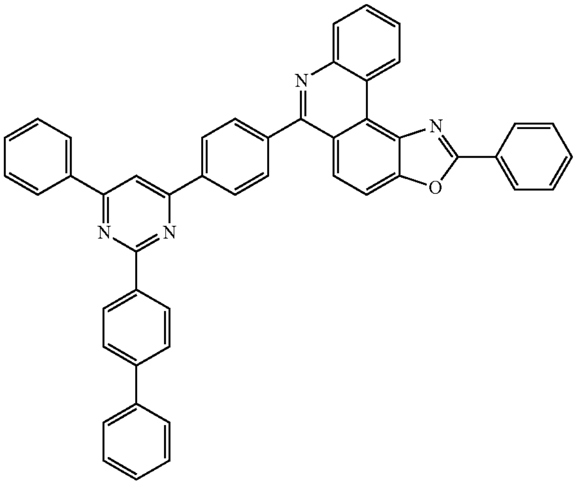
18
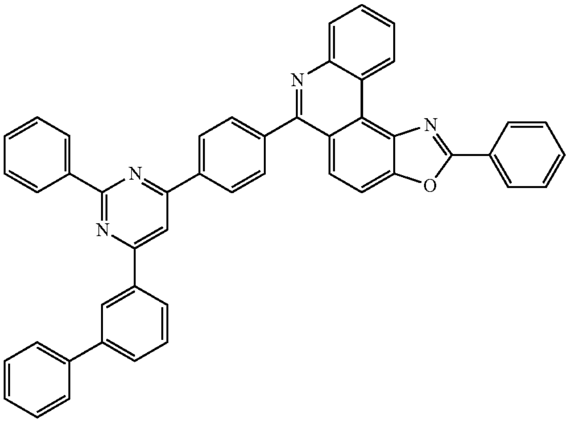

-continued
19
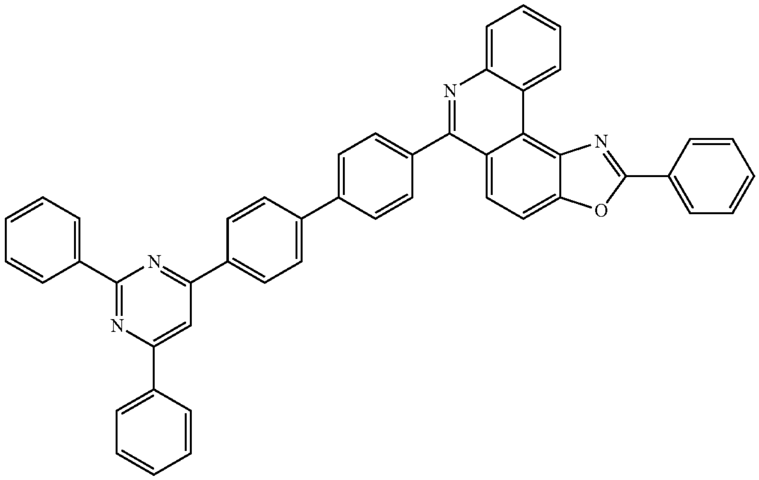
20
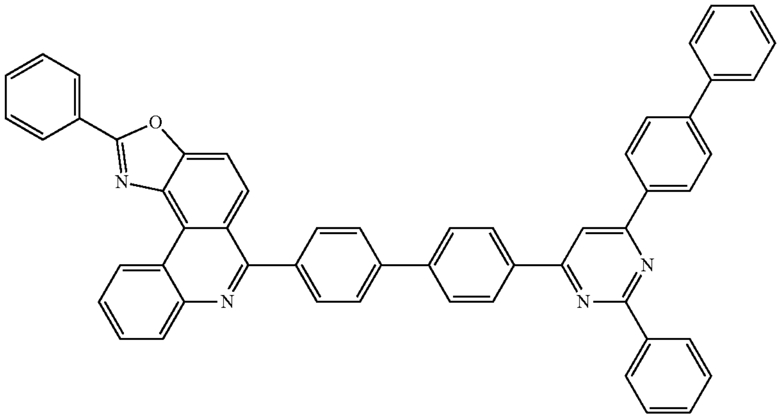
21
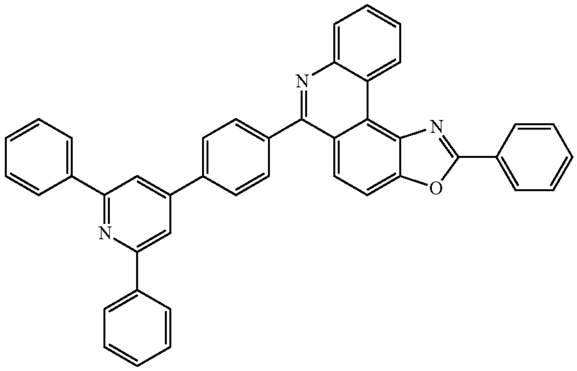
22
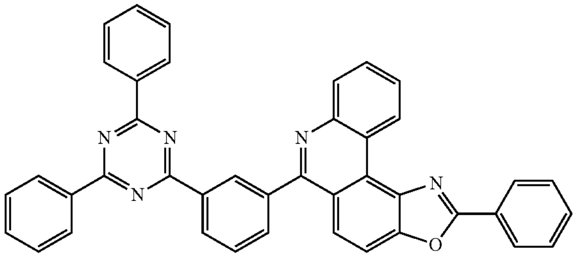
23
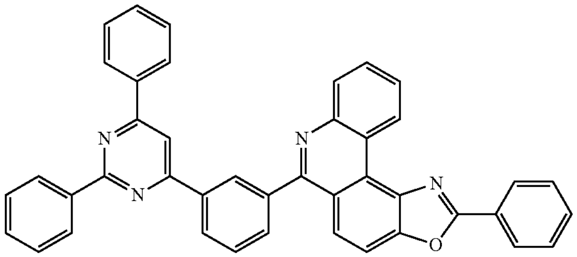

-continued
24
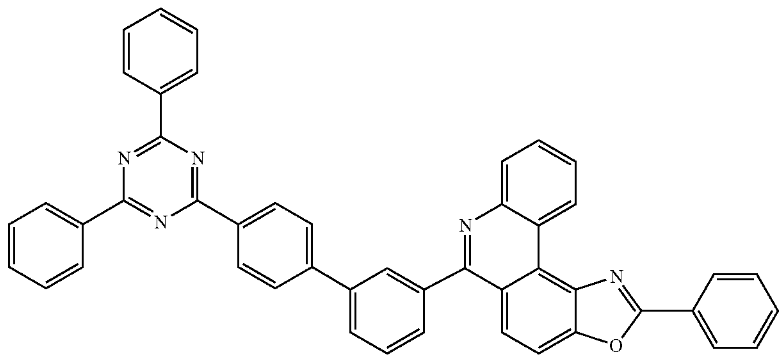
25
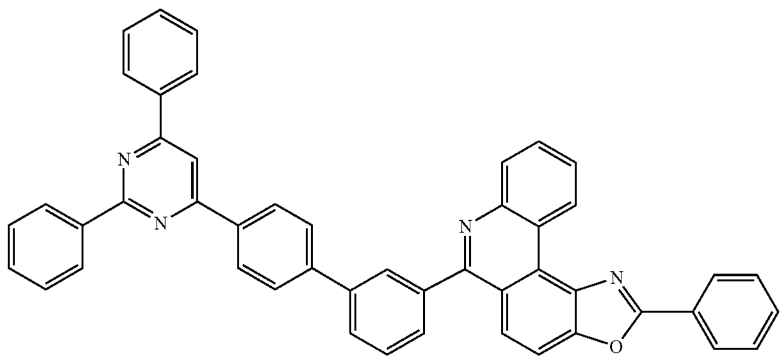
26
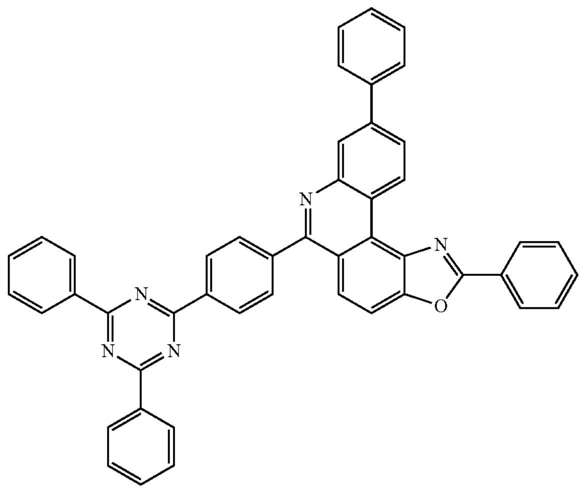
27
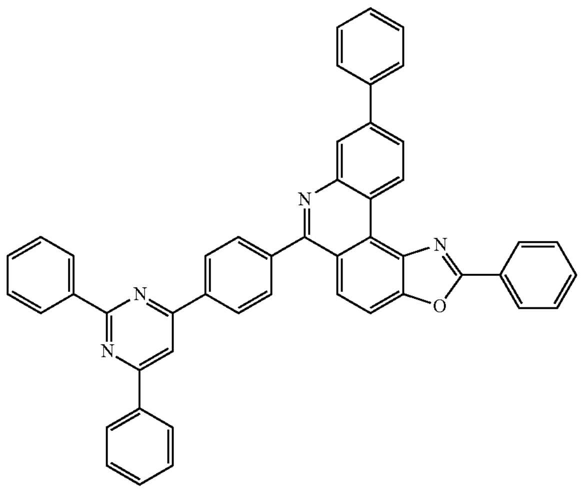

-continued
28
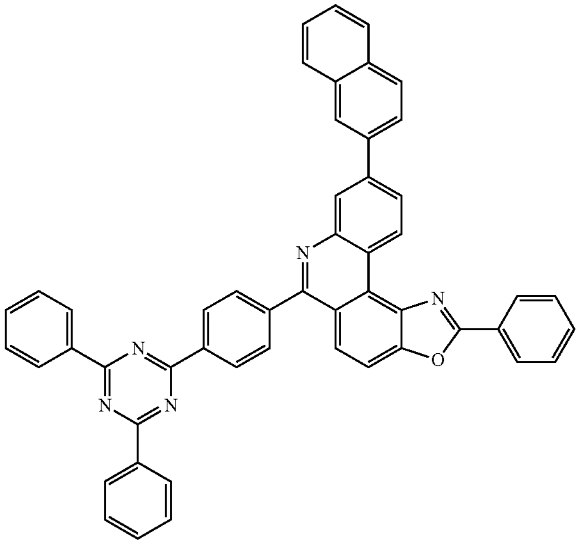
29
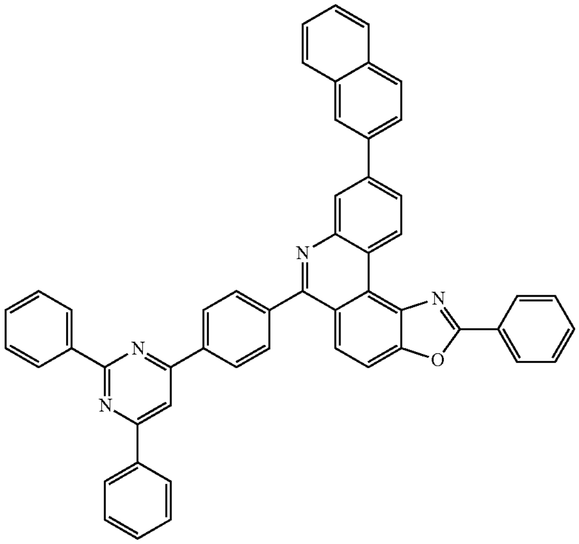
30
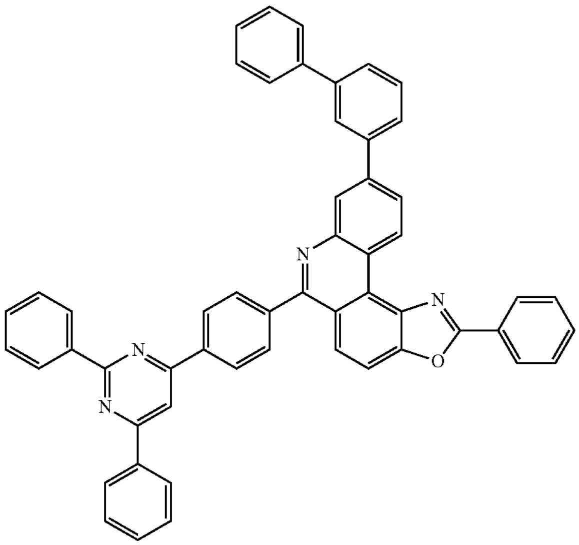
31
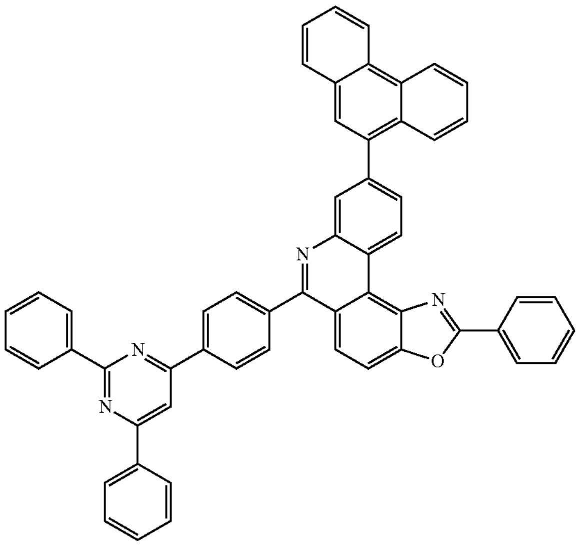

-continued
32
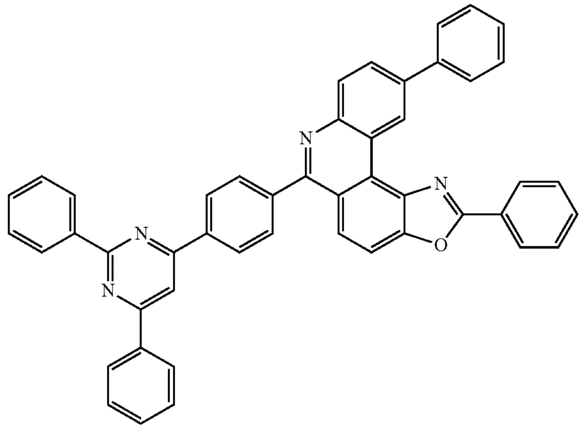
33
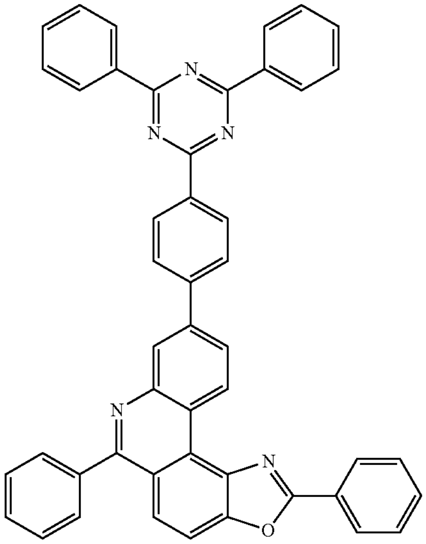
34
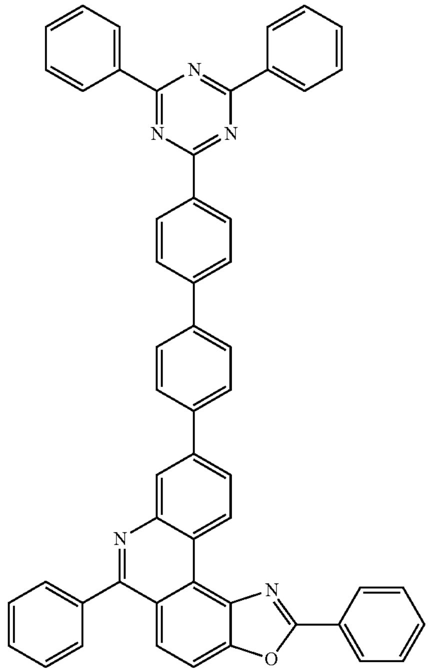
35
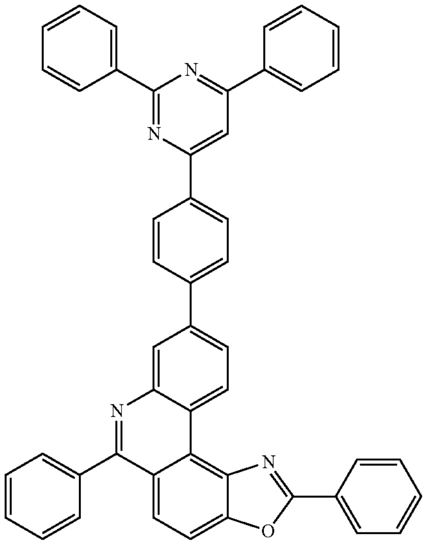

-continued
36
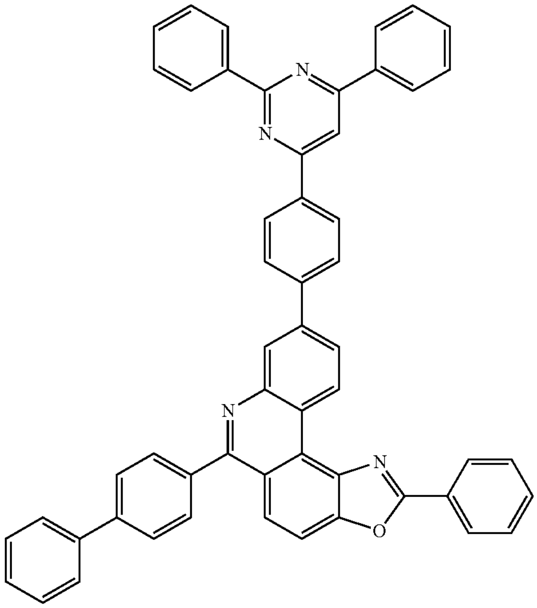
37
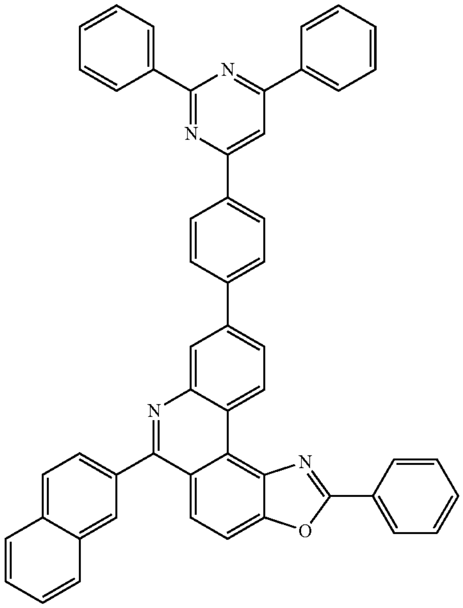
38
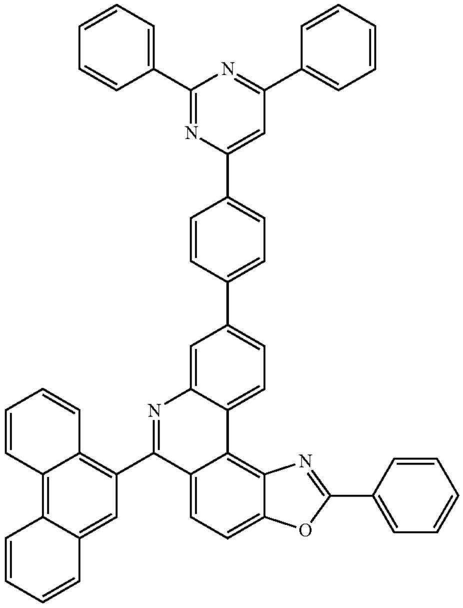
39
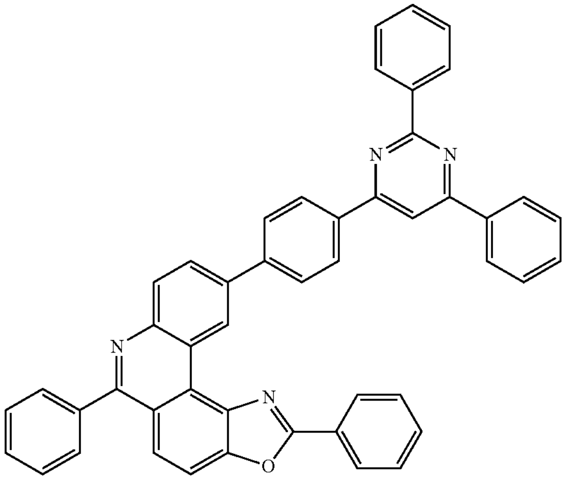
40
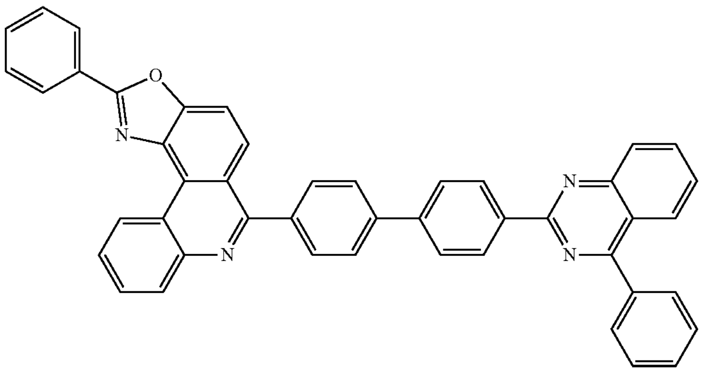

-continued
41
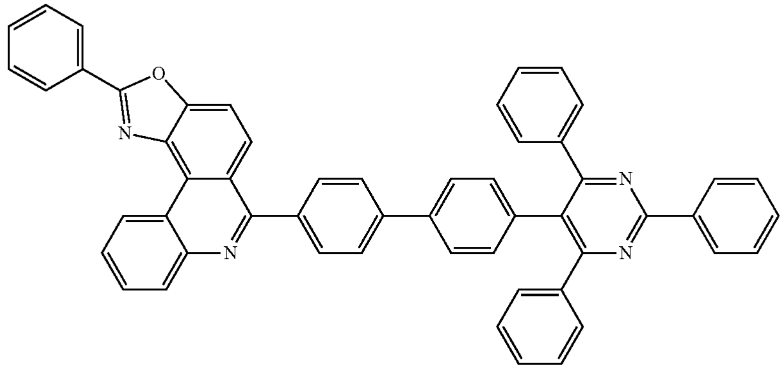
42
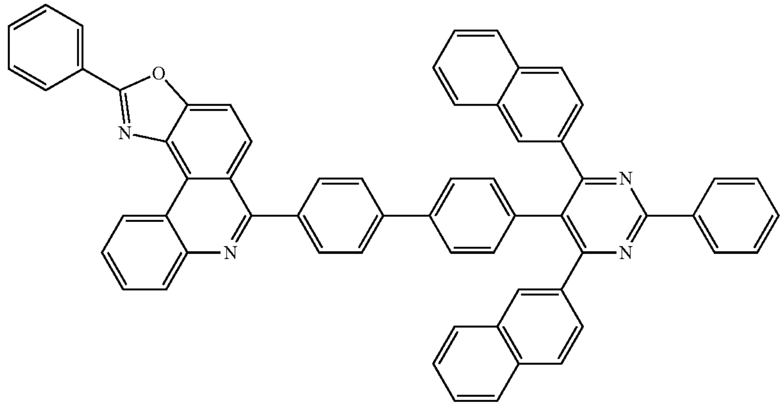
43
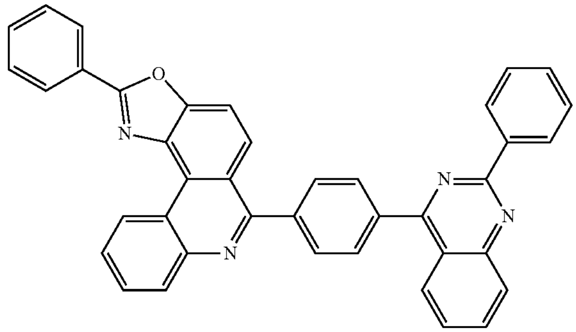
44
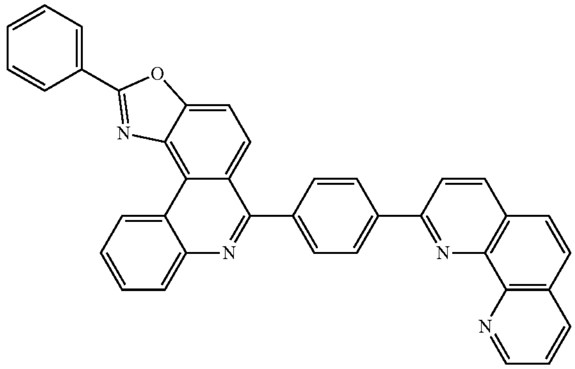

-continued
45
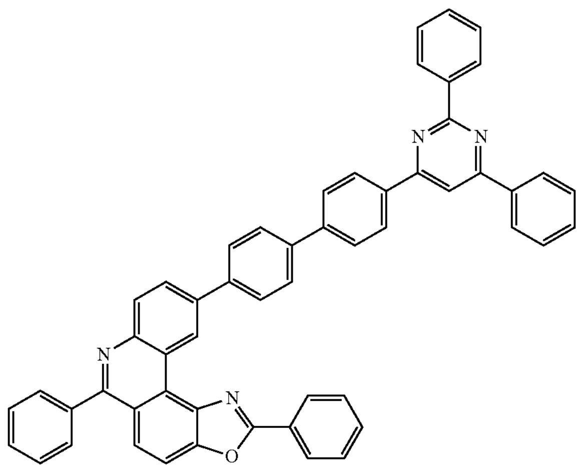
46
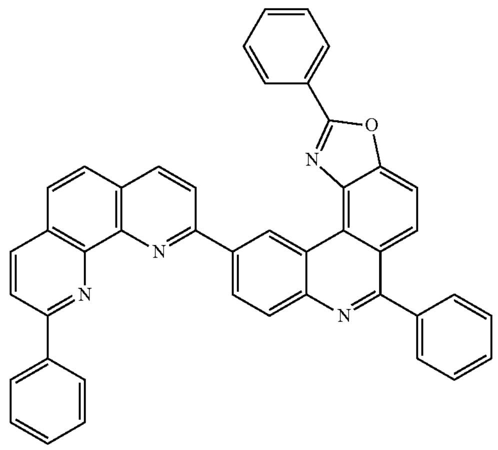
47
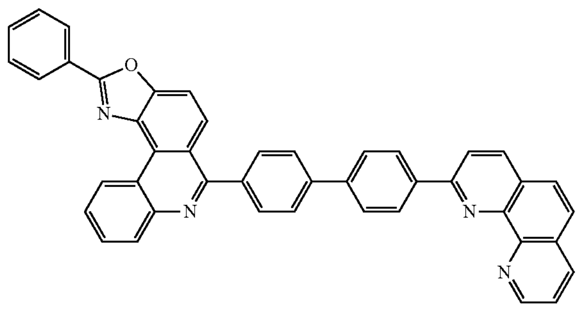
48
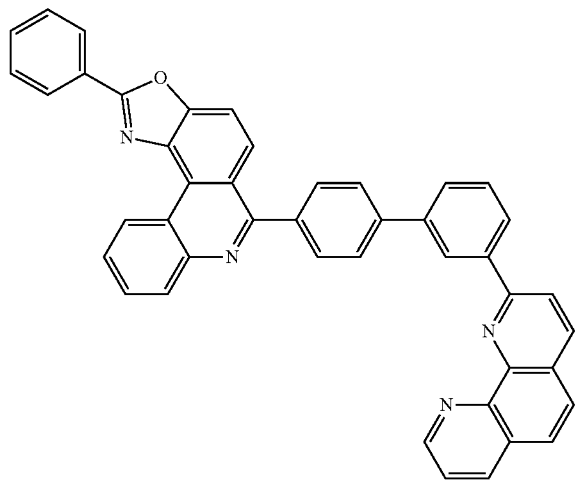
49
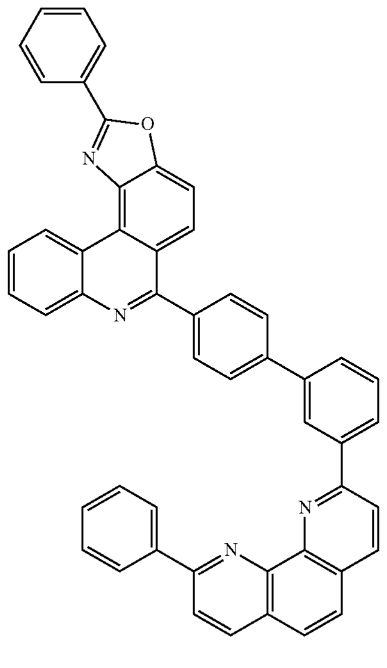
50
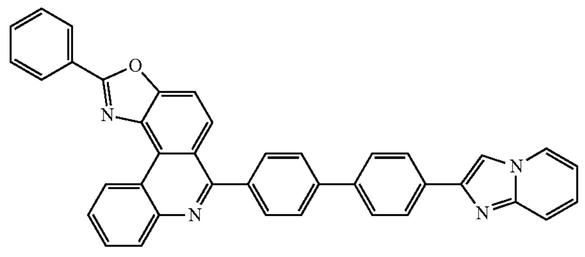

-continued
51
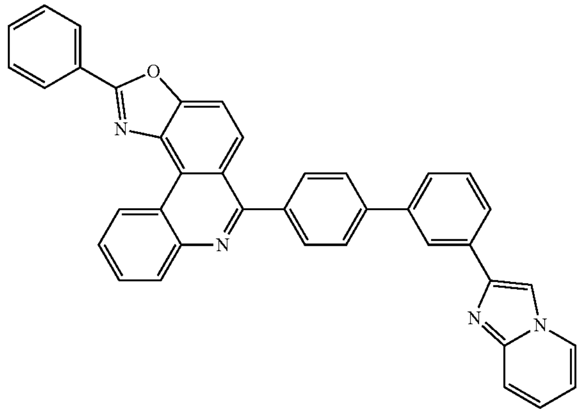
52
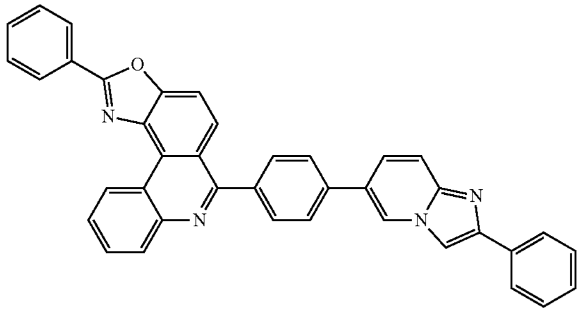
53
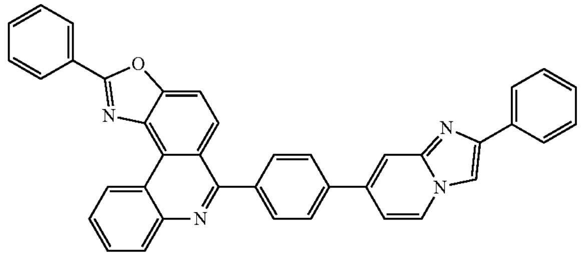
54
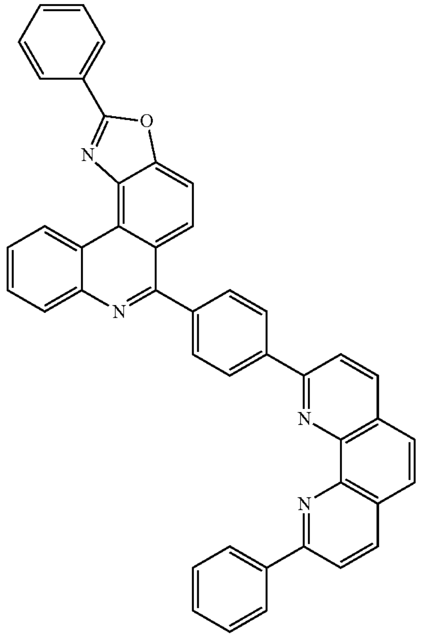
55
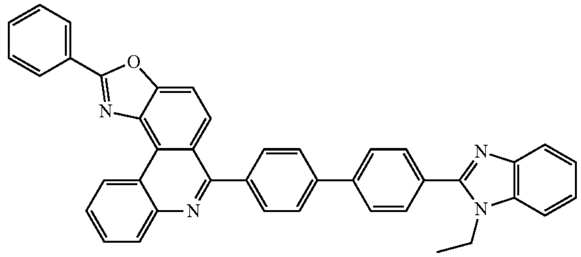
56
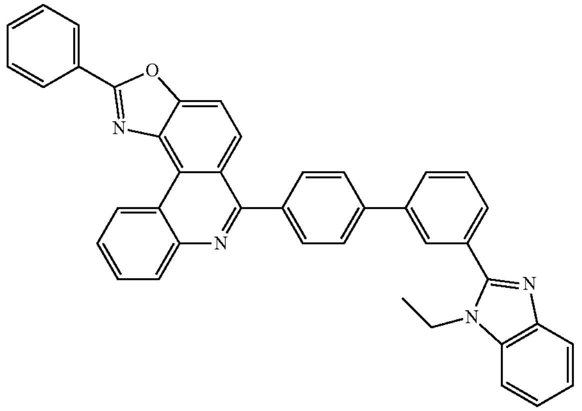

-continued
57
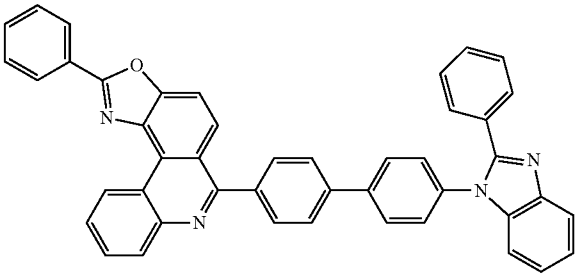
58
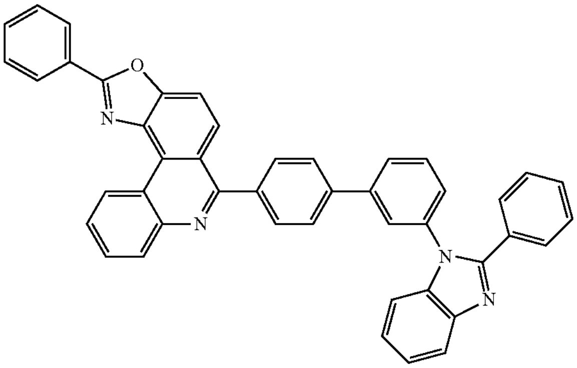
59
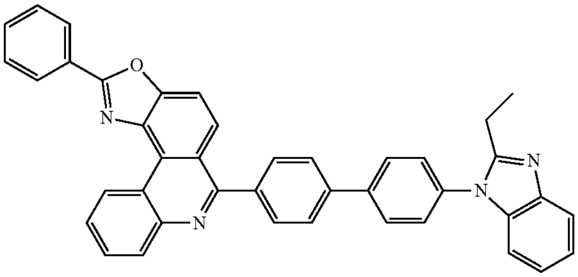
60
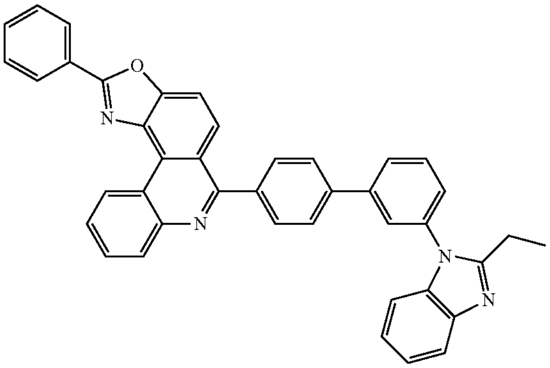
61
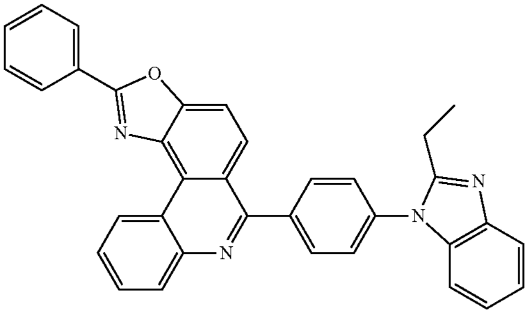
62
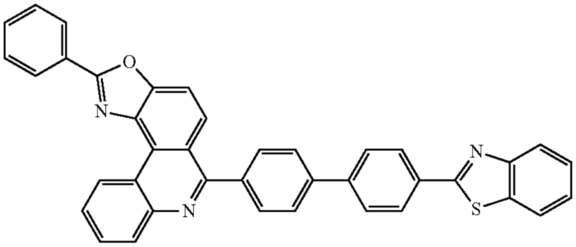
63
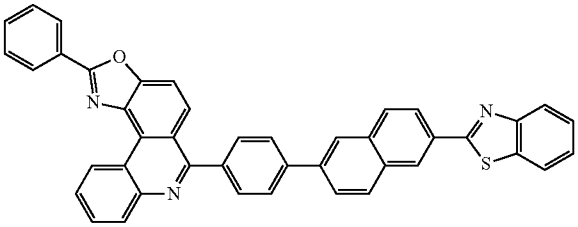
64
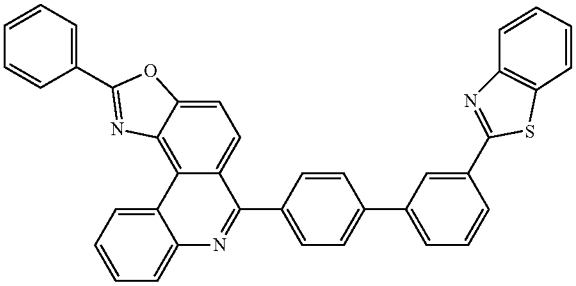

-continued
65
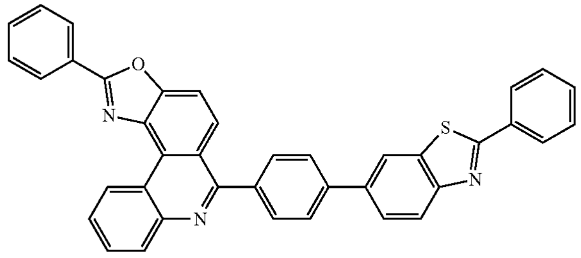
66
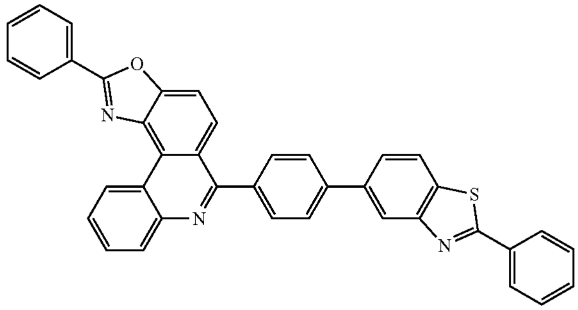
67
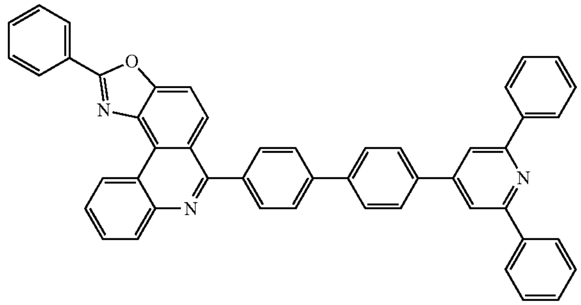
68
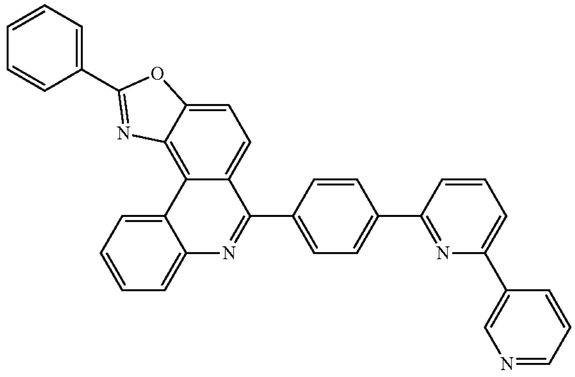
69
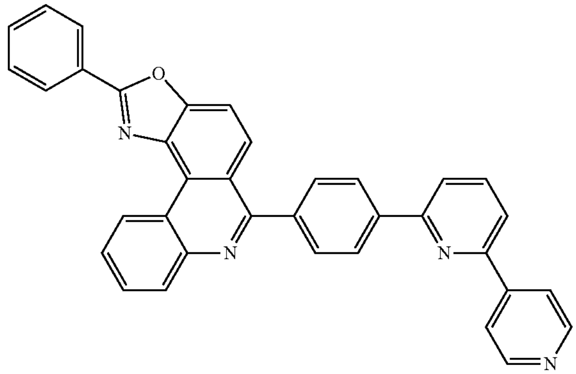
70
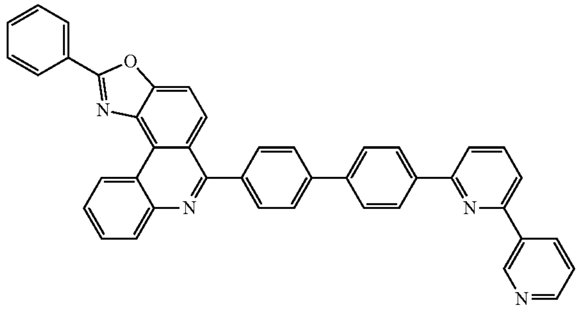

-continued
71
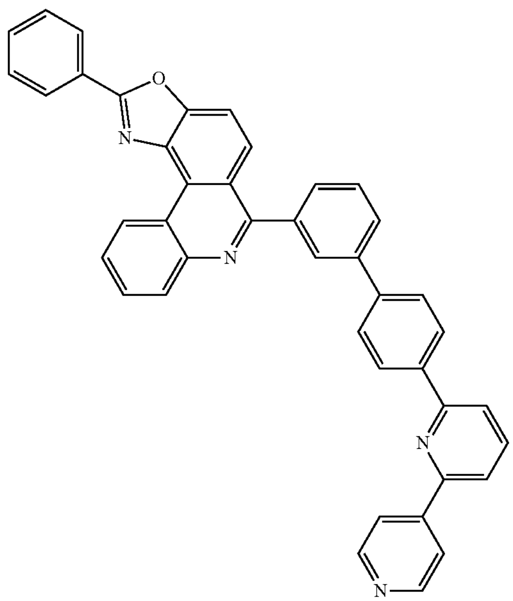
72
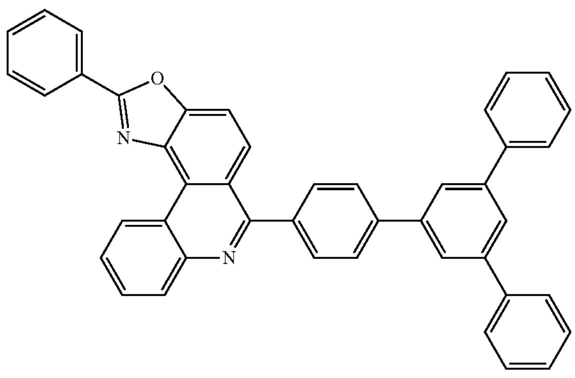
73
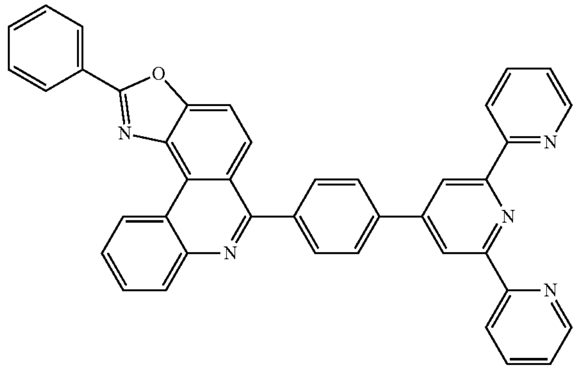
74
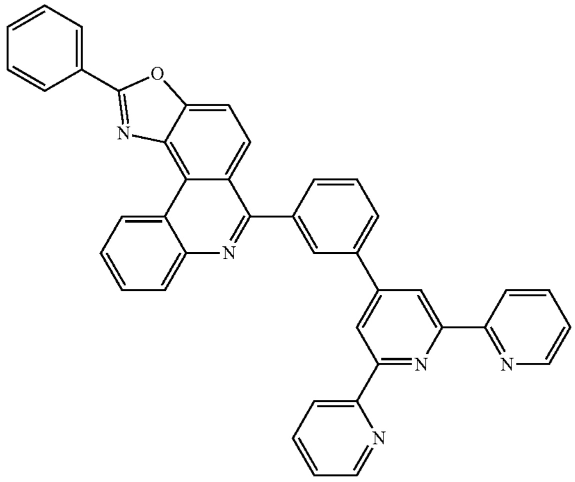

-continued
75
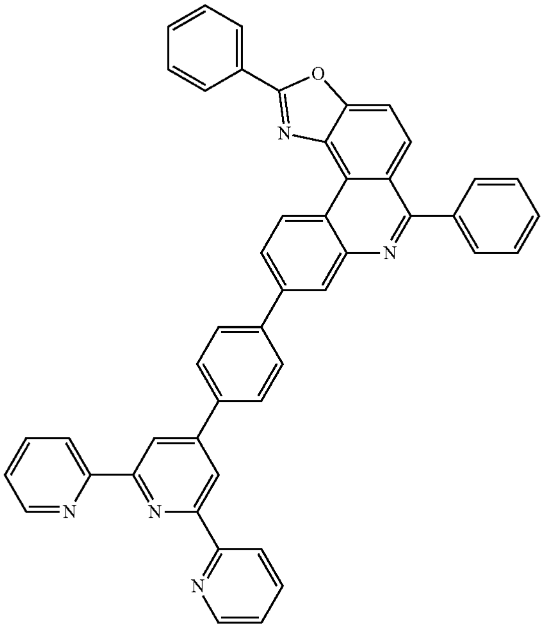
76
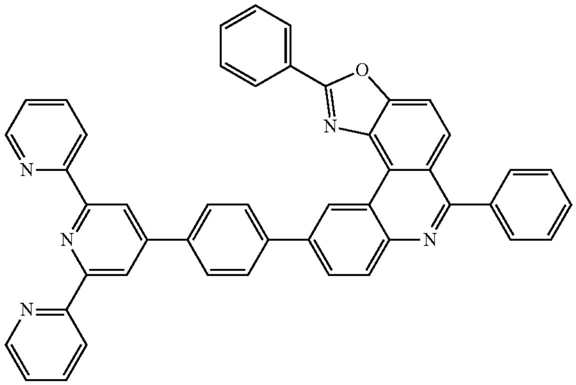
77
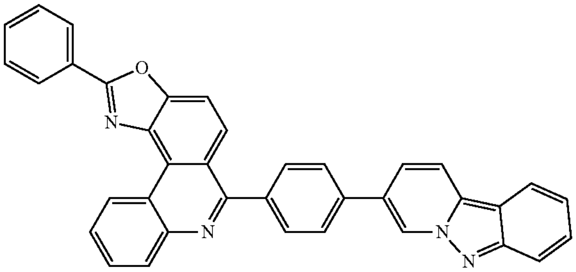
78
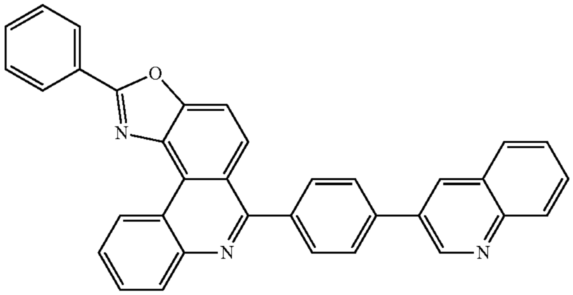
79
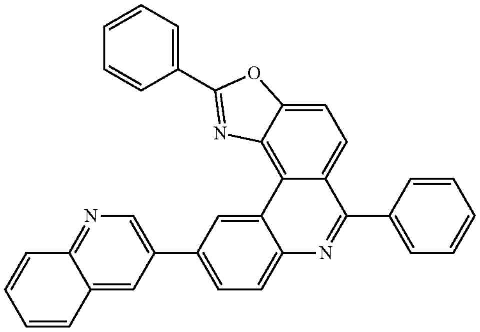
80
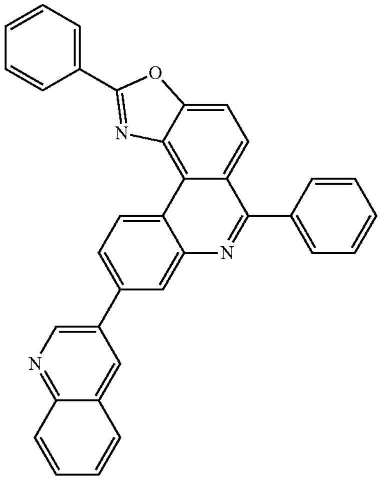

-continued
81
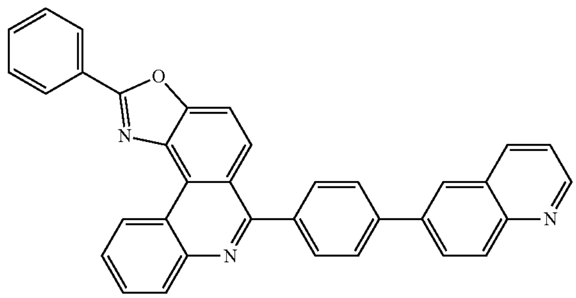
82
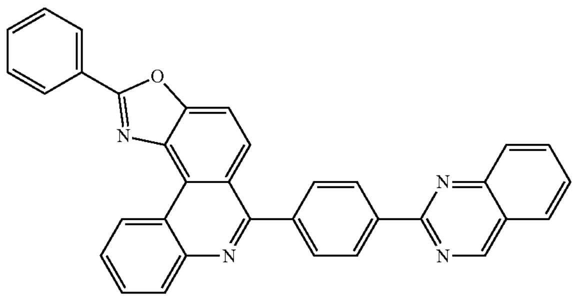
83
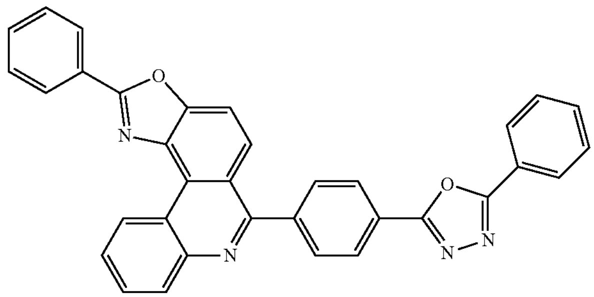
84
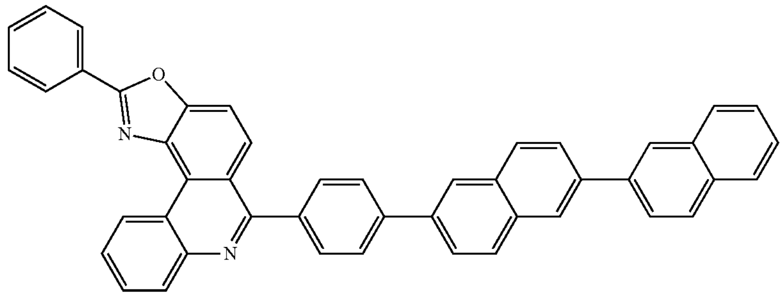
85
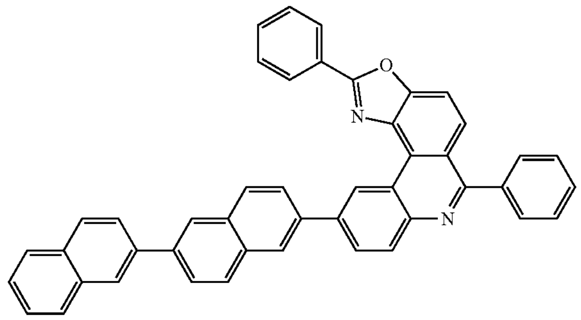
86
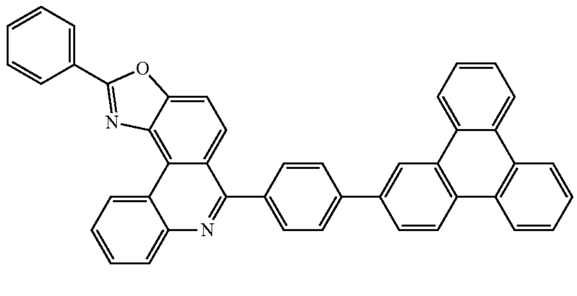

-continued
87
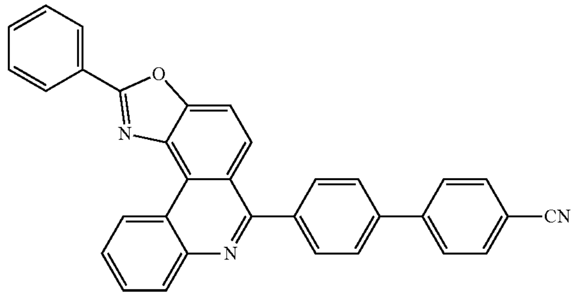
88
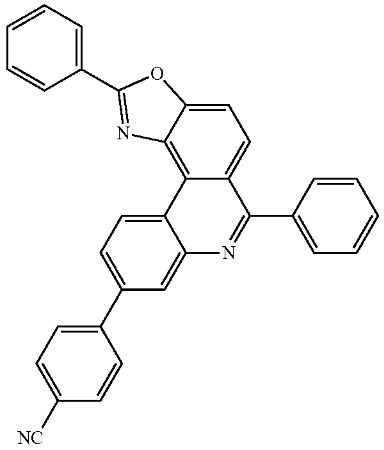
89
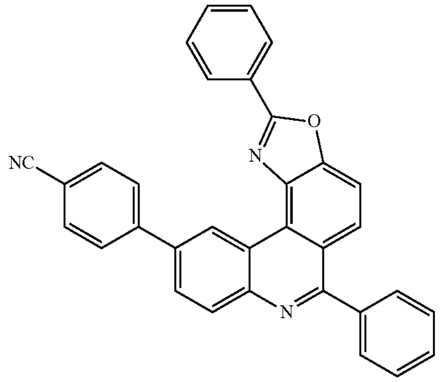
90
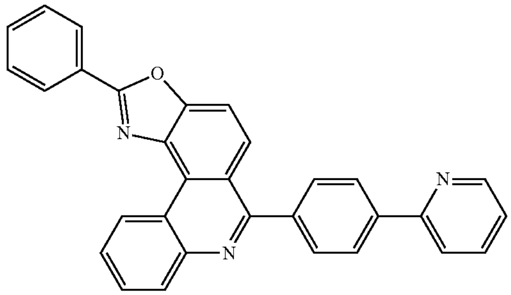
91
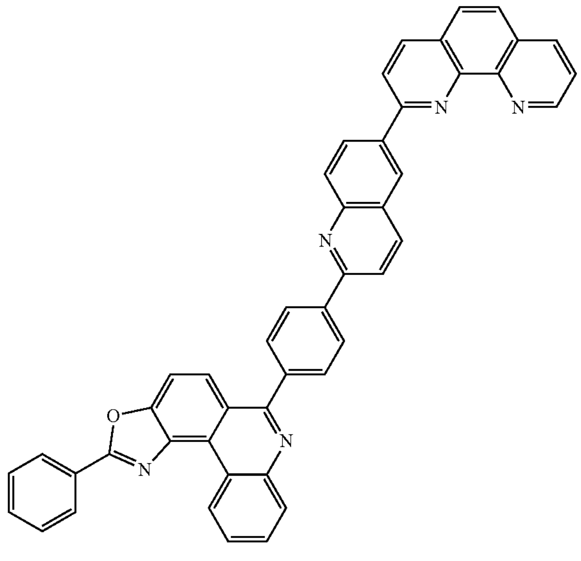
92
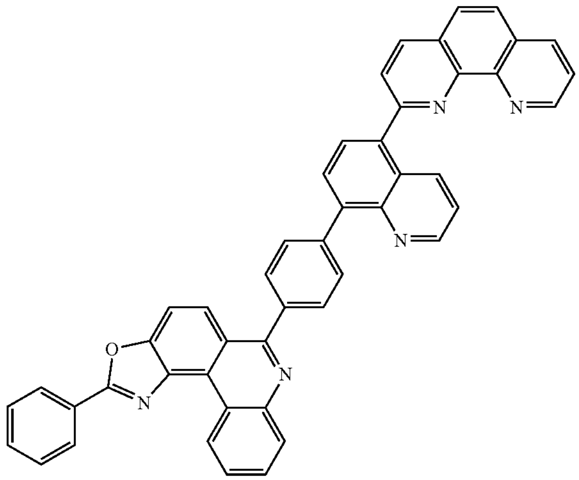

-continued
93
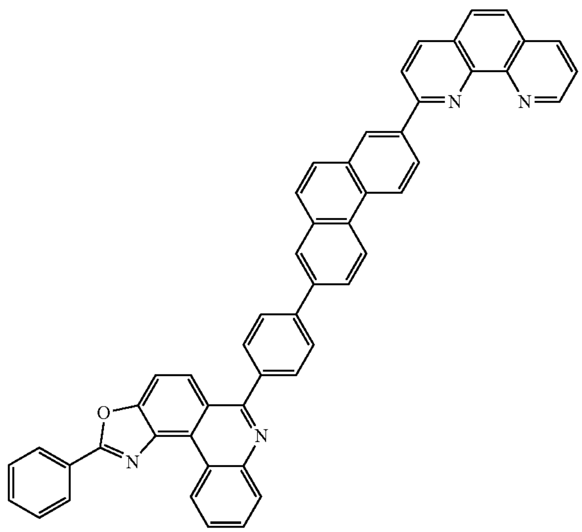
94
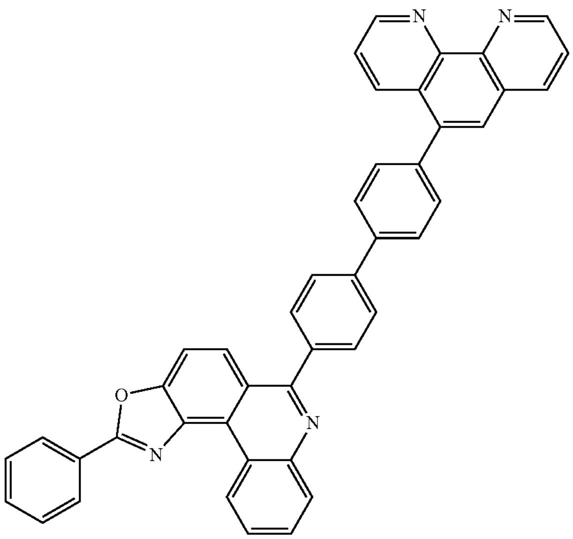
95
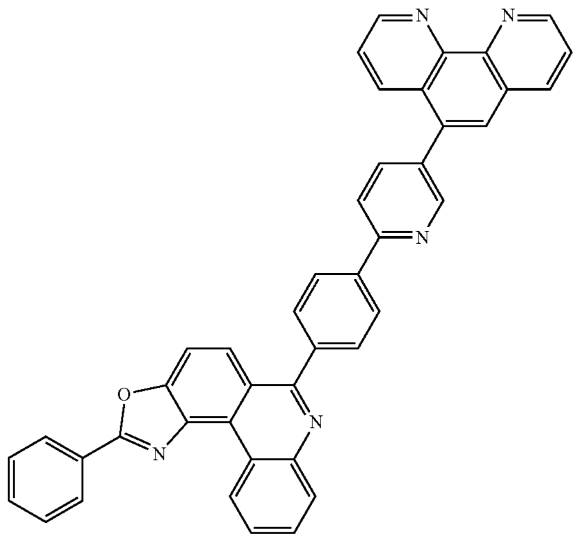
96
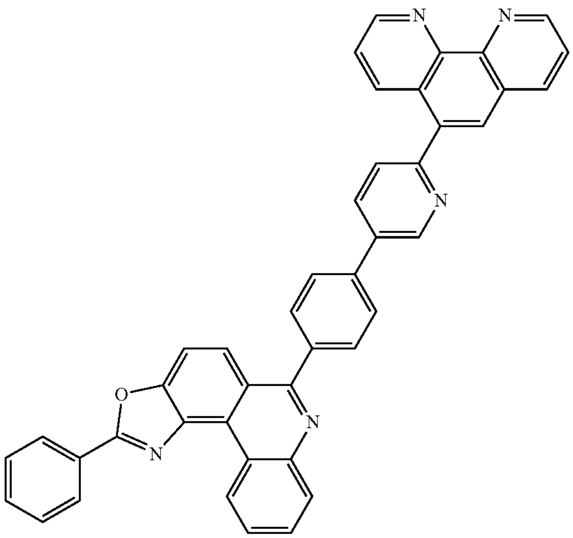
97
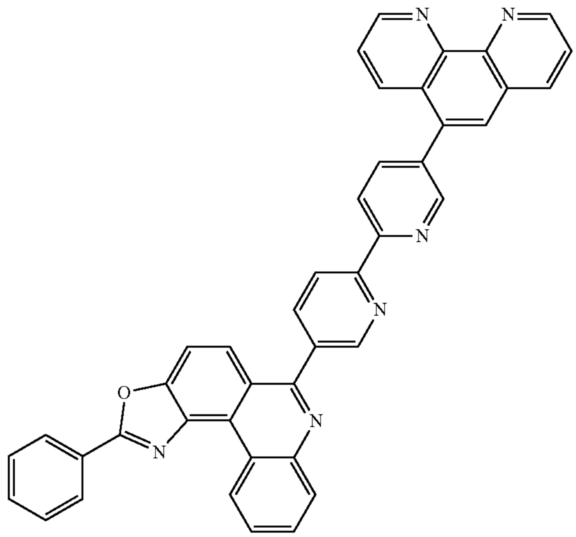
98
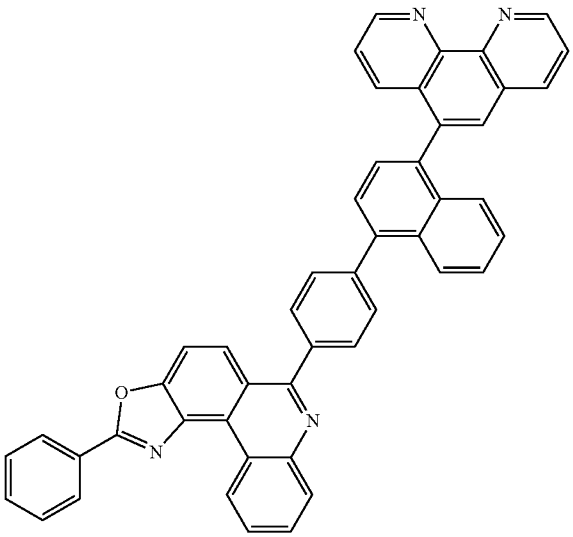

-continued
99
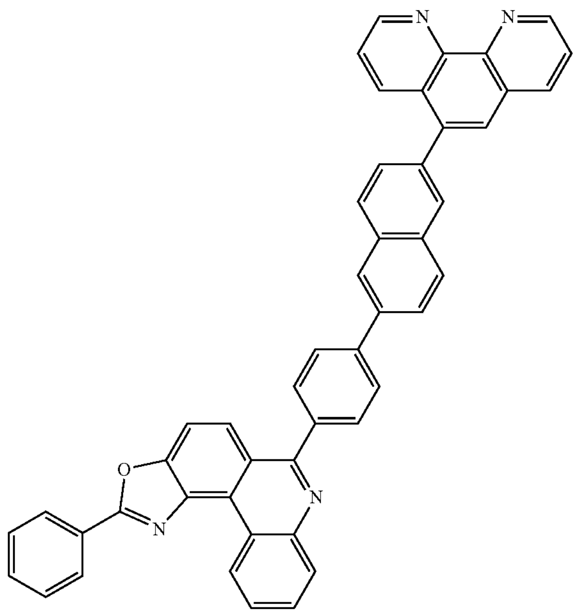
100
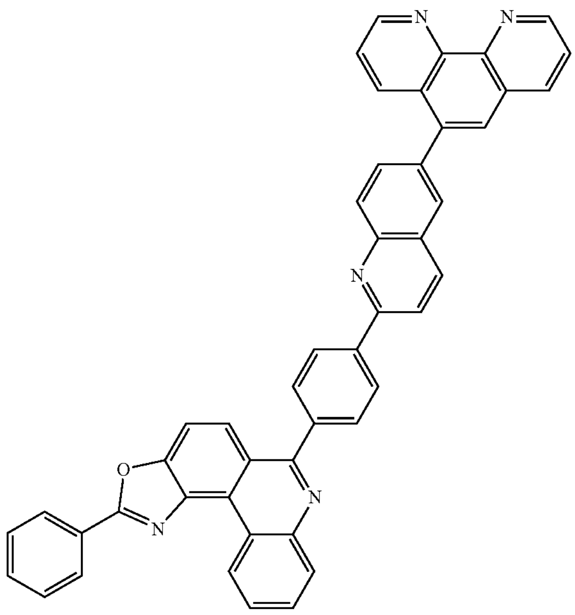
101
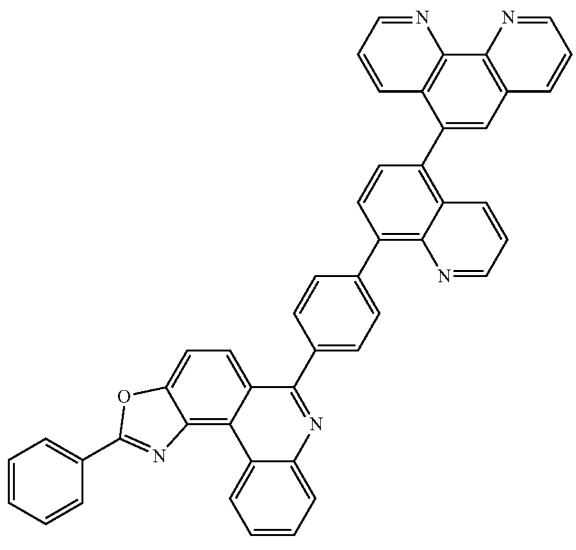
102
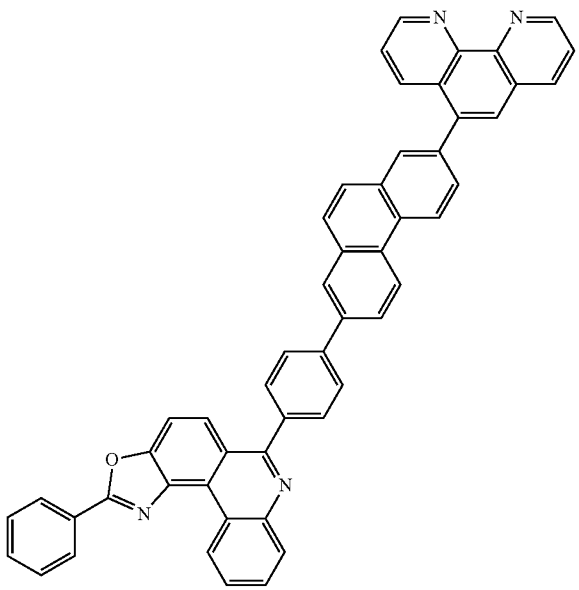

-continued
103
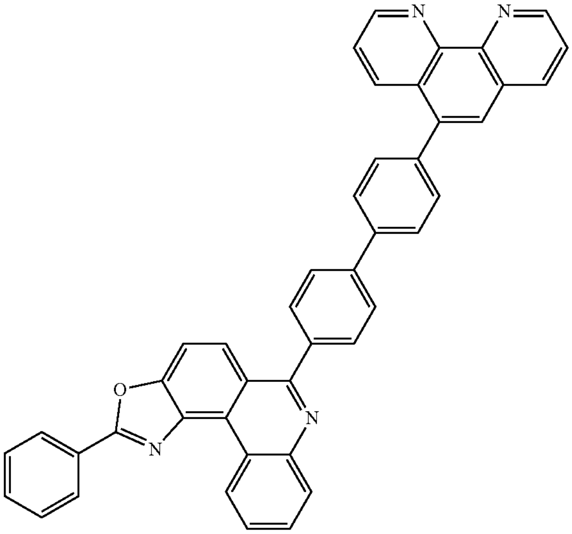
104
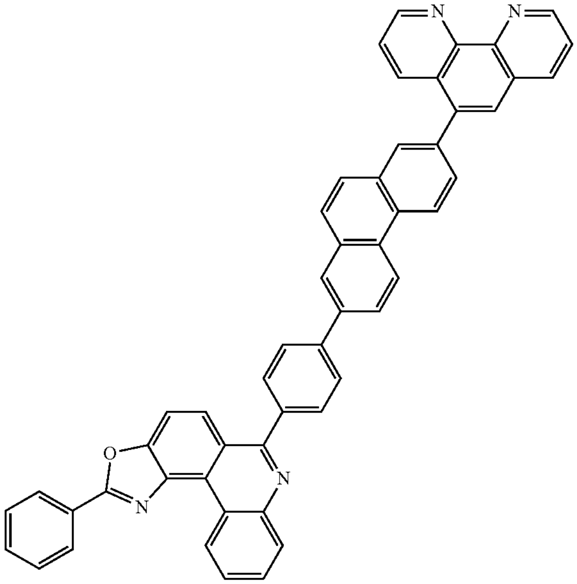
105
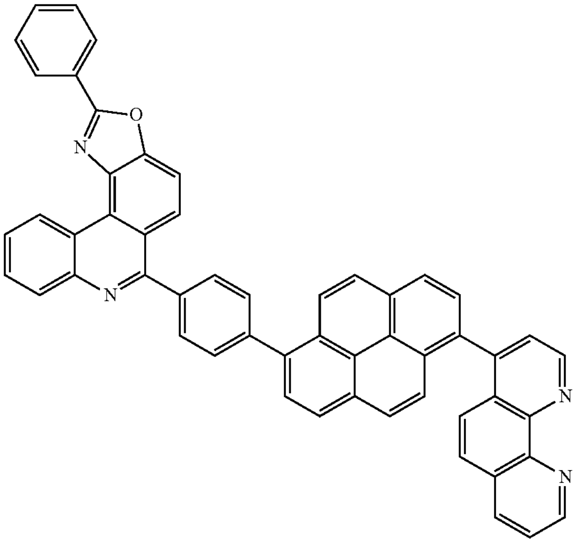
106
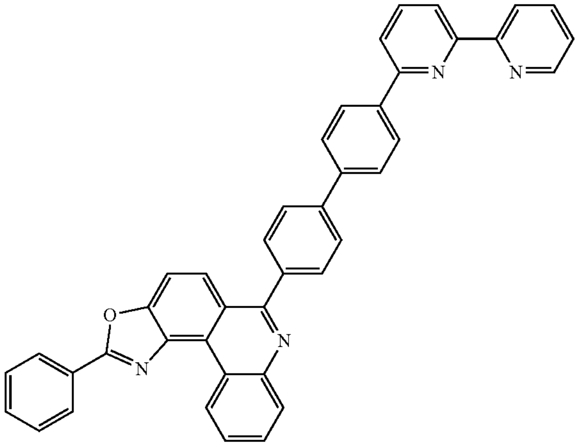
107
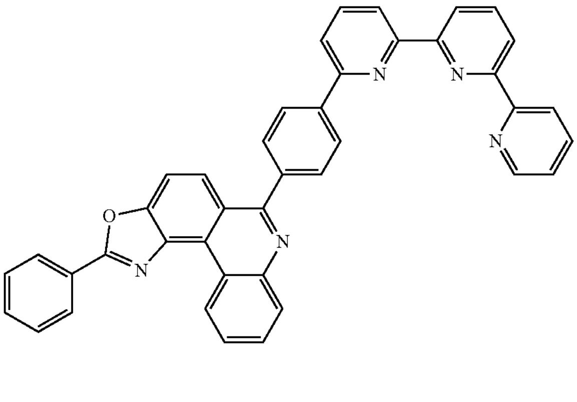
108
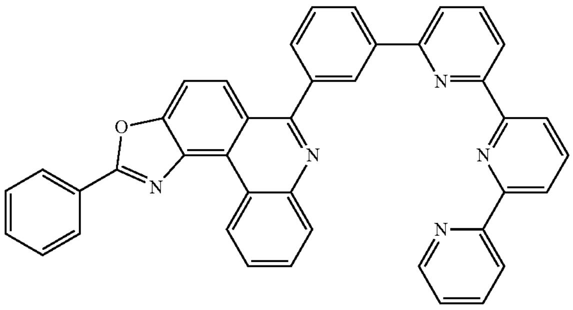

-continued
109
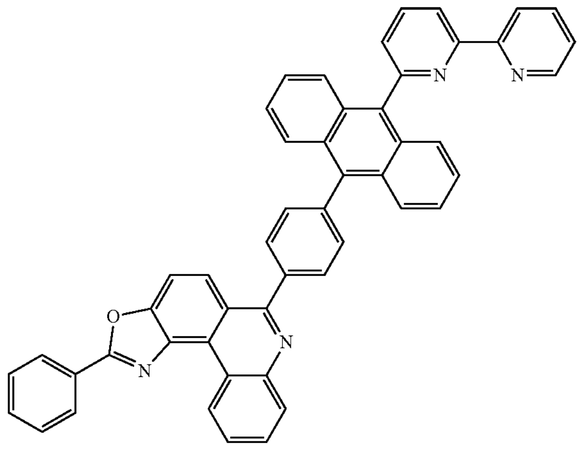
110
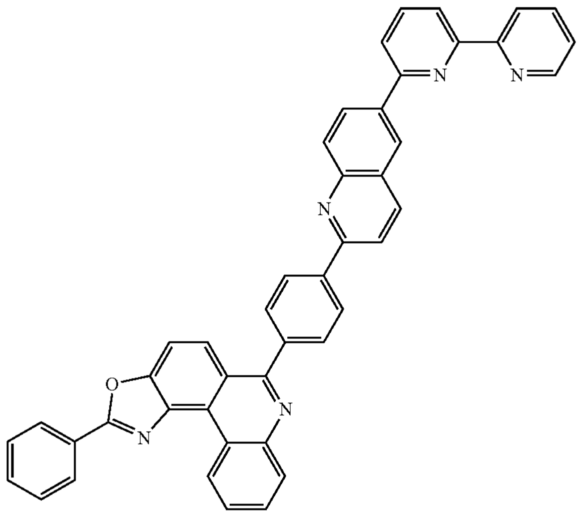
111
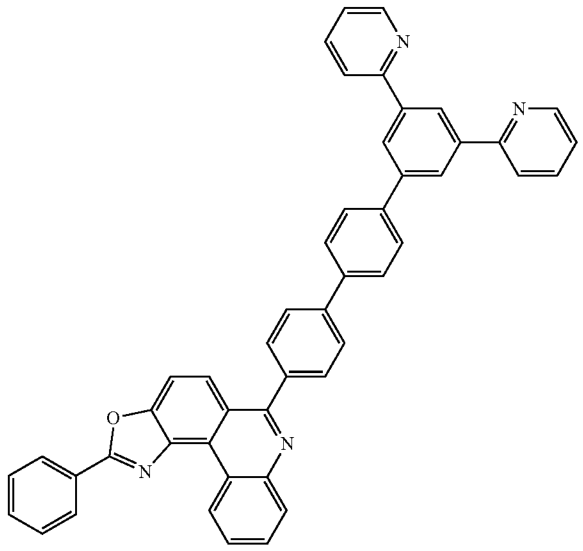
112
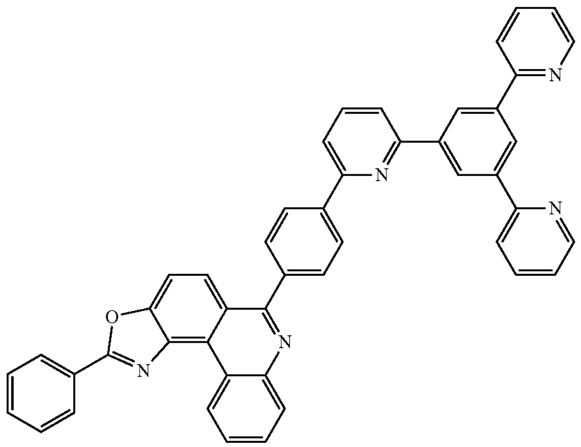

-continued
113
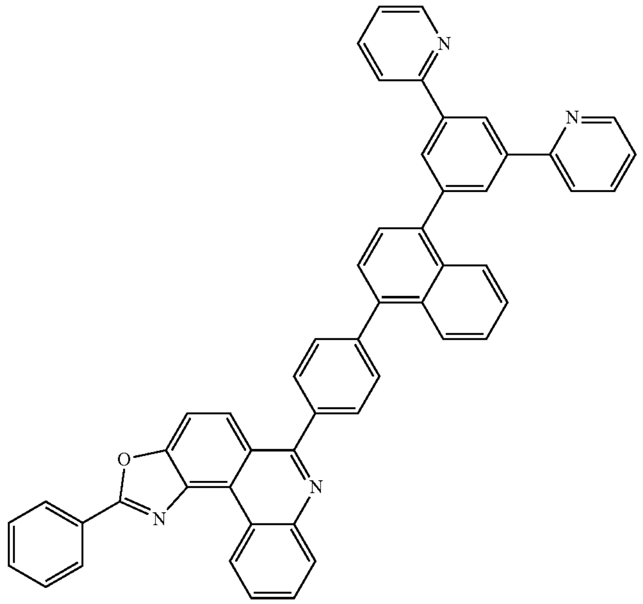
114
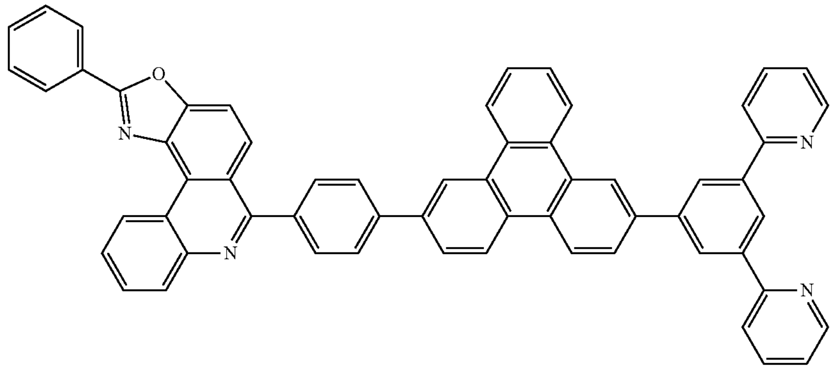
115
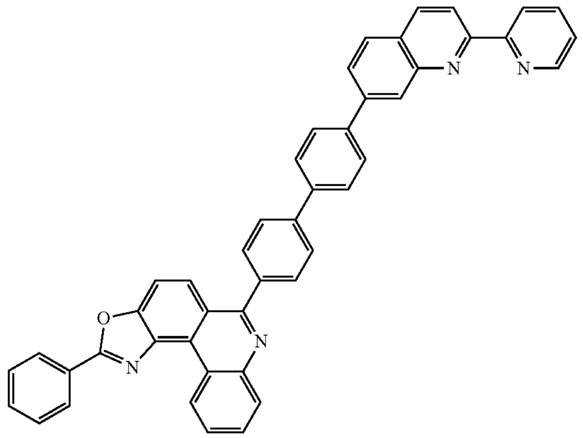
116
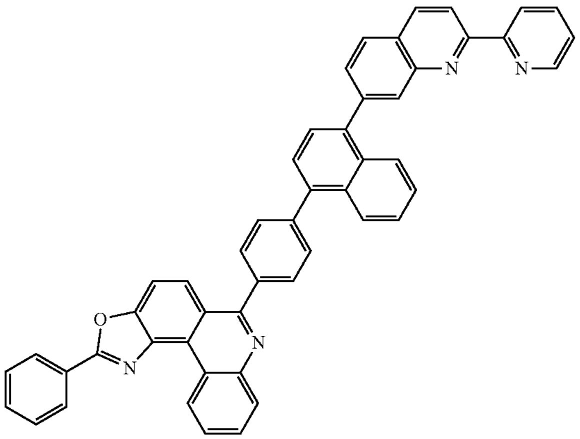

-continued
117
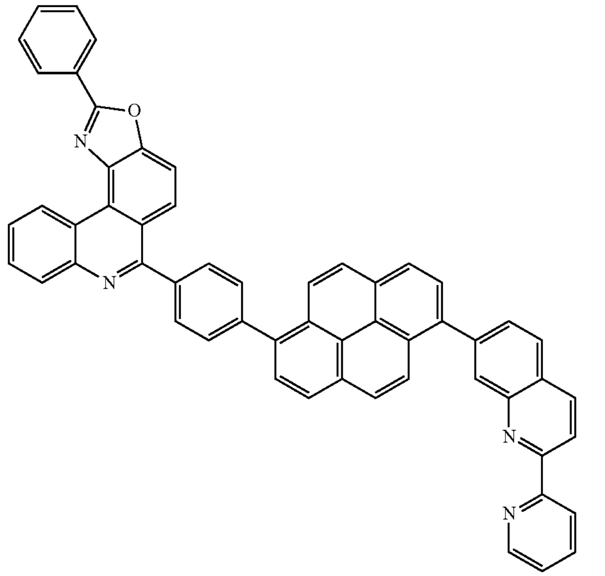
118
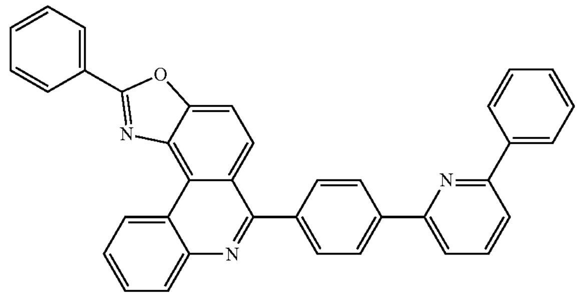
119
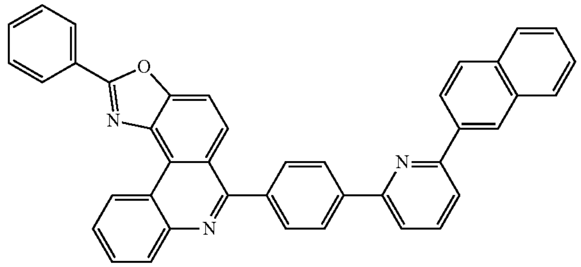
120
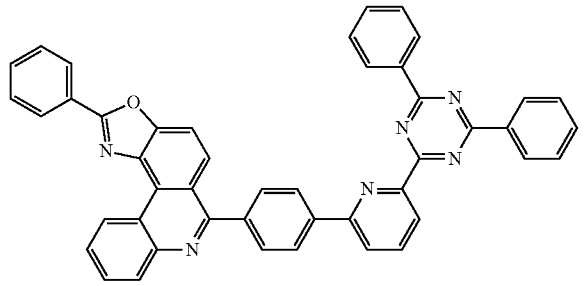
121
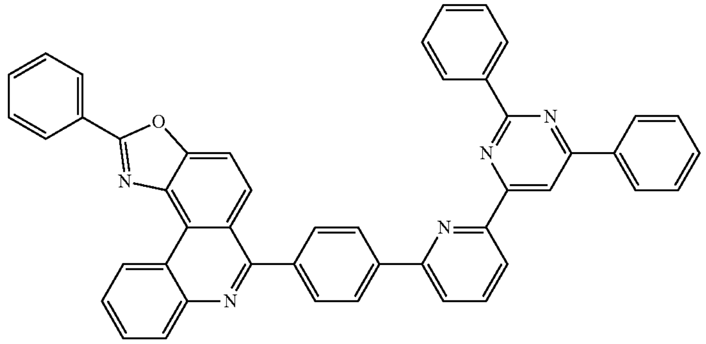
122
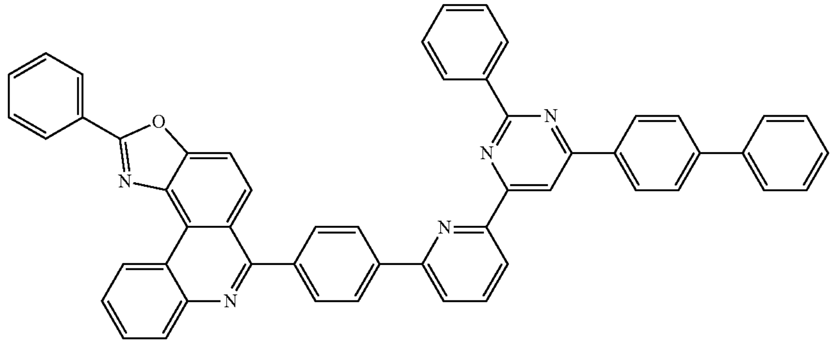

-continued
123
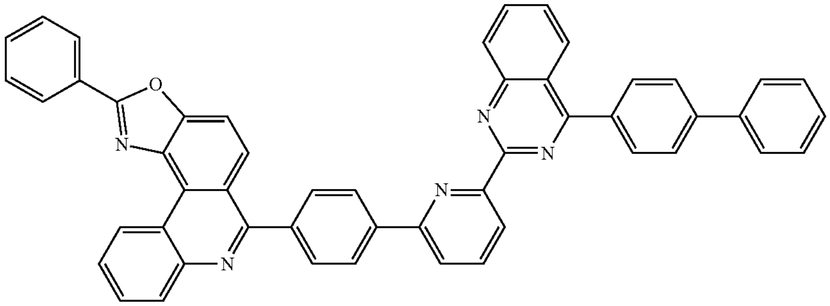
124
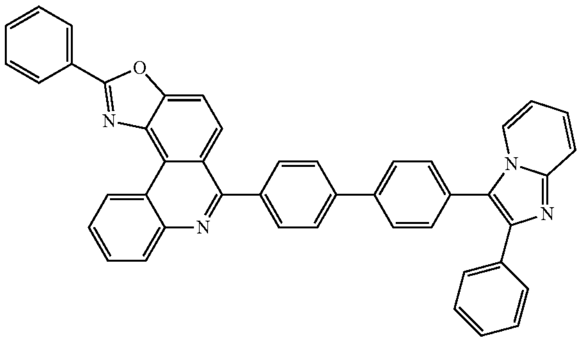
125
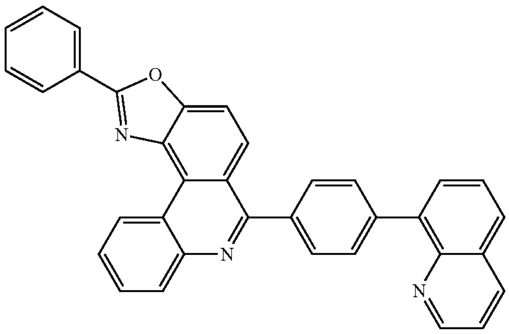
126
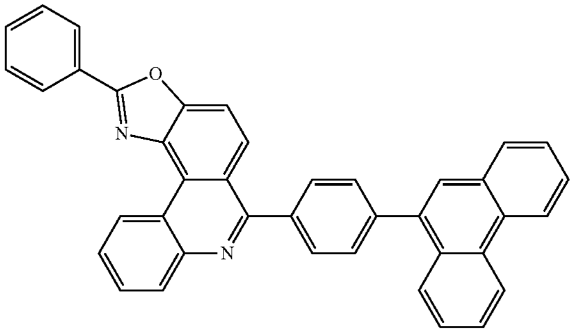
127
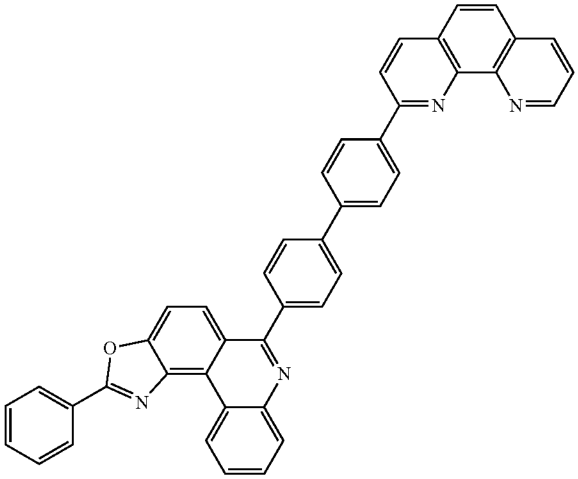

-continued
128
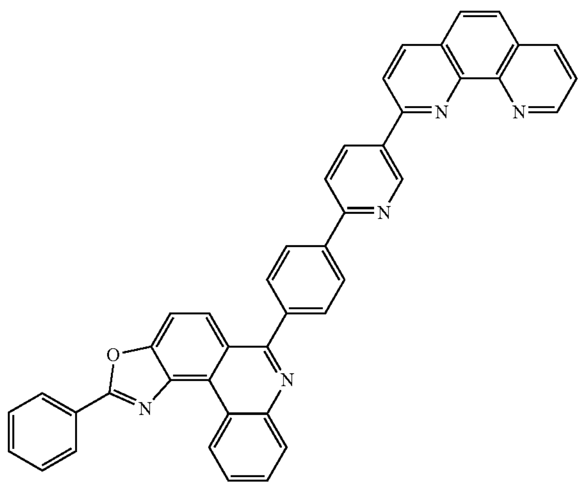
129
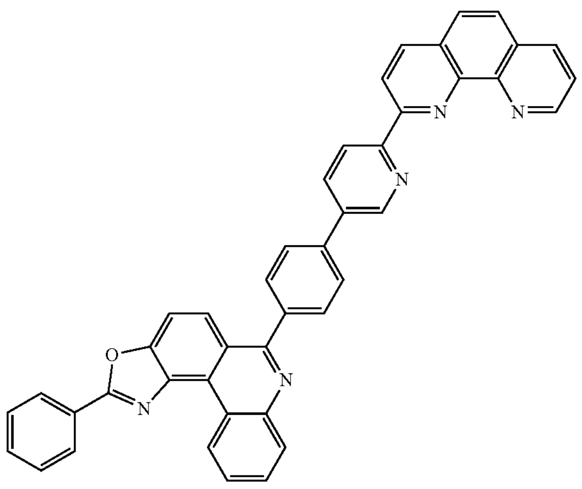
130
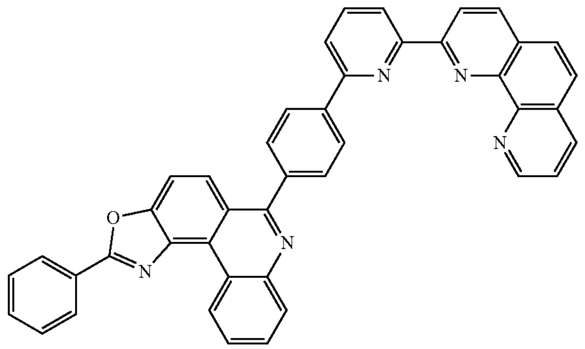
131
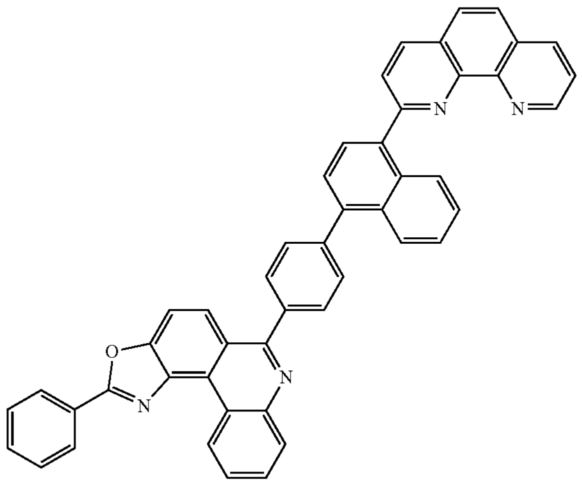
132
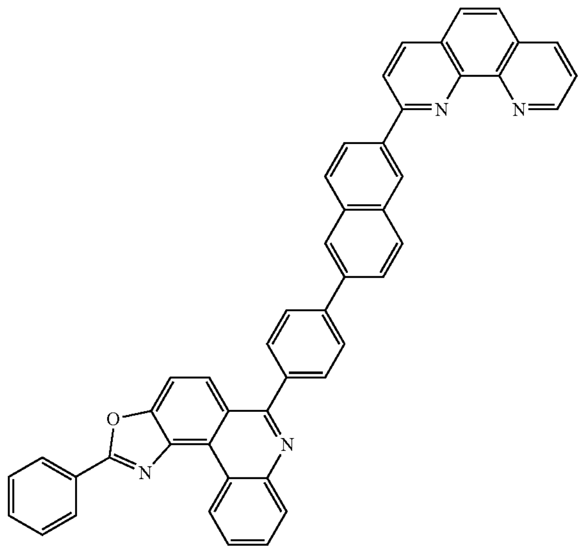
133
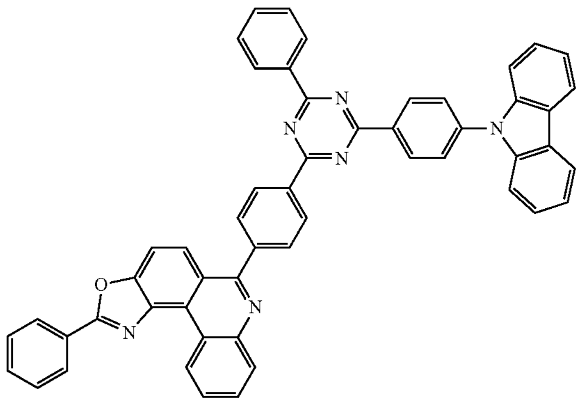

-continued
134
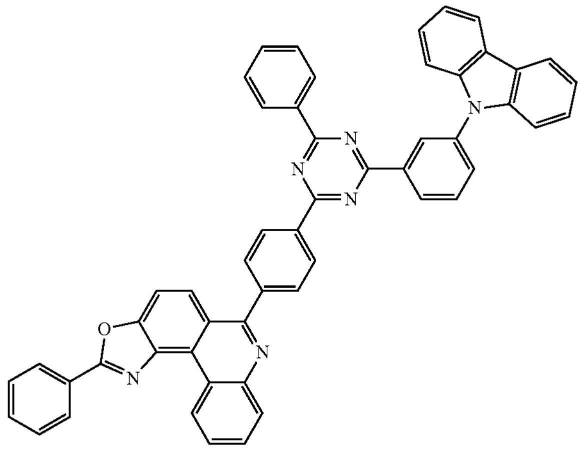
135
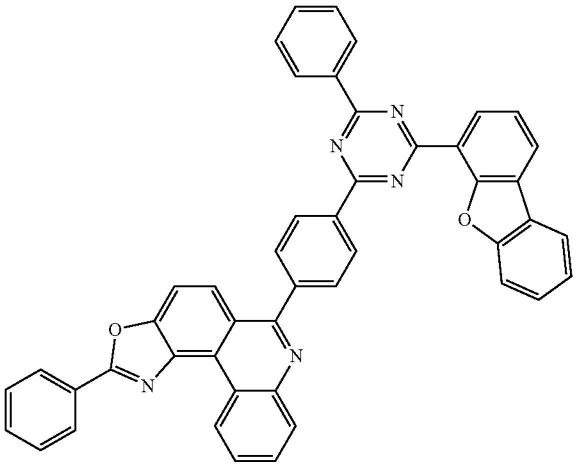
136
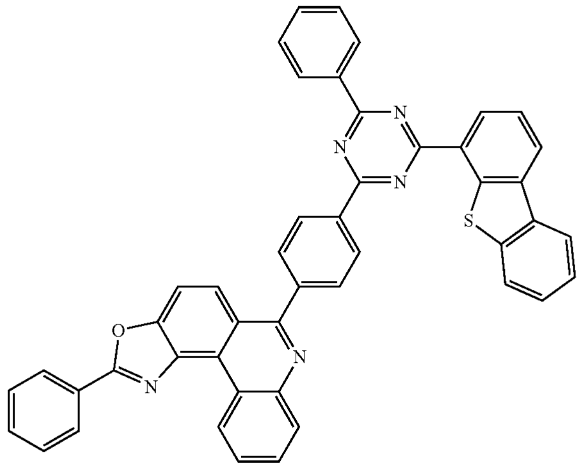
137
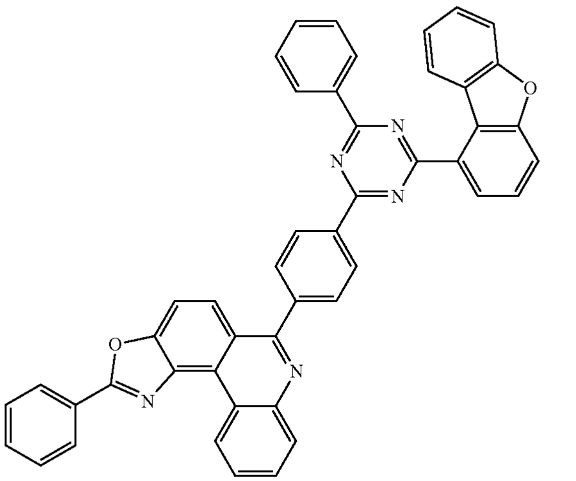
138
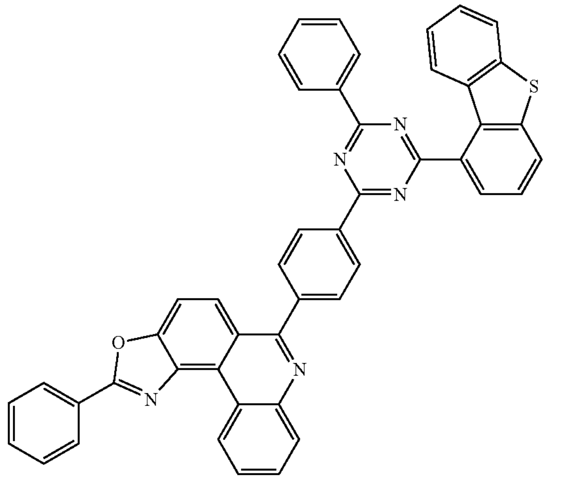
139
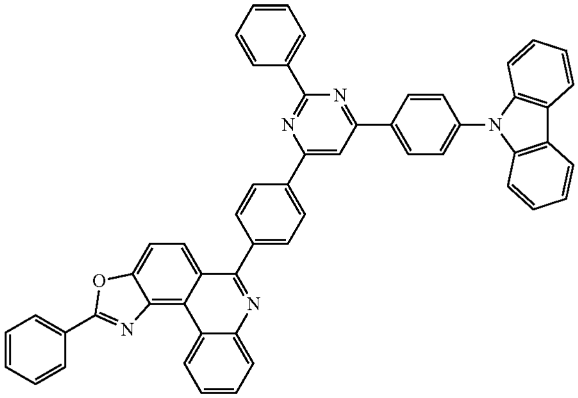

-continued
140
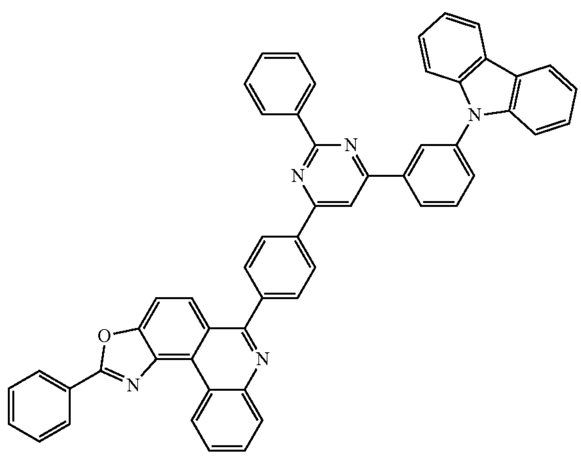
141
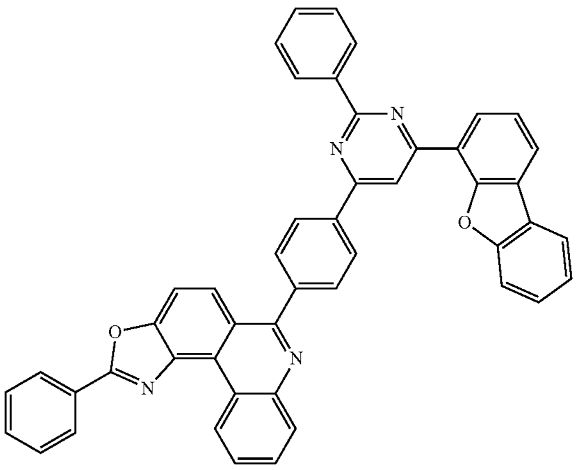
142
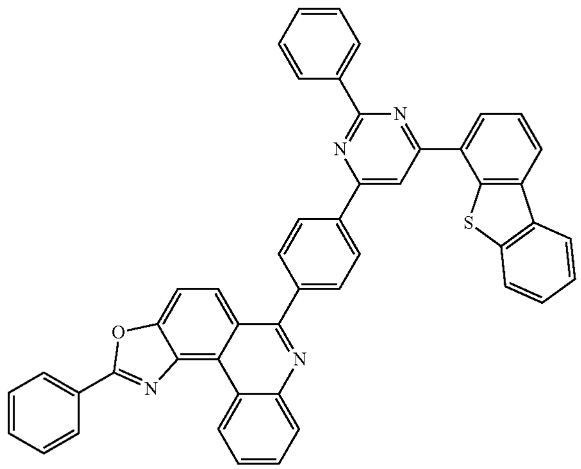
143
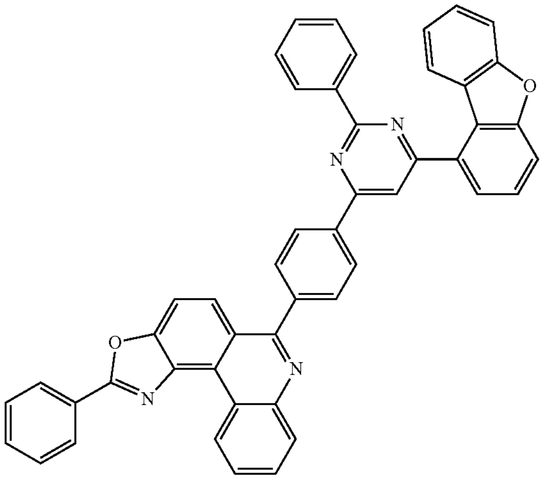
144
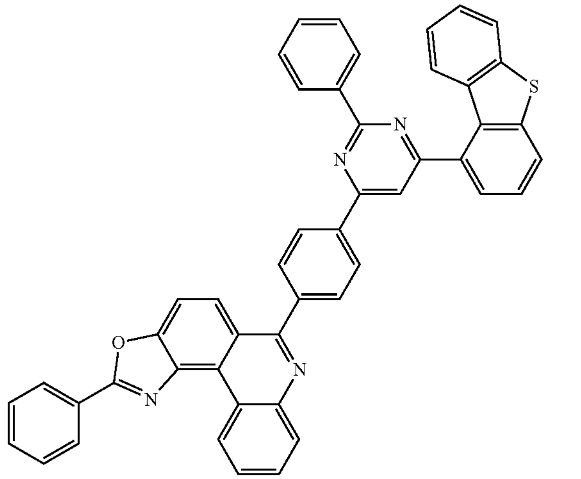
145
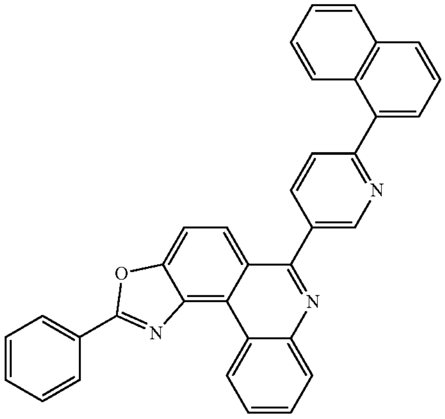

-continued
146
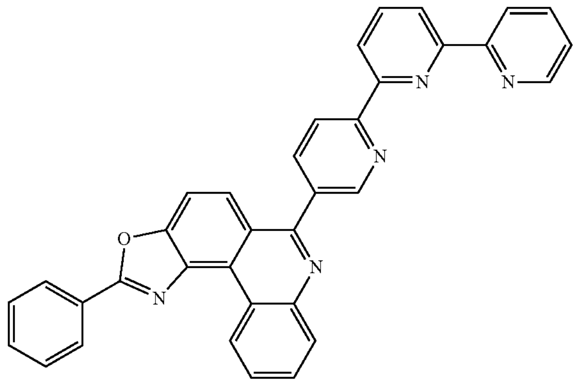
147
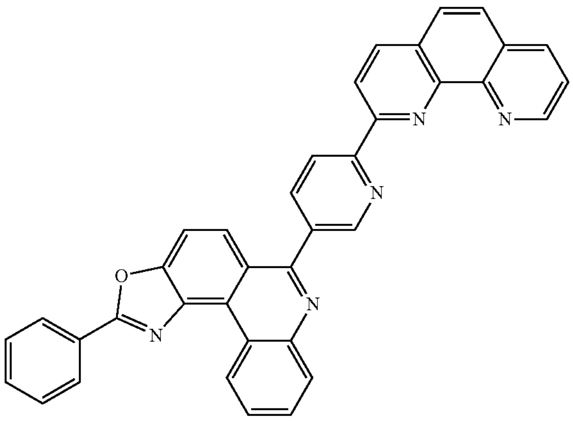
148
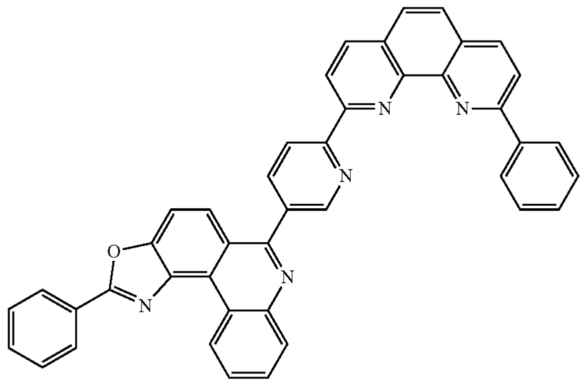
149
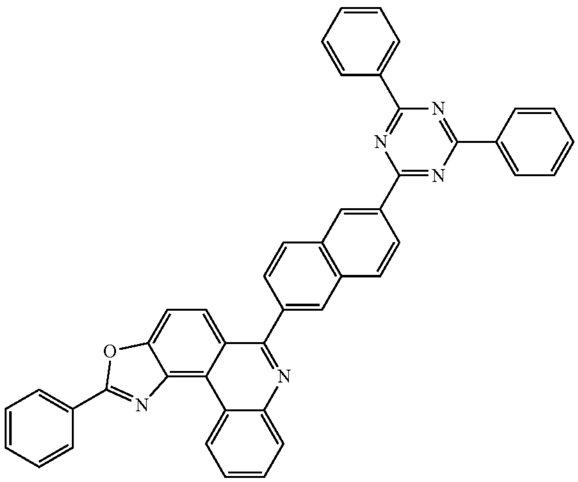
150
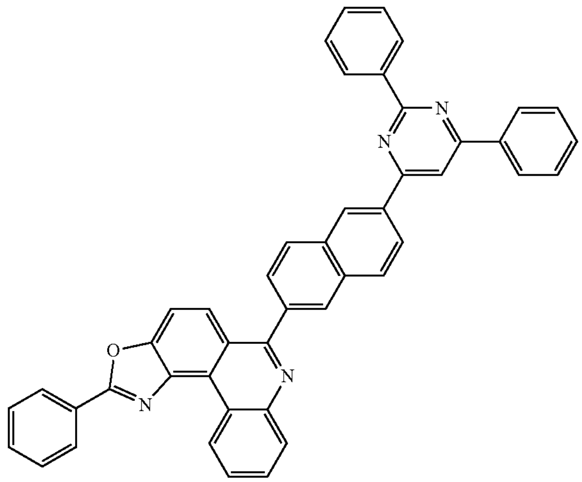
151
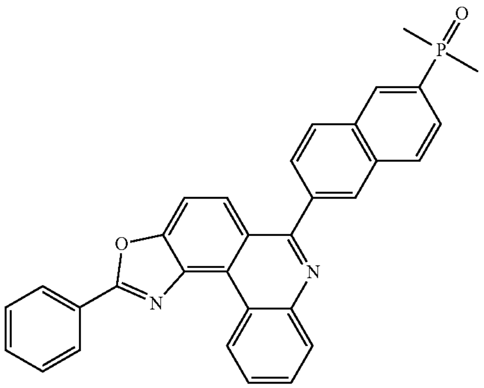

-continued
152
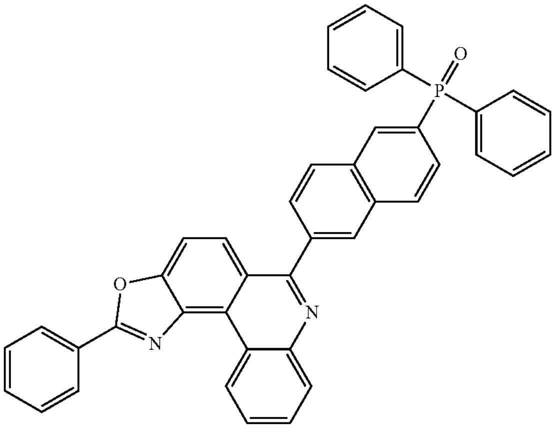
153
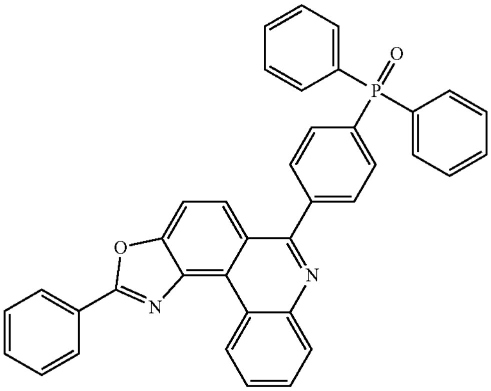
154
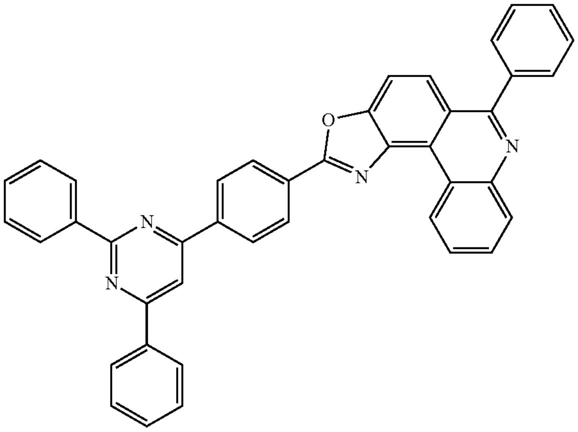
155
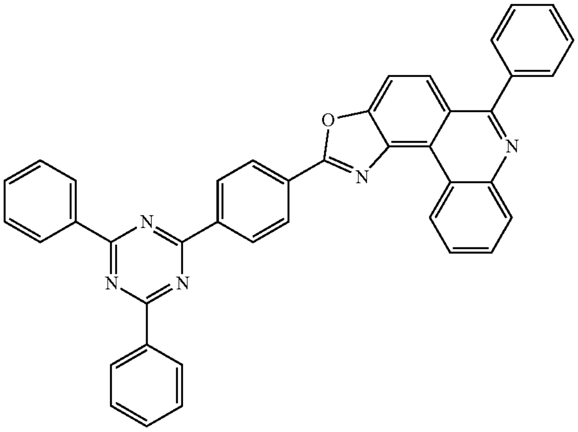
156
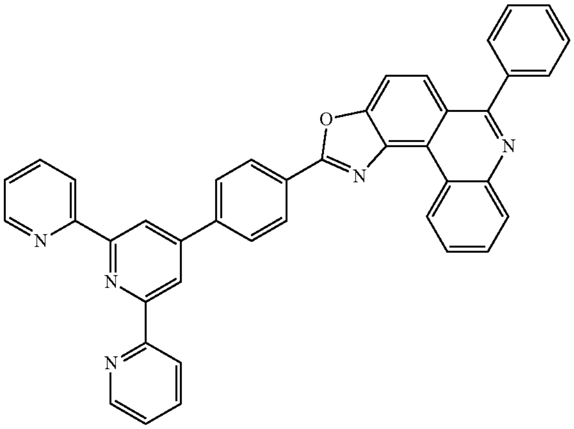
157
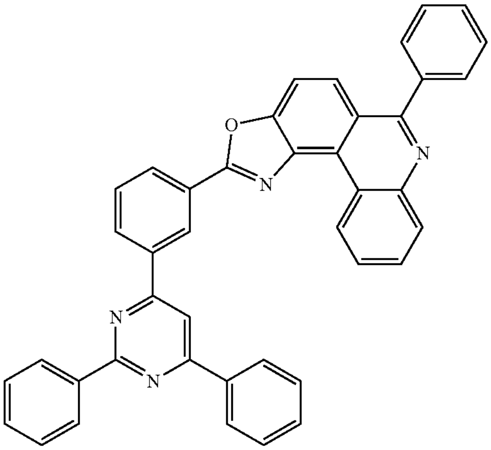

-continued
158
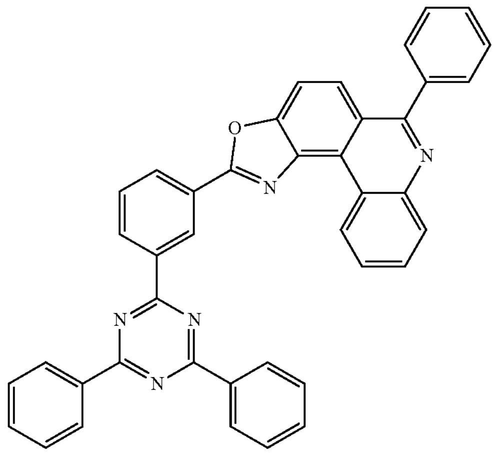
159
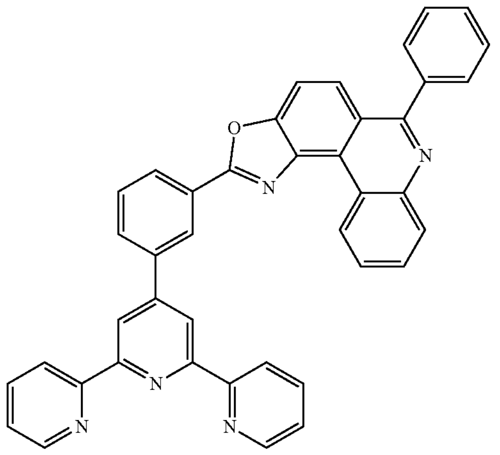
160
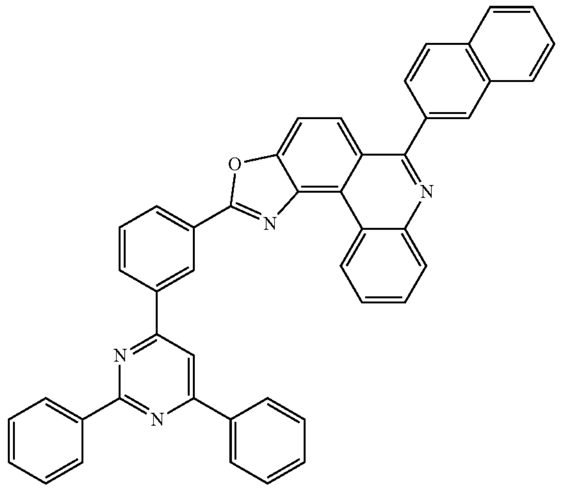
161
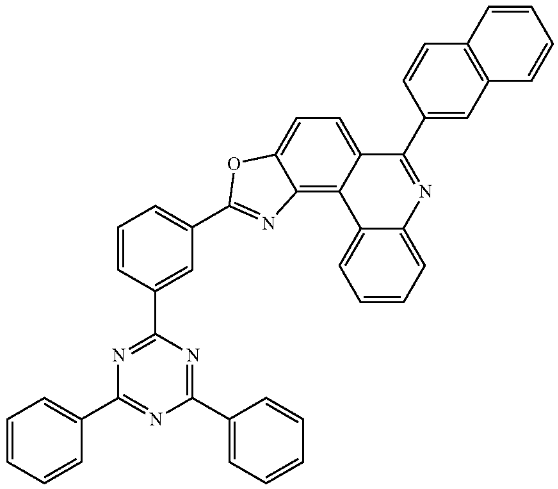
162
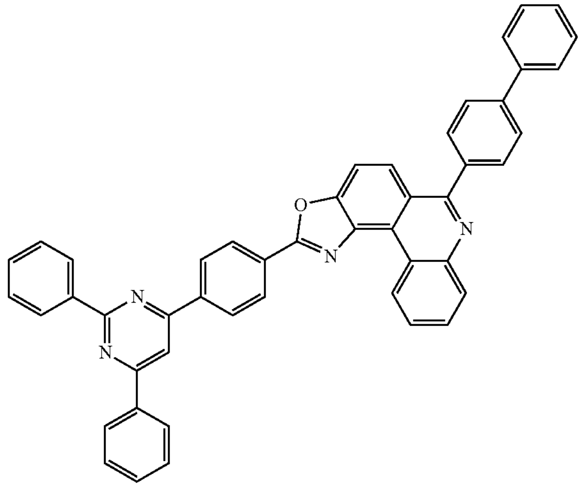
163
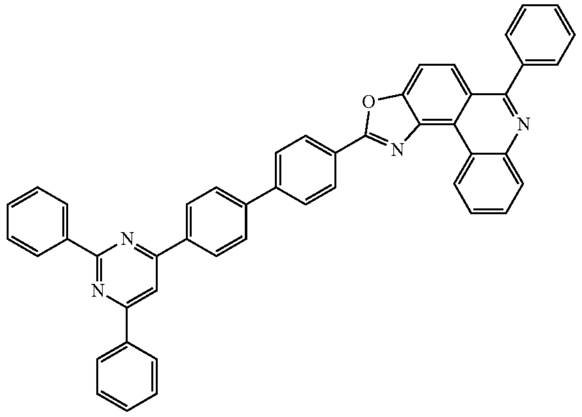

-continued
164
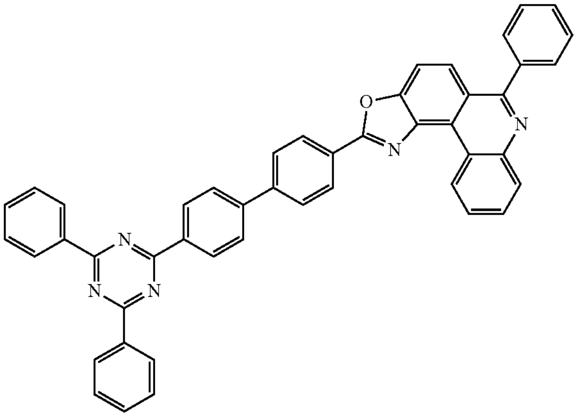
165
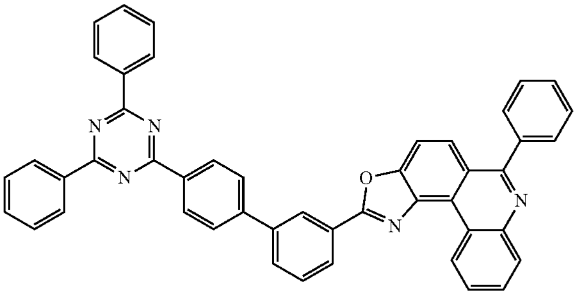
166
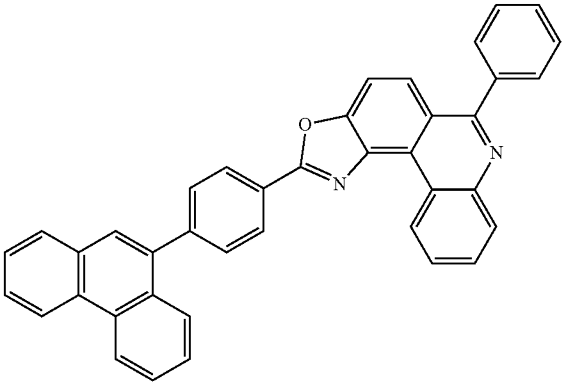
167
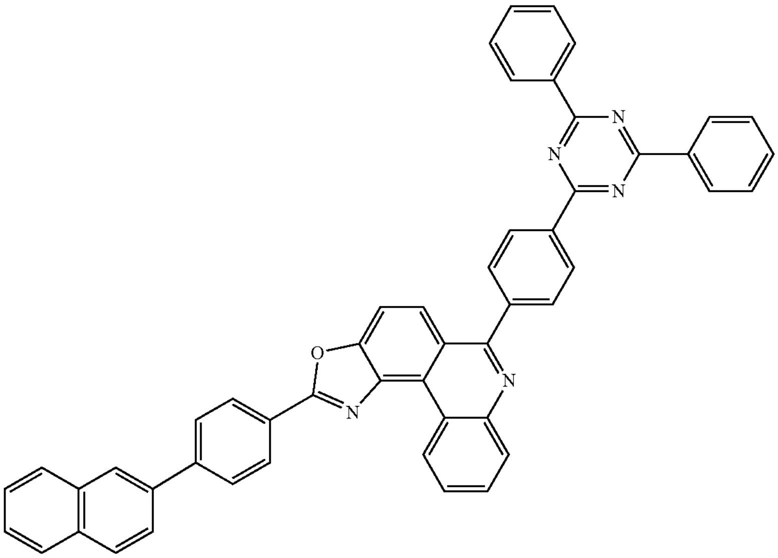

-continued

168

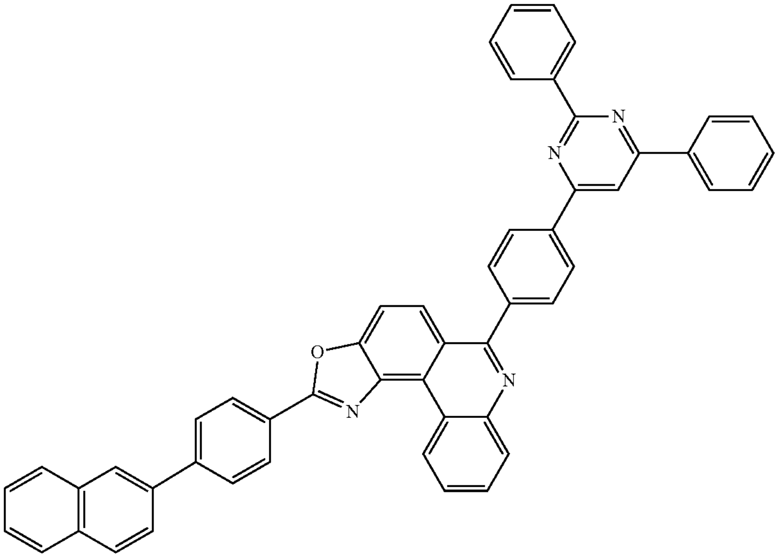

In addition, by introducing various substituents to the structure of Chemical Formula 1, compounds having unique properties of the introduced substituents may be synthesized. For example, by introducing substituents normally used as hole injection layer materials, hole transfer layer materials, light emitting layer materials, electron transfer layer materials and charge generation layer materials used for manufacturing an organic light emitting device to the core structure, materials satisfying conditions required for each organic material layer may be synthesized.

In addition, by introducing various substituents to the structure of Chemical Formula 1, the energy band gap may be finely controlled, and meanwhile, properties at interfaces between organic materials are enhanced, and material applications may become diverse.

Another embodiment of the present specification provides an organic light emitting device including a first electrode; a second electrode; and one or more organic material layers provided between the first electrode and the second electrode, wherein one or more layers of the organic material layers include the heterocyclic compound represented by Chemical Formula 1.

In one embodiment of the present specification, the first electrode may be an anode, and the second electrode may be a cathode.

In another embodiment of the present specification, the first electrode may be a cathode, and the second electrode may be an anode.

In one embodiment of the present specification, the organic light emitting device may be a blue organic light emitting device, and the heterocyclic compound according to Chemical Formula 1 may be used as a material of the blue organic light emitting device.

In another embodiment of the present specification, the organic light emitting device may be a green organic light emitting device, and the heterocyclic compound according to Chemical Formula 1 may be used as a material of the green organic light emitting device.

In another embodiment of the present specification, the organic light emitting device may be a red organic light emitting device, and the heterocyclic compound according to Chemical Formula 1 may be used as a material of the red organic light emitting device.

Specific details on the heterocyclic compound represented by Chemical Formula 1 are the same as the descriptions provided above.

The organic light emitting device of the present specification may be manufactured using common organic light emitting device manufacturing methods and materials except that one or more organic material layers are formed using the heterocyclic compound described above.

The heterocyclic compound may be formed into an organic material layer through a solution coating method as well as a vacuum deposition method when manufacturing the organic light emitting device. Herein, the solution coating method means spin coating, dip coating, inkjet printing, screen printing, a spray method, roll coating and the like, but is not limited thereto.

The organic material layer of the organic light emitting device of the present specification may be formed in a single layer structure, or may also be formed in a multilayer structure in which two or more organic material layers are laminated. For example, the organic light emitting device according to one embodiment of the present disclosure may have a structure including a hole injection layer, a hole transfer layer, a light emitting layer, an electron transfer layer, an electron injection layer and the like as the organic material layer. However, the structure of the organic light emitting device is not limited thereto, and may include a smaller number of organic material layers.

In the organic light emitting device of the present specification, the organic material layer includes an electron transfer layer, and the electron transfer layer may include the heterocyclic compound.

In another organic light emitting device of the present specification, the organic material layer includes a hole blocking layer, and the hole blocking layer may include the heterocyclic compound.

The organic light emitting device of the present disclosure may further include one, two or more layers selected from the group consisting of a light emitting layer, a hole injection layer, a hole transfer layer, an electron injection layer, an electron transfer layer, an electron blocking layer and a hole blocking layer.

FIGS. 1 to 4 illustrate a lamination order of electrodes and organic material layers of an organic light emitting device according to one embodiment of the present specification. However, the scope of the present application is not limited to these diagrams, and structures of organic light emitting devices known in the art may also be used in the present application.

FIG. 1 illustrates an organic light emitting device in which an anode (200), an organic material layer (300) and a cathode (400) are consecutively laminated on a substrate (100). However, the structure is not limited to such a structure, and as illustrated in FIG. 2, an organic light emitting device in which a cathode, an organic material layer and an anode are consecutively laminated on a substrate may also be obtained.

FIG. 3 illustrates a case of the organic material layer being a multilayer. The organic light emitting device according to FIG. 3 includes a hole injection layer (301), a hole transfer layer (302), a light emitting layer (303), a hole blocking layer (304), an electron transfer layer (305) and an electron injection layer (306). However, the scope of the present application is not limited to such a lamination structure, and as necessary, other layers except the light emitting layer may not be included, and other necessary functional layers may be further included.

The organic material layer including the heterocyclic compound represented by Chemical Formula 1 may further include other materials as necessary.

In addition, the organic light emitting device according to one embodiment of the present specification includes an anode, a cathode, and two or more stacks provided between the anode and the cathode, and the two or more stacks each independently include a light emitting layer, a charge generation layer is included between the two or more stacks, and the charge generation layer includes the heterocyclic compound represented by Chemical Formula 1.

In addition, the organic light emitting device according to one embodiment of the present specification includes an anode, a first stack provided on the anode and including a first light emitting layer, a charge generation layer provided on the first stack, a second stack provided on the charge generation layer and including a second light emitting layer, and a cathode provided on the second stack. Herein, the charge generation layer may include the heterocyclic compound represented by Chemical Formula 1. In addition, the first stack and the second stack may each independently further include one or more types of the hole injection layer, the hole transfer layer, the hole blocking layer, the electron transfer layer, the electron injection layer and the like described above.

The charge generation layer may be an N-type charge generation layer, and the charge generation layer may further include a dopant known in the art in addition to the heterocyclic compound represented by Chemical Formula 1.

The charge generation layer may further include a P-type charge generation layer.

As the organic light emitting device according to one embodiment of the present specification, an organic light emitting device having a 2-stack tandem structure is illustrated in FIG. 4.

Herein, the first electron blocking layer, the first hole blocking layer, the second hole blocking layer and the like described in FIG. 4 may not be included in some cases.

In the organic light emitting device according to one embodiment of the present specification, materials other than the heterocyclic compound of Chemical Formula 1 are illustrated below, however, these are for illustrative purposes only and not for limiting the scope of the present application, and may be replaced by materials known in the art.

As the anode material, materials having relatively large work function may be used, and transparent conductive oxides, metals, conductive polymers or the like may be used. Specific examples of the anode material include metals such as vanadium, chromium, copper, zinc and gold, or alloys thereof; metal oxides such as zinc oxide, indium oxide, indium tin oxide (ITO) and indium zinc oxide (IZO); combinations of metals and oxides such as ZnO:Al or $SnO_2$:Sb; conductive polymers such as poly(3-methylthiophene), poly [3,4-(ethylene-1,2-dioxy)thiophene] (PEDOT), polypyrrole and polyaniline, and the like, but are not limited thereto.

As the cathode material, materials having relatively small work function may be used, and metals, metal oxides, conductive polymers or the like may be used. Specific examples of the cathode material include metals such as magnesium, calcium, sodium, potassium, titanium, indium, yttrium, lithium, gadolinium, aluminum, silver, tin and lead, or alloys thereof; multilayer structure materials such as LiF/Al or $LiO_2$/Al, and the like, but are not limited thereto.

As the hole injection material, known hole injection materials may be used, and for example, phthalocyanine compounds such as copper phthalocyanine disclosed in U.S. Pat. No. 4,356,429, or starburst-type amine derivatives such as tris(4-carbazoyl-9-ylphenyl)amine (TCTA), 4,4',4"-tri [phenyl(m-tolyl)amino]triphenylamine (m-MTDATA) or 1,3,5-tris[4-(3-methylphenylphenylamino)phenyl]benzene (m-MTDAPB) described in the literature [Advanced Material, 6, p. 677 (1994)], polyaniline/dodecylbenzene sulfonic acid, poly(3,4-ethylenedioxythiophene)/poly(4-styrene-sulfonate), polyaniline/camphor sulfonic acid or polyaniline/poly(4-styrene-sulfonate) that are conductive polymers having solubility, and the like, may be used.

As the hole transfer material, pyrazoline derivatives, arylamine-based derivatives, stilbene derivatives, triphenyldiamine derivatives and the like may be used, and low molecular or high molecular materials may also be used.

As the electron transfer material, metal complexes of oxadiazole derivatives, anthraquinodimethane and derivatives thereof, benzoquinone and derivatives thereof, naphthoquinone and derivatives thereof, anthraquinone and derivatives thereof, tetracyanoanthraquinodimethane and derivatives thereof, fluorenone derivatives, diphenyldicyanoethylene and derivatives thereof, diphenoquinone derivatives, 8-hydroxyquinoline and derivatives thereof, and the like, may be used, and high molecular materials may also be used as well as low molecular materials.

As examples of the electron injection material, LiF is typically used in the art, however, the present application is not limited thereto.

As the light emitting material, red, green or blue light emitting materials may be used, and as necessary, two or more light emitting materials may be mixed and used. Herein, two or more light emitting materials may be used by being deposited as individual sources of supply or by being premixed and deposited as one source of supply. In addition, fluorescent materials may also be used as the light emitting material, however, phosphorescent materials may also be used. As the light emitting material, materials emitting light by bonding electrons and holes injected from an anode and a cathode, respectively, may be used alone, however, materials having a host material and a dopant material involving in light emission together may also be used.

When mixing light emitting material hosts, same series hosts may be mixed, or different series hosts may be mixed. For example, any two or more types of materials among n-type host materials or p-type host materials may be selected, and used as a host material of a light emitting layer.

The organic light emitting device according to one embodiment of the present specification may be a top-emission type, a bottom-emission type or a dual-emission type depending on the materials used.

The heterocyclic compound according to one embodiment of the present specification may also be used in an organic electronic device including an organic solar cell, an organic photo conductor, an organic transistor and the like under a similar principle used in the organic light emitting device.

Hereinafter, the present specification will be described in more detail with reference to examples, however, these are for illustrative purposes only, and the scope of the present application is not limited thereto.

[Preparation Example 1] Preparation of Compound 1

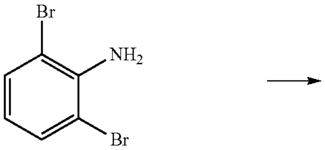

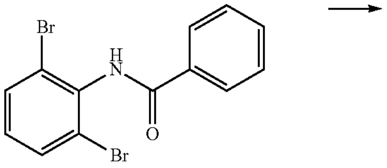

1-1

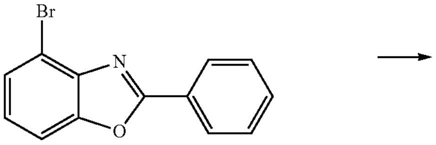

1-2

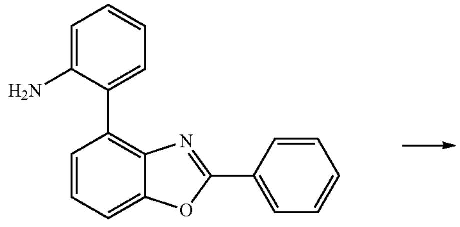

1-3

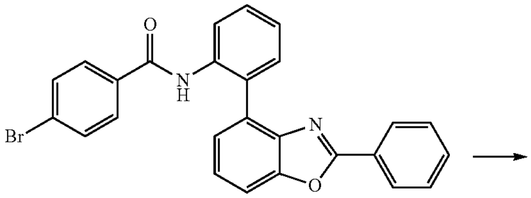

1-4

-continued

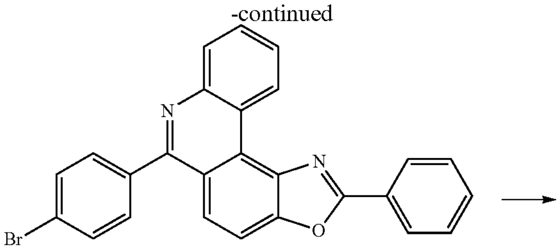

1-5

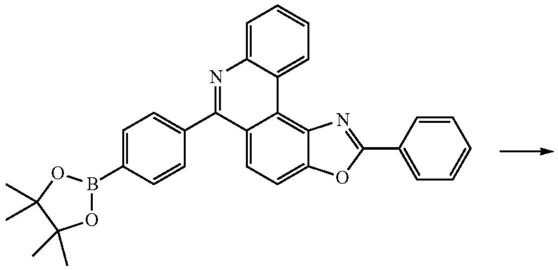

1-6

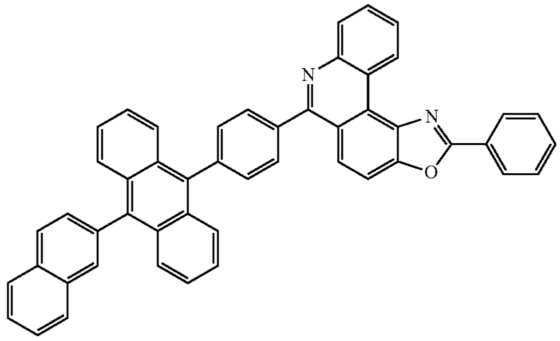

1

1) Preparation of Compound 1-1

After dissolving compound 2,6-dibromoaniline (20 g, 79.7 mmol, 1 eq.) in tetrahydrofuran (THF), benzoyl chloride (9.7 ml, 1.05 eq.) was added thereto, and the result was stirred for 24 hours at room temperature. After the reaction was finished, an aqueous sodium bicarbonate solution was added thereto, and the result was extracted with ethyl acetate. The organic layer was dried with anhydrous $MgSO_4$, and, after removing the solvent using a rotary evaporator, recrystallized using dichloromethane and hexane to obtain target Compound 1-1 (15 g, yield: 53%).

2) Preparation of Compound 1-2

After dissolving Compound 1-1 (15 g, 42.2 mmol) in dimethyl sulfoxide (DMSO) (150 ml), $K_2CO_3$ (17.5 g, 3.0 eq.) was added thereto, and the result was stirred for 17 hours at 150° C. After the reaction was finished, the layers were separated using distilled water and ethyl acetate at room temperature, and the organic layer was dried with anhydrous $MgSO_4$. After removing the solvent using a rotary evaporator, the result was purified with column chromatography using dichloromethane and hexane as a developing solvent to obtain target Compound 1-2 (8.6 g, yield: 74%).

3) Preparation of Compound 1-3

After dissolving Compound 1-2 (8.6 g, 31.3 mmol) in toluene, ethanol and $H_2O$, 2-(4,4,5,5-tetramethyl-1,3,2-dioxaborolan-2-yl)aniline (8.2 g, 1.2 eq.), $Pd(PPh_3)_4$ (1.8 g, 0.05 eq.) and $K_2CO_3$ (13.0 g, 3.0 eq.) were added thereto, and the result was stirred for 5 hours at 110° C. After the reaction was completed, the result was cooled to room temperature, and extracted with distilled water and ethyl acetate. The organic layer was dried with anhydrous $MgSO_4$, and, after removing the solvent using a rotary evaporator, purified with column chromatography using ethyl acetate and hexane as a developing solvent to obtain target Compound 1-3 (8.1 g, yield: 90%).

4) Preparation of Compound 1-4

After dissolving Compound 1-3 (8.1 g, 28.2 mmol) in tetrahydrofuran (THF), 4-bromobenzoyl chloride (9.3 g, 1.5 eq.) and triethylamine (TEA) (12 ml, 3.0 eq.) were added thereto at 0° C., and the result was stirred for 2 hours at room temperature. After the reaction was completed, ethyl acetate and distilled water were added to the reaction vessel for solidification, and produced solids were collected to obtain target Compound 1-4 (14 g, yield: 100%).

5) Preparation of Compound 1-5

After dissolving Compound 1-4 (14 g, 30.9 mmol) in nitrobenzene, $POCl_3$ (4.3 ml, 1.5 eq.) was added thereto, and the result was stirred for 17 hours at 150° C. After the reaction was completed, the result was neutralized by adding an aqueous sodium bicarbonate solution thereto at room temperature, and produced solids were filtered to obtain target Compound 1-5 (10.8 g, yield: 77%).

6) Preparation of Compound 1-6

After dissolving Compound 1-5 (10.8 g, 30.9 mmol) in 1,4-dioxane, bis(pinacolato)diboron, $Pd(dppf)Cl_2$ and potassium acetate were added thereto, and the result was stirred for 2 hours at 110° C. After the reaction was completed, the result was extracted with distilled water and ethyl acetate. The organic layer was dried with anhydrous $MgSO_4$, and, after removing the solvent using a rotary evaporator, target Compound 1-6 (15.1 g, yield: 98%) was obtained without further purification.

7) Preparation of Compound 1

After adding 9-bromo-10-(naphthalen-2-yl)anthracene (12.7 g, 1.1 eq.), $Pd(PPh_3)_4$ (1.7 g, 0.05 eq.), $K_2CO_3$ (12.5 g, 3.0 eq.), toluene, ethanol and $H_2O$ to Compound 1-6 (15.1 g, 30.2 mmol), the result was stirred for 2 hours at 110° C. After the reaction was completed, the result was cooled to room temperature, and extracted with distilled water and ethyl acetate. The organic layer was dried with anhydrous $MgSO_4$, and, after removing the solvent using a rotary evaporator, purified with column chromatography using dichloromethane and hexane as a developing solvent to obtain target Compound 1 (17 g, yield: 86%).

[Preparation Example 2] Preparation of Compound 5

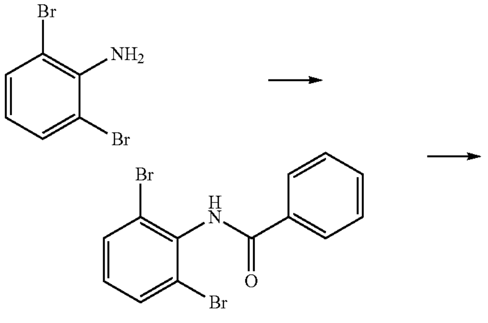

1-1

-continued

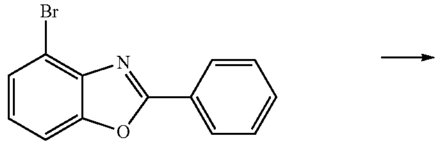

1-2

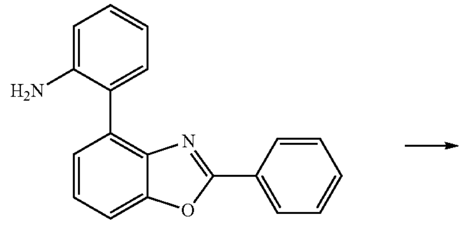

1-3

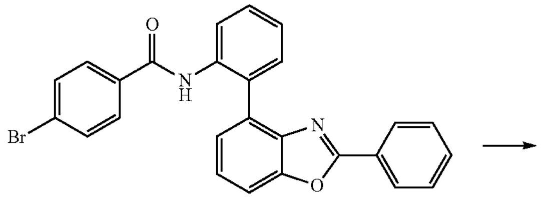

1-4

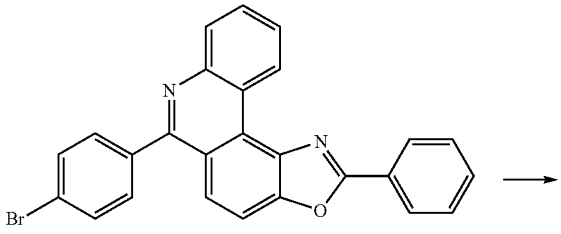

1-5

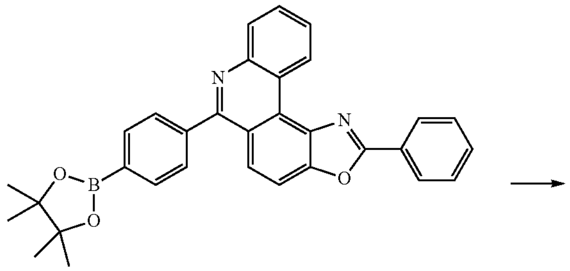

1-6

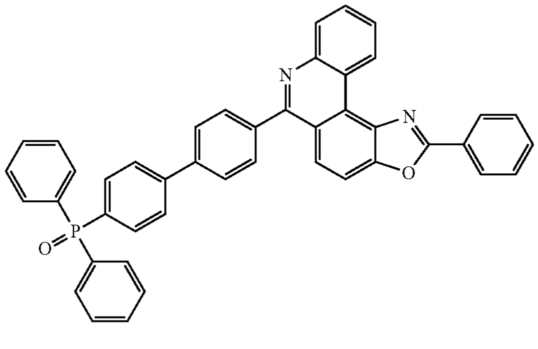

5

Target Compound 5 was obtained in the same manner as in the preparation of Compound 1 in Preparation Example 1 except that (4-bromophenyl)diphenylphosphine oxide was used instead of 9-bromo-10-(naphthalen-2-yl)anthracene.

[Preparation Example 3] Preparation of Compound 7

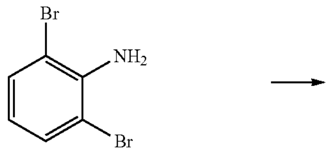

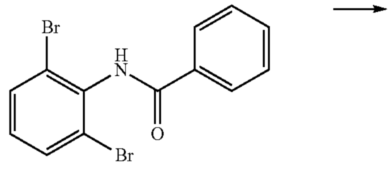

1-1

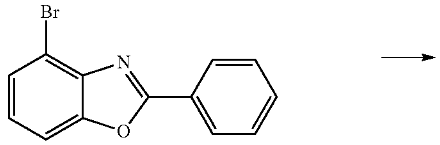

1-2

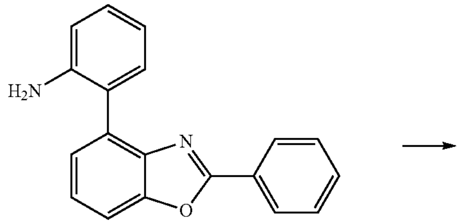

1-3

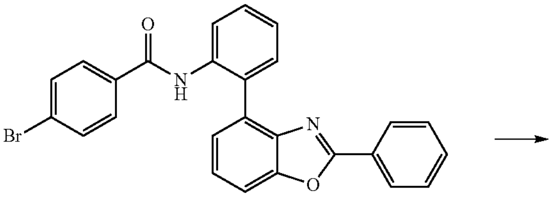

1-4

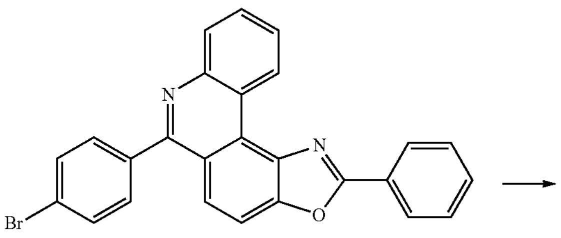

1-5

-continued

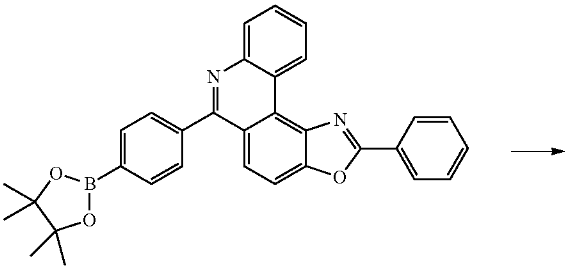

1-6

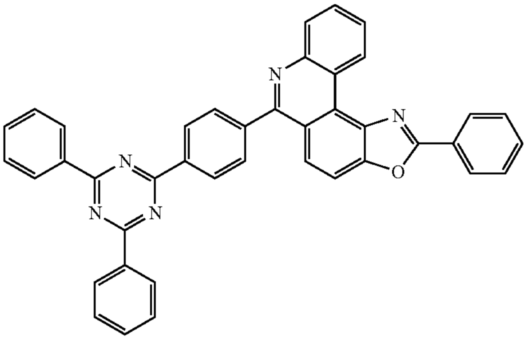

7

Target Compound 7 was obtained in the same manner as in the preparation of Compound 1 in Preparation Example 1 except that 2-chloro-4,6-diphenyl-1,3,5-triazine was used instead of 9-bromo-10-(naphthalen-2-yl)anthracene.

[Preparation Example 4] Preparation of Compound 9

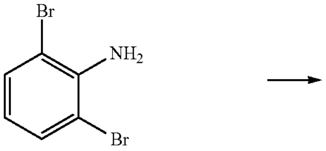

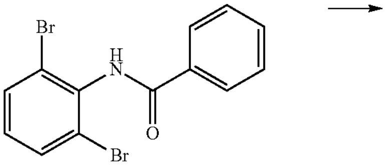

1-1

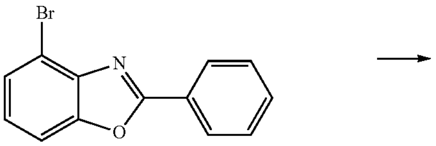

1-2

-continued
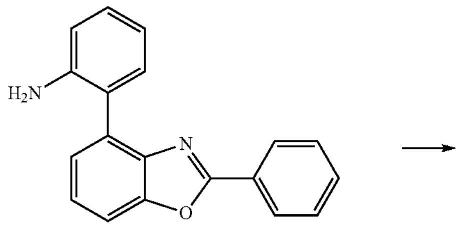
1-3
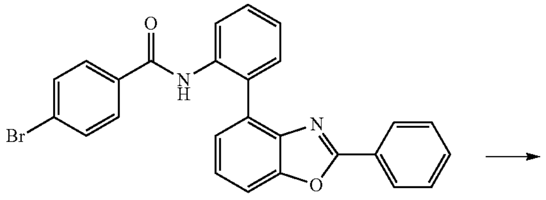
1-4
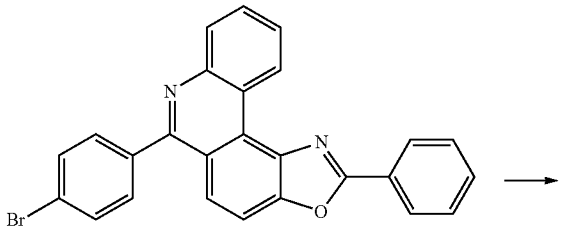
1-5
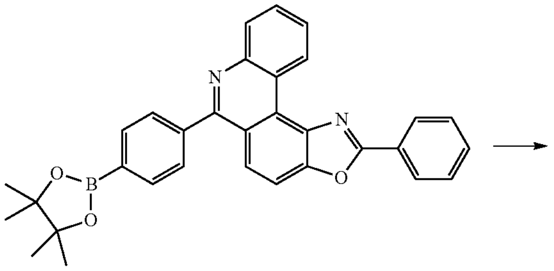
1-6
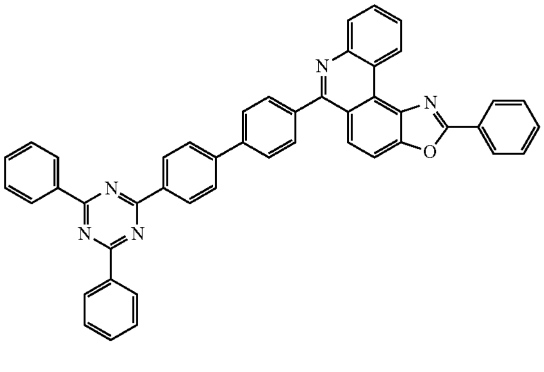
9
Target Compound 9 was obtained in the same manner as in the preparation of Compound 1 in Preparation Example 1 except that 2-(4-bromophenyl)-4,6-diphenyl-1,3,5-triazine was used instead of 9-bromo-10-(naphthalen-2-yl)anthracene.
[Preparation Example 5] Preparation of Compound 16
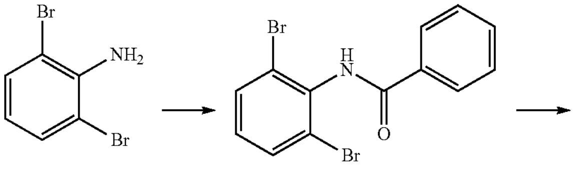
1-1
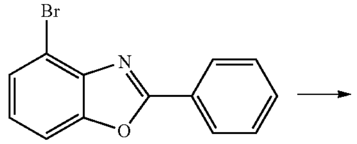
1-2
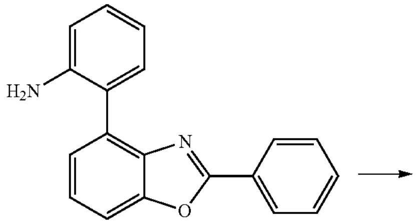
1-3
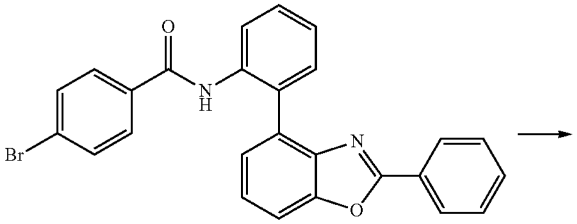
1-4
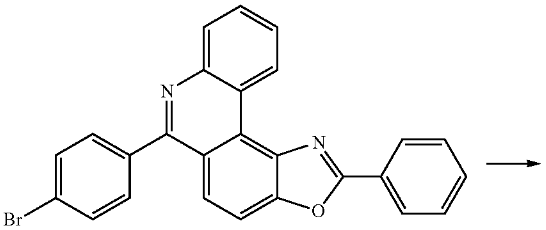
1-5
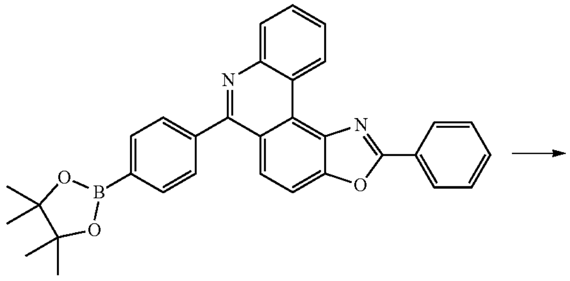
1-6

-continued

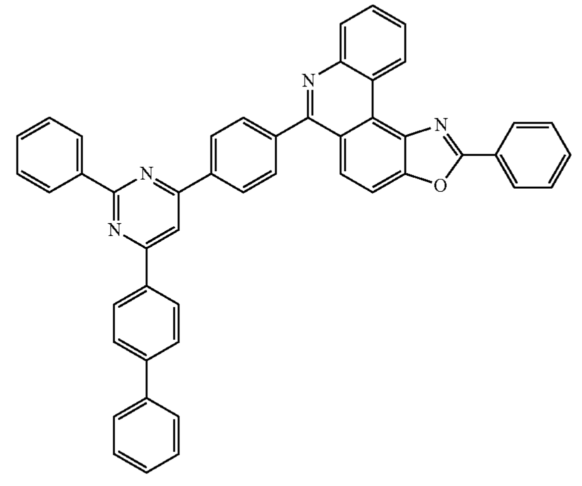

16

Target Compound 16 was obtained in the same manner as in the preparation of Compound 1 in Preparation Example 1 except that 4-([1,1'-biphenyl]-4-yl)-6-chloro-2-phenylpyrimidine was used instead of 9-bromo-10-(naphthalen-2-yl) anthracene.

[Preparation Example 6] Preparation of Compound 25

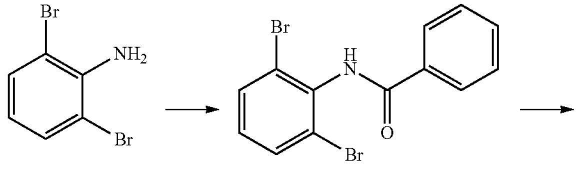

1-1

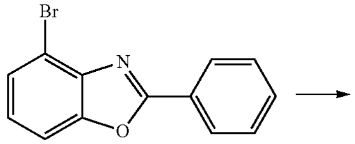

1-2

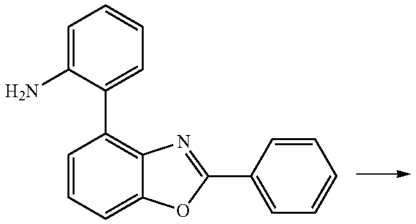

1-3

-continued

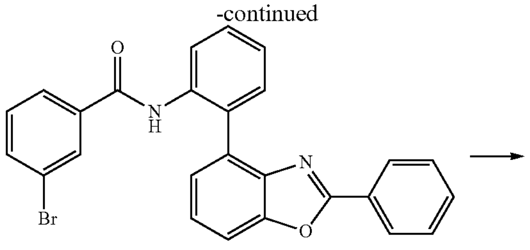

25-1

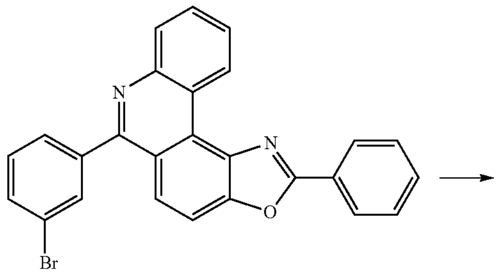

25-2

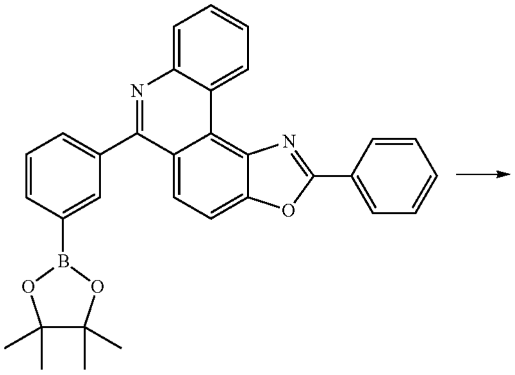

25-3

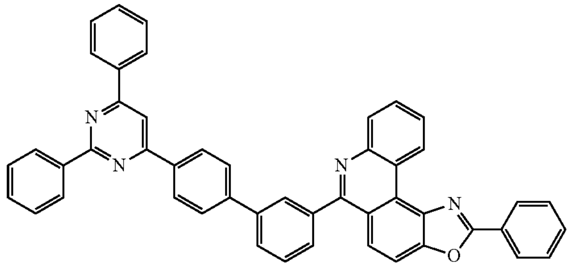

25

1) Preparation of Compound 25-1

After dissolving Compound 1-3 (10.0 g, 34.9 mmol) in tetrahydrofuran (THF), 4-bromobenzoyl chloride (11.5 g, 1.5 eq.) and triethylamine (TEA) (15 ml, 3.0 eq.) were added thereto at 0° C., and the result was stirred for 2 hours at room temperature. After the reaction was completed, ethyl acetate and distilled water were added to the reaction vessel for solidification, and produced solids were collected to obtain target Compound 25-1 (15.4 g, yield: 94%).

2) Preparation of Compound 25-2

After dissolving Compound 25-1 (15.4 g, 32.8 mmol) in nitrobenzene, $POCl_3$ (4.6 ml, 1.5 eq.) was added thereto, and the result was stirred for 17 hours at 150° C. After the reaction was completed, the result was neutralized by adding an aqueous sodium bicarbonate solution thereto at room temperature, and produced solids were filtered to obtain target Compound 25-2 (9.6 g, yield: 65%).

3) Preparation of Compound 25-3

After dissolving Compound 25-2 (9.6 g, 21.3 mmol) in 1,4-dioxane, bis(pinacolato)diboron, Pd(dppf)$Cl_2$ and potassium acetate were added thereto, and the result was stirred for 2 hours at 110° C. After the reaction was completed, the result was extracted with distilled water and ethyl acetate. The organic layer was dried with anhydrous $MgSO_4$, and, after removing the solvent using a rotary evaporator, target Compound 25-3 (10.4 g, yield: 98%) was obtained without further purification.

4) Preparation of Compound 25

After adding 4-(4-bromophenyl)-2,6-diphenylpyrimidine (8.5 g, 1.1 eq.), $Pd(PPh_3)_4$ (1.1 g, 0.05 eq.), $K_2CO_3$ (8.3 g, 3.0 eq.), toluene, ethanol and $H_2O$ to Compound 25-3 (10.0 g, 20.0 mmol), the result was stirred for 2 hours at 110° C. After the reaction was completed, the result was cooled to room temperature, and extracted with distilled water and ethyl acetate. The organic layer was dried with anhydrous $MgSO_4$, and, after removing the solvent using a rotary evaporator, purified with column chromatography using dichloromethane and hexane as a developing solvent to obtain target Compound 25 (11.4 g, yield: 84%).

[Preparation Example 7] Preparation of Compound 29

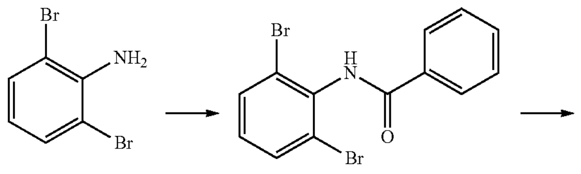

1-1

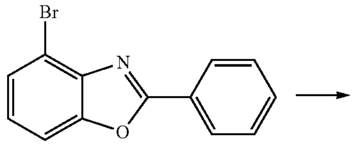

1-2

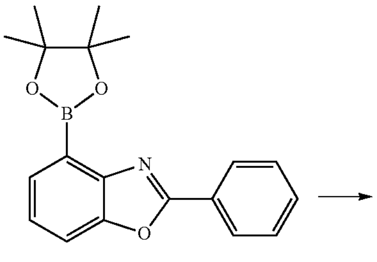

29-1

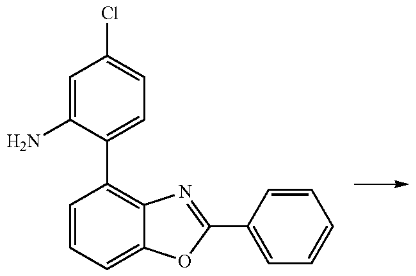

29-2

-continued

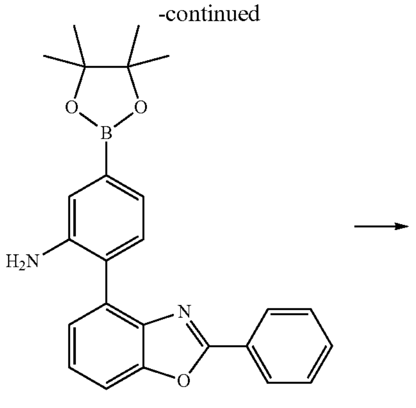

29-3

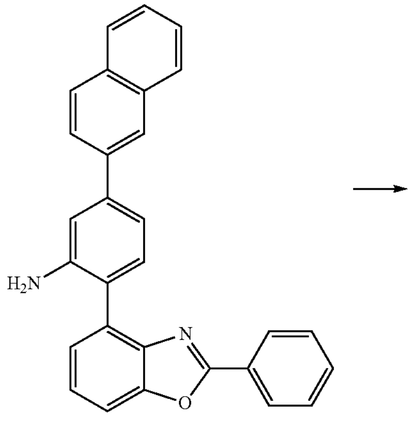

29-4

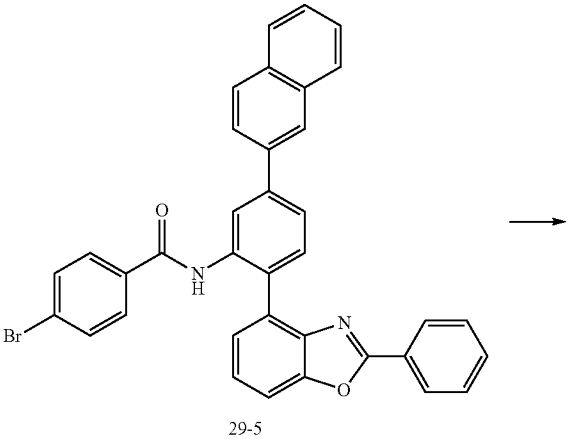

29-5

-continued

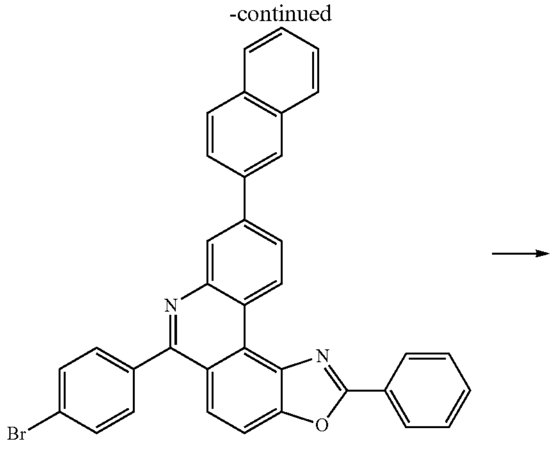

29-6

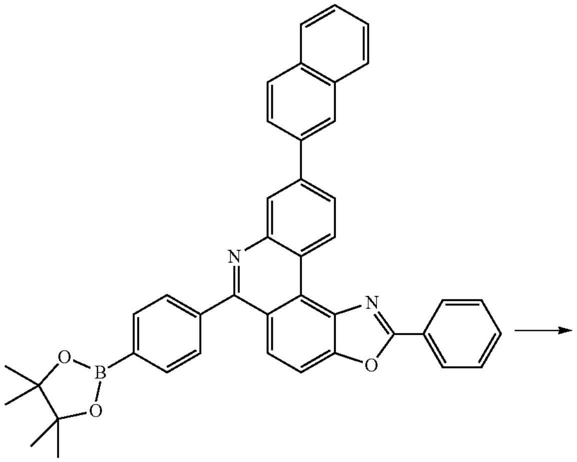

29-7

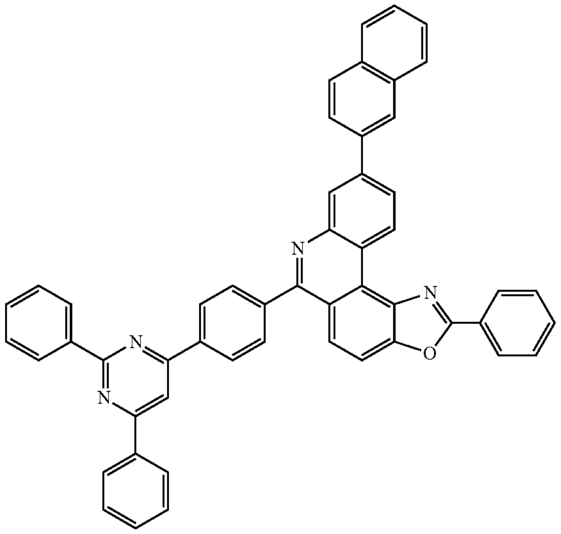

29

1) Preparation of Compound 29-1

After dissolving Compound 1-2 (10.0 g, 36.4 mmol) in 1,4-dioxane, bis(pinacolato)diboron (9.2 g, 2.0 eq.), Pd(dppf)$Cl_2$ (1.3 g, 0.05 eq.) and potassium acetate (10.7 g, 3.0 eq.) were added thereto, and the result was stirred for 2 hours at 110° C. After the reaction was completed, the result was extracted with distilled water and ethyl acetate. The organic layer was dried with anhydrous $MgSO_4$, and, after removing the solvent using a rotary evaporator, target Compound 29-1 (11.5 g, yield: 99%) was obtained without further purification.

2) Preparation of Compound 29-2

After dissolving Compound 29-1 (11.5 g, 36.0 mmol) in toluene, ethanol and $H_2O$, 2-bromo-5-chloroaniline (8.9 g, 1.2 eq.), $Pd(PPh_3)_4$ (2.0 g, 0.05 eq.) and $K_2CO_3$ (15.0 g, 3.0 eq.) were added thereto, and the result was stirred for 5 hours at 110° C. After the reaction was completed, the result was cooled to room temperature, and extracted with distilled water and ethyl acetate. The organic layer was dried with anhydrous $MgSO_4$, and, after removing the solvent using a rotary evaporator, purified with column chromatography using ethyl acetate and hexane as a developing solvent to obtain target Compound 29-2 (10.4 g, yield: 90%).

3) Preparation of Compound 29-3

After dissolving Compound 29-2 (10.4 g, 32.4 mmol) in 1,4-dioxane, bis(pinacolato)diboron (16.4 g, 2.0 eq.), Pd(dppf)$Cl_2$ (1.1 g, 0.05 eq.) and potassium acetate (9.5 g, 3.0 eq.) were added thereto, and the result was stirred for 2 hours at 110° C. After the reaction was completed, the result was extracted with distilled water and ethyl acetate. The organic layer was dried with anhydrous $MgSO_4$, and, after removing the solvent using a rotary evaporator, target Compound 29-3 (13.0 g, yield: 98%) was obtained without further purification.

4) Preparation of Compound 29-4

After dissolving Compound 29-3 (13.0 g, 31.7 mmol) in toluene, ethanol and $H_2O$, 2-bromonaphthalene (7.9 g, 1.2 eq.), $Pd(PPh_3)_4$ (1.8 g, 0.05 eq.) and $K_2CO_3$ (13.1 g, 3.0 eq.) were added thereto, and the result was stirred for 5 hours at 110° C. After the reaction was completed, the result was cooled to room temperature, and extracted with distilled water and ethyl acetate. The organic layer was dried with anhydrous $MgSO_4$, and, after removing the solvent using a rotary evaporator, purified with column chromatography using ethyl acetate and hexane as a developing solvent to obtain target Compound 29-4 (12.4 g, yield: 95%).

5) Preparation of Compound 29-5

After dissolving Compound 29-4 (12.4 g, 30.1 mmol) in tetrahydrofuran (THF), 4-bromobenzoyl chloride (9.9 g, 1.5 eq.) and triethylamine (TEA) (12 ml, 3.0 eq.) were added thereto at 0° C., and the result was stirred for 2 hours at room temperature. After the reaction was completed, ethyl acetate and distilled water were added to the reaction vessel for solidification, and produced solids were collected to obtain target Compound 29-5 (17.7 g, yield: 99%).

6) Preparation of Compound 29-6

After dissolving Compound 29-5 (17.7 g, 29.8 mmol) in nitrobenzene, $POCl_3$ (4.1 ml, 1.5 eq.) was added thereto, and the result was stirred for 17 hours at 150° C. After the reaction was completed, the result was neutralized by adding an aqueous sodium bicarbonate solution thereto at room temperature, and produced solids were filtered to obtain target Compound 29-6 (10.8 g, yield: 62%).

7) Preparation of Compound 29-7

After dissolving Compound 29-6 (10.8 g, 18.4 mmol) in 1,4-dioxane, bis(pinacolato)diboron, Pd(dppf)$Cl_2$ and potassium acetate were added thereto, and the result was stirred for 2 hours at 110° C. After the reaction was completed, the result was extracted with distilled water and ethyl acetate. The organic layer was dried with anhydrous $MgSO_4$, and, after removing the solvent using a rotary evaporator, target Compound 29-7 (15.1 g, yield: 98%) was obtained without further purification.

8) Preparation of Compound 29

After adding 4-chloro-2,6-diphenylpyrimidine (5.3 g, 1.1 eq.), $Pd(PPh_3)_4$ (1.0 g, 0.05 eq.), $K_2CO_3$ (7.5 g, 3.0 eq.), toluene, ethanol and $H_2O$ to Compound 29-7 (15.1 g, 18.1 mmol), the result was stirred for 2 hours at 110° C. After the reaction was completed, the result was cooled to room temperature, and extracted with distilled water and ethyl acetate. The organic layer was dried with anhydrous $MgSO_4$, and, after removing the solvent using a rotary evaporator, purified with column chromatography using dichloromethane and hexane as a developing solvent to obtain target Compound 29 (11 g, yield: 84%).

[Preparation Example 8] Preparation of Compound 34

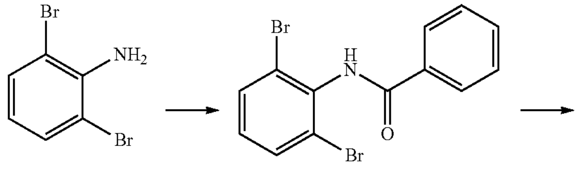

1-1

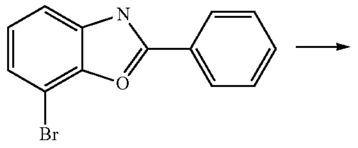

1-2

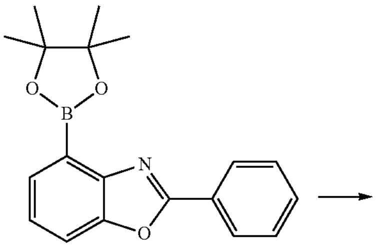

29-1

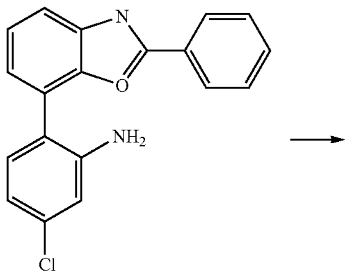

29-2

-continued

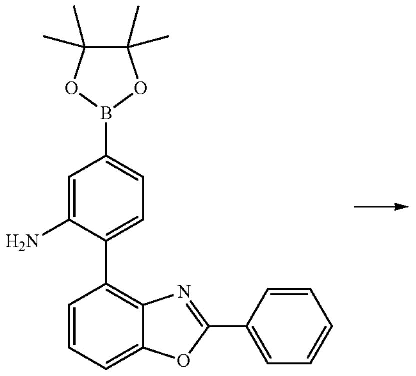

29-3

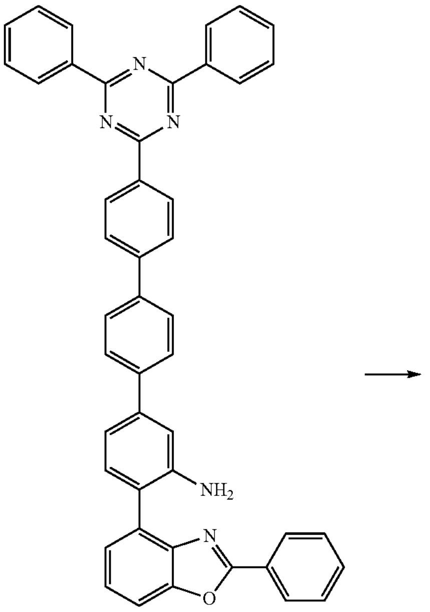

34-1

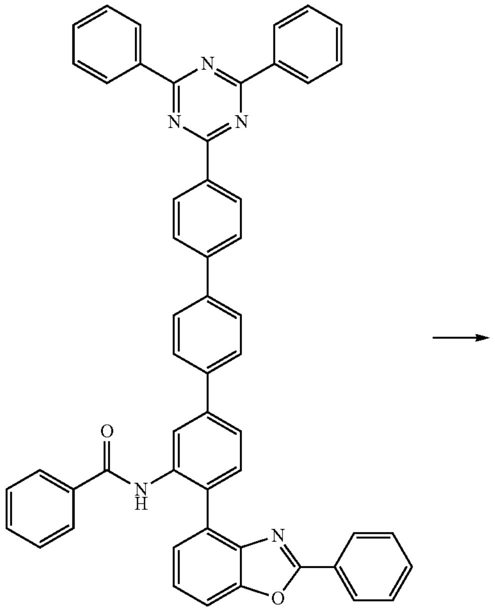

34-2

-continued

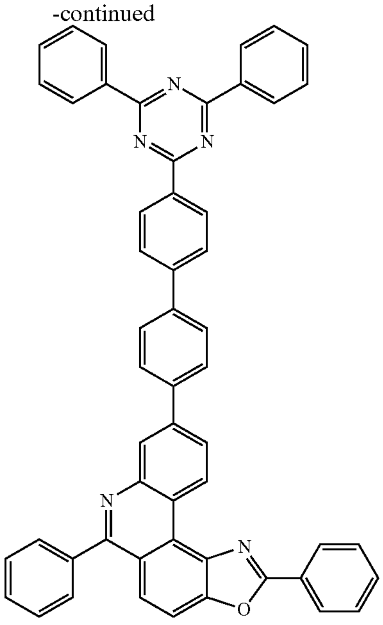

34

1) Preparation of Compound 34-1

After dissolving Compound 29-3 (10.0 g, 24.2 mmol) in toluene, ethanol and $H_2O$, 2-(4'-bromo-[1,1'-biphenyl]-4-yl)-4,6-diphenyl-1,3,5-triazine (10.3 g, 1.1 eq.), $Pd(PPh_3)_4$ (1.4 g, 0.05 eq.) and $K_2CO_3$ (10.0 g, 3.0 eq.) were added thereto, and the result was stirred for 5 hours at 110° C. After the reaction was completed, the result was cooled to room temperature, and extracted with distilled water and ethyl acetate. The organic layer was dried with anhydrous $MgSO_4$, and, after removing the solvent using a rotary evaporator, purified with column chromatography using ethyl acetate and hexane as a developing solvent to obtain target Compound 34-1 (14.9 g, yield: 92%).

2) Preparation of Compound 34-2

After dissolving Compound 34-1 (14.9 g, 22.2 mmol) in tetrahydrofuran (THF), benzoyl chloride (3.8 ml, 1.5 eq.) and triethylamine (TEA) (9.3 ml, 3.0 eq.) were added thereto at 0° C., and the result was stirred for 2 hours at room temperature. After the reaction was completed, ethyl acetate and distilled water were added to the reaction vessel for solidification, and produced solids were collected to obtain target Compound 34-2 (17.0 g, yield: 99%).

3) Preparation of Compound 34

After dissolving Compound 34-2 (17.0 g, 21.9 mmol) in nitrobenzene, $POCl_3$ (3.0 ml, 1.5 eq.) was added thereto, and the result was stirred for 18 hours at 150° C. After the reaction was completed, the result was neutralized by adding an aqueous sodium bicarbonate solution thereto at room temperature, and produced solids were filtered to obtain target Compound 34 (10.7 g, yield: 65%).

[Preparation Example 9] Preparation of Compound 45

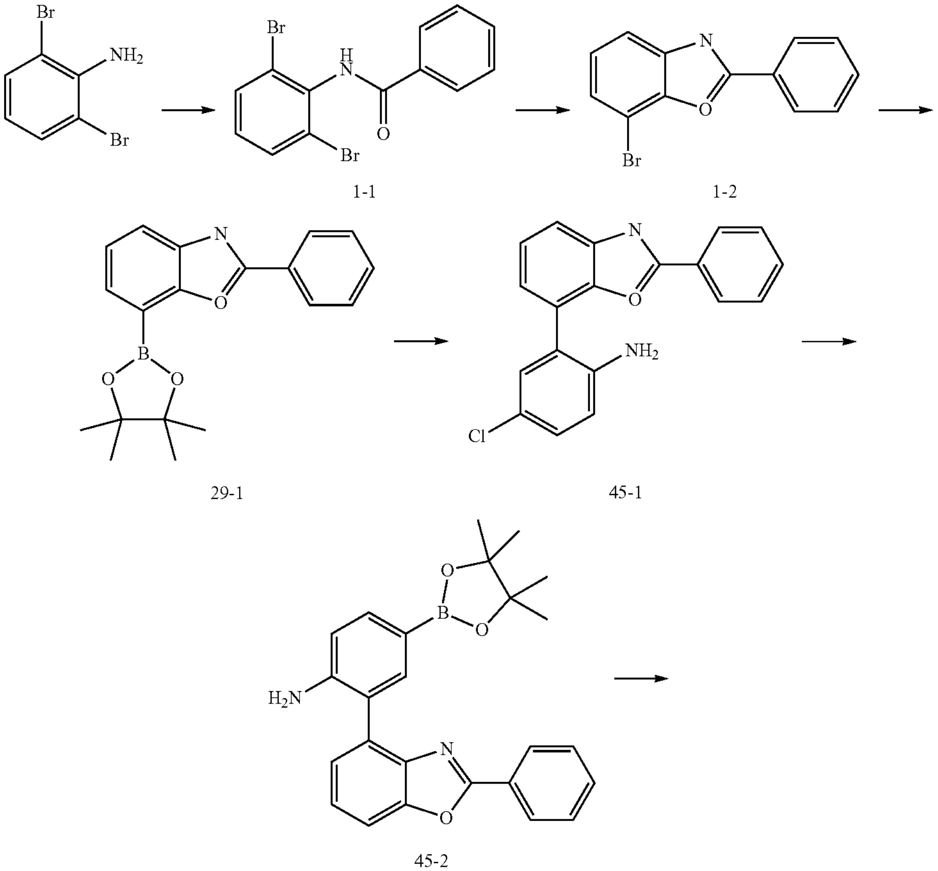

1-1

1-2

29-1

45-1

45-2

-continued
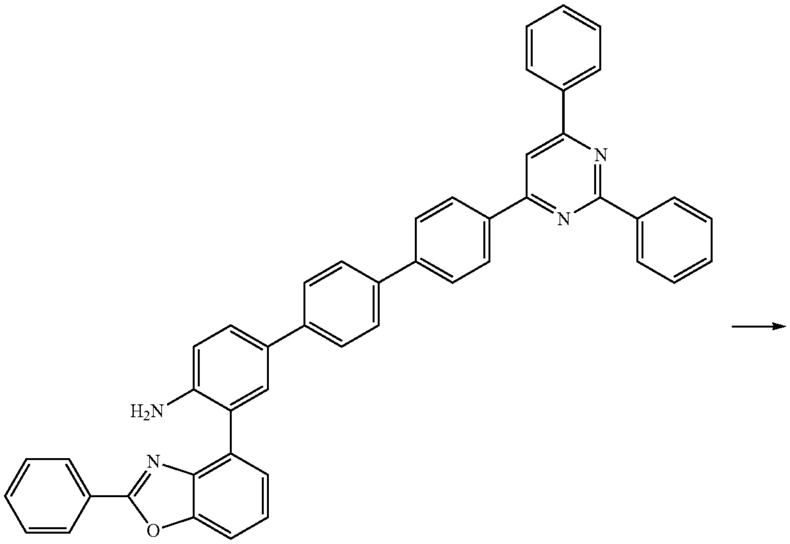
45-3
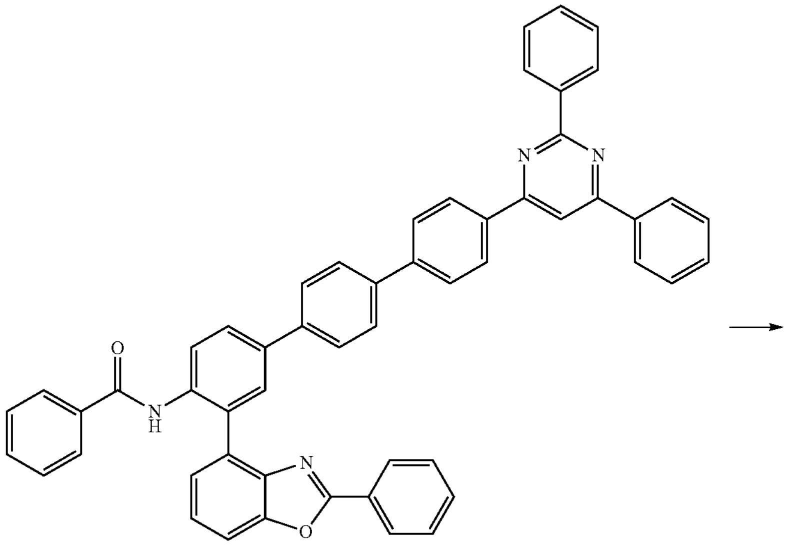
45-4

-continued

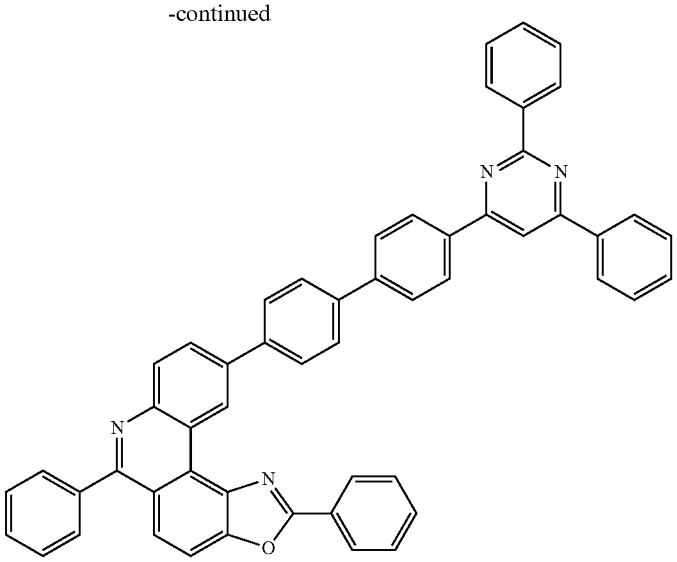

45

1) Preparation of Compound 45-1

After dissolving Compound 29-1 (10.0 g, 31.1 mmol) in toluene, ethanol and $H_2O$, 2-bromo-4-chloroaniline (7.7 g, 1.2 eq.), $Pd(PPh_3)_4$ (1.8 g, 0.05 eq.) and $K_2CO_3$ (12.9 g, 3.0 eq.) were added thereto, and the result was stirred for 5 hours at 110° C. After the reaction was completed, the result was cooled to room temperature, and extracted with distilled water and ethyl acetate. The organic layer was dried with anhydrous $MgSO_4$, and, after removing the solvent using a rotary evaporator, purified with column chromatography using ethyl acetate and hexane as a developing solvent to obtain target Compound 45-1 (8.7 g, yield: 88%).

2) Preparation of Compound 45-2

After dissolving Compound 45-1 (8.7 g, 27.3 mmol) in 1,4-dioxane, bis(pinacolato)diboron, $Pd(dppf)Cl_2$ and potassium acetate were added thereto, and the result was stirred for 2 hours at 110° C. After the reaction was completed, the result was extracted with distilled water and ethyl acetate. The organic layer was dried with anhydrous $MgSO_4$, and, after removing the solvent using a rotary evaporator, target Compound 45-2 (11.2 g, yield: 100%) was obtained without further purification.

3) Preparation of Compound 45-3

After dissolving Compound 45-2 (11.2 g, 27.3 mmol) in toluene, ethanol and $H_2O$, 4-(4'-bromo-[1,1'-biphenyl]-4-yl)-2,6-diphenylpyrimidine (13.9 g, 1.1 eq.), $Pd(PPh_3)_4$ (1.5 g, 0.05 eq.) and $K_2CO_3$ (11.3 g, 3.0 eq.) were added thereto, and the result was stirred for 5 hours at 110° C. After the reaction was completed, the result was cooled to room temperature, and extracted with distilled water and ethyl acetate. The organic layer was dried with anhydrous $MgSO_4$, and, after removing the solvent using a rotary evaporator, purified with column chromatography using ethyl acetate and hexane as a developing solvent to obtain target Compound 45-3 (16.4 g, yield: 90%).

4) Preparation of Compound 45-4

After dissolving Compound 45-3 (16.4 g, 24.5 mmol) in tetrahydrofuran (THF), benzoyl chloride (4.2 ml, 1.5 eq.) and triethylamine (TEA) (10.3 ml, 3.0 eq.) were added thereto at 0° C., and the result was stirred for 2 hours at room temperature. After the reaction was completed, ethyl acetate and distilled water were added to the reaction vessel for solidification, and produced solids were collected to obtain target Compound 45-4 (18.7 g, yield: 99%).

5) Preparation of Compound 45

After dissolving Compound 45-4 (18.7 g, 24.2 mmol) in nitrobenzene, $POCl_3$ (3.3 ml, 1.5 eq.) was added thereto, and the result was stirred for 18 hours at 150° C. After the reaction was completed, the result was neutralized by adding an aqueous sodium bicarbonate solution thereto at room temperature, and produced solids were filtered to obtain target Compound 45 (11.7 g, yield: 64%).

[Preparation Example 10] Preparation of Compound 46

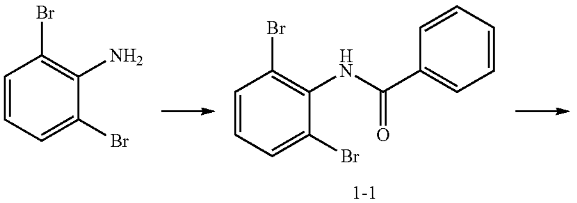

1-1

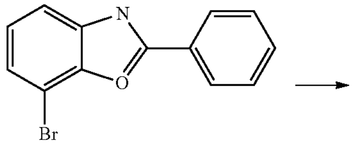

1-2

-continued

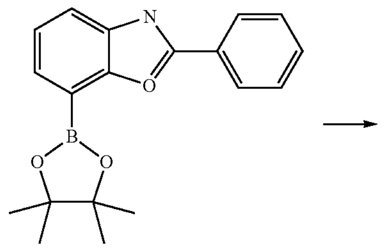

29-1

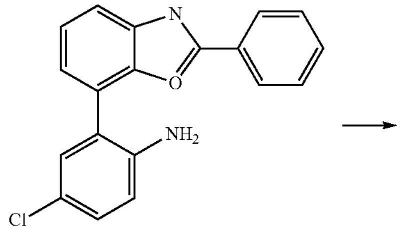

45-1

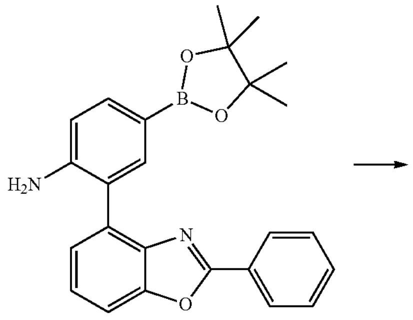

45-2

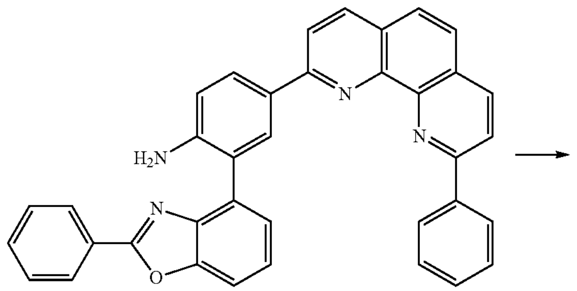

46-1

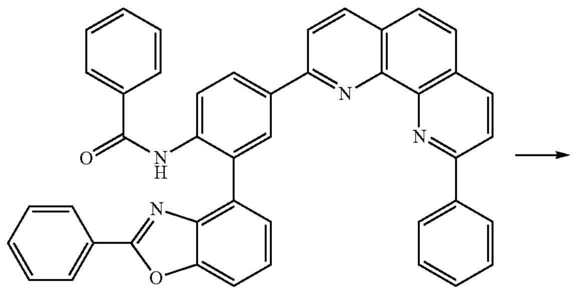

46-2

-continued

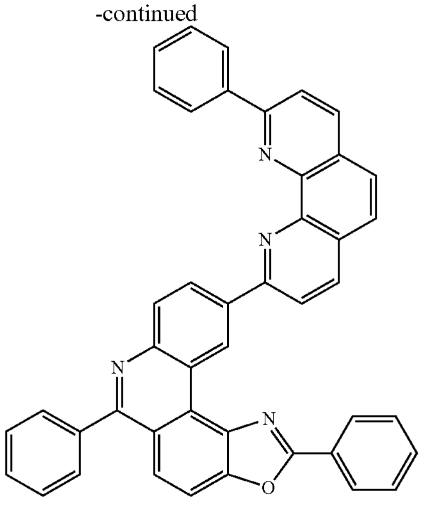

46

1) Preparation of Compound 46-1

After dissolving Compound 45-2 (10.0 g, 27.3 mmol) in toluene, ethanol and $H_2O$, 2-bromo-9-phenyl-1,10-phenanthroline (13.9 g, 1.1 eq.), $Pd(PPh_3)_4$ (1.5 g, 0.05 eq.) and $K_2CO_3$ (11.3 g, 3.0 eq.) were added thereto, and the result was stirred for 5 hours at 110° C. After the reaction was completed, the result was cooled to room temperature, and extracted with distilled water and ethyl acetate. The organic layer was dried with anhydrous $MgSO_4$, and, after removing the solvent using a rotary evaporator, purified with column chromatography using ethyl acetate and hexane as a developing solvent to obtain target Compound 46-1 (13.2 g, yield: 90%).

2) Preparation of Compound 46-2

After dissolving Compound 46-1 (13.2 g, 24.5 mmol) in tetrahydrofuran (THF), benzoyl chloride (4.2 ml, 1.5 eq.) and triethylamine (TEA) (10.2 ml, 3.0 eq.) were added thereto at 0° C., and the result was stirred for 2 hours at room temperature. After the reaction was completed, ethyl acetate and distilled water were added to the reaction vessel for solidification, and produced solids were collected to obtain target Compound 46-2 (15.6 g, yield: 99%).

3) Preparation of Compound 46

After dissolving Compound 46-2 (15.6 g, 24.2 mmol) in nitrobenzene, $POCl_3$ (5.5 ml, 1.5 eq.) was added thereto, and the result was stirred for 18 hours at 150° C. After the reaction was completed, the result was neutralized by adding an aqueous sodium bicarbonate solution thereto at room temperature, and produced solids were filtered to obtain target Compound 46 (10.3 g, yield: 68%).

[Preparation Example 11] Preparation of Compound 49

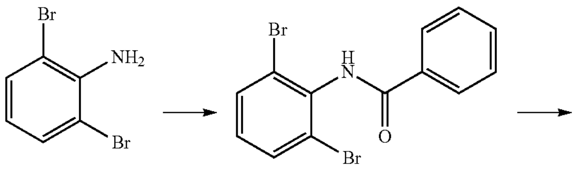

1-1

-continued
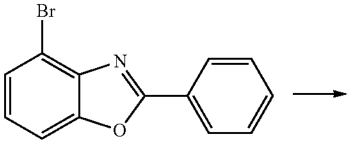
1-2
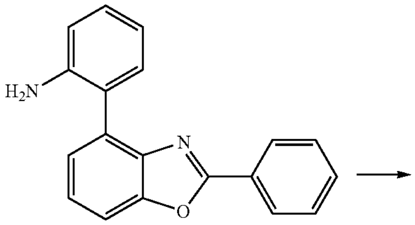
1-3
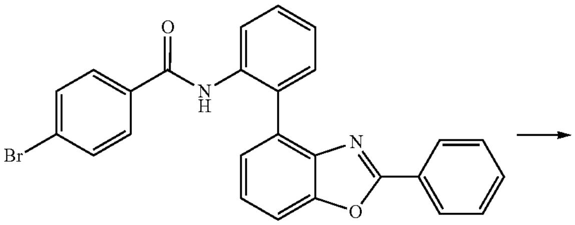
1-4
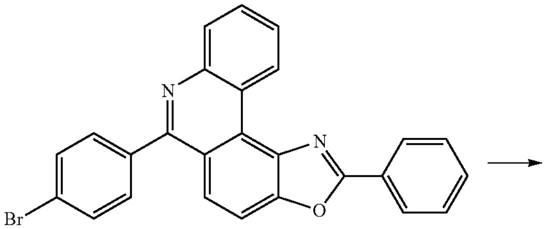
1-5
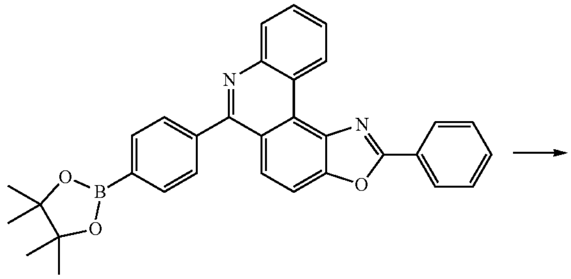
1-6
-continued
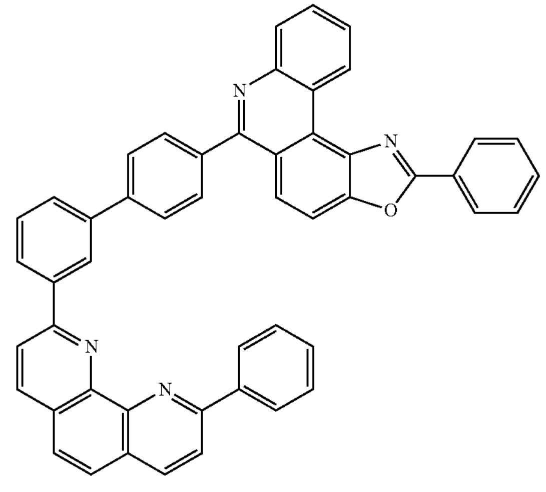
49
Target Compound 49 was obtained in the same manner as in the preparation of Compound 1 in Preparation Example 1 except that 2-(3-bromophenyl)-9-phenyl-1,10-phenanthroline was used instead of 9-bromo-10-phenylanthracene.
[Preparation Example 12] Preparation of Compound 54
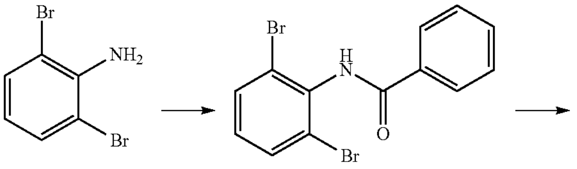
1-1
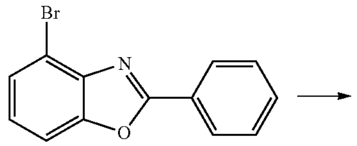
1-2
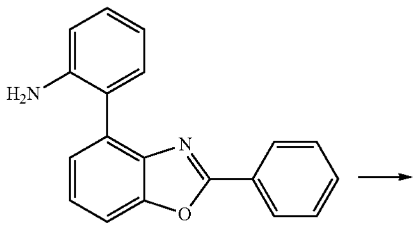
1-3
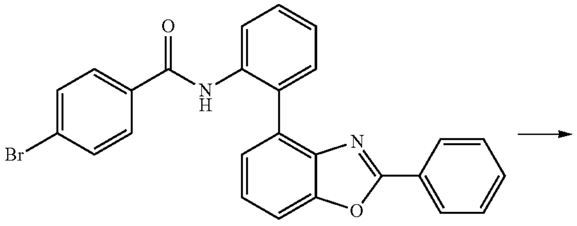
1-4

-continued
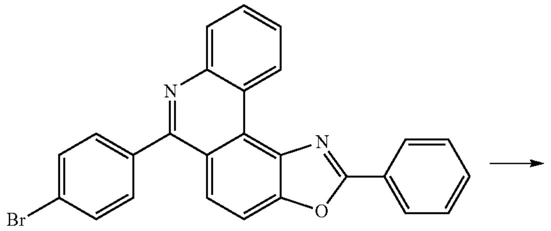
1-5
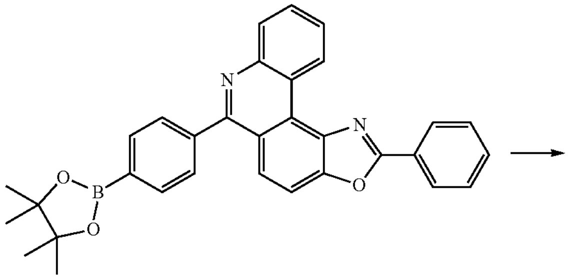
1-6
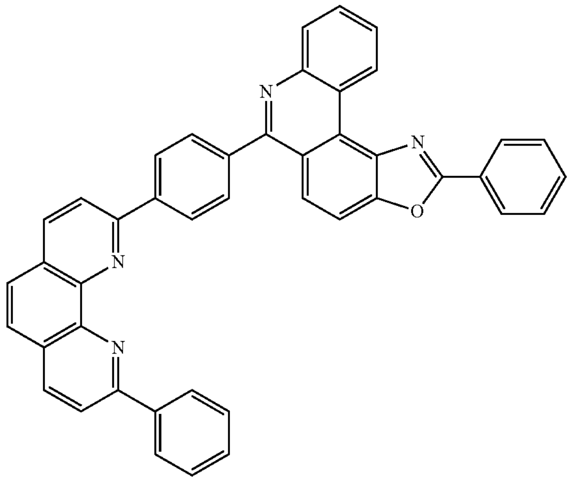
54
Target Compound 54 was obtained in the same manner as in the preparation of Compound 1 in Preparation Example 1 except that 2-bromo-9-phenyl-1,10-phenanthroline was used instead of 9-bromo-10-phenylanthracene.
[Preparation Example 13] Preparation of Compound 59
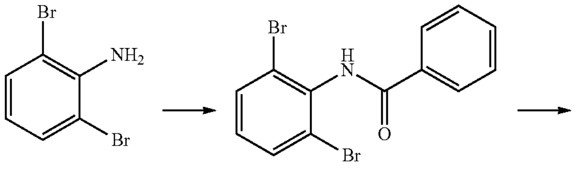
1-1
-continued
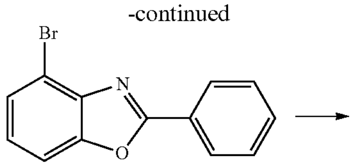
1-2
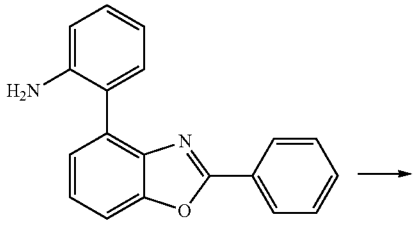
1-3
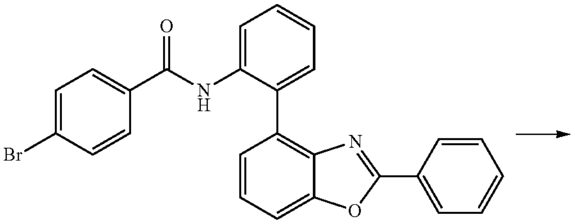
1-4
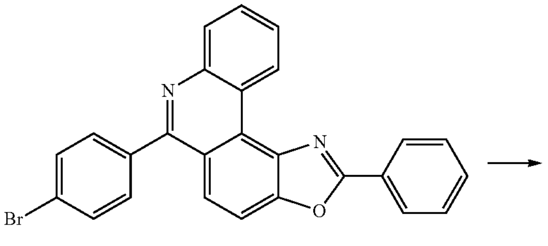
1-5
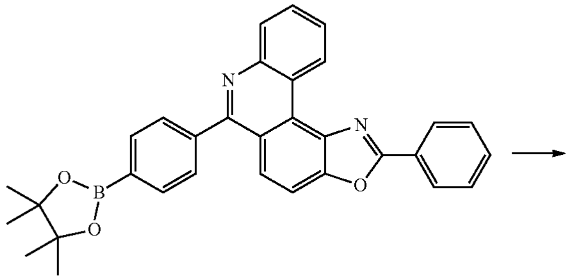
1-6
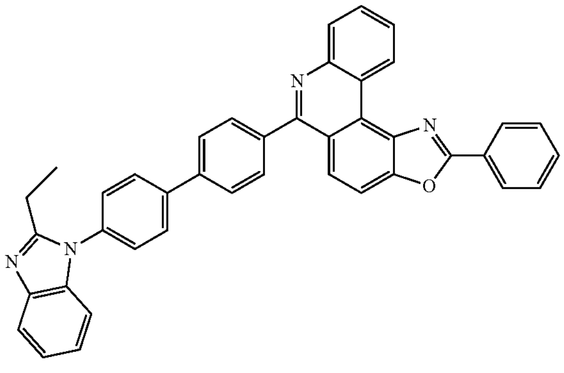
59

Target Compound 59 was obtained in the same manner as in the preparation of Compound 1 in Preparation Example 1 except that 1-(4-bromophenyl)-2-ethyl-1H-benzo[d]imidazole was used instead of 9-bromo-10-phenylanthracene.

[Preparation Example 14] Preparation of Compound 62

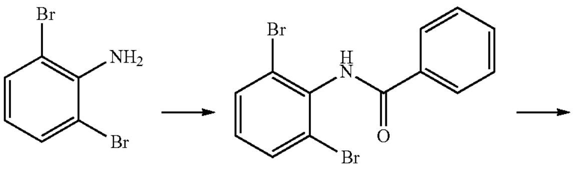

1-1

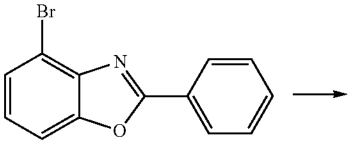

1-2

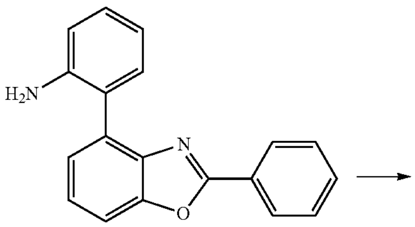

1-3

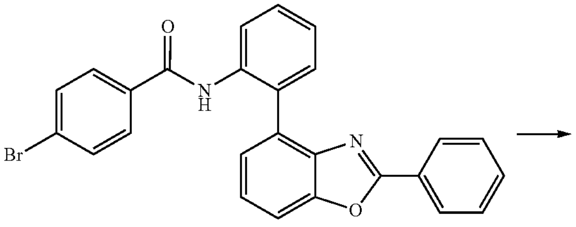

1-4

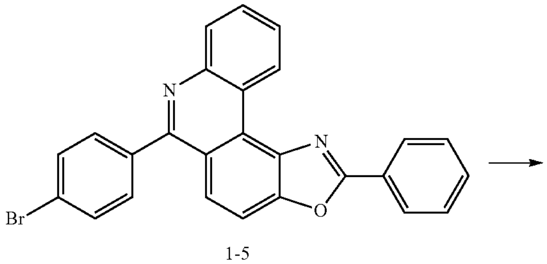

1-5

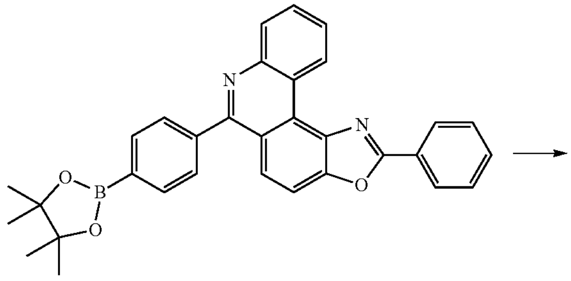

1-6

-continued

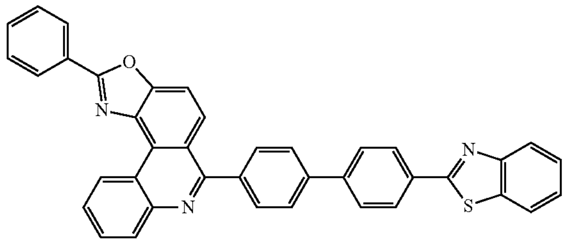

62

Target Compound 62 was obtained in the same manner as in the preparation of Compound 1 in Preparation Example 1 except that 2-(4-bromophenyl)benzo[d]thiazole was used instead of 9-bromo-10-phenylanthracene.

[Preparation Example 15] Preparation of Compound 67

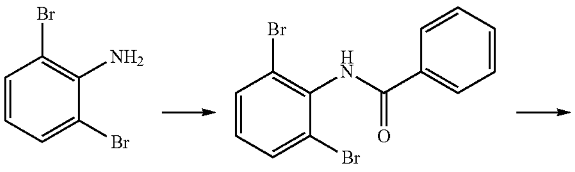

1-1

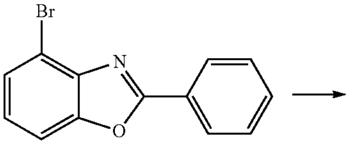

1-2

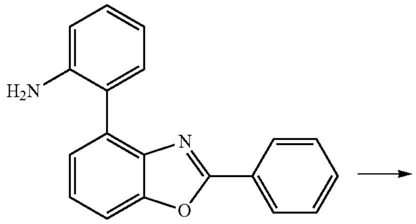

1-3

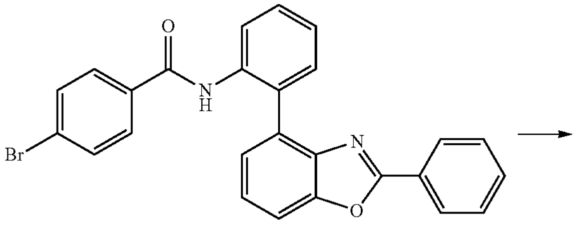

1-4

-continued

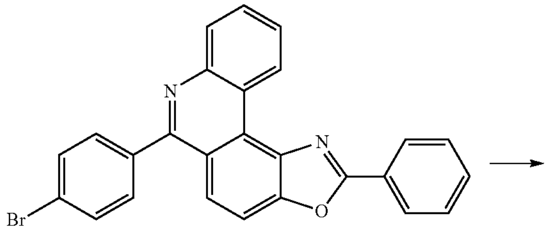

1-5

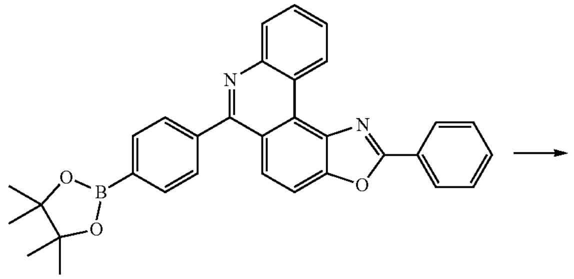

1-6

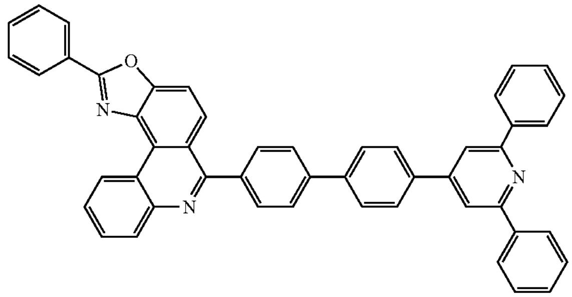

67

Target Compound 67 was obtained in the same manner as in the preparation of Compound 1 in Preparation Example 1 except that 4-(4-bromophenyl)-2,6-diphenylpyridine was used instead of 9-bromo-10-phenylanthracene.

[Preparation Example 16] Preparation of Compound 73

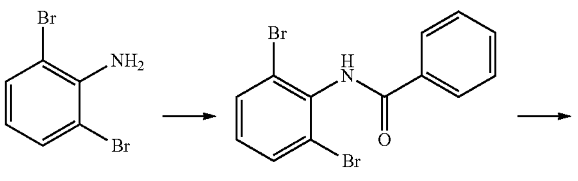

1-1

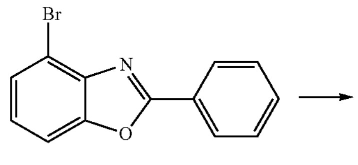

1-2

-continued

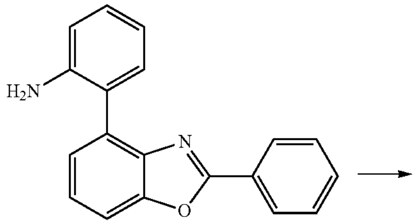

1-3

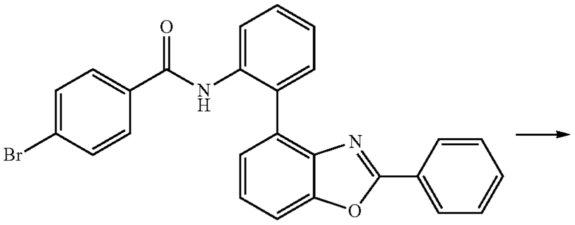

1-4

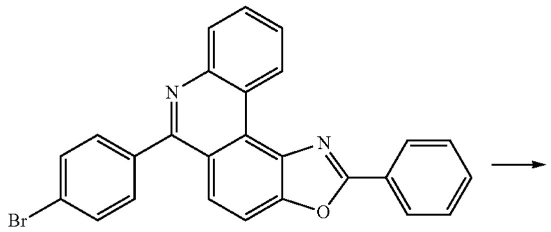

1-5

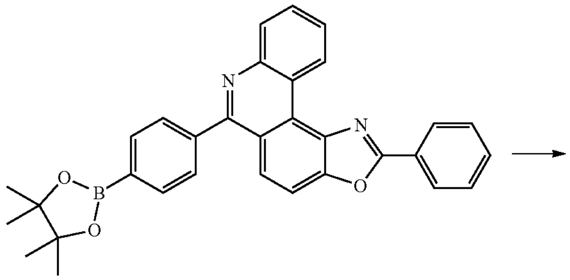

1-6

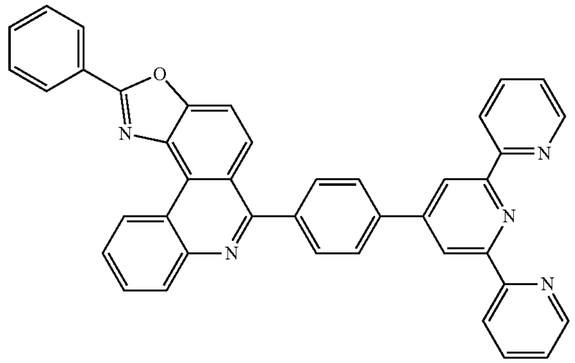

73

Target Compound 73 was obtained in the same manner as in the preparation of Compound 1 in Preparation Example 1 except that 4'-chloro-2,2':6',2"-terpyridine was used instead of 9-bromo-10-(naphthalen-2-yl)anthracene.

[Preparation Example 17] Preparation of Compound 87
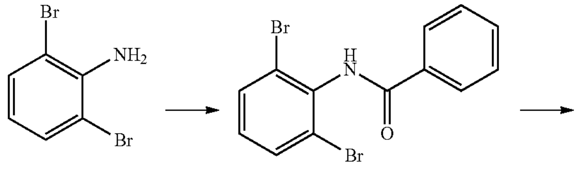
1-1
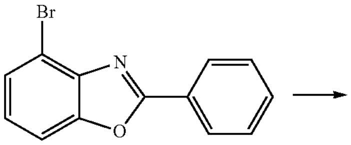
1-2
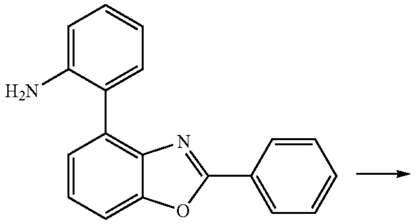
1-3
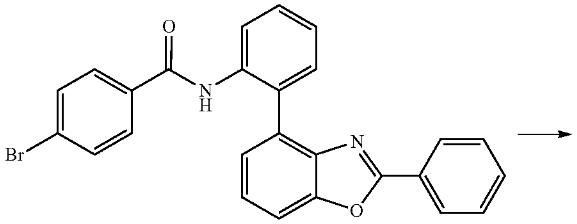
1-4
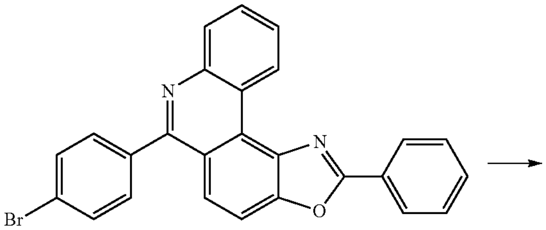
1-5
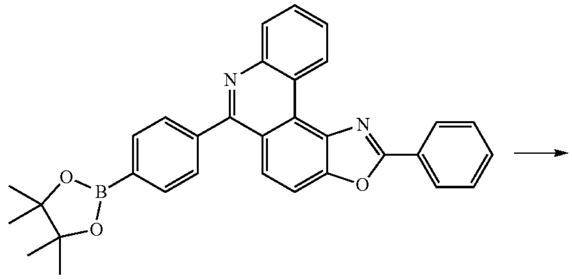
1-6
-continued
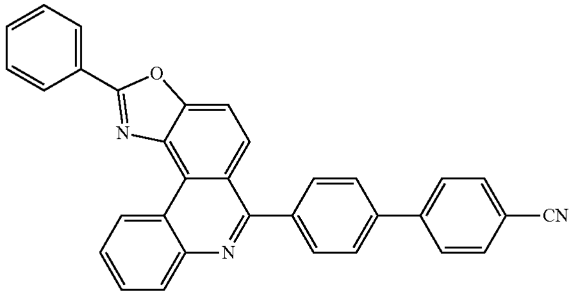
87
Target Compound 87 was obtained in the same manner as in the preparation of Compound 1 in Preparation Example 1 except that 4-bromobenzonitrile was used instead of 9-bromo-10-(naphthalen-2-yl)anthracene.
[Preparation Example 18] Preparation of Compound 94
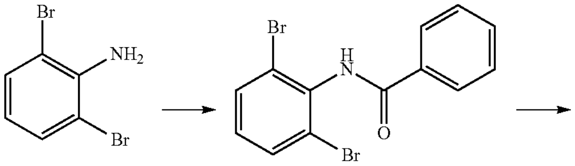
1-1
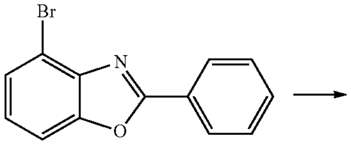
1-2
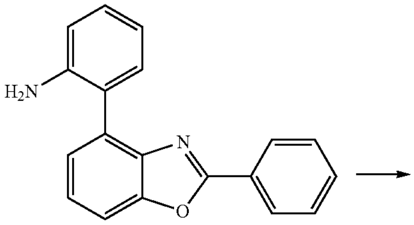
1-3
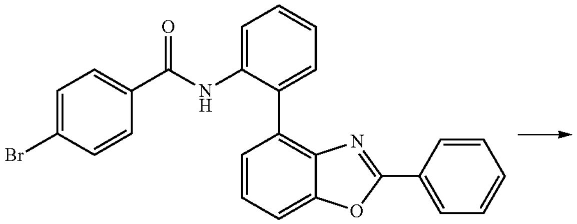
1-4

-continued

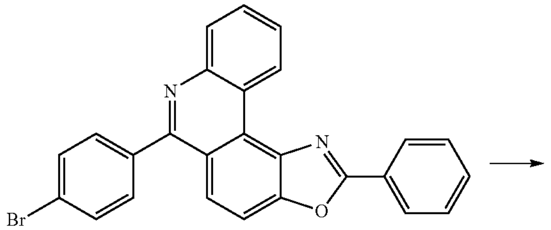

1-5

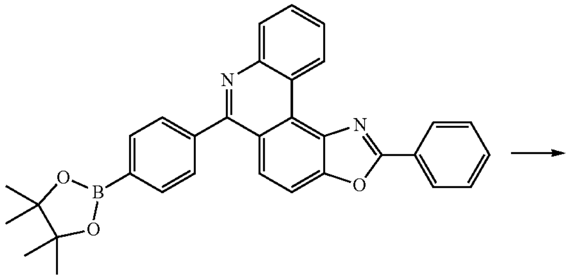

1-6

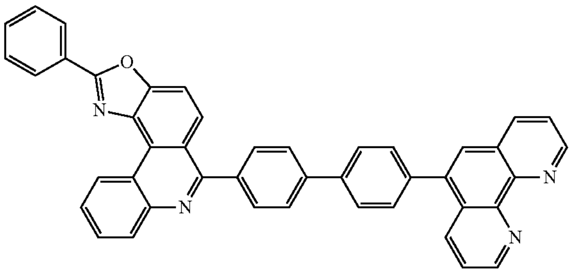

94

Target Compound 94 was obtained in the same manner as in the preparation of Compound 1 in Preparation Example 1 except that 5-(4-bromophenyl)-1,10-phenanthroline was used instead of 9-bromo-10-(naphthalen-2-yl)anthracene.

[Preparation Example 19] Preparation of Compound 107

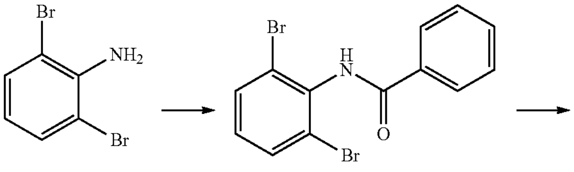

1-1

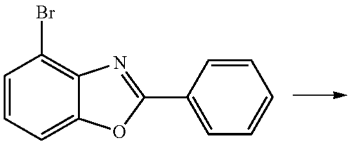

1-2

-continued

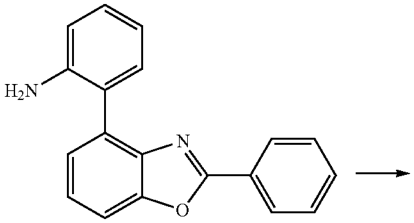

1-3

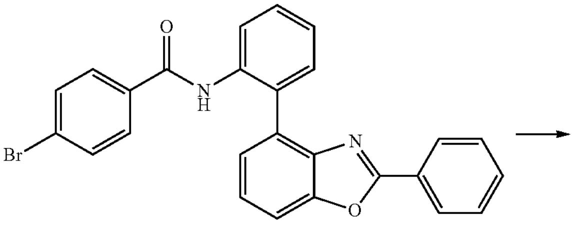

1-4

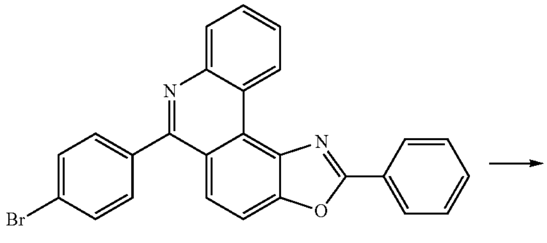

1-5

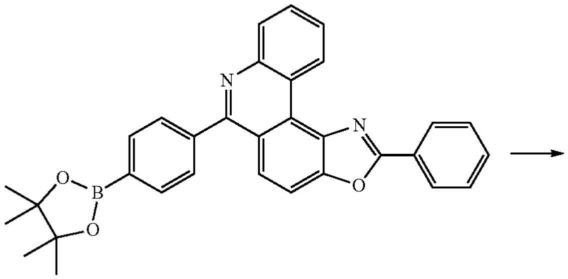

1-6

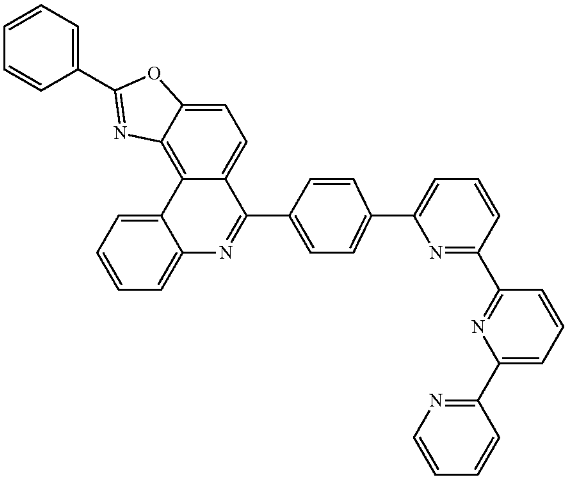

107

Target Compound 107 was obtained in the same manner as in the preparation of Compound 1 in Preparation Example 1 except that 6-bromo-2,2':6',2"-terpyridine was used instead of 9-bromo-10-(naphthalen-2-yl)anthracene.

[Preparation Example 20] Preparation of Compound 108

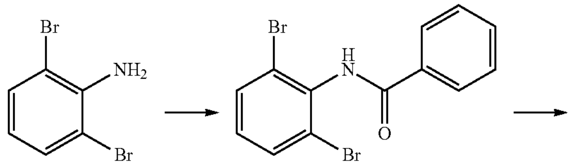

1-1

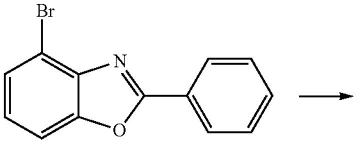

1-2

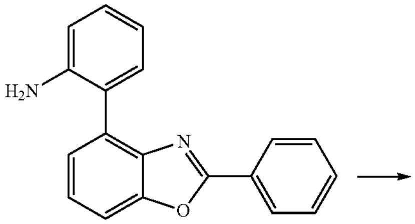

1-3

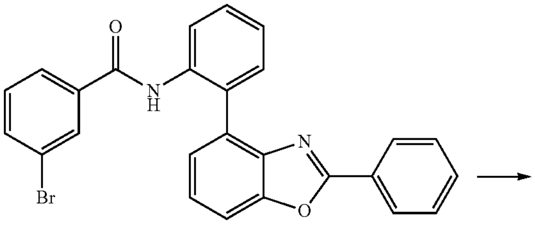

25-1

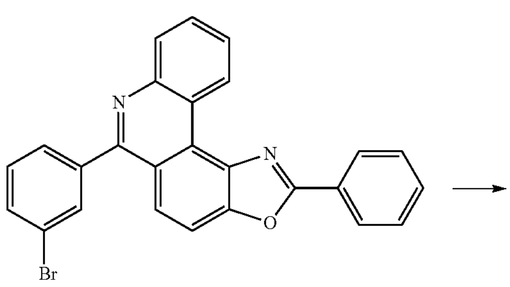

25-2

-continued

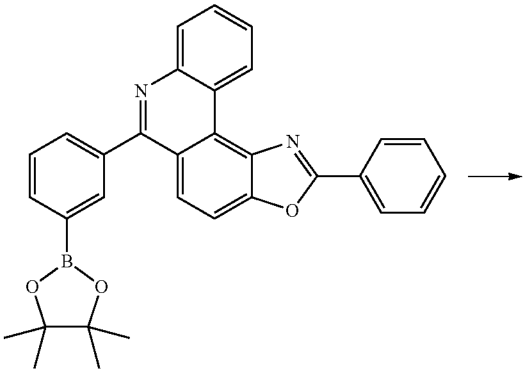

25-3

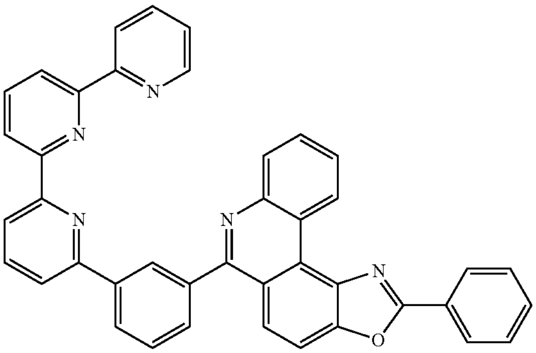

108

Target Compound 108 was obtained in the same manner as in the preparation of Compound 25 in Preparation Example 6 except that 6-bromo-2,2':6',2"-terpyridine was used instead of 4-(4-bromophenyl)-2,6-diphenylpyrimidine.

[Preparation Example 21] Preparation of Compound 129

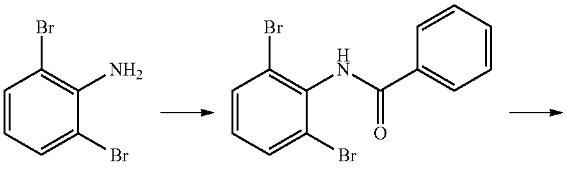

1-1

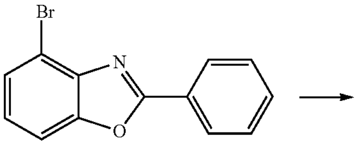

1-2

-continued
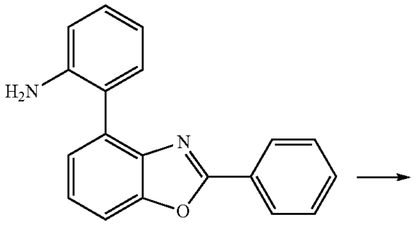
1-3
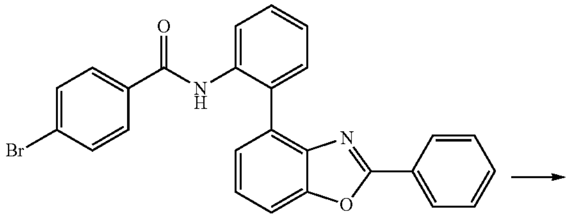
1-4
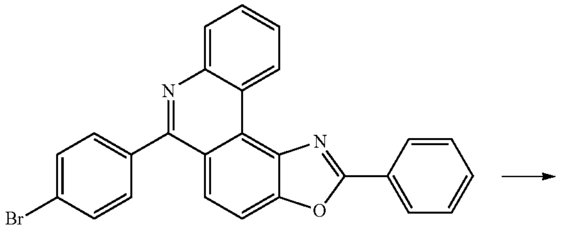
1-5
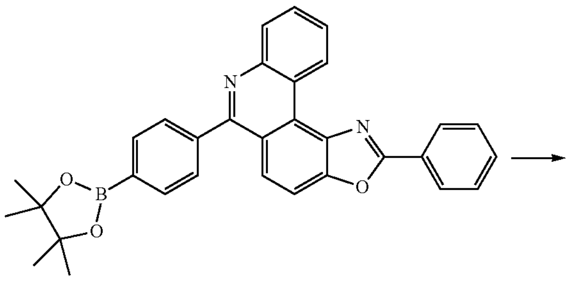
1-6
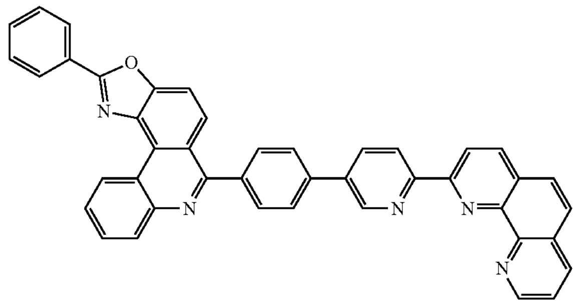
129
Target Compound 129 was obtained in the same manner as in the preparation of Compound 1 in Preparation Example 1 except that 2-(5-bromopyridin-2-yl)-1,10-phenanthroline was used instead of 9-bromo-10-(naphthalen-2-yl)anthracene.
[Preparation Example 22] Preparation of Compound 130
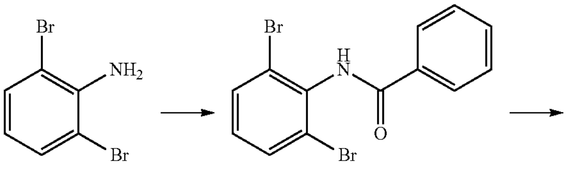
1-1
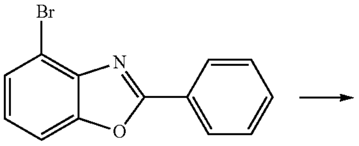
1-2
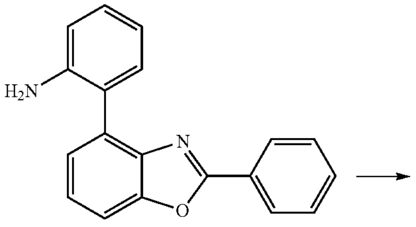
1-3
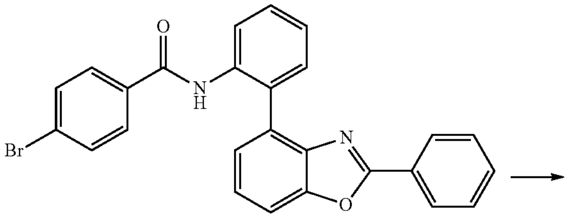
1-4
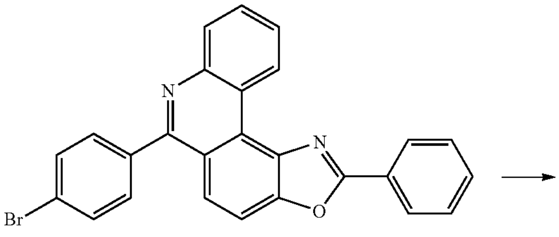
1-5
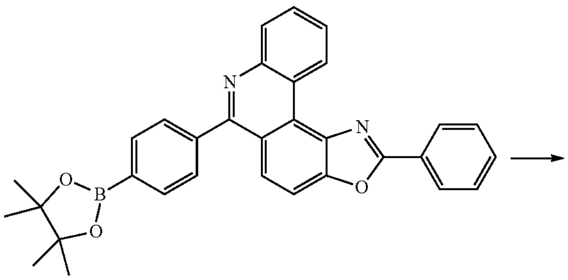
1-6

-continued

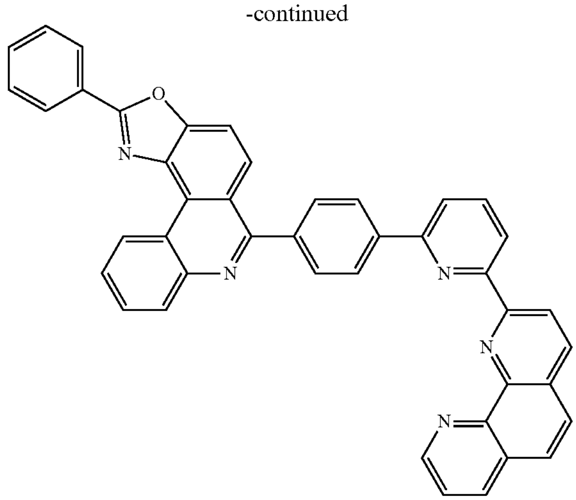

130

Target Compound 130 was obtained in the same manner as in the preparation of Compound 1 in Preparation Example 1 except that 2-(6-bromopyridin-2-yl)-1,10-phenanthroline was used instead of 9-bromo-10-(naphthalen-2-yl)anthracene.

[Preparation Example 23] Preparation of Compound 134

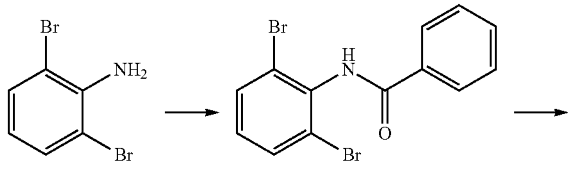

1-1

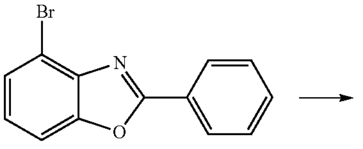

1-2

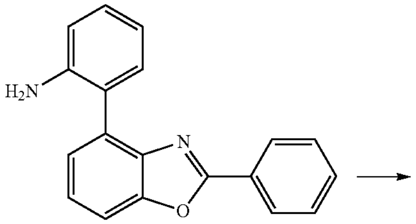

1-3

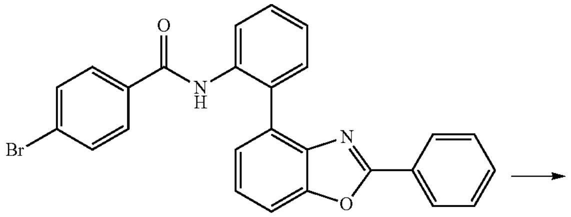

1-4

-continued

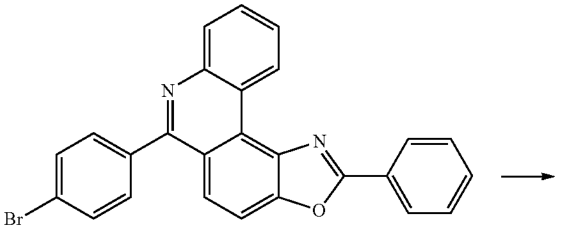

1-5

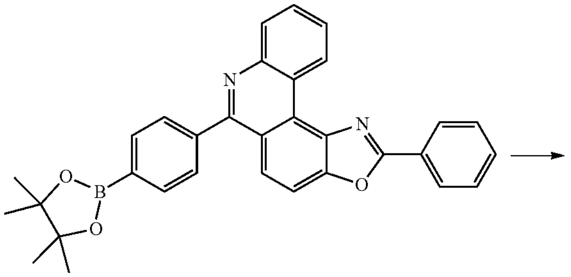

1-6

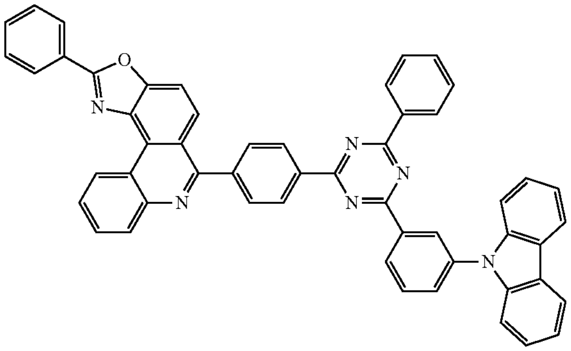

134

Target Compound 134 was obtained in the same manner as in the preparation of Compound 1 in Preparation Example 1 except that 9-(3-(4-chloro-6-phenyl-1,3,5-triazin-2-yl)phenyl)-9H-carbazole was used instead of 9-bromo-10-(naphthalen-2-yl)anthracene.

[Preparation Example 24] Preparation of Compound 135

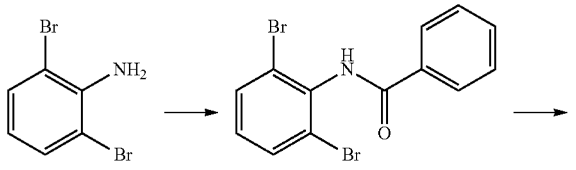

1-1

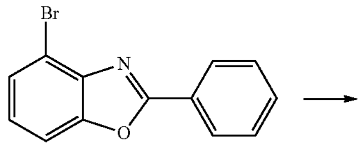

1-2

-continued
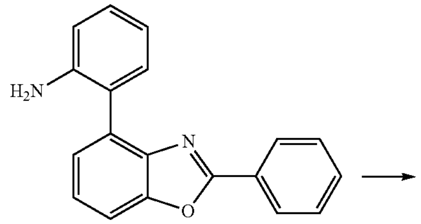
1-3
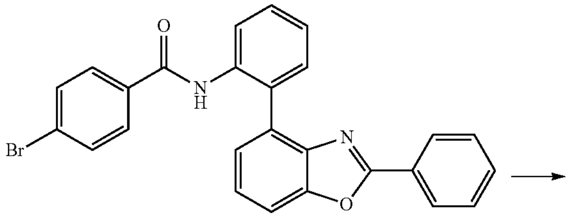
1-4
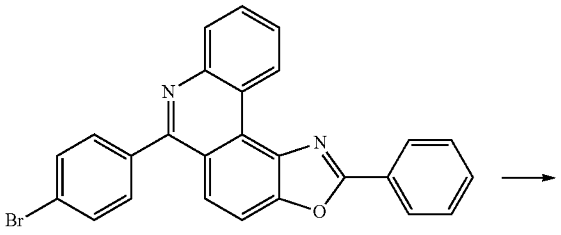
1-5
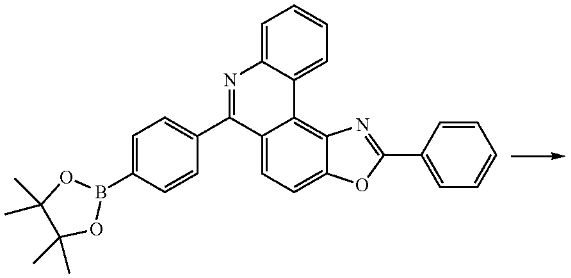
1-6
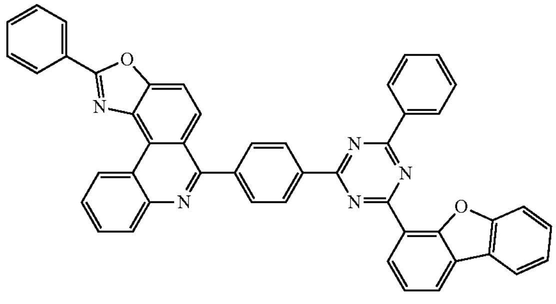
135
Target Compound 135 was obtained in the same manner as in the preparation of Compound 1 in Preparation Example 1 except that 2-chloro-4-(dibenzo[b,d]furan-4-yl)-6-phenyl-1,3,5-triazine was used instead of 9-bromo-10-(naphthalen-2-yl)anthracene.
[Preparation Example 25] Preparation of Compound 140
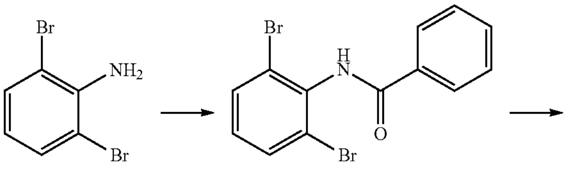
1-1
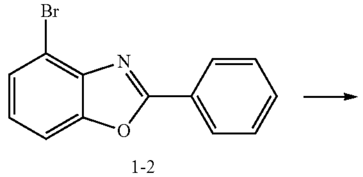
1-2
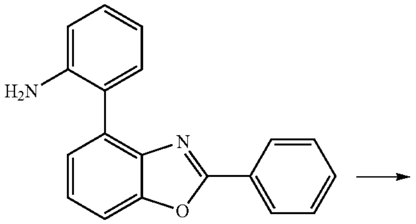
1-3
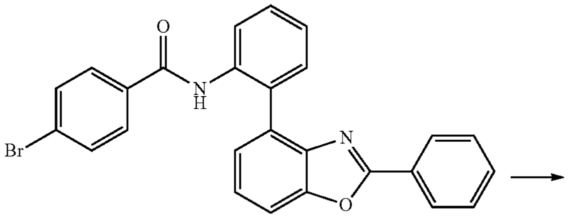
1-4
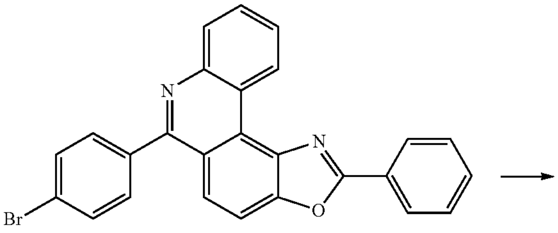
1-5
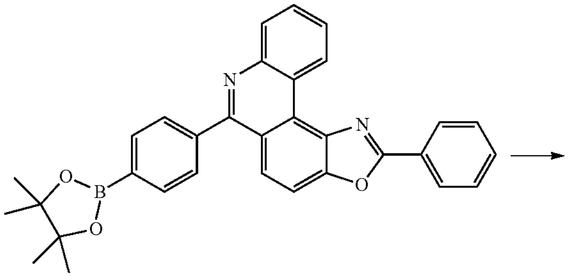
1-6

-continued

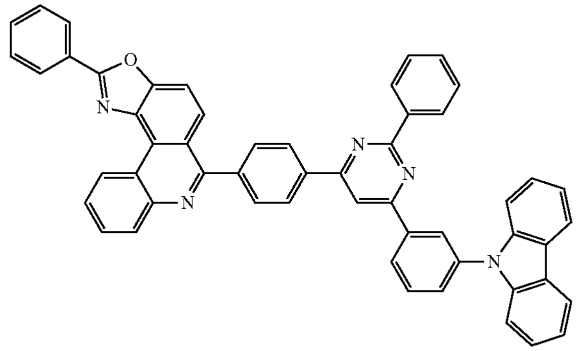

140

Target Compound 140 was obtained in the same manner as in the preparation of Compound 1 in Preparation Example 1 except that 9-(3-(6-chloro-2-phenylpyrimidin-4-yl)phenyl)-9H-carbazole was used instead of 9-bromo-10-(naphthalen-2-yl)anthracene.

[Preparation Example 26] Preparation of Compound 141

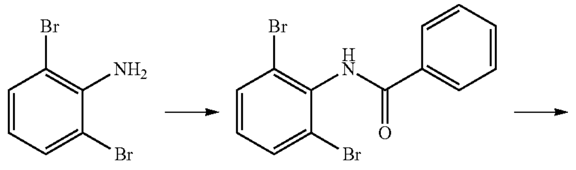

1-1

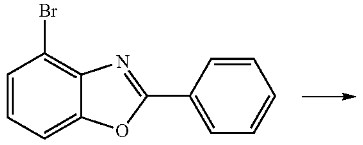

1-2

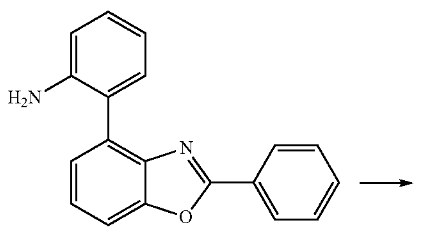

1-3

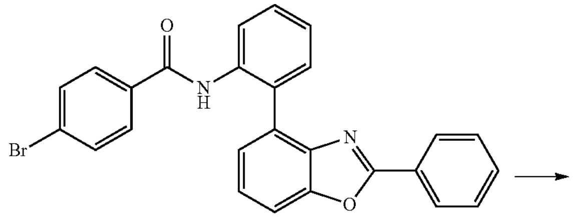

1-4

-continued

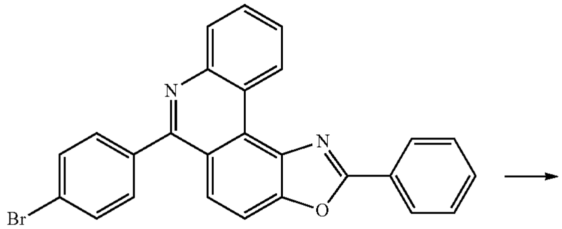

1-5

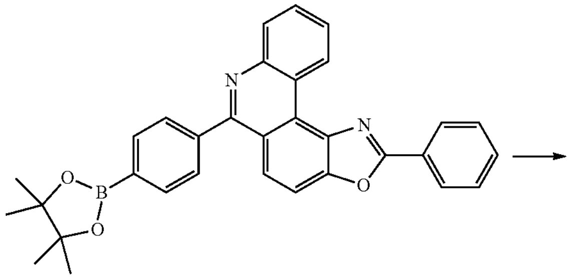

1-6

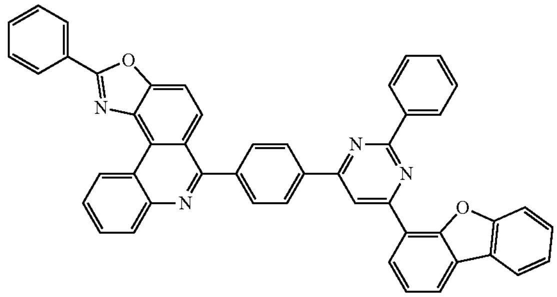

141

Target Compound 141 was obtained in the same manner as in the preparation of Compound 1 in Preparation Example 1 except that 4-chloro-6-(dibenzo[b,d]furan-4-yl)-2-phenylpyrimidine was used instead of 9-bromo-10-(naphthalen-2-yl)anthracene.

[Preparation Example 27] Preparation of Compound 146

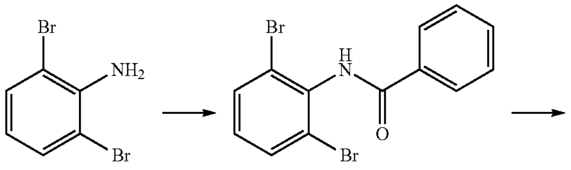

1-1

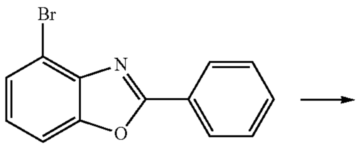

1-2

-continued

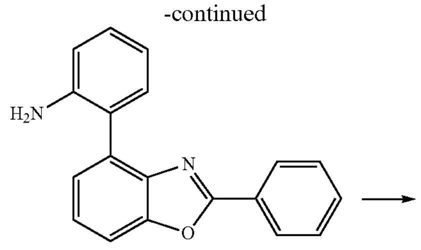

1-3

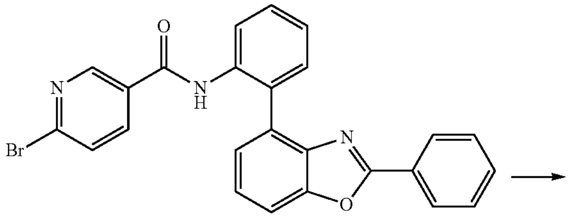

146-1

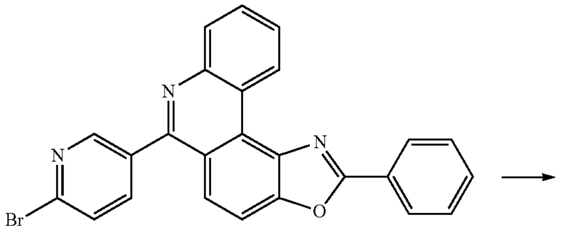

146-2

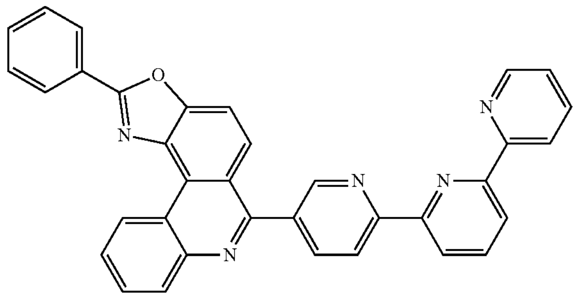

146

1) Preparation of Compound 146-1

After dissolving Compound 1-3 (10.0 g, 34.9 mmol) in tetrahydrofuran (THF), 6-bromonicotinoyl chloride (7.7 g, 1.5 eq.) and triethylamine (TEA) (14.6 ml, 3.0 eq.) were added thereto at 0° C., and the result was stirred for 2 hours at room temperature. After the reaction was completed, ethyl acetate and distilled water were added to the reaction vessel for solidification, and produced solids were collected to obtain target Compound 146-1 (13.7 g, yield: 84%).

2) Preparation of Compound 146-2

After dissolving Compound 146-1 (13.7 g, 29.3 mmol) in nitrobenzene, $POCl_3$ (4.1 ml, 1.5 eq.) was added thereto, and the result was stirred for 17 hours at 150° C. After the reaction was completed, the result was neutralized by adding an aqueous sodium bicarbonate solution thereto at room temperature, and produced solids were filtered to obtain target Compound 146-2 (7.28 g, yield: 55%).

3) Preparation of Compound 146

After dissolving Compound 146-2 (7.28 g, 16.1 mmol) in toluene, n-BuLi (2.0 eq.) was slowly added dropwise thereto at −78° C. After stirring the result for 30 minutes at −78° C., 6-bromo-2,2'-bipyridine (4.1 g, 1.1 eq.) was slowly added thereto, and the result was stirred for 2 hours at room temperature. After the reaction was finished, the result was extracted with distilled water and ethyl acetate, and then the organic layer was concentrated. The concentrated residue was dissolved in MC, then $MnO_2$ (1.5 eq.) was added thereto at room temperature, and the result was stirred for 1 hour and then passed through celite. Methanol was added to the concentrated residue for solidification, and as a result, target Compound 146 (7.09 g, yield: 73%) was obtained.

[Preparation Example 28] Preparation of Compound 148

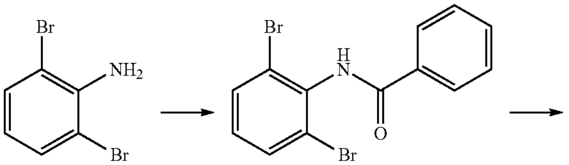

1-1

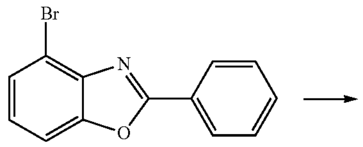

1-2

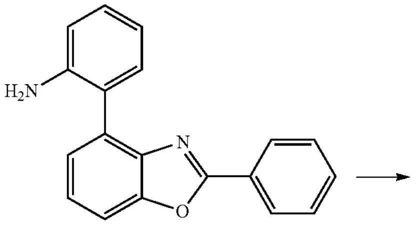

1-3

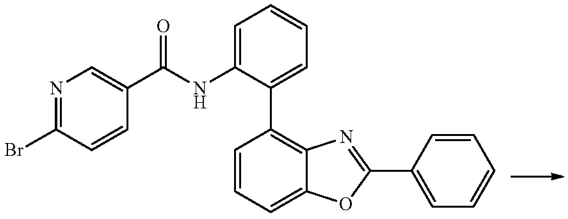

146-1

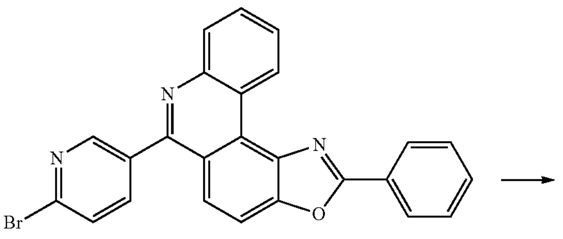

146-2

-continued

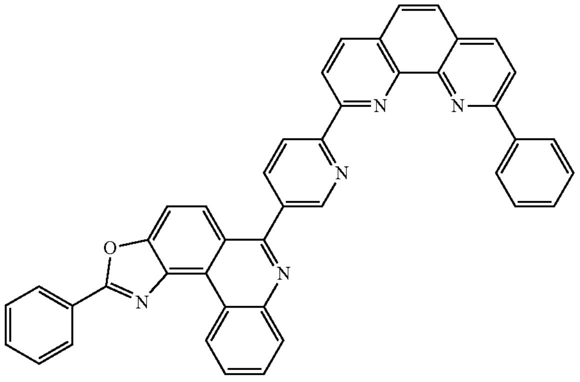

148

Target Compound 148 was obtained in the same manner as in the preparation of Compound 146 in Preparation Example 27 except that 2-bromo-9-phenyl-1,10-phenanthroline was used instead of 6-bromo-2,2'-bipyridine.

[Preparation Example 29] Preparation of Compound 152

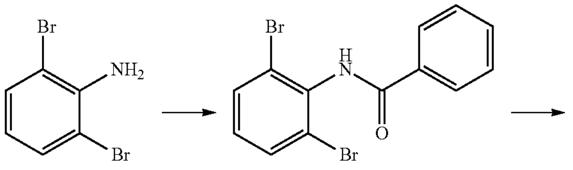

1-1

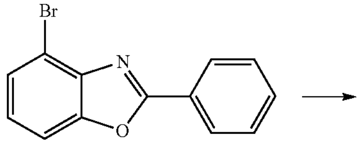

1-2

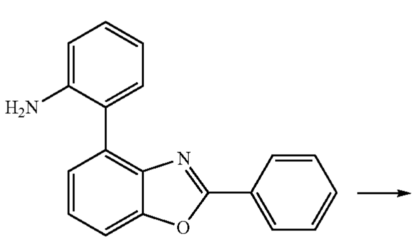

1-3

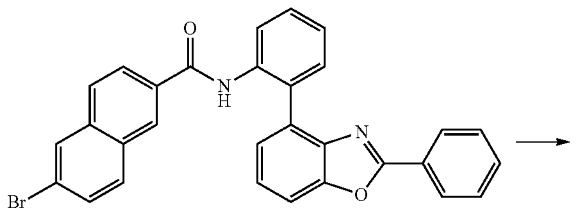

152-1

-continued

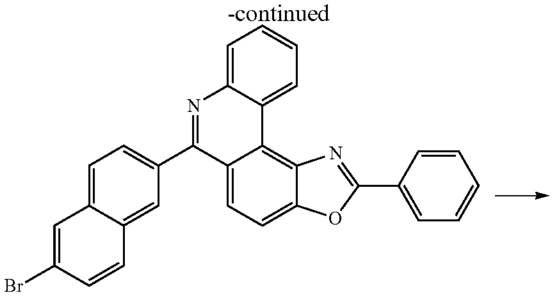

152-2

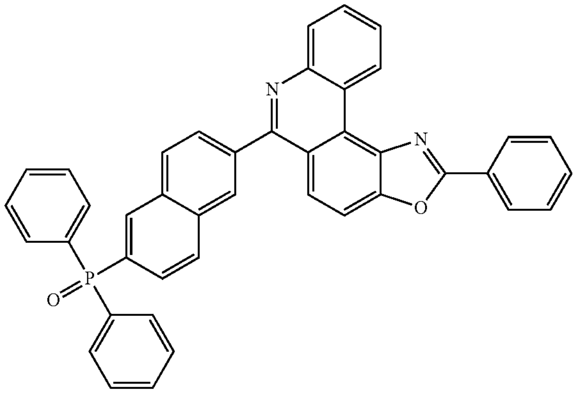

152

1) Preparation of Compound 152-1

After dissolving Compound 1-3 (10.0 g, 34.9 mmol) in tetrahydrofuran (THF), 6-bromo-2-naphthoyl chloride (14.1 g, 1.5 eq.) and triethylamine (TEA) (14.5 ml, 3.0 eq.) were added thereto at 0° C., and the result was stirred for 2 hours at room temperature. After the reaction was completed, ethyl acetate and distilled water were added to the reaction vessel for solidification, and produced solids were collected to obtain target Compound 152-1 (18.1 g, yield: 100%).

2) Preparation of Compound 152-2

After dissolving Compound 152-1 (18.1 g, 34.9 mmol) in nitrobenzene, $POCl_3$ (4.8 ml, 1.5 eq.) was added thereto, and the result was stirred for 17 hours at 150° C. After the reaction was completed, the result was neutralized by adding an aqueous sodium bicarbonate solution thereto at room temperature, and produced solids were filtered to obtain target Compound 152-2 (10.8 g, yield: 62%).

3) Preparation of Compound 152

After dissolving Compound 152-2 (10.8 g, 21.6 mmol) in tetrahydrofuran (THF), 2.5 M n-BuLi (11.2 ml, 1.3 eq.) was slowly added dropwise thereto at −78° C., and then the result was stirred for 30 minutes. After adding chlorodiphenylphosphine (4.76 g, 1.3 eq.) thereto, the result was stirred for 1 hour.

After the reaction was completed, methanol was added thereto, the result was stirred for 1 hour, and the result was extracted with distilled water and ethyl acetate. The organic layer was dried with anhydrous $MgSO_4$, and the solvent was removed using a rotary evaporator. After dissolving the concentrated solution by adding dichloromethane thereto, hydrogen peroxide was added thereto, and the result was stirred for 3 hours. After the reaction was terminated, the result was extracted with distilled water and ethyl acetate. The organic layer was dried with anhydrous $MgSO_4$, and, after removing the solvent using a rotary evaporator, the result was heated and dissolved by adding toluene thereto, and then recrystallized to obtain target Compound 152 (10.9 g, 81%).

[Preparation Example 30] Preparation of Compound 154

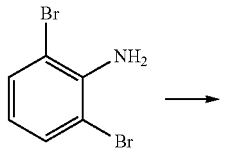

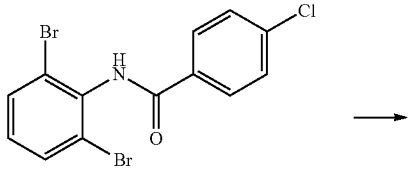

154-1

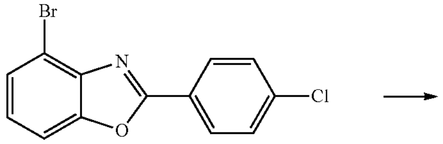

154-2

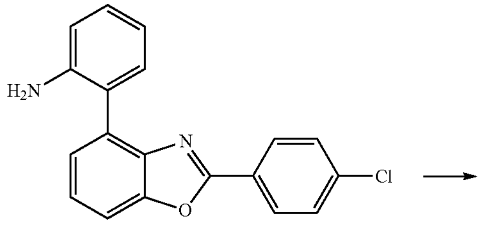

154-3

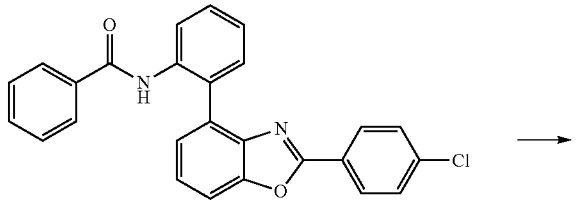

154-4

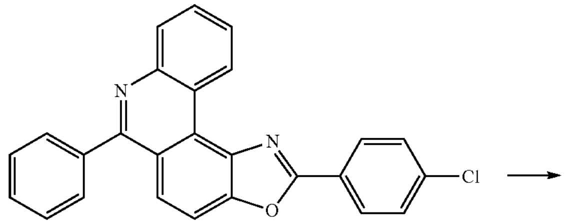

154-5

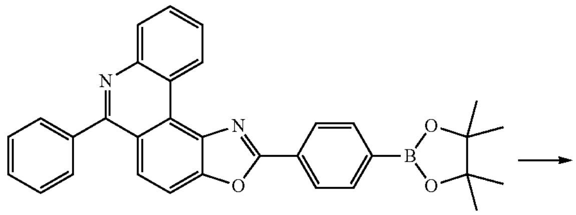

154-6

-continued

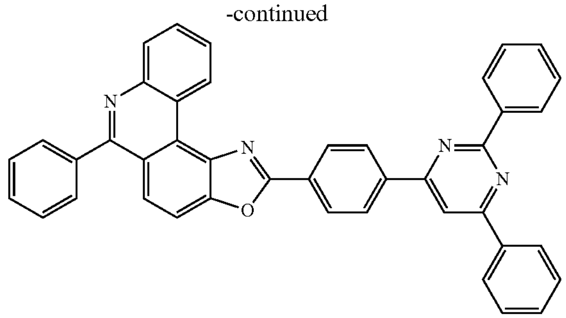

154

1) Preparation of Compound 154-1

After dissolving compound 2,6-dibromoaniline (20 g, 79.7 mmol, 1 eq.) in tetrahydrofuran (THF), 4-chlorobenzoyl chloride (18.3 g, 1.05 eq.) was added thereto, and the result was stirred for 24 hours at room temperature. After the reaction was finished, an aqueous sodium bicarbonate solution was added thereto, and the result was extracted with ethyl acetate. The organic layer was dried with anhydrous $MgSO_4$, and, after removing the solvent using a rotary evaporator, recrystallized using dichloromethane and hexane to obtain target Compound 154-1 (14.8 g, yield: 48%).

2) Preparation of Compound 154-2

After dissolving Compound 154-1 (14.8 g, 38.2 mmol) in dimethyl sulfoxide (DMSO) (150 ml), $K_2CO_3$ (17.5 g, 3.0 eq.) was added thereto, and the result was stirred for 17 hours at 150° C. After the reaction was finished, the layers were separated using distilled water and ethyl acetate at room temperature, and the organic layer was dried with anhydrous $MgSO_4$. After removing the solvent using a rotary evaporator, the result was purified with column chromatography using dichloromethane and hexane as a developing solvent to obtain target Compound 154-2 (8.48 g, yield: 72%).

3) Preparation of Compound 154-3

After dissolving Compound 154-2 (8.48 g, 27.5 mmol) in toluene, ethanol and $H_2O$, 2-(4,4,5,5-tetramethyl-1,3,2-dioxaborolan-2-yl)aniline (6.6 g, 1.1 eq.), $Pd(PPh_3)_4$ (1.6 g, 0.05 eq.) and $K_2CO_3$ (11.4 g, 3.0 eq.) were added thereto, and the result was stirred for 5 hours at 110° C. After the reaction was completed, the result was cooled to room temperature, and extracted with distilled water and ethyl acetate. The organic layer was dried with anhydrous $MgSO_4$, and, after removing the solvent using a rotary evaporator, purified with column chromatography using ethyl acetate and hexane as a developing solvent to obtain target Compound 154-3 (8.3 g, yield: 94%).

4) Preparation of Compound 154-4

After dissolving Compound 154-3 (8.3 g, 25.8 mmol) in tetrahydrofuran (THF), benzoyl chloride (4.4 ml, 1.5 eq.) and triethylamine (TEA) (10.7 ml, 3.0 eq.) were added thereto at 0° C., and the result was stirred for 2 hours at room temperature. After the reaction was completed, ethyl acetate and distilled water were added to the reaction vessel for solidification, and produced solids were collected to obtain target Compound 154-4 (10.8 g, yield: 99%).

5) Preparation of Compound 154-5

After dissolving Compound 154-4 (10.8 g, 25.5 mmol) in nitrobenzene, $POCl_3$ (3.5 ml, 1.5 eq.) was added thereto, and the result was stirred for 18 hours at 150° C. After the reaction was completed, the result was neutralized by adding an aqueous sodium bicarbonate solution thereto at room temperature, and produced solids were filtered to obtain target Compound 154-5 (6.5 g, yield: 63%).

6) Preparation of Compound 154-6

After dissolving Compound 154-5 (6.5 g, 16.0 mmol) in 1,4-dioxane, bis(pinacolato)diboron, Pd(dppf)$Cl_2$ and potassium acetate were added thereto, and the result was stirred for 2 hours at 110° C. After the reaction was completed, the result was extracted with distilled water and ethyl acetate. The organic layer was dried with anhydrous $MgSO_4$, and, after removing the solvent using a rotary evaporator, target Compound 154-6 (8.0 g, yield: 100%) was obtained without further purification.

7) Preparation of Compound 154

After dissolving Compound 154-6 (8.0 g, 16.0 mmol) in toluene, ethanol and $H_2O$, 4-chloro-2,6-diphenylpyrimidine (4.7 g, 1.1 eq.), $Pd(PPh_3)_4$ (0.9 g, 0.05 eq.) and $K_2CO_3$ (6.6 g, 3.0 eq.) were added thereto, and the result was stirred for 5 hours at 110° C. After the reaction was completed, the result was cooled to room temperature, and extracted with distilled water and ethyl acetate. The organic layer was dried with anhydrous $MgSO_4$, and, after removing the solvent using a rotary evaporator, purified with column chromatography using ethyl acetate and hexane as a developing solvent to obtain target Compound 154 (8.8 g, yield: 92%).

[Preparation Example 31] Preparation of Compound 155

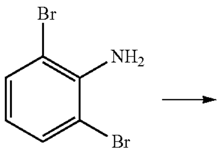

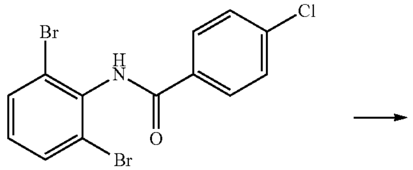

154-1

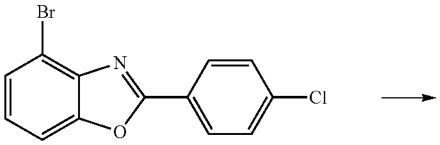

154-2

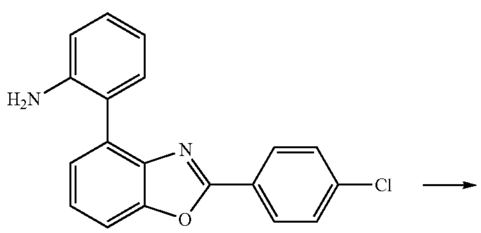

154-3

-continued

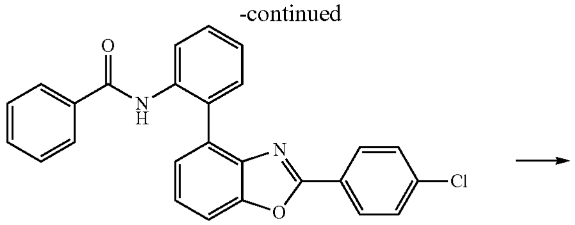

154-4

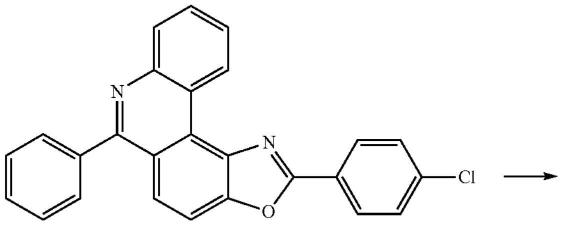

154-5

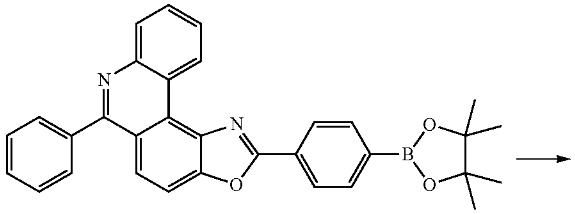

154-6

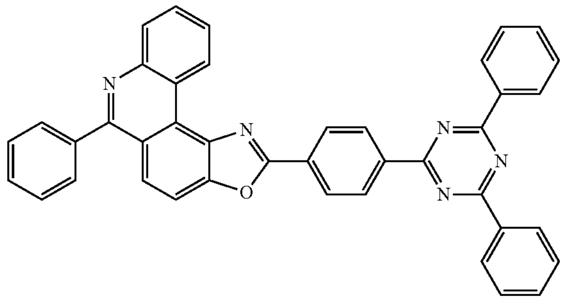

155

Target Compound 155 was obtained in the same manner as in the preparation of Compound 154 in Preparation Example 30 except that 2-chloro-4,6-diphenyl-1,3,5-triazine was used instead of 4-chloro-2,6-diphenylpyrimidine.

[Preparation Example 32] Preparation of Compound 163

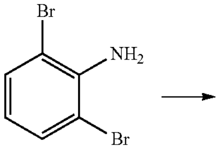

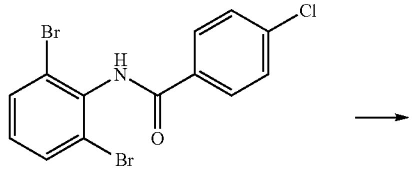

154-1

-continued
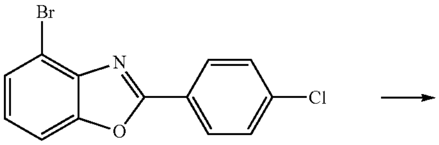
154-2
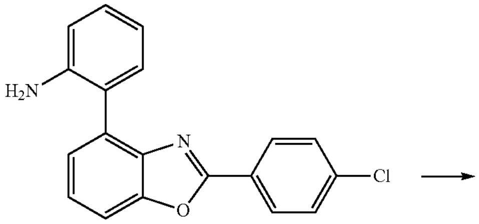
154-3
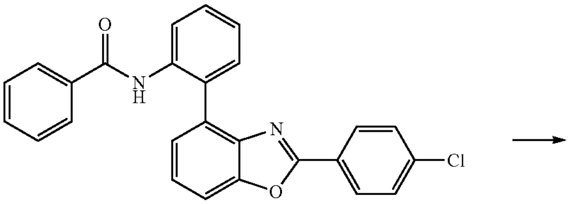
154-4
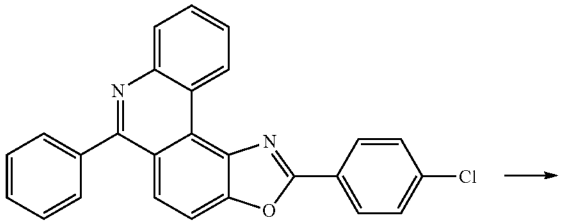
154-5
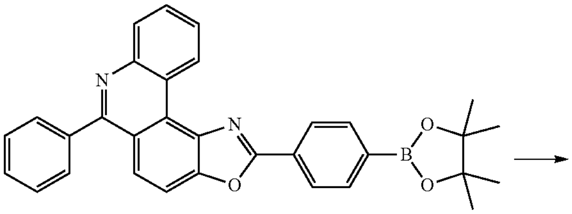
154-6
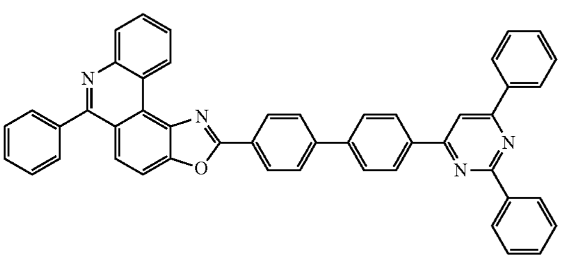
163
Target Compound 163 was obtained in the same manner as in the preparation of Compound 154 in Preparation Example 30 except that 4-(4-bromophenyl)-2,6-diphenylpyrimidine was used instead of 4-chloro-2,6-diphenylpyrimidine.
[Preparation Example 33] Preparation of Compound 164
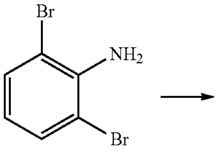
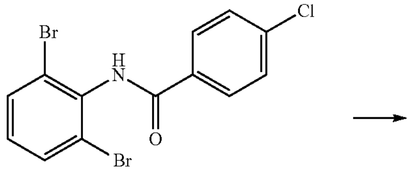
154-1
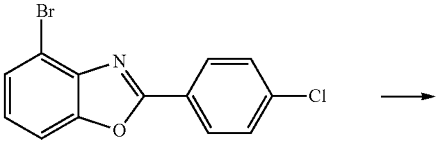
154-2
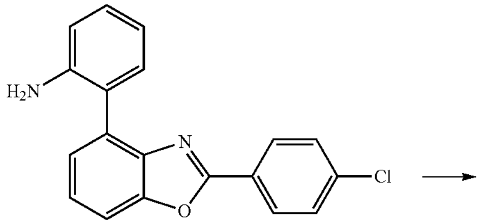
154-3
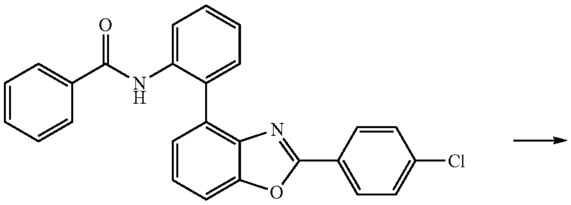
154-4
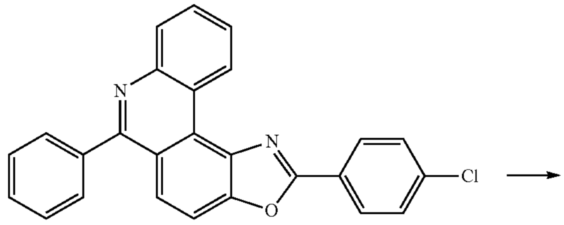
154-5
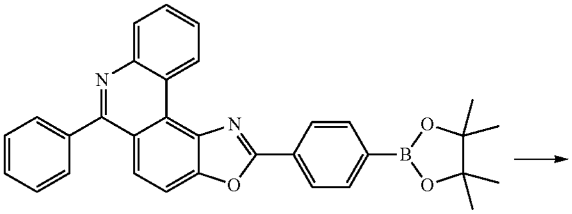
154-6

-continued

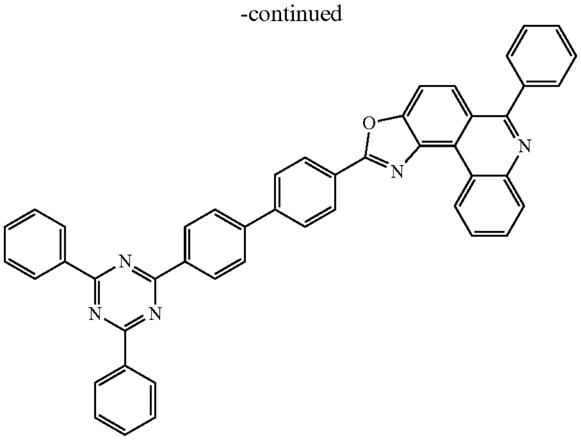

164

Target Compound 164 was obtained in the same manner as in the preparation of Compound 154 in Preparation Example 30 except that 2-(4-bromophenyl)-4,6-diphenyl-1,3,5-triazine was used instead of 4-chloro-2,6-diphenylpyrimidine.

Compounds other than the compounds described in Preparation Examples 1 to 33 were also prepared in the same manner as the compounds described in Preparation Examples 1 to 33, and the synthesis identification results are shown in the following Table 1 and Table 2.

TABLE 1

| NO | $^1$H NMR ($CDCl_3$, 300 Mz) |
|---|---|
| 1 | δ = 8.81(2H, d), 7.91~8.05(12H, m), 7.73~7.78(2H, m), 7.39~7.60(12H, m), 7.28(2H, d) |
| 5 | δ = 8.81(2H, d), 7.77~8.06(16H, m), 7.60(1H, m), 7.51~7.41(10H, m) |
| 7 | δ = 8.81(2H, d), 8.28(4H, d), 7.88~8.06(7H, m), 7.78(1H, m), 7.41~7.60(11H, m) |
| 9 | δ = 8.81(2H, d), 8.28(4H, d), 7.78~8.05(10H, m), 7.41~7.60(11H, m), 7.25(2H, d) |
| 16 | δ = 8.81(2H, d), 8.23~8.33(7H, m), 7.78~8.06(8H, m), 7.41~7.60(13H, m) |
| 25 | δ = 8.21~8.30(7H, m), 7.79~8.05(10H, m), 7.41~7.60(13H, m) |
| 29 | δ = 8.81(2H, d), 8.27~8.33(6H, m), 7.92~8.12(8H, m), 7.73~7.79(3H, m), 7.41~7.59(13H, m) |
| 34 | δ = 8.21~8.30(8H, m), 8.05(2H, m), 7.79~7.92(6H, m), 7.41~7.54(13H, m), 7.25(4H, s) |
| 45 | δ = 8.72(1H, d), 8.41(1H, s), 8.30(4H, m), 8.05~8.10(6H, m), 7.92(1H, d), 7.81(1H, d), 7.35~7.54(12H, m) |
| 46 | δ = 8.81(1H, d), 8.21~8.30(4H, m), 7.78~8.10(12H, m), 7.35~7.60(12H, m) |
| 49 | δ = 8.84(4H, s), 8.30(2H, d), 7.92~8.10(8H, m), 7.78(1H, m), 7.35~7.60(10H, m) |
| 54 | δ = 8.81(2H, d), 8.56(1H, m), 7.41~8.06(18H, m), 7.22(2H, m), 2.85(2H, m), 1.25(3H, t) |
| 59 | δ = 8.81(2H, d), 8.18(1H, m), 7.78~8.05(11H, m), 7.41~7.60(7H, m), 7.25(2H, d) |
| 62 | δ = 8.81(2H, d), 8.30(4H, d), 8.20(2H, s), 7.88~8.05(7H, m), 7.78(1H, m), 7.41~7.60(11H, m), 7.25(4H, s) |
| 67 | δ = 9.30(2H, d), 9.15(2H, s), 8.81(2H, d), 8.53(2H, d), 7.41~8.06(15H, m), 7.14(2H, t) |
| 73 | δ = 8.81(2H, d), 7.78~8.06(12H, m), 7.41~7.60(5H, m) |
| 87 | δ = 8.81~8.83(4H, m), 8.38(2H, d), 7.88~8.06(7H, m), 7.78(1H, m), 7.41~7.65(8H, m), 7.25(4H, s) |
| 94 | δ = 9.30(1H, d), 9.04(2H, d), 8.90(1H, d), 8.84(4H, s), 8.53(1H, d), 7.92~8.06(5H, m), 7.41~7.82(9H, m), 7.14(1H, m), 7.00(1H, d) |
| 107 | δ = 9.30(1H, m), 9.04(2H, d), 8.90(1H, d), 8.72(1H, s), 8.53(1H, d), 8.32(2H, d), 7.92~8.06(5H, m), 7.41~7.82(10H, m), 7.14(1H, m), 7.00(1H, d) |
| 108 | δ = 8.99(1H, d), 8.81~8.83(4H, m), 8.29~8.38(3H, m), 7.78~8.06(9H, m), 7.41~7.60(6H, m), 7.28(2H, d) |
| 129 | δ = 8.90(1H, d), 8.84(4H, s), 8.83(1H, d), 8.31(1H, d), 8.29(1H, d), 7.92~8.06(6H, m), 7.78~7.81(2H, m), 7.50~7.63(6H, m), 7.41(1H, m), 7.00(1H, d) |
| 130 | δ = 8.81(2H, d), 8.55(1H, d), 8.28(3H, d), 7.88~8.12(10H, m), 7.78(1H, m), 7.25~7.63(15H, m) |
| 134 | δ = 8.81(2H, d), 8.28(2H, d), 7.78~8.09(11H, m), 7.32~7.66(12H, m) |
| 135 | δ = 8.81(2H, d), 8.55(1H, d), 8.23~8.33(5H, m), 7.94~8.12(8H, m), 7.78~7.79(2H, m), 7.25~7.60(15H, m) |
| 140 | δ = 8.81(2H, d), 8.23~8.33(5H, m), 7.78~8.06(8H, m), 7.32~7.60(13H, m) |
| 141 | δ = 9.30~9.32(2H, d), 9.02~9.04(3H, m), 8.53(1H, d), 8.39(1H, d), 7.92~8.06(5H, m), 7.41~7.82(8H, m), 7.14(1H, m) |
| 146 | δ = 9.32(1H, s), 9.02(1H, d), 8.29~8.39(5H, m), 7.92~8.10(7H, m), 7.78~7.81(2H, m), 7.35~7.60(9H, m) |

TABLE 1-continued

| NO | $^1$H NMR ($CDCl_3$, 300 Mz) |
|---|---|
| 148 | δ = 8.85(1H, s), 8.38(1H, d), 7.92~8.06(8H, m), 7.77(4H, d), 7.45~7.51(12H, m) |
| 152 | 5 = 8.23~8.30(7H, m), 8.06(1H, d), 7.78~7.98(7H, m), 7.41~7.60(11H, m) |
| 154 | 5 = 8.28~8.30(6H, m), 8.06(1H, d), 7.78~7.92(7H, m), 7.41~7.60(11H, m) |
| 155 | δ = 8.44(1H, d), 8.21~8.30(8H, m), 8.03~8.12(4H, m), 7.90(1H, s), 7.35~7.54(11H, m) |
| 163 | δ = 8.23~8.30(7H, m), 8.06(1H, d), 7.78~7.98(9H, m), 7.41~7.54(11H, m), 7.25(2H, d) |
| 164 | δ = 8.28~8.30(6H, m), 8.06(1H, d), 7.78~7.98(7H, m), 7.41~7.60(11H, m), 7.25(4H, d) |

TABLE 2

| Compound | FD-MS | Compound | FD-MS |
|---|---|---|---|
| 1 | m/z = 674.79 (C50H30N2O = 674.24) | 2 | m/z = 572.59 (C38H25N2O2P = 572.17) |
| 3 | m/z = 548.63 (C40H24N2O = 548.19) | 4 | m/z = 698.75 (C48H31N2O2P = 698.21) |
| 5 | m/z = 648.69 (C44H29N2O2P = 648.20) | 6 | m/z = 778.90 (C56H34N4O = 778.27) |
| 7 | m/z = 603.67 (C41H25N5O = 603.21) | 8 | m/z = 703.79 (C49H29N5O = 703.24) |
| 9 | m/z = 679.77 (C47H29N5O = 679.24) | 10 | m/z = 729.82 (C51H31N5O = 729.25) |
| 11 | m/z = 602.68 (C42H26N4O = 602.21) | 12 | m/z = 702.80 (C50H30N4O = 702.24) |
| 13 | m/z = 678.78 (C48H30N4O = 678.24) | 14 | m/z = 602.68 (C42H26N4O = 602.21) |
| 15 | m/z = 702.80 (C50H30N4O = 702.24) | 16 | m/z = 678.78 (C48H30N4O = 678.24) |
| 17 | m/z = 678.78 (C48H30N4O = 678.24) | 18 | m/z = 678.78 (C48H30N4O = 678.24) |
| 19 | m/z = 678.78 (C48H30N4O = 678.24) | 20 | m/z = 754.87 (C54H34N4O = 754.27) |
| 21 | m/z = 601.69 (C43H27N3O = 601.22) | 22 | m/z = 603.67 (C41H25N5O = 603.21) |
| 23 | m/z = 602.68 (C42H26N4O = 602.21) | 24 | m/z = 679.77 (C47H29N5O = 679.24) |
| 25 | m/z = 678.78 (C48H30N4O = 678.24) | 26 | m/z = 679.77 (C47H29N5O = 679.24) |
| 27 | m/z = 678.78 (C48H30N4O = 678.24) | 28 | m/z = 729.82 (C51H31N5O = 729.25) |
| 29 | m/z = 728.84 (C52H32N4O = 728.26) | 30 | m/z = 754.87 (C54H34N4O = 754.27) |
| 31 | m/z = 778.90 (C56H34N4O = 778.27) | 32 | m/z = 678.78 (C48H30N4O = 678.24) |
| 33 | m/z = 679.77 (C47H29N5O = 679.24) | 34 | m/z = 755.86 (C53H33N5O = 755.27) |
| 35 | m/z = 678.78 (C48H30N4O = 678.24) | 36 | m/z = 754.87 (C54H34N4O = 754.27) |
| 37 | m/z = 728.84 (C52H32N4O = 728.26) | 38 | m/z = 778.90 (C56H34N4O = 778.27) |
| 39 | m/z = 678.78 (C48H30N4O = 678.24) | 40 | m/z = 652.74 (C46H28N4O = 652.23) |
| 41 | m/z = 754.87 (C54H34N4O = 754.27) | 42 | m/z = 854.99 (C62H38N4O = 854.30) |
| 43 | m/z = 576.64 (C40H24N4O = 576.20) | 44 | m/z = 550.61 (C38H22N4O = 550.18) |
| 45 | m/z = 754.87 (C54H34N4O = 754.27) | 46 | m/z = 626.70 (C44H26N4O = 626.21) |
| 47 | m/z = 626.70 (C44H26N4O = 626.21) | 48 | m/z = 626.70 (C44H26N4O = 626.21) |
| 49 | m/z = 637.73 (C50H30N4O = 702.24) | 50 | m/z = 564.63 (C39H24N4O = 564.20) |
| 51 | m/z = 564.63 (C39H24N4O = 564.20) | 52 | m/z = 564.63 (C39H24N4O = 564.20) |
| 53 | m/z = 564.63 (C39H24N4O = 564.20) | 54 | m/z = 626.70 (C44H26N4O = 626.21) |
| 55 | m/z = 592.69 (C41H28N4O = 592.23) | 56 | m/z = 592.69 (C41H28N4O = 592.23) |
| 57 | m/z = 640.73 (C45H28N4O = 640.23) | 58 | m/z = 640.73 (C45H28N4O = 640.23) |
| 59 | m/z = 592.69 (C41H28N4O = 592.23) | 60 | m/z = 592.69 (C41H28N4O = 592.23) |
| 61 | m/z = 516.59 (C35H24N4O = 516.20) | 62 | m/z = 581.68 (C39H23N3OS = 581.16) |
| 63 | m/z = 631.74 (C43H25N3OS = 631.17) | 64 | m/z = 581.68 (C39H23N3OS = 581.16) |
| 65 | m/z = 581.68 (C39H23N3OS = 581.16) | 66 | m/z = 581.68 (C39H23N3OS = 581.16) |
| 67 | m/z = 677.79 (C49H31N3O = 677.25) | 68 | m/z = 526.59 (C36H22N4O = 526.18) |
| 69 | m/z = 526.59 (C36H22N4O = 526.18) | 70 | m/z = 602.68 (C42H26N4O = 602.21) |
| 71 | m/z = 602.68 (C42H26N4O = 602.21) | 72 | m/z = 600.71 (C44H28N2O = 600.22) |
| 73 | m/z = 603.67 (C41H25N5O = 603.21) | 74 | m/z = 603.67 (C41H25N5O = 603.21) |
| 75 | m/z = 679.77 (C47H29N5O = 679.24) | 76 | m/z = 679.77 (C47H29N5O = 679.24) |
| 77 | m/z = 538.60 (C37H22N4O = 538.18) | 78 | m/z = 499.56 (C35H21N3O = 499.17) |
| 79 | m/z = 499.56 (C35H21N3O = 499.17) | 80 | m/z = 499.56 (C35H21N3O = 499.17) |
| 81 | m/z = 499.56 (C35H21N3O = 499.17) | 82 | m/z = 500.55 (C34H20N4O = 500.16) |
| 83 | m/z = 516.55 (C34H20N4O2 = 516.16) | 84 | m/z = 624.73 (C46H28N2O = 624.22) |
| 85 | m/z = 624.73 (C46H28N2O = 624.22) | 86 | m/z = 598.69 (C44H26N2O = 598.20) |
| 87 | m/z = 473.52 (C33H19N3O = 473.15) | 88 | m/z = 473.52 (C33H19N3O = 473.15) |
| 89 | m/z = 473.52 (C33H19N3O = 473.15) | 90 | m/z = 449.50 (C31H19N3O = 449.15) |
| 91 | m/z = 677.75 (C47H27N5O = 677.22) | 92 | m/z = 677.75 (C47H27N5O = 677.22) |
| 93 | m/z = 726.82 (C52H30N4O = 726.24) | 94 | m/z = 626.70 (C44H26N4O = 626.21) |
| 95 | m/z = 627.69 (C43H25N5O = 627.21) | 96 | m/z = 627.69 (C43H25N5O = 627.21) |
| 97 | m/z = 628.68 (C42H24N6O = 628.21) | 98 | m/z = 676.76 (C48H28N4O = 676.23) |
| 99 | m/z = 676.76 (C48H28N4O = 676.23) | 100 | m/z = 677.75 (C47H27N5O = 677.22) |
| 101 | m/z = 677.75 (C47H27N5O = 677.22) | 102 | m/z = 726.82 (C52H30N4O = 726.24) |
| 103 | m/z = 626.70 (C44H26N4O = 626.21) | 104 | m/z = 726.82 (C52H30N4O = 726.24) |
| 105 | m/z = 752.86 (C54H32N4O = 752.26) | 106 | m/z = 602.68 (C42H26N4O = 602.21) |
| 107 | m/z = 603.67 (C41H25N5O = 603.21) | 108 | m/z = 603.67 (C41H25N5O = 603.21) |
| 109 | m/z = 702.80 (C50H30N4O = 702.24) | 110 | m/z = 653.73 (C45H27N5O = 653.22) |
| 111 | m/z = 678.78 (C48H30N4O = 678.24) | 112 | m/z = 679.77 (C47H29N5O = 679.24) |
| 113 | m/z = 728.84 (C52H32N4O = 728.26) | 114 | m/z = 828.95 (C60H36N4O = 828.29) |
| 115 | m/z = 652.74 (C46H28N4O = 652.23) | 116 | m/z = 702.80 (C50H30N4O = 702.24) |
| 117 | m/z = 778.90 (C56H34N4O = 778.27) | 118 | m/z = 525.60 (C37H23N3O = 525.18) |
| 119 | m/z = 575.66 (C41H25N3O = 575.20) | 120 | m/z = 680.75 (C46H28N6O = 680.23) |

TABLE 2-continued

| Compound | FD-MS | Compound | FD-MS |
|---|---|---|---|
| 121 | m/z = 679.77 (C47H29N5O = 679.24) | 122 | m/z = 755.86 (C53H33N5O = 755.27) |
| 123 | m/z = 729.82 (C51H31N5O = 729.25) | 124 | m/z = 640.73 (C45H28N4O = 640.23) |
| 125 | m/z = 499.56 (C35H21N3O = 499.17) | 126 | m/z = 548.63 (C40H24N2O = 548.19) |
| 127 | m/z = 626.70 (C44H26N4O = 626.21) | 128 | m/z = 627.69 (C43H25N5O = 627.21) |
| 129 | m/z = 627.69 (C43H25N5O = 627.21) | 130 | m/z = 627.69 (C43H25N5O = 627.21) |
| 131 | m/z = 676.76 (C48H28N4O = 676.23) | 132 | m/z = 676.76 (C48H28N4O = 676.23) |
| 133 | m/z = 768.86 (C53H32N6O = 768.26) | 134 | m/z = 768.86 (C53H32N6O = 768.26) |
| 135 | m/z = 693.75 (C47H27N5O2 = 693.22) | 136 | m/z = 709.82 (C47H27N5OS = 709.19) |
| 137 | m/z = 693.75 (C47H27N5O2 = 693.22) | 138 | m/z = 709.82 (C47H27N5OS = 709.19) |
| 139 | m/z = 767.87 (C54H33N5O = 767.27) | 140 | m/z = 767.87 (C54H33N5O = 767.27) |
| 141 | m/z = 692.76 (C48H28N4O2 = 692.22) | 142 | m/z = 708.83 (C48H28N4OS = 708.20) |
| 143 | m/z = 692.76 (C48H28N4O2 = 692.22) | 144 | m/z = 708.83 (C48H28N4OS = 708.20) |
| 145 | m/z = 499.56 (C35H21N3O = 499.17) | 146 | m/z = 527.57 (C35H21N5O = 527.17) |
| 147 | m/z = 551.60 (C37H21N5O = 551.17) | 148 | m/z = 627.69 (C43H25N5O = 627.21) |
| 149 | m/z = 653.73 (C45H27N5O = 653.22) | 150 | m/z = 652.74 (C46H28N4O = 652.23) |
| 151 | m/z = 498.51 (C32H23N2O2P = 498.15) | 152 | m/z = 622.65 (C42H27N2O2P = 622.18) |
| 153 | m/z = 572.59 (C38H25N2O2P = 572.17) | 154 | m/z = 602.68 (C42H26N4O = 602.21) |
| 155 | m/z = 603.67 (C41H25N5O = 603.21) | 156 | m/z = 603.67 (C41H25N5O = 603.21) |
| 157 | m/z = 602.68 (C42H26N4O = 602.21) | 158 | m/z = 603.67 (C41H25N5O = 603.21) |
| 159 | m/z = 603.67 (C41H25N5O = 603.21) | 160 | m/z = 652.74 (C46H28N4O = 652.23) |
| 161 | m/z = 653.73 (C45H27N5O = 653.22) | 162 | m/z = 678.78 (C48H30N4O = 678.24) |
| 163 | m/z = 678.78 (C48H30N4O = 678.24) | 164 | m/z = 679.77 (C47H29N5O = 679.24) |
| 165 | m/z = 679.77 (C47H29N5O = 679.24) | 166 | m/z = 548.63 (C40H24N2O = 548.19) |
| 167 | m/z = 729.82 (C51H31N5O = 729.25) | 168 | m/z = 728.84 (C52H32N4O = 728.26) |

[Experimental Example 1] Manufacture of Organic Light Emitting Device

1) Manufacture of Organic Light Emitting Device

A transparent indium tin oxide (ITO) electrode thin film obtained from glass for an organic light emitting device (OLED) (manufactured by Samsung-Corning Co., Ltd.) was ultrasonic cleaned using trichloroethylene, acetone, ethanol and distilled water consecutively for 5 minutes each, stored in isopropanol, and used.

Next, an ITO substrate was installed in a substrate folder of a vacuum deposition apparatus, and the following 4,4',4"-tris(N,N-(2-naphthyl)-phenylamino)triphenylamine (2-TNATA) was introduced to a cell in the vacuum deposition apparatus.

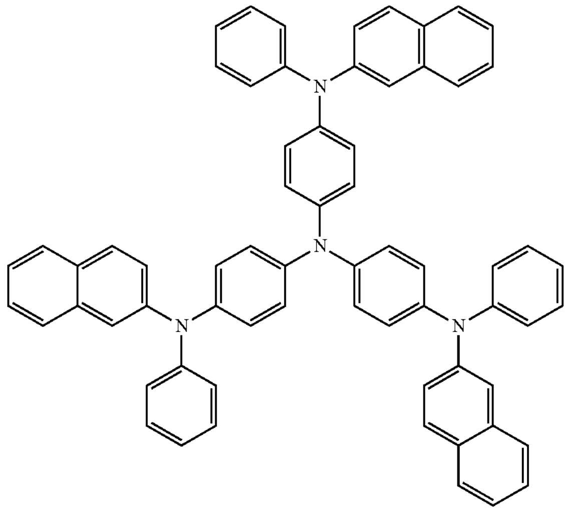

2-TNATA

Subsequently, the chamber was evacuated until the degree of vacuum therein reached $10^{-6}$ torr, and then 2-TNATA was evaporated by applying a current to the cell to deposit a hole injection layer having a thickness of 600 Å on the ITO substrate.

To another cell of the vacuum deposition apparatus, the following N,N'-bis(α-naphthyl)-N,N'-diphenyl-4,4'-diamine (NPB) was introduced, and evaporated by applying a current to the cell to deposit a hole transfer layer having a thickness of 300 Å on the hole injection layer.

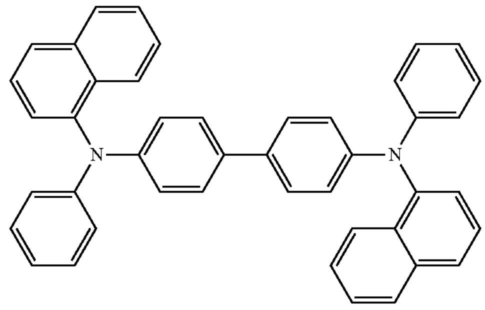

NPB

After forming the hole injection layer and the hole transfer layer as above, a blue light emitting material having a structure as below was deposited thereon as a light emitting layer. Specifically, in one side cell in the vacuum deposition apparatus, the following H1, a blue light emitting host material, was vacuum deposited to a thickness of 200 Å, and the following D1, a blue light emitting dopant material, was vacuum deposited thereon by 5% with respect to the host material.

H1
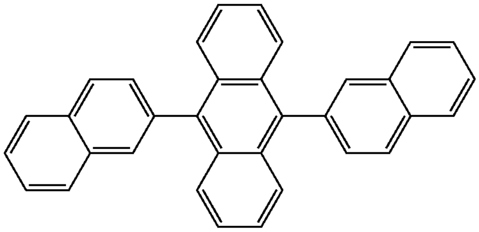
D1
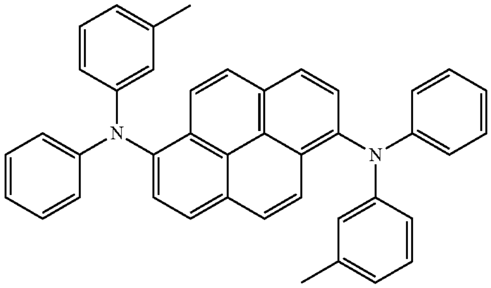
E1
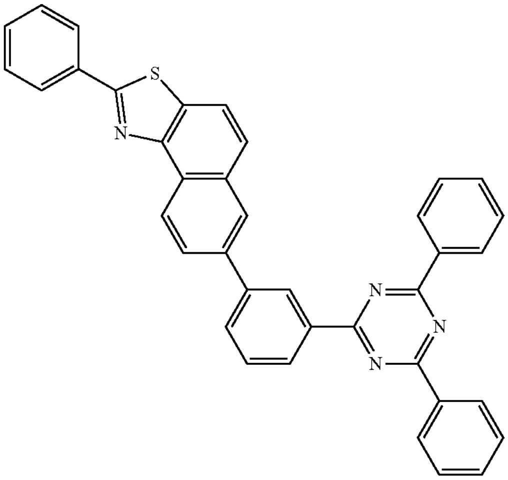
E2
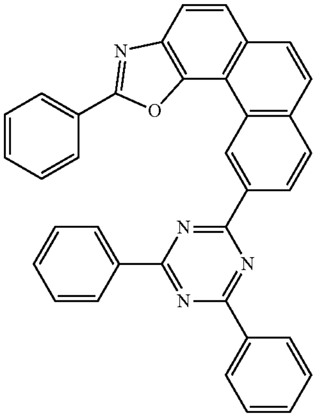
-continued
E3
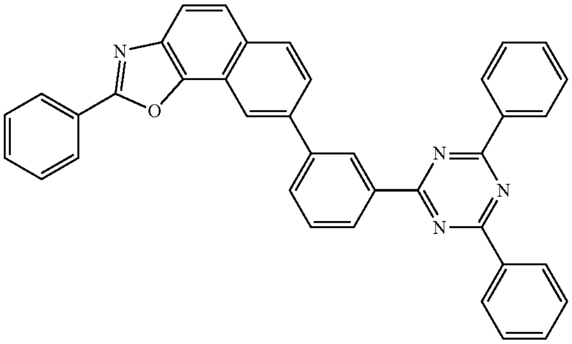
E4
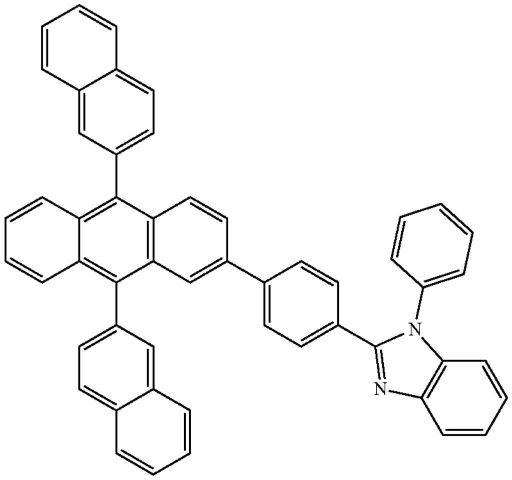
E5
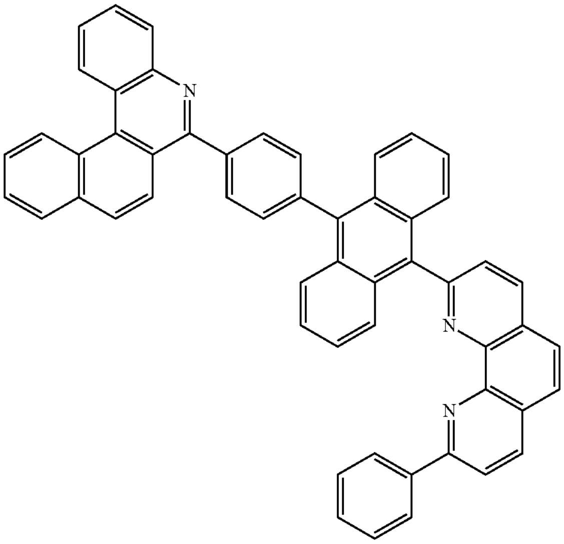

-continued

E6

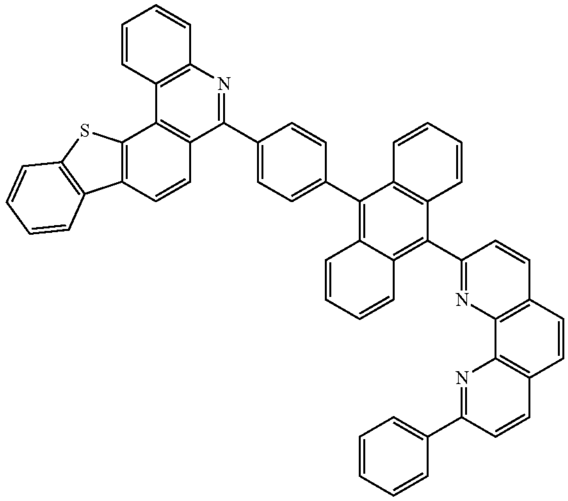

Subsequently, one of compounds described in the following Table 3 was deposited to a thickness of 300 Å as an electron transfer layer.

As an electron injection layer, lithium fluoride (LiF) was deposited to a thickness of 10 Å, and an Al cathode was employed to a thickness of 1,000 Å, and as a result, an OLED was manufactured.

Meanwhile, all the organic compounds required to manufacture the OLED were vacuum sublimation purified under $10^{-6}$ torr to $10^{-8}$ torr by each material to be used in the OLED manufacture.

Results of measuring driving voltage, light emission efficiency, color coordinate (CIE) and lifetime of the blue organic light emitting devices manufactured according to the present disclosure are as shown in Table 3.

TABLE 3

| | Compound | Driving Voltage (V) | Light Emission Efficiency (cd/A) | CIE (x, y) | Lifetime ($T_{95}$) |
|---|---|---|---|---|---|
| Comparative Example 1 | E1 | 4.90 | 6.50 | (0.141, 0.092) | 35 |
| Comparative Example 2 | E2 | 4.83 | 6.30 | (0.139, 0.094) | 34 |
| Comparative Example 3 | E3 | 4.96 | 6.50 | (0.139, 0.088) | 36 |
| Comparative Example 4 | E4 | 5.51 | 5.94 | (0.134, 0.100) | 31 |
| Comparative Example 5 | E5 | 4.85 | 6.49 | (0.133, 0.010) | 34 |
| Comparative Example 6 | E6 | 4.87 | 6.50 | (0.134, 0.102) | 35 |
| Example 1 | 1 | 4.80 | 6.58 | (0.134, 0.101) | 39 |
| Example 2 | 5 | 4.46 | 6.61 | (0.134, 0.102) | 38 |
| Example 3 | 7 | 4.63 | 6.93 | (0.135, 0.103) | 41 |
| Example 4 | 9 | 4.81 | 6.55 | (0.134, 0.100) | 39 |
| Example 5 | 16 | 4.61 | 6.59 | (0.133, 0.102) | 38 |
| Example 6 | 25 | 4.77 | 6.61 | (0.134, 0.102) | 43 |
| Example 7 | 29 | 4.48 | 6.50 | (0.134, 0.101) | 39 |
| Example 8 | 34 | 4.46 | 6.52 | (0.134, 0.102) | 43 |
| Example 9 | 45 | 4.65 | 6.65 | (0.135, 0.102) | 40 |
| Example 10 | 46 | 4.42 | 6.50 | (0.133, 0.103) | 45 |
| Example 11 | 49 | 4.61 | 6.55 | (0.134, 0.101) | 42 |
| Example 12 | 54 | 4.44 | 6.71 | (0.134, 0.101) | 37 |
| Example 13 | 59 | 4.77 | 6.63 | (0.132, 0.100) | 41 |
| Example 14 | 62 | 4.63 | 6.54 | (0.134, 0.103) | 39 |

TABLE 3-continued

| | Compound | Driving Voltage (V) | Light Emission Efficiency (cd/A) | CIE (x, y) | Lifetime ($T_{95}$) |
|---|---|---|---|---|---|
| Example 15 | 67 | 4.71 | 6.73 | (0.134, 0.100) | 43 |
| Example 16 | 73 | 4.81 | 6.60 | (0.134, 0.102) | 41 |
| Example 17 | 87 | 4.79 | 6.61 | (0.133, 0.100) | 38 |
| Example 18 | 94 | 4.63 | 6.74 | (0.134, 0.101) | 39 |
| Example 19 | 107 | 4.40 | 6.51 | (0.134, 0.102) | 38 |
| Example 20 | 108 | 4.37 | 6.60 | (0.134, 0.101) | 40 |
| Example 21 | 129 | 4.36 | 6.62 | (0.133, 0.102) | 39 |
| Example 22 | 130 | 4.40 | 6.50 | (0.134, 0.101) | 42 |
| Example 23 | 134 | 4.75 | 6.52 | (0.134, 0.101) | 39 |
| Example 24 | 135 | 4.81 | 6.55 | (0.133, 0.101) | 37 |
| Example 25 | 140 | 4.81 | 6.63 | (0.132, 0.100) | 43 |
| Example 26 | 141 | 4.67 | 6.51 | (0.134, 0.102) | 38 |
| Example 27 | 146 | 4.63 | 6.62 | (0.134, 0.101) | 41 |
| Example 28 | 148 | 4.40 | 6.54 | (0.133, 0.100) | 38 |
| Example 29 | 152 | 4.37 | 6.53 | (0.134, 0.101) | 39 |
| Example 30 | 154 | 4.39 | 6.55 | (0.133, 0.101) | 41 |
| Example 31 | 155 | 4.38 | 6.60 | (0.132, 0.102) | 40 |
| Example 32 | 163 | 4.39 | 6.52 | (0.134, 0.102) | 43 |
| Example 33 | 164 | 4.77 | 6.60 | (0.134, 0.101) | 38 |

As seen from the results of Table 3, the organic light emitting device using the electron transfer layer material of the blue organic light emitting device of the present disclosure had lower driving voltage and significantly improved light emission efficiency and lifetime compared to Comparative Examples 1 to 6. Particularly, it was identified that Examples 3, 12, 21, 30 and 32 were superior in all aspects of driving voltage, light emission efficiency and lifetime.

Such a result is considered to be due to the fact that, when using the disclosed compound having proper length and strength, and flatness as an electron transfer layer, a compound in an excited state is made by receiving electrons under a specific condition, and particularly when a hetero-skeleton site of the compound is formed in an excited state, excited energy moves to a stable state before the excited hetero-skeleton site goes through other reactions, and a relatively stabilized compound is capable of efficiently transferring electrons without the compound being decomposed or destroyed. For reference, compounds that are stable when excited are considered to be aryl or acene-based compounds or polycyclic hetero-compounds. Accordingly, it is considered that excellent results in all aspects of driving, efficiency and lifetime were obtained by the compound of the present disclosure enhancing enhanced electron-transfer properties or improved stability.

[Experimental Example 2] Manufacture of Organic Light Emitting Device

1) Manufacture of Organic Light Emitting Device

A transparent indium tin oxide (ITO) electrode thin film obtained from glass for an organic light emitting device (OLED) (manufactured by Samsung-Corning Co., Ltd.) was ultrasonic cleaned using trichloroethylene, acetone, ethanol and distilled water consecutively for 5 minutes each, stored in isopropanol, and used.

Next, an ITO substrate was installed in a substrate folder of a vacuum deposition apparatus, and the following 4,4',4''-tris(N,N-(2-naphthyl)-phenylamino)triphenylamine (2-TNATA) was introduced to a cell in the vacuum deposition apparatus.

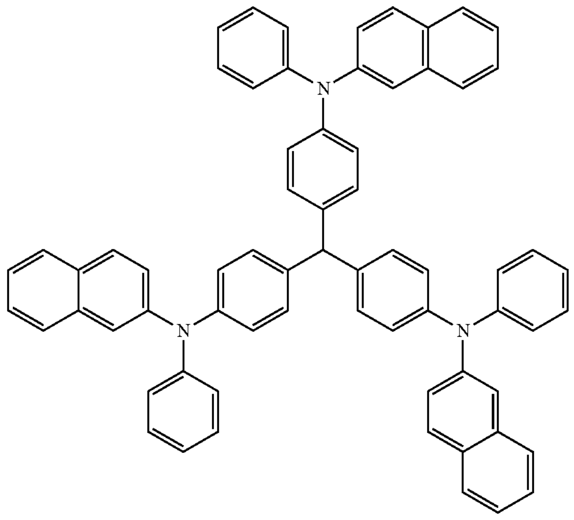

2-TNATA

Subsequently, the chamber was evacuated until the degree of vacuum therein reached $10^{-6}$ torr, and then 2-TNATA was evaporated by applying a current to the cell to deposit a hole injection layer having a thickness of 600 Å on the ITO substrate.

To another cell of the vacuum deposition apparatus, the following N,N'-bis(α-naphthyl)-N,N'-diphenyl-4,4'-diamine (NPB) was introduced, and evaporated by applying a current to the cell to deposit a hole transfer layer having a thickness of 300 Å on the hole injection layer.

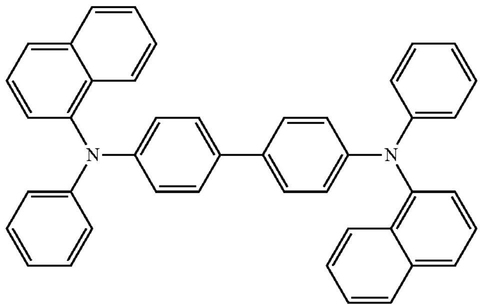

NPB

After forming the hole injection layer and the hole transfer layer as above, a blue light emitting material having a structure as below was deposited thereon as a light emitting layer. Specifically, in one side cell in the vacuum deposition apparatus, the following H1, a blue light emitting host material, was vacuum deposited to a thickness of 200 Å, and the following D1, a blue light emitting dopant material, was vacuum deposited thereon by 5% with respect to the host material.

H1

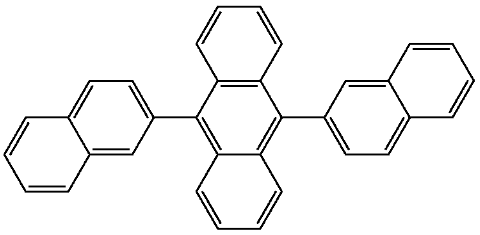

D1

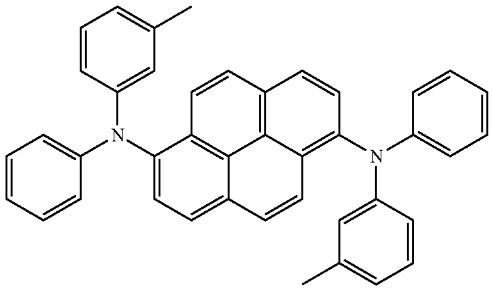

Subsequently, a compound of the following Structural Formula E4 was deposited to a thickness of 300 Å as an electron transfer layer.

E1

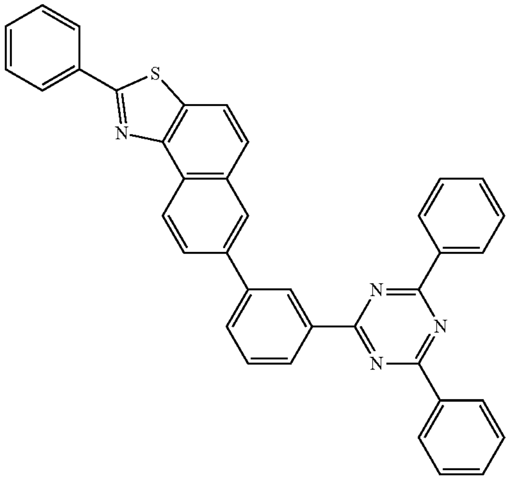

E2

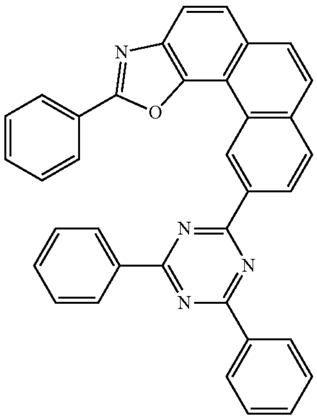

-continued

E3

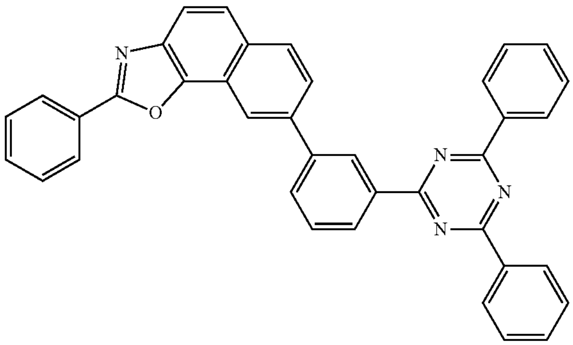

E4

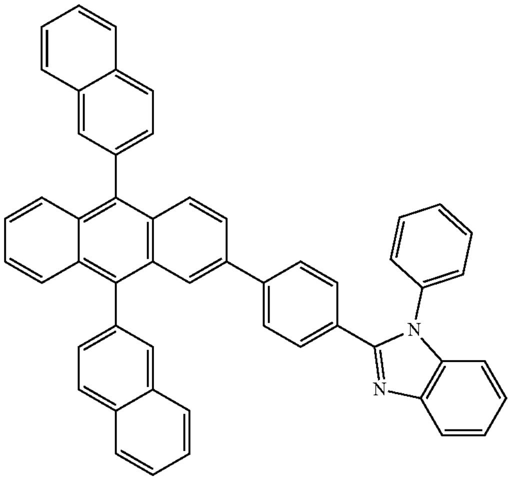

E5

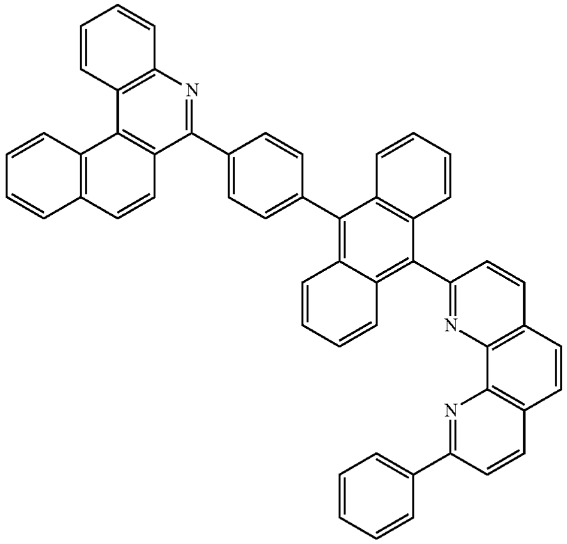

-continued

E6

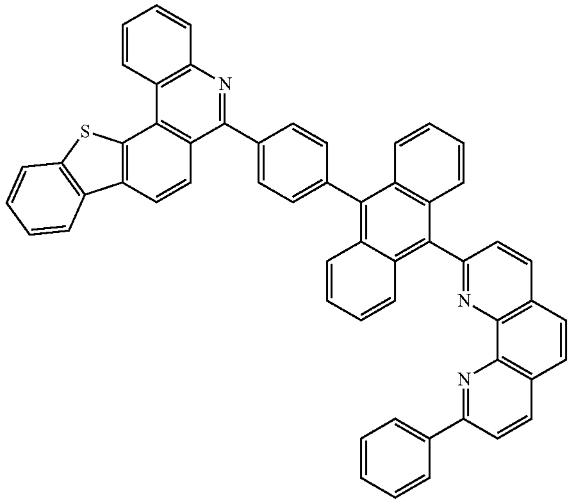

As an electron injection layer, lithium fluoride (LiF) was deposited to a thickness of 10 Å, and an Al cathode was employed to a thickness of 1,000 Å, and as a result, an OLED was manufactured.

Meanwhile, all the organic compounds required to manufacture the OLED were vacuum sublimation purified under $10^{-6}$ torr to $10^{-8}$ torr by each material to be used in the OLED manufacture.

Organic light emitting devices were manufactured in the same manner as in Experimental Example 2 except that, after forming the electron transfer layer E4 to a thickness of 250 Å, a hole blocking layer was formed on the electron transfer layer using a compound presented in Table 4 to a thickness of 50 Å.

Results of measuring driving voltage, light emission efficiency, color coordinate (CIE) and lifetime of the blue organic light emitting devices manufactured according to the present disclosure are as shown in Table 4.

TABLE 4

| | Compound | Driving Voltage (V) | Light Emission Efficiency (cd/A) | CIE (x, y) | Lifetime ($T_{95}$) |
|---|---|---|---|---|---|
| Comparative Example 7 | E1 | 4.90 | 6.50 | (0.141, 0.092) | 35 |
| Comparative Example 8 | E2 | 4.83 | 6.30 | (0.139, 0.094) | 34 |
| Comparative Example 9 | E3 | 4.96 | 6.50 | (0.139, 0.088) | 36 |
| Comparative Example 10 | E4 | 5.51 | 5.94 | (0.134, 0.100) | 31 |
| Comparative Example 11 | E5 | 4.85 | 6.49 | (0.133, 0.010) | 34 |
| Comparative Example 12 | E6 | 4.87 | 6.50 | (0.134, 0.102) | 35 |
| Example 34 | 1 | 4.81 | 6.57 | (0.134, 0.101) | 39 |
| Example 35 | 5 | 4.46 | 6.61 | (0.134, 0.102) | 38 |
| Example 36 | 7 | 4.62 | 6.94 | (0.135, 0.103) | 41 |
| Example 37 | 9 | 4.81 | 6.58 | (0.134, 0.100) | 39 |
| Example 38 | 16 | 4.63 | 6.59 | (0.133, 0.102) | 40 |
| Example 39 | 25 | 4.72 | 6.62 | (0.134, 0.102) | 43 |
| Example 40 | 29 | 4.48 | 6.50 | (0.134, 0.101) | 39 |
| Example 41 | 34 | 4.45 | 6.53 | (0.134, 0.102) | 42 |
| Example 42 | 45 | 4.65 | 6.64 | (0.135, 0.102) | 40 |
| Example 43 | 46 | 4.46 | 6.50 | (0.133, 0.103) | 44 |

TABLE 4-continued

| | Compound | Driving Voltage (V) | Light Emission Efficiency (cd/A) | CIE (x, y) | Lifetime ($T_{95}$) |
|---|---|---|---|---|---|
| Example 44 | 49 | 4.61 | 6.56 | (0.134, 0.101) | 42 |
| Example 45 | 54 | 4.44 | 6.71 | (0.134, 0.101) | 38 |
| Example 46 | 59 | 4.76 | 6.67 | (0.132, 0.100) | 41 |
| Example 47 | 62 | 4.63 | 6.55 | (0.134, 0.103) | 39 |
| Example 48 | 67 | 4.70 | 6.73 | (0.134, 0.100) | 42 |
| Example 49 | 73 | 4.81 | 6.61 | (0.134, 0.102) | 41 |
| Example 50 | 87 | 4.78 | 6.61 | (0.133, 0.100) | 39 |
| Example 51 | 94 | 4.63 | 6.74 | (0.134, 0.101) | 39 |
| Example 52 | 107 | 4.41 | 6.52 | (0.134, 0.102) | 38 |
| Example 53 | 108 | 4.39 | 6.60 | (0.134, 0.101) | 41 |
| Example 54 | 129 | 4.36 | 6.63 | (0.133, 0.102) | 39 |
| Example 55 | 130 | 4.42 | 6.50 | (0.134, 0.101) | 42 |
| Example 56 | 134 | 4.71 | 6.53 | (0.134, 0.101) | 39 |
| Example 57 | 135 | 4.81 | 6.55 | (0.133, 0.101) | 38 |
| Example 58 | 140 | 4.80 | 6.66 | (0.132, 0.100) | 43 |
| Example 59 | 141 | 4.67 | 6.51 | (0.134, 0.102) | 38 |
| Example 60 | 146 | 4.61 | 6.65 | (0.134, 0.101) | 42 |
| Example 61 | 148 | 4.40 | 6.54 | (0.133, 0.100) | 38 |
| Example 62 | 152 | 4.39 | 6.54 | (0.134, 0.101) | 39 |
| Example 63 | 154 | 4.39 | 6.55 | (0.133, 0.101) | 42 |
| Example 64 | 155 | 4.36 | 6.61 | (0.132, 0.102) | 40 |
| Example 65 | 163 | 4.39 | 6.52 | (0.134, 0.102) | 42 |
| Example 66 | 164 | 4.76 | 6.62 | (0.134, 0.101) | 38 |

As seen from the results of Table 4, the organic light emitting device using the hole blocking layer material of the organic light emitting device of the present disclosure had lower driving voltage and significantly improved light emission efficiency and lifetime compared to Comparative Examples 7 to 12.

[Experimental Example 3] Manufacture of Organic Light Emitting Device

1) Manufacture of Organic Light Emitting Device

A glass substrate on which indium tin oxide (ITO) was coated as a thin film to a thickness of 1500 Å was cleaned with distilled water ultrasonic waves. After the cleaning with distilled water was finished, the substrate was ultrasonic cleaned with solvents such as acetone, methanol and isopropyl alcohol, then dried, and UVO treated for 5 minutes using UV in a UV cleaner. After that, the substrate was transferred to a plasma cleaner (PT), and after conducting plasma treatment under vacuum for ITO work function and residual film removal, the substrate was transferred to a thermal deposition apparatus for organic deposition.

On the transparent ITO electrode (anode), organic materials were formed in a 2-stack white organic light emitting device (WOLED) structure. As for the first stack, TAPC was thermal vacuum deposited first to a thickness of 300 Å to form a hole transfer layer. After forming the hole transfer layer, a light emitting layer was thermal vacuum deposited thereon as follows. As the light emitting layer, the following TCz1, a host, was 8% doped with the following FIrpic, a blue phosphorescent dopant, and deposited to 300 Å. After forming an electron transfer layer to 400 Å using the following TmPyPB, the compound described in the following Table 5 was 20% doped with $Cs_2CO_3$ to form a charge generation layer to 100 Å.

As for the second stack, $MoO_3$ was thermal vacuum deposited first to a thickness of 50 Å to form a hole injection layer. A hole transfer layer, a common layer, was formed to 100 Å by 20% doping $MoO_3$ to the following TAPC and then depositing TAPC to 300 Å. A light emitting layer was formed by 8% doping the following $Ir(ppy)_3$, a green phosphorescent dopant, to the following TCz1, a host, and depositing the result to 300 Å, and then an electron transfer layer was formed to 600 Å using the following TmPyPB. Lastly, an electron injection layer was formed on the electron transfer layer by depositing lithium fluoride (LiF) to a thickness of 10 Å, and then a cathode was formed on the electron injection layer by depositing an aluminum (Al) cathode to a thickness of 1,200 Å, and as a result, an organic electroluminescent device was manufactured.

Meanwhile, all the organic compounds required to manufacture the OLED were vacuum sublimation purified under $10^{-6}$ torr to $10^{-8}$ torr for each material to be used in the OLED manufacture.

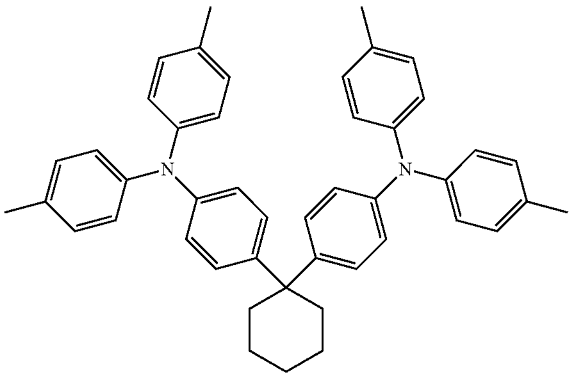

TAPC

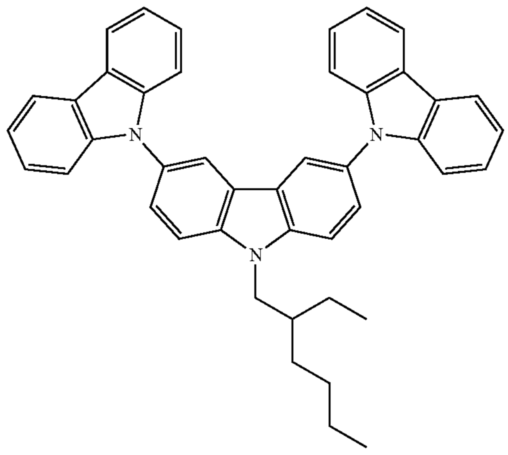

TCz1

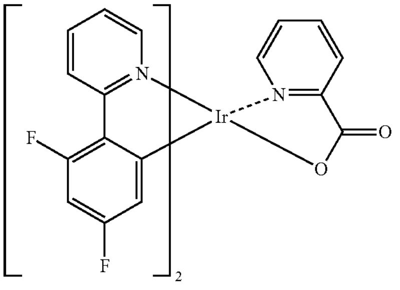

Firpic

-continued
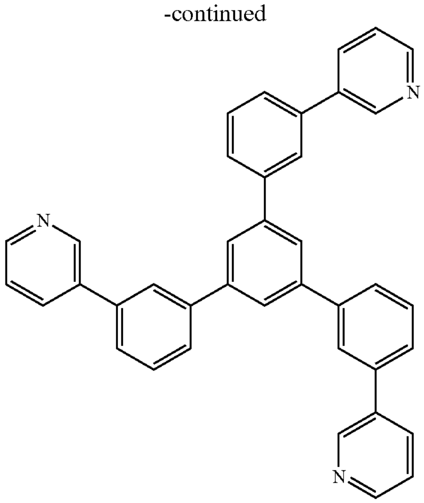
TmPyPB
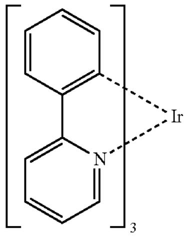
Ir(ppy)3
E1
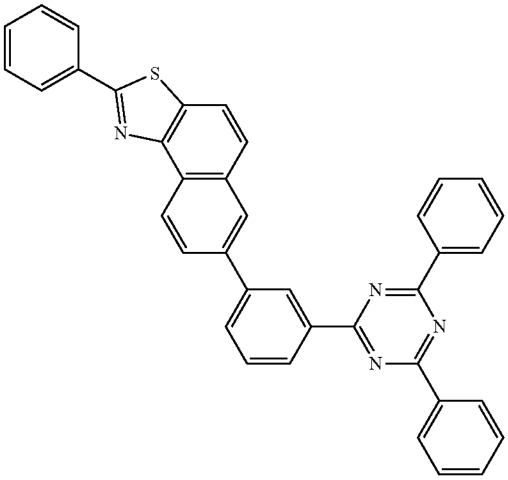
E2
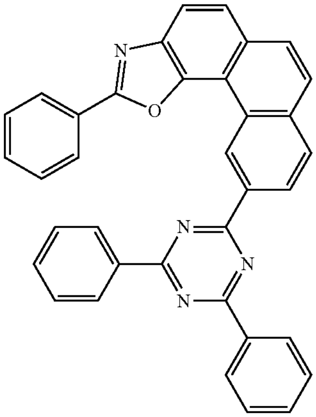
-continued
E3
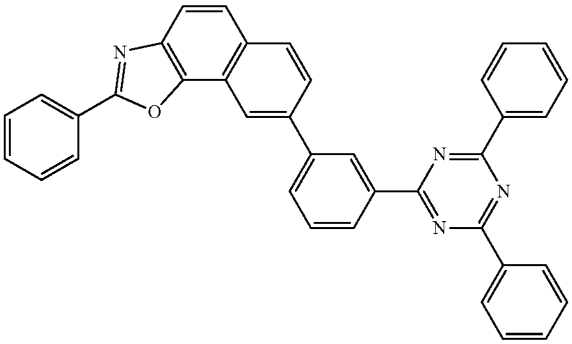
E4
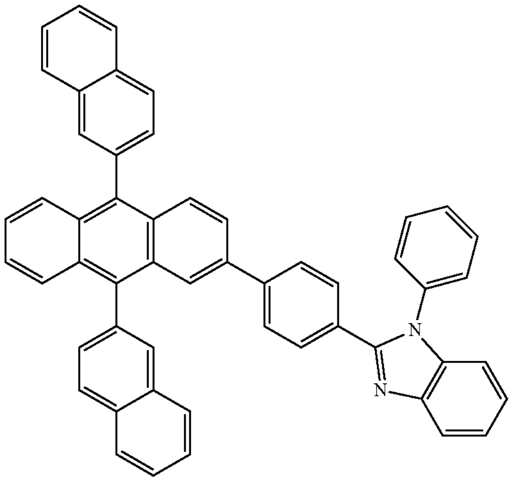
E5
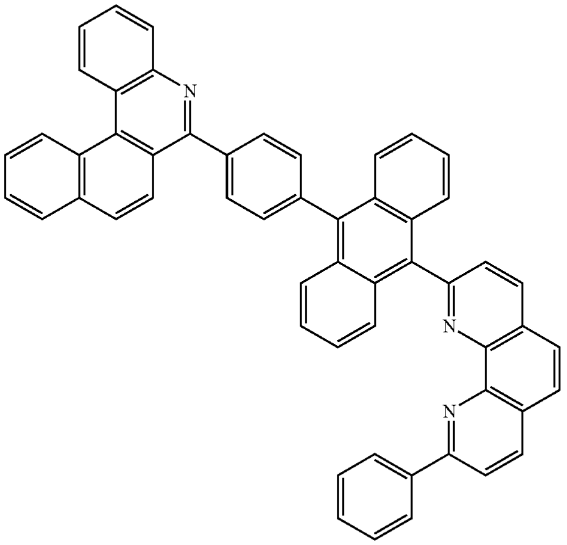

-continued

E6

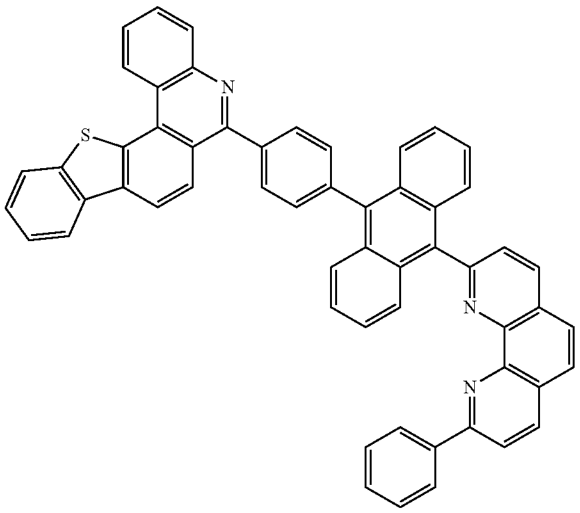

Results of measuring driving voltage, light emission efficiency, color coordinate (CIE) and lifetime of the white organic light emitting devices manufactured according to the present disclosure are as shown in Table 5.

TABLE 5

| | Compound | Driving Voltage (V) | Light Emission Efficiency (cd/A) | CIE (x, y) | Lifetime ($T_{95}$) |
|---|---|---|---|---|---|
| Comparative Example 13 | E1 | 4.90 | 6.50 | (0.141, 0.092) | 35 |
| Comparative Example 14 | E2 | 4.83 | 6.30 | (0.139, 0.094) | 34 |
| Comparative Example 15 | E3 | 4.96 | 6.50 | (0.139, 0.088) | 36 |
| Comparative Example 16 | E4 | 5.51 | 5.94 | (0.134, 0.100) | 31 |
| Comparative Example 17 | E5 | 4.85 | 6.49 | (0.133, 0.010) | 34 |
| Comparative Example 18 | E6 | 4.87 | 6.50 | (0.134, 0.102) | 35 |
| Example 67 | 44 | 4.78 | 6.61 | (0.133, 0.100) | 39 |
| Example 68 | 49 | 4.63 | 6.74 | (0.134, 0.101) | 39 |
| Example 69 | 54 | 4.41 | 6.52 | (0.134, 0.102) | 38 |
| Example 70 | 148 | 4.39 | 6.52 | (0.134, 0.102) | 42 |

As seen from the results of Table 5, the organic light emitting device using the charge generation layer material of the 2-stack white organic light emitting device of the present disclosure had lower driving voltage and improved light emission efficiency compared to Comparative Examples 13 to 18.

Such a result is considered to be due to the fact that the compound of the present disclosure used as an N-type charge generation layer formed with the disclosed skeleton having proper length and strength, and flatness and a proper hetero-compound capable of binding to metals forms a gap state in the N-type charge generation layer by doping an alkali metal or an alkaline earth metal, and electrons produced from a P-type charge generation layer are readily injected into an electron transfer layer through the gap state produced in the N-type charge generation layer. Accordingly, the P-type charge generation layer may favorably inject and transfer electrons to the N-type charge generation layer, and as a result, driving voltage was lowered, and light emission efficiency and lifetime were improved in the organic light emitting device.

The invention claimed is:

1. A heterocyclic compound represented by the following Chemical Formula 1:

[Chemical Formula 1]

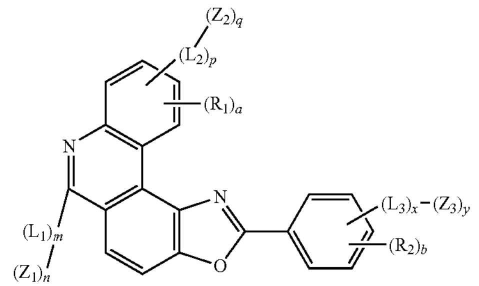

wherein, in Chemical Formula 1, $L_1$ to $L_3$ are the same as or different from each other, and each independently a direct bond; a substituted or unsubstituted arylene group; or a substituted or unsubstituted heteroarylene group;

$Z_1$ to $Z_3$ are the same as or different from each other, and each independently selected from the group consisting of hydrogen; deuterium; a halogen group; a cyano group; a substituted or unsubstituted alkyl group; a substituted or unsubstituted alkenyl group; a substituted or unsubstituted alkynyl group; a substituted or unsubstituted alkoxy group; a substituted or unsubstituted cycloalkyl group; a substituted or unsubstituted heterocycloalkyl group; a substituted or unsubstituted aryl group; a substituted or unsubstituted heteroaryl group; a substituted or unsubstituted phosphine oxide group; and a substituted or unsubstituted amine group;

$R_1$ and $R_2$ are the same as or different from each other, and each independently selected from the group consisting of hydrogen; deuterium; a halogen group; a cyano group; a substituted or unsubstituted alkyl group; a substituted or unsubstituted alkenyl group; a substituted or unsubstituted alkynyl group; a substituted or unsubstituted alkoxy group; a substituted or unsubstituted cycloalkyl group; a substituted or unsubstituted heterocycloalkyl group; a substituted or unsubstituted aryl group; a substituted or unsubstituted heteroaryl group; a substituted or unsubstituted phosphine oxide group; and a substituted or unsubstituted amine group, or two or more groups adjacent to each other bond to each other to form a substituted or unsubstituted aliphatic or aromatic hydrocarbon ring or heteroring;

m, p, x, n, q and y are each an integer of 1 to 5;

a is an integer of 1 to 3;

b is an integer of 1 to 4; and when m, p, x, n, q, y, a and b are an integer of 2 or greater, substituents in the parentheses are the same as or different from each other.

2. The heterocyclic compound of claim 1, wherein Chemical Formula 1 is represented by one of the following Chemical Formula 2 to Chemical Formula 4:

[Chemical Formula 2]

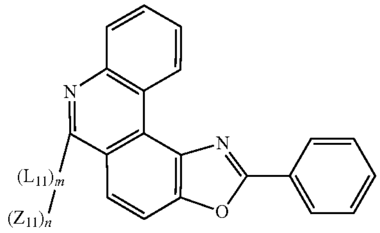

[Chemical Formula 3]

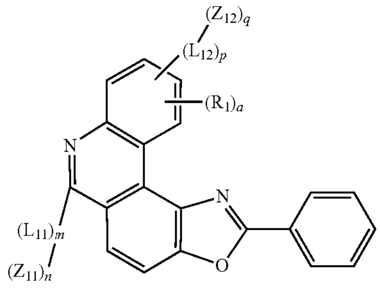

-continued

[Chemical Formula 4]

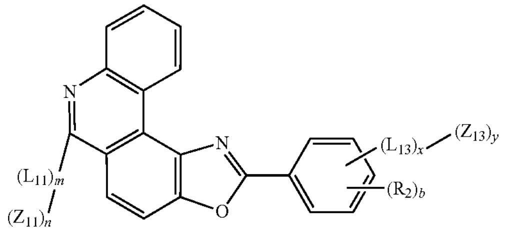

in Chemical Formula 2 to Chemical Formula 4, $R_1$, $R_2$, m, p, x, n, q, y, a and b have the same definitions as in Chemical Formula 1;

$L_{11}$ to $L_{13}$ are the same as or different from each other, and each independently a direct bond; a substituted or unsubstituted arylene group; or a substituted or unsubstituted heteroarylene group; and $Z_{11}$ to $Z_{13}$ are the same as or different from each other, and each independently selected from the group consisting of a cyano group; a substituted or unsubstituted aryl group; a substituted or unsubstituted heteroaryl group; and a substituted or unsubstituted phosphine oxide group.

3. The heterocyclic compound of claim 1, wherein $R_1$ and $R_2$ are hydrogen.

4. The heterocyclic compound of claim 1, wherein $Z_1$ to $Z_3$ are the same as or different from each other, and each independently hydrogen; deuterium; a cyano group; a substituted or unsubstituted C6 to C40 aryl group; a substituted or unsubstituted C2 to C40 heteroaryl group; or a substituted or unsubstituted phosphine oxide group.

5. The heterocyclic compound of claim 1, wherein Chemical Formula 1 is represented by any one of the following compounds:

1

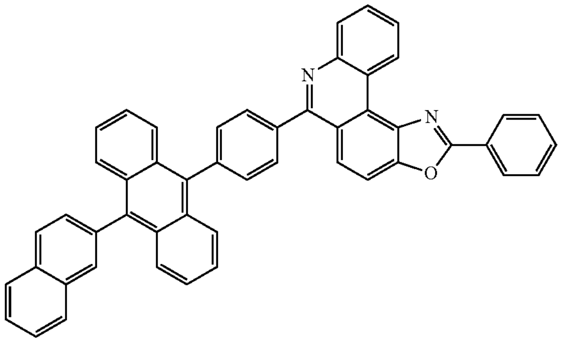

2

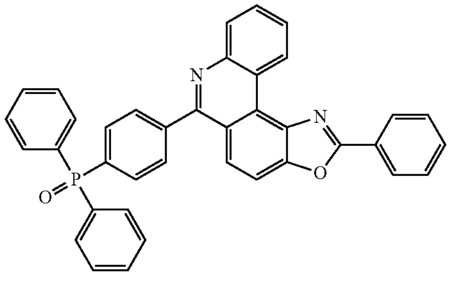

3

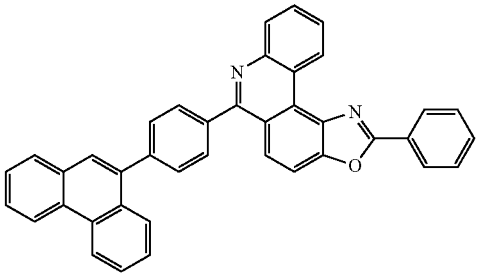

4

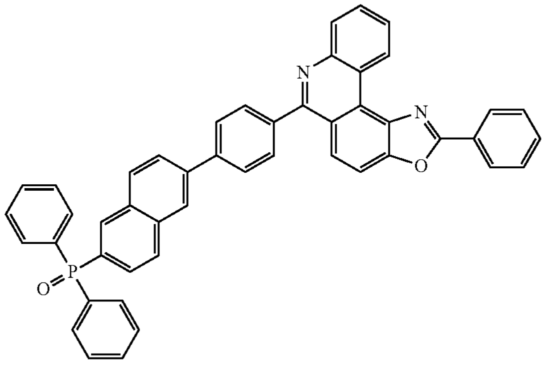

-continued
5
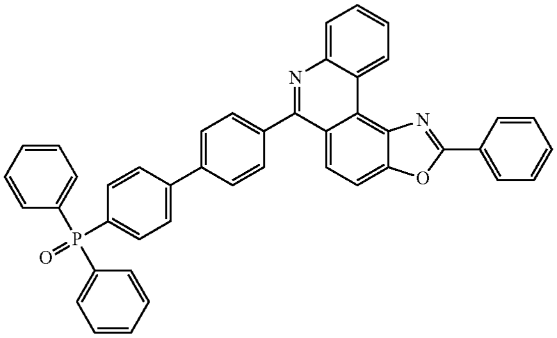
6
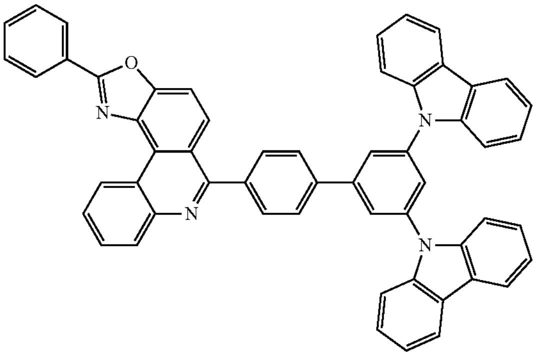
7
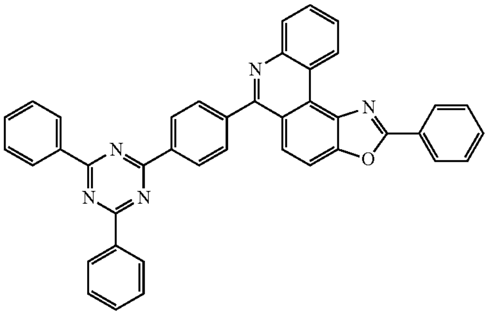
8
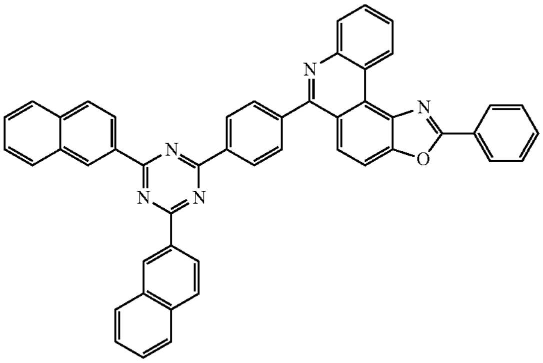
9
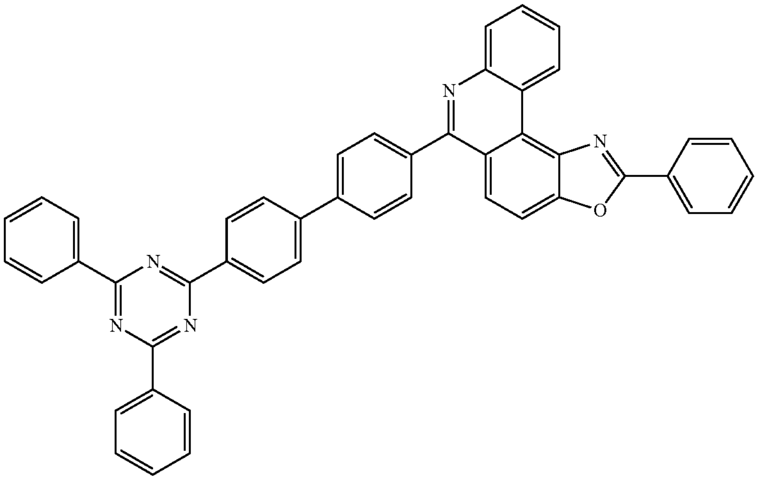

-continued
10
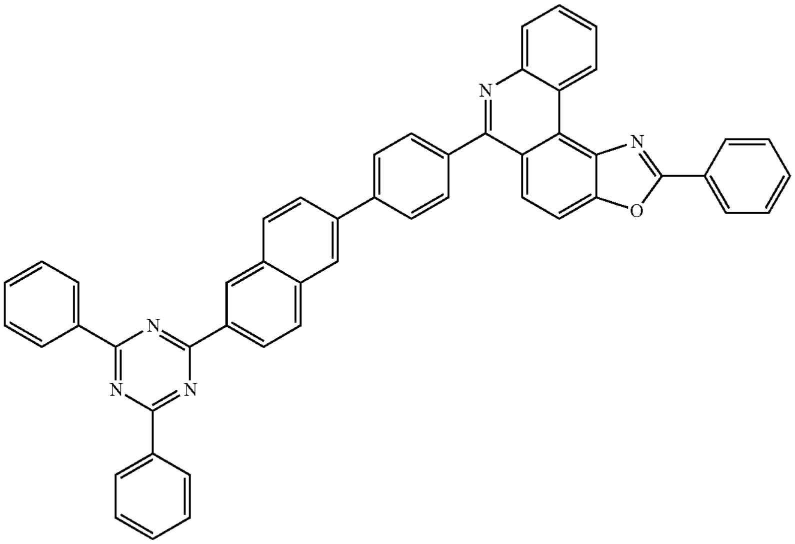
11
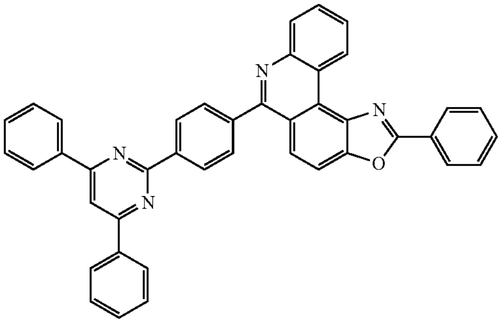
12
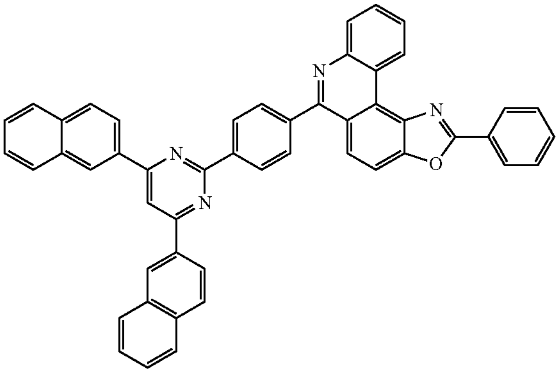
13
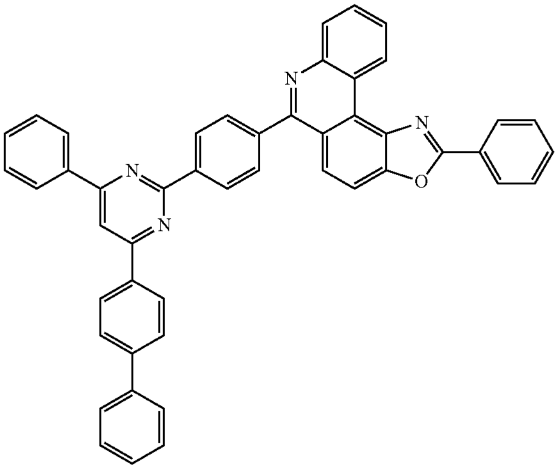
14
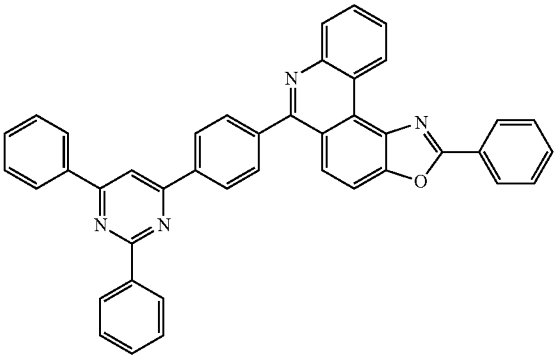

-continued
15
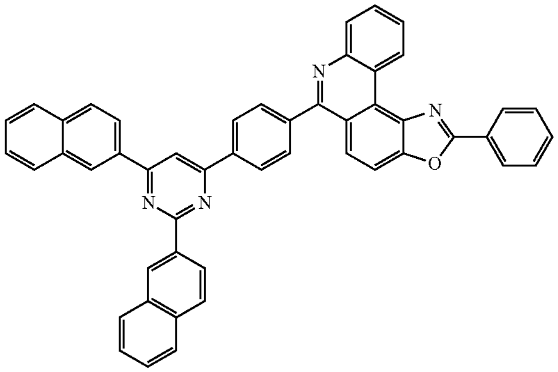
16
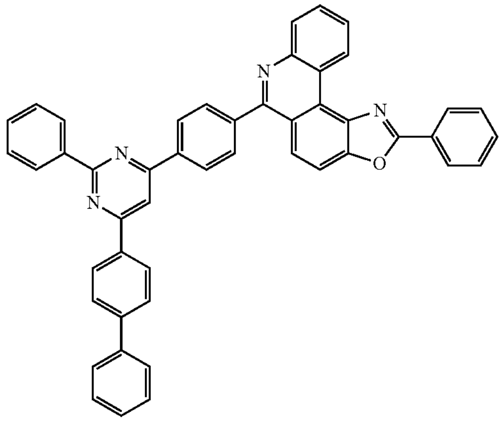
17
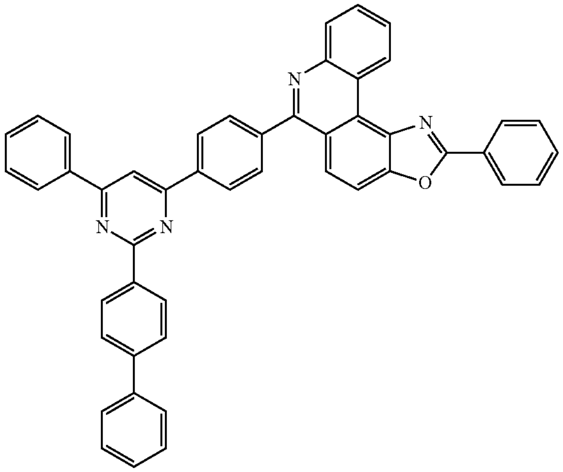
18
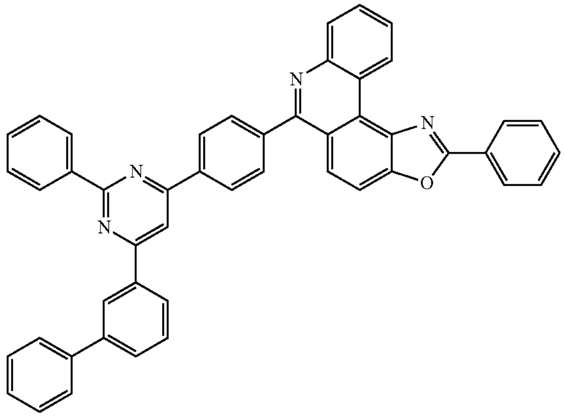
19
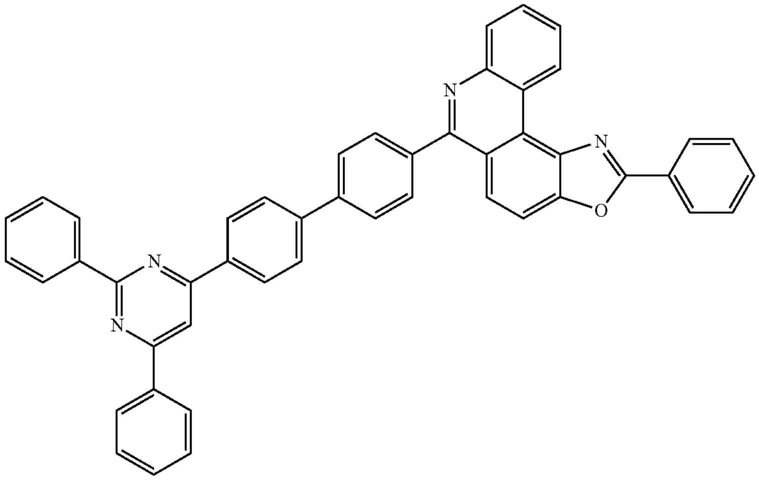

-continued
20
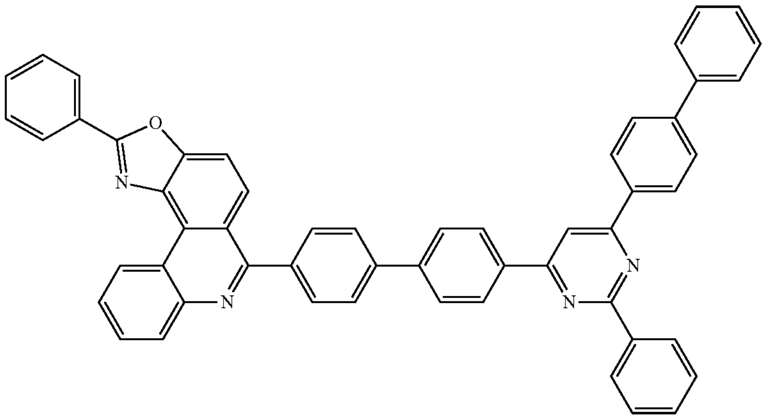
21
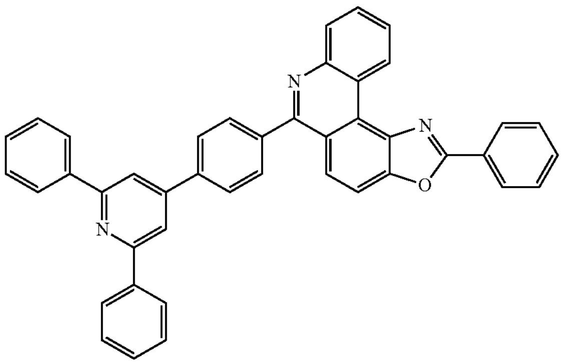
22
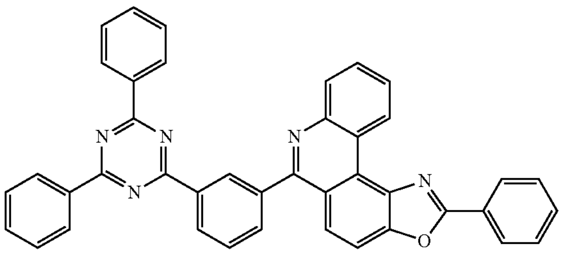
23
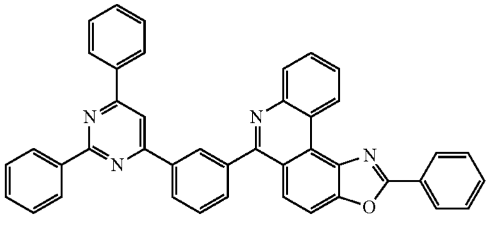
24
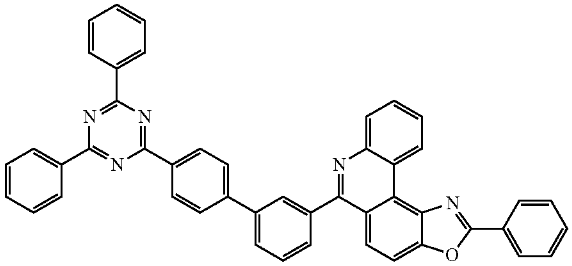
25
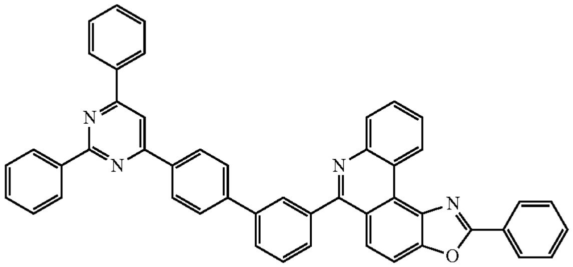
26
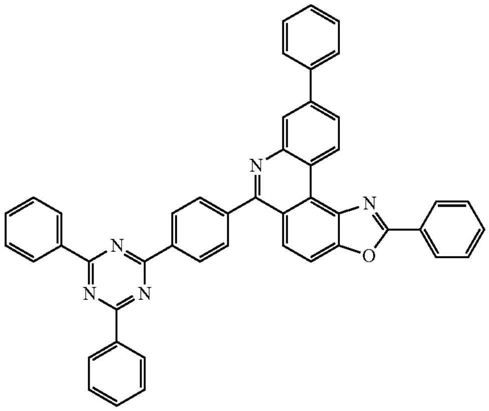

-continued
27
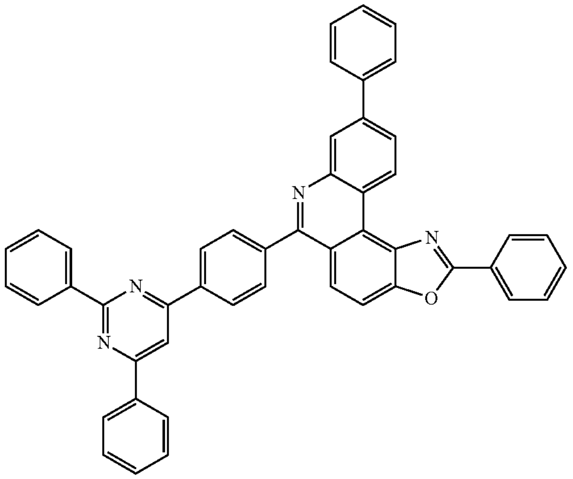
28
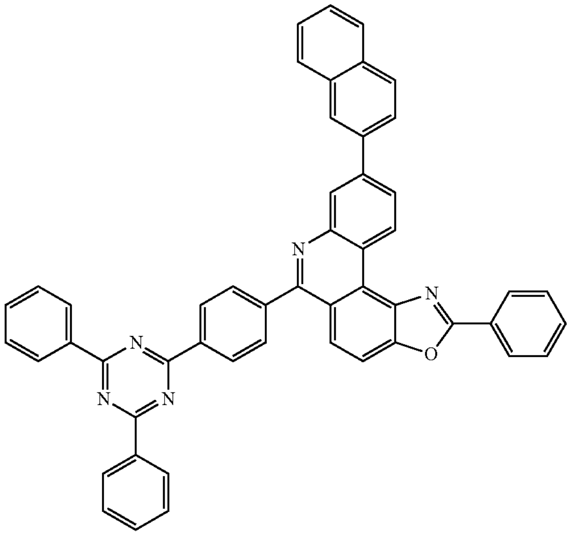
29
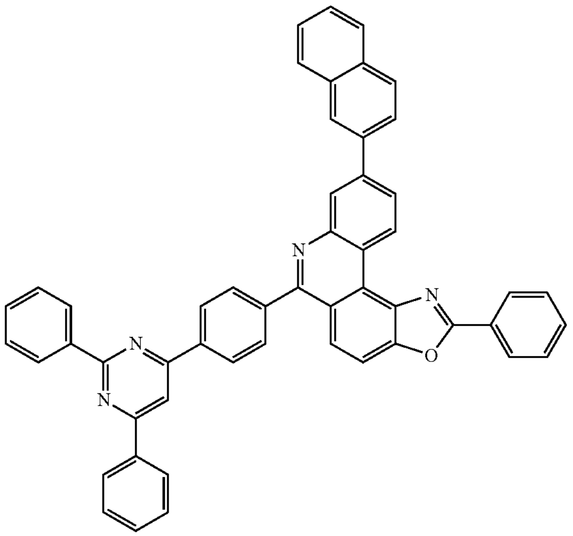
30
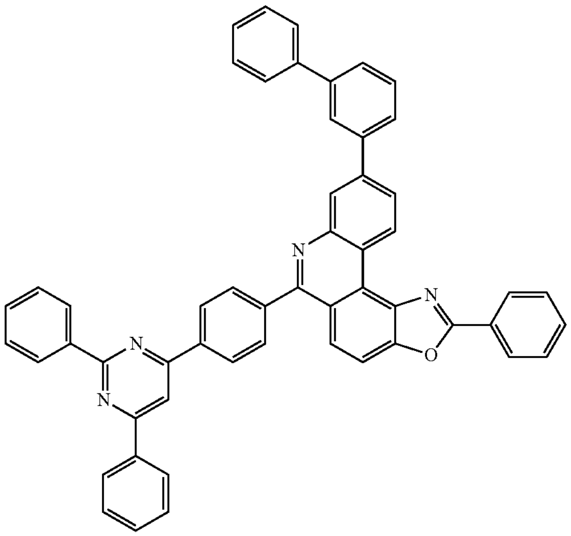
31
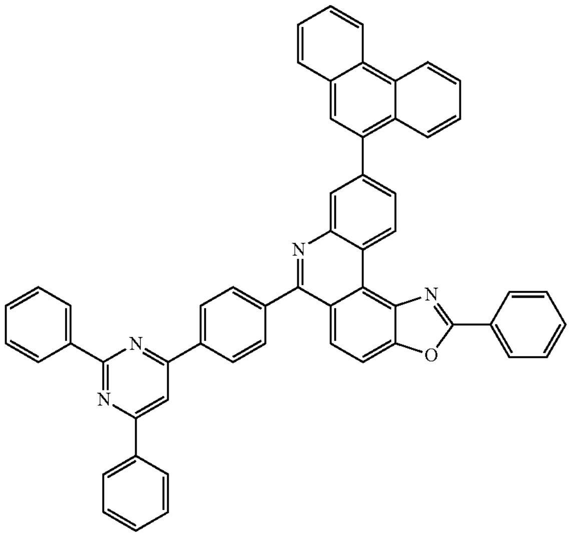
32
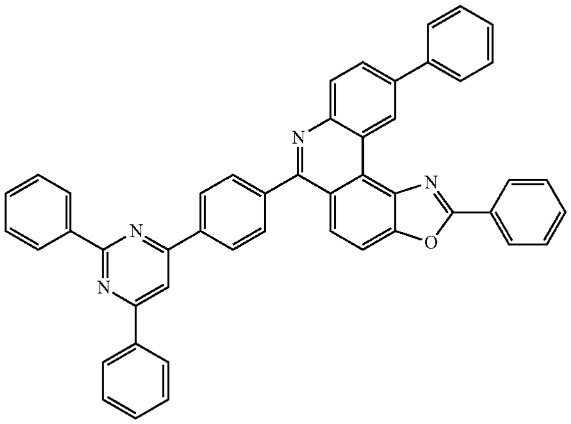

-continued
33
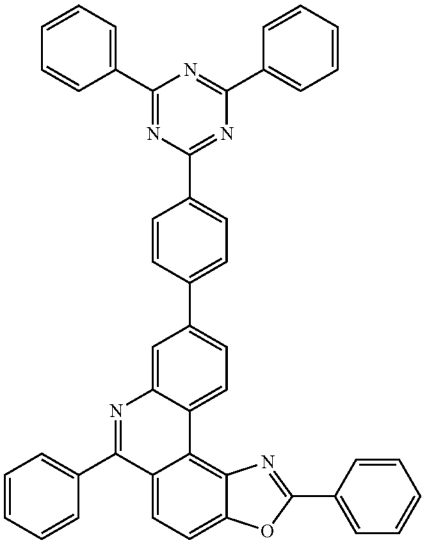
34
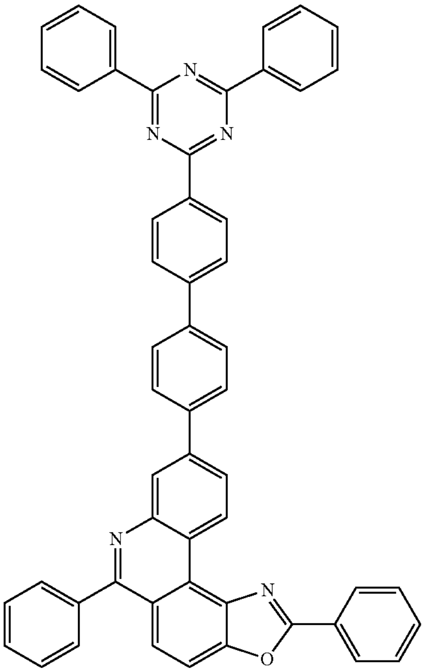
35
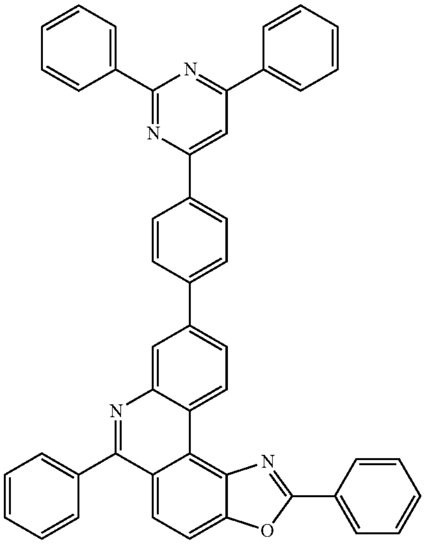
36
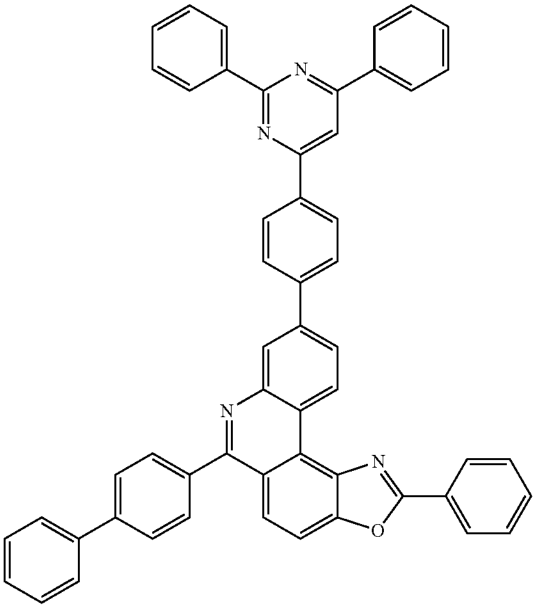

-continued
37
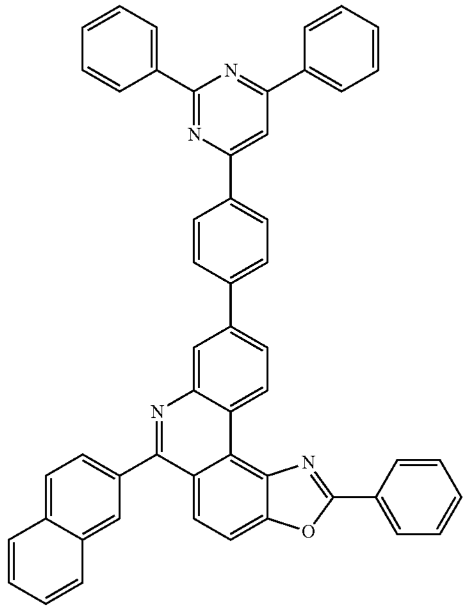
38
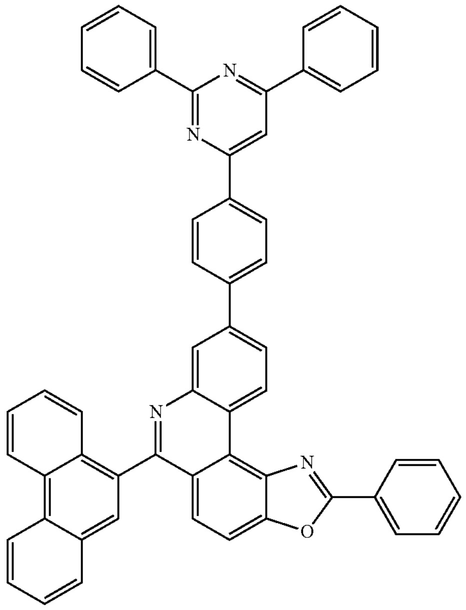
39
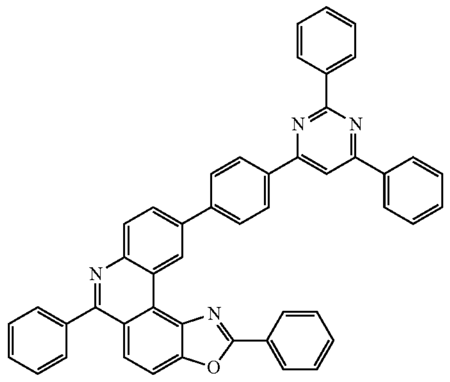
40
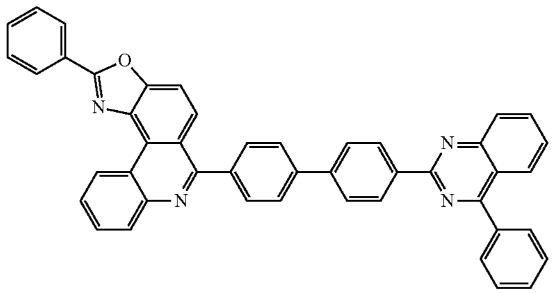
41
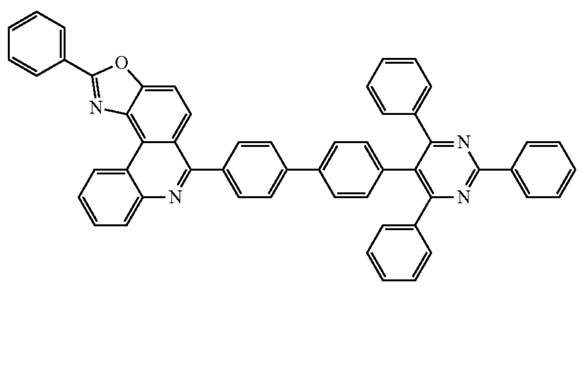
42
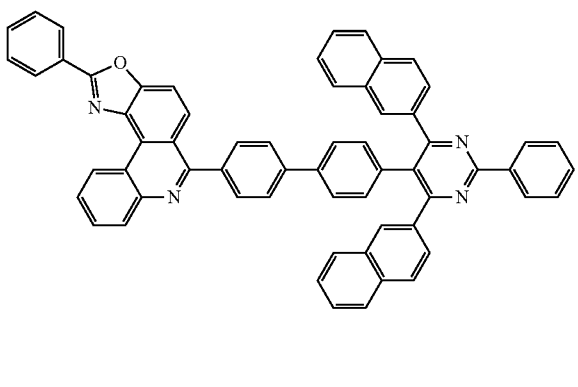

-continued
43
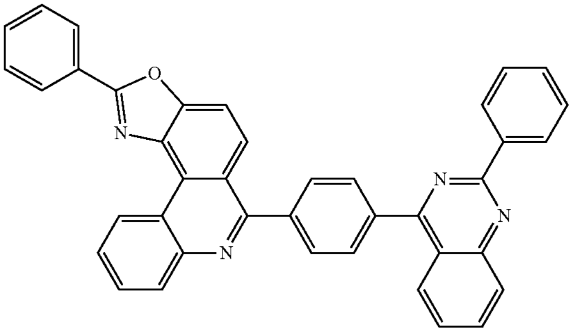
44
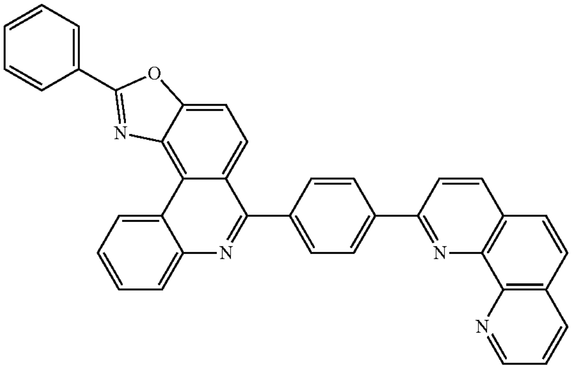
45
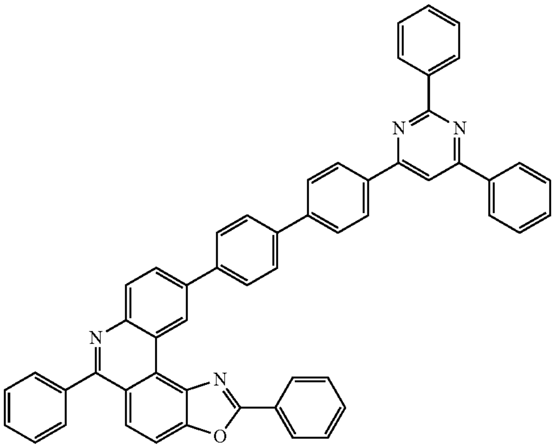
46
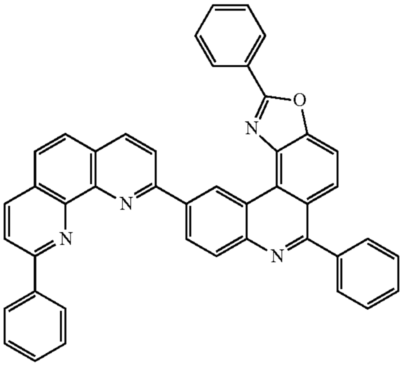
47
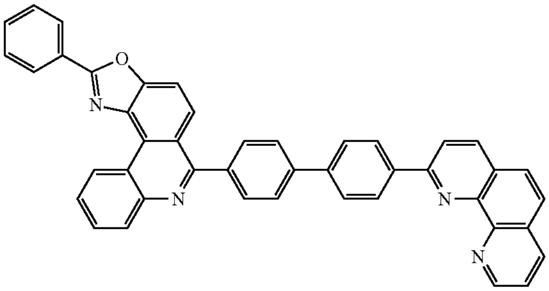
48
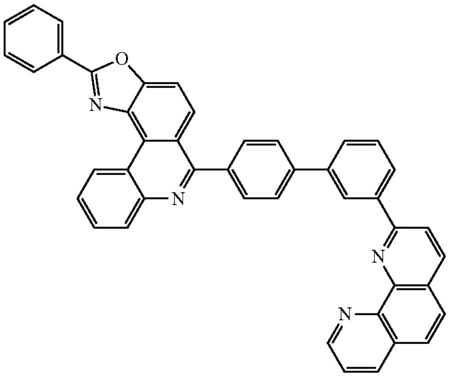

-continued
49
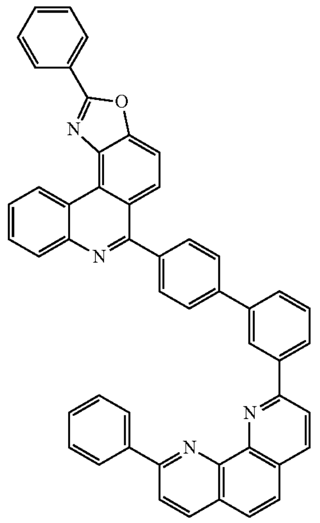
50
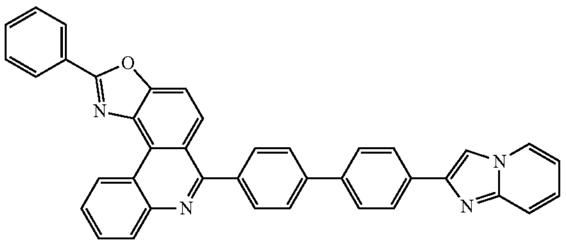
51
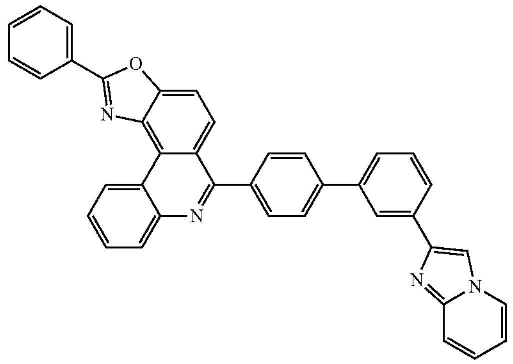
52
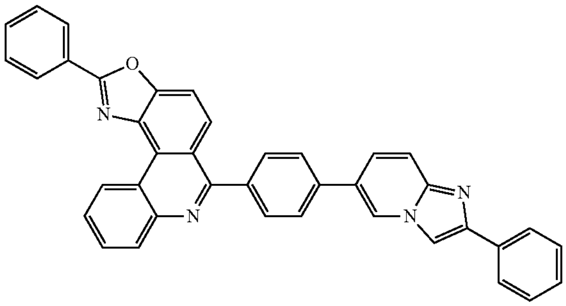
53
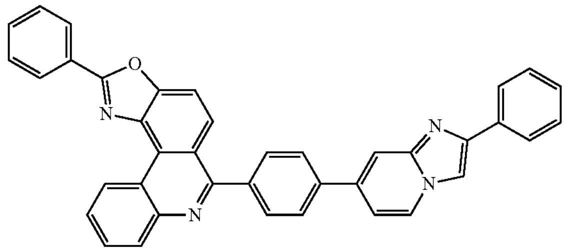
54
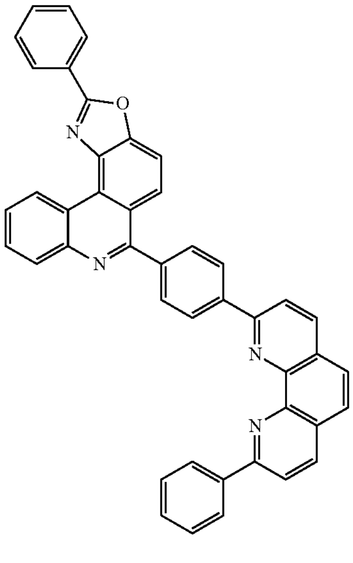

-continued
55
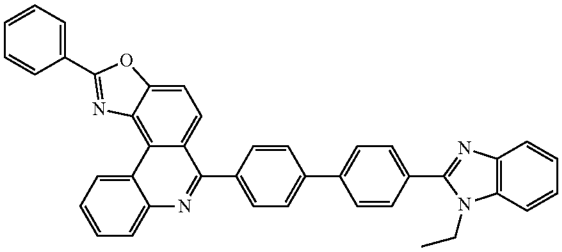
56
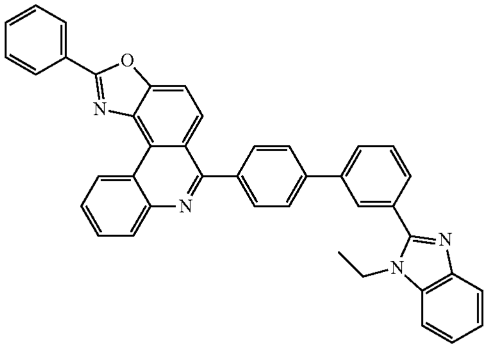
57
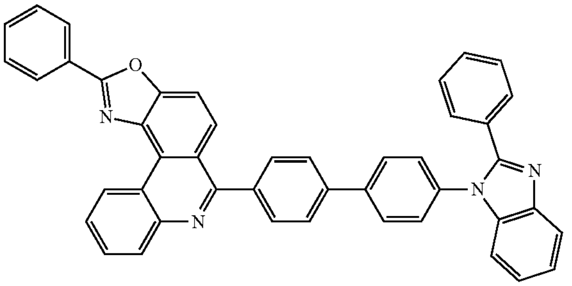
58
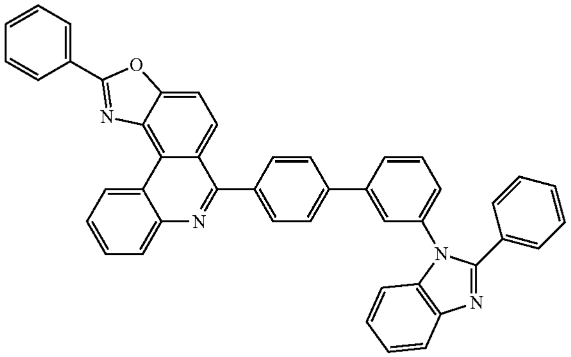
59
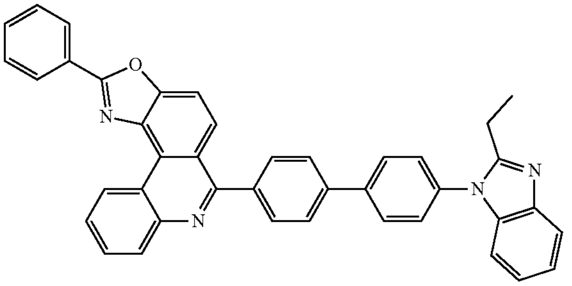
60
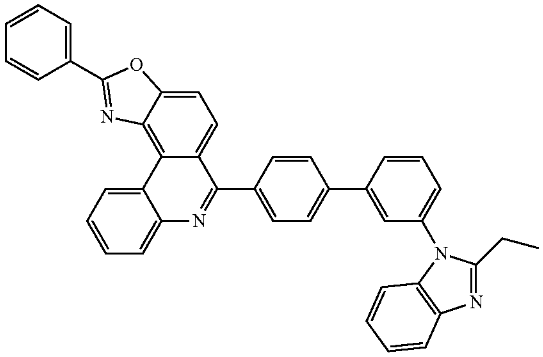
61
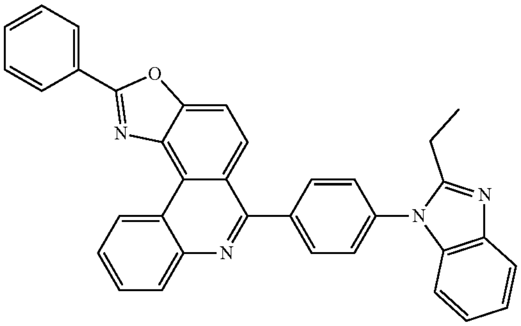

-continued
62
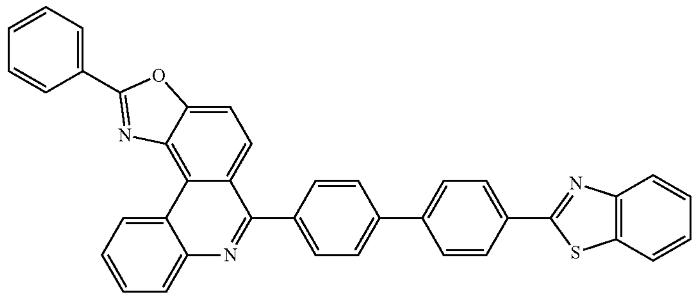
63
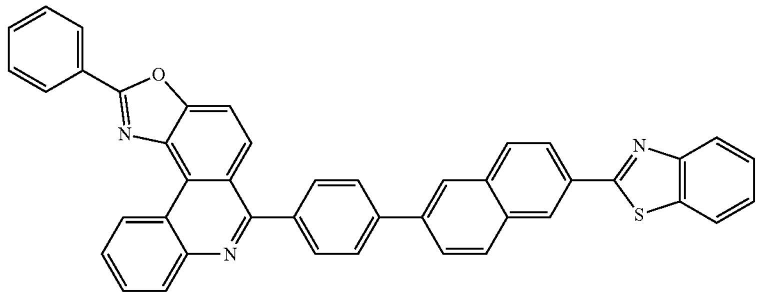
64
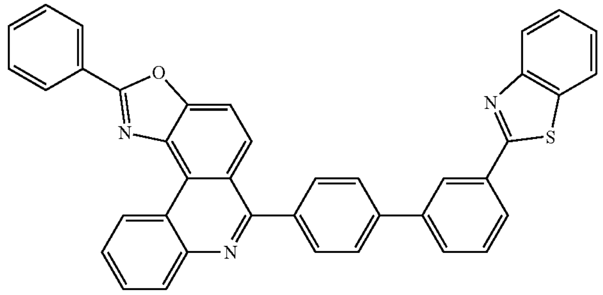
65
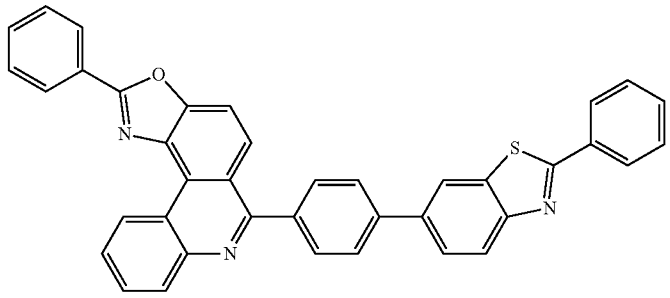
66
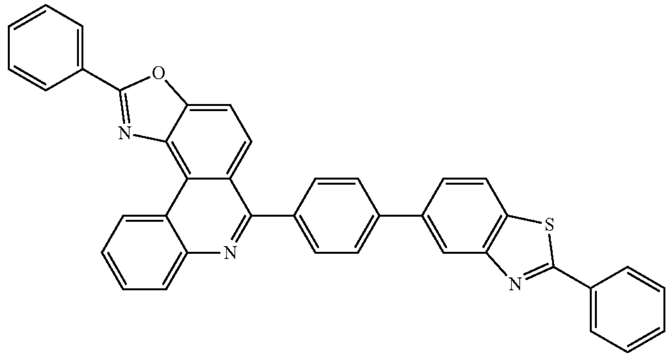

-continued
67
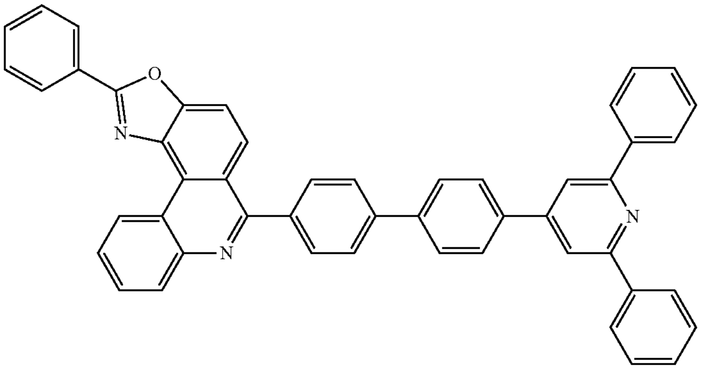
68
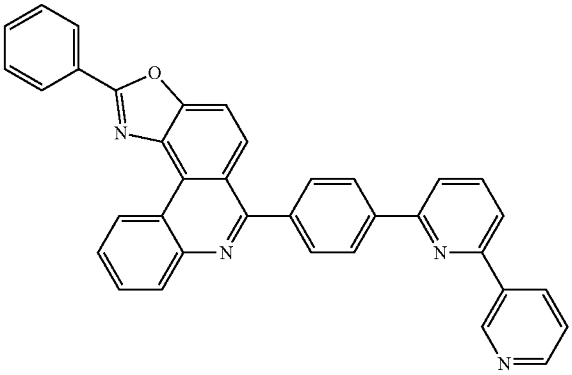
69
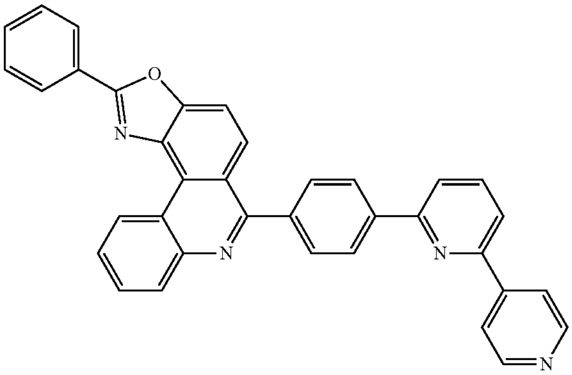
70
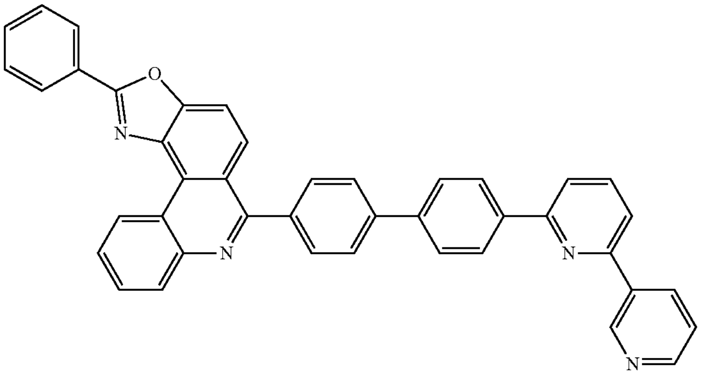

-continued
71
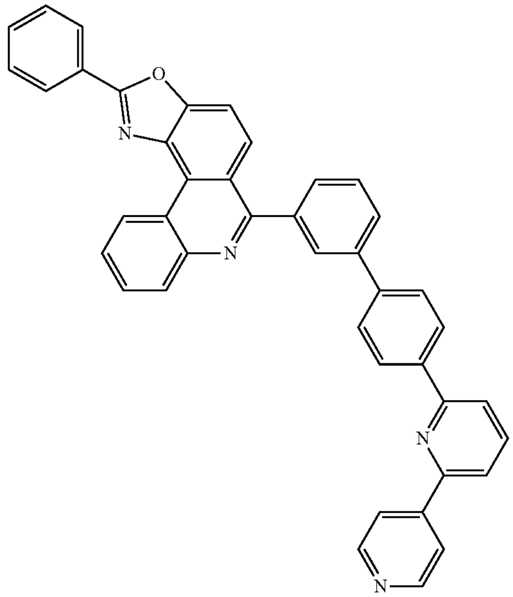
72
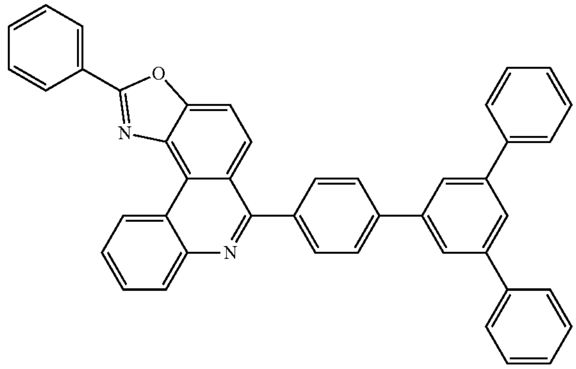
73
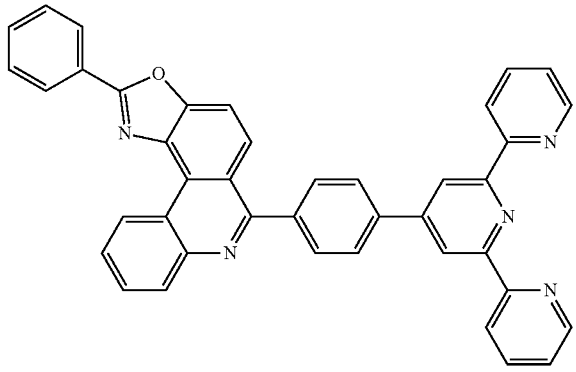

-continued
74
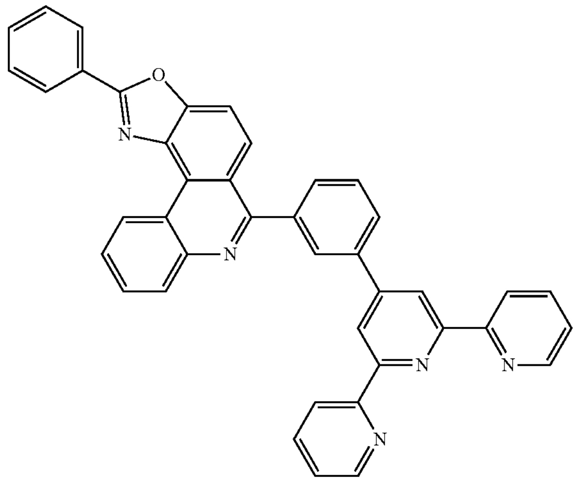
75
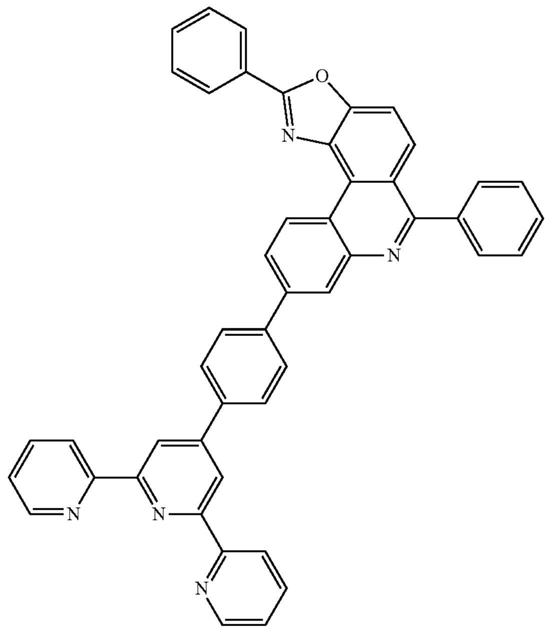
76
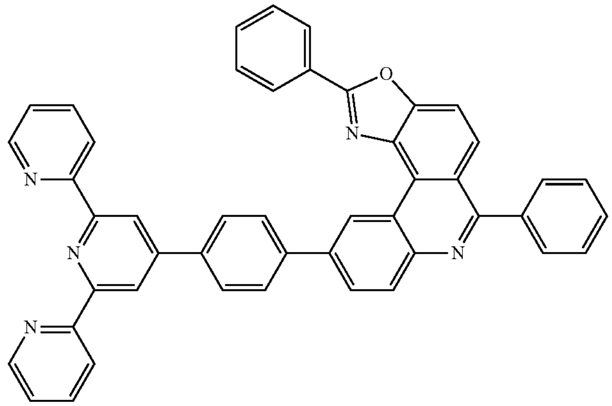

-continued
77
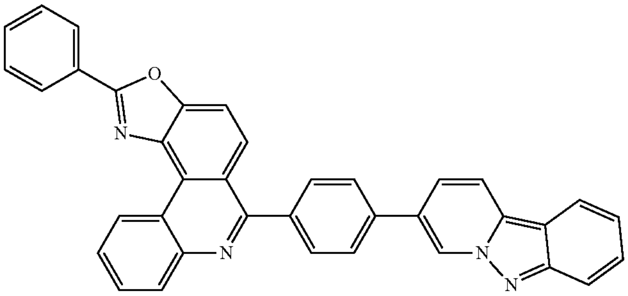
78
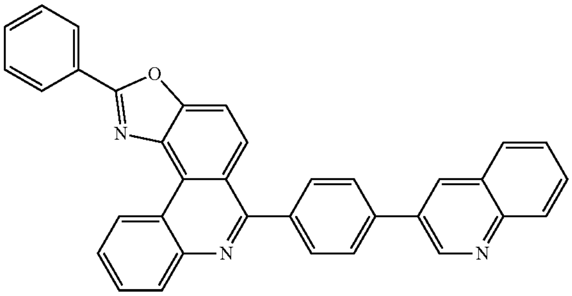
79
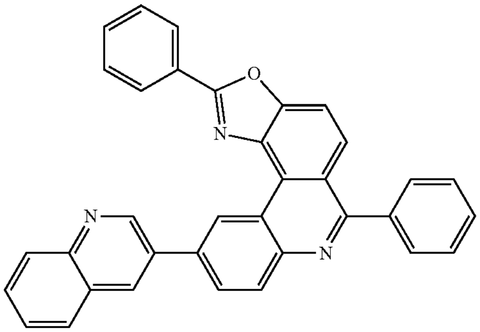
80
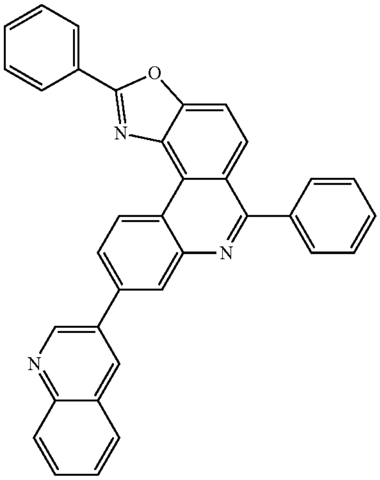

-continued
81
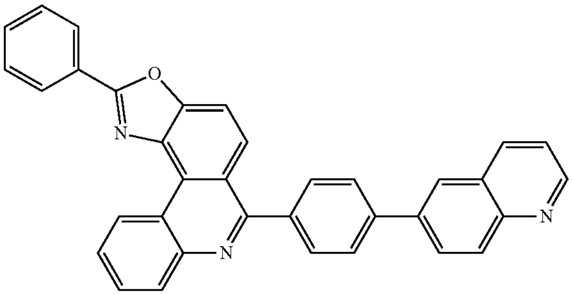
82
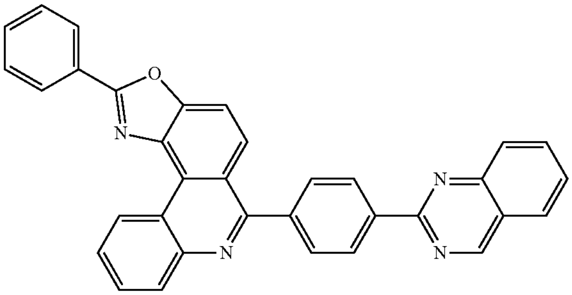
83
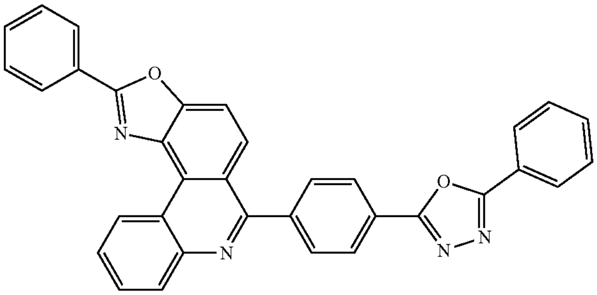
84
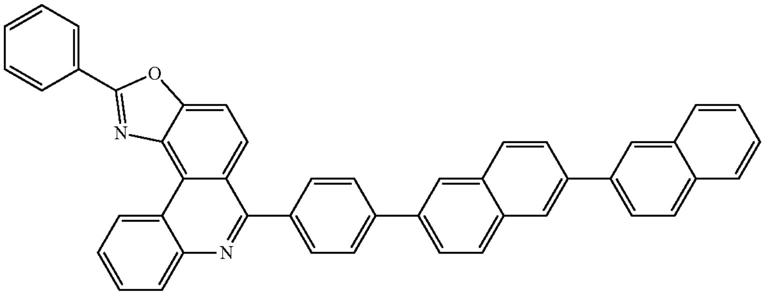
85
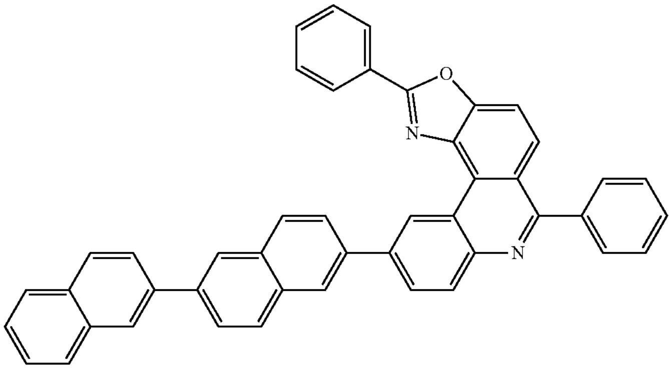

-continued
86
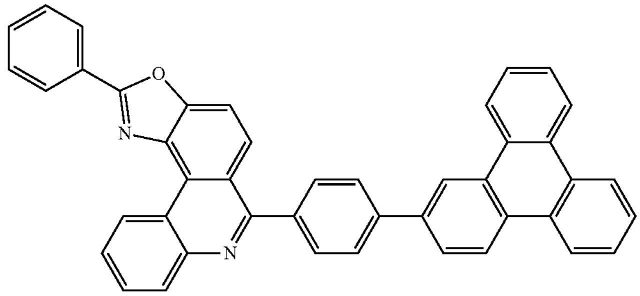
87
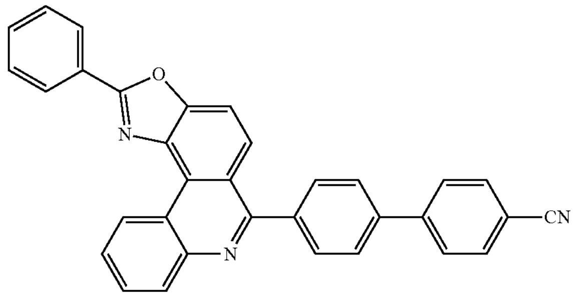
88
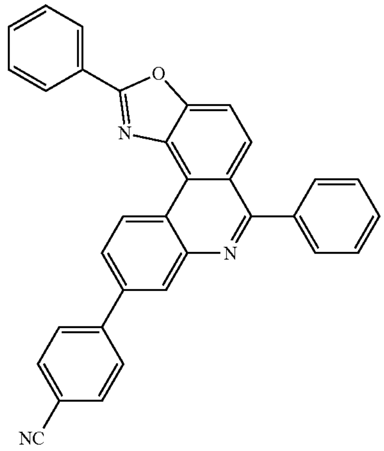
89
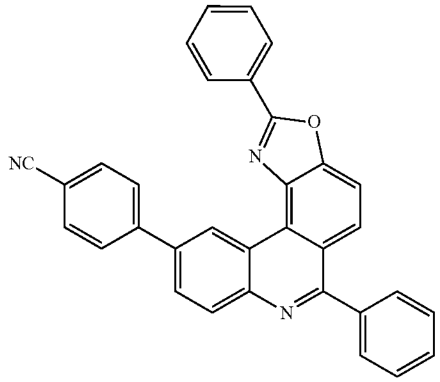

-continued
90
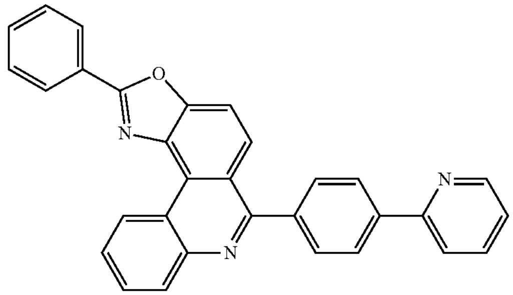
91
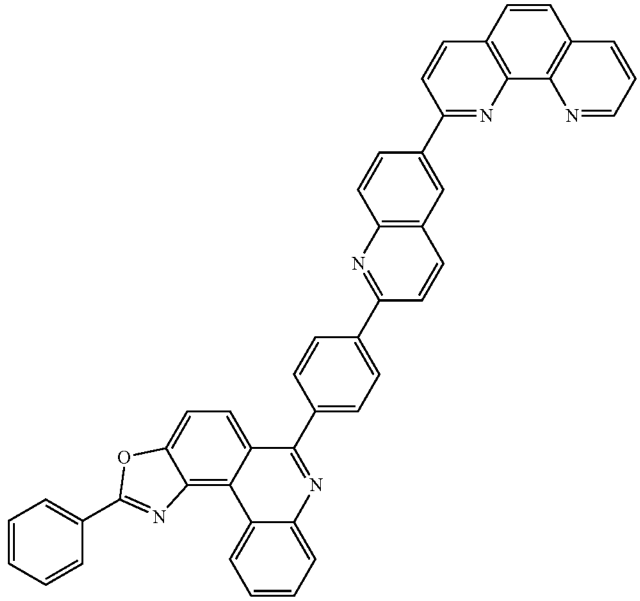
92
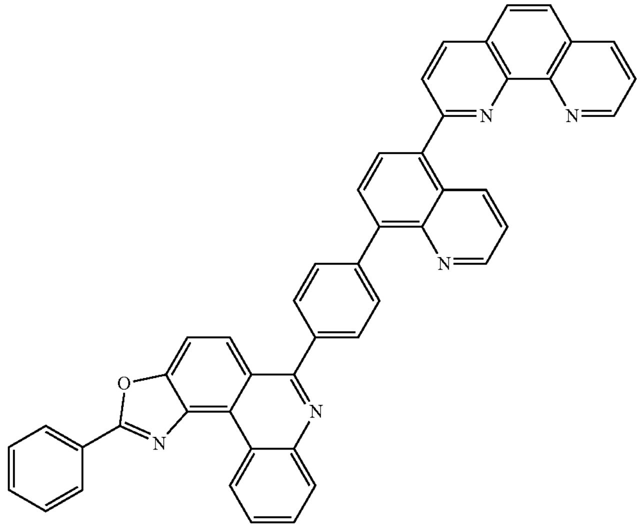

-continued
93
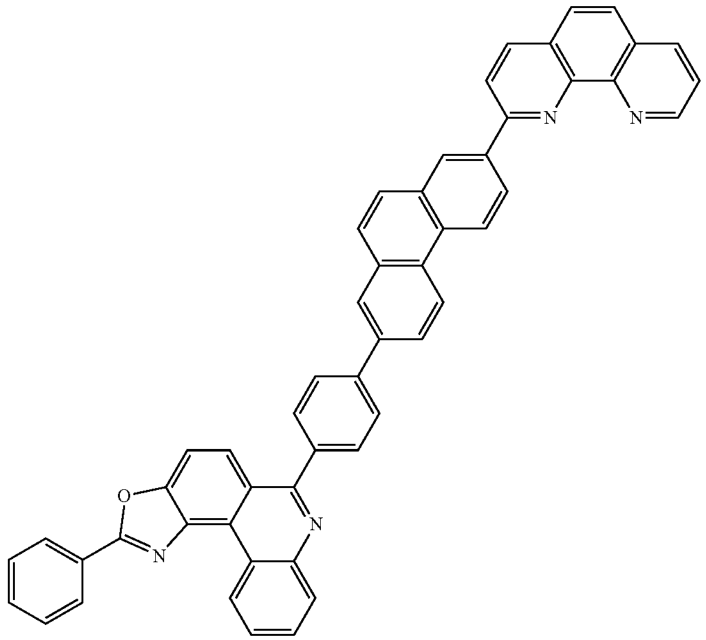
94
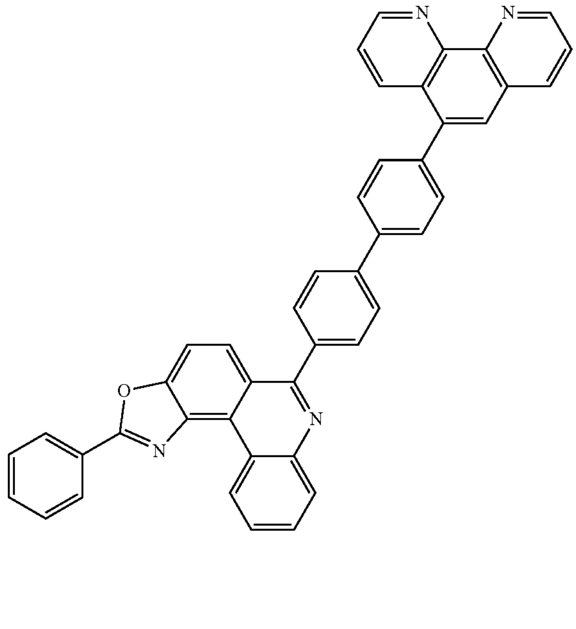

-continued
95
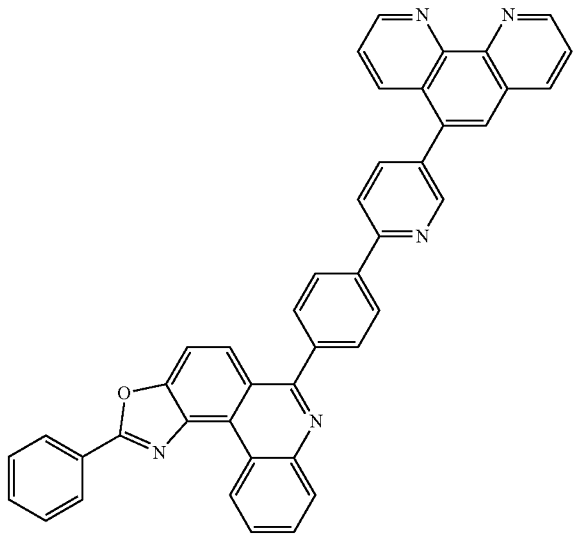
96
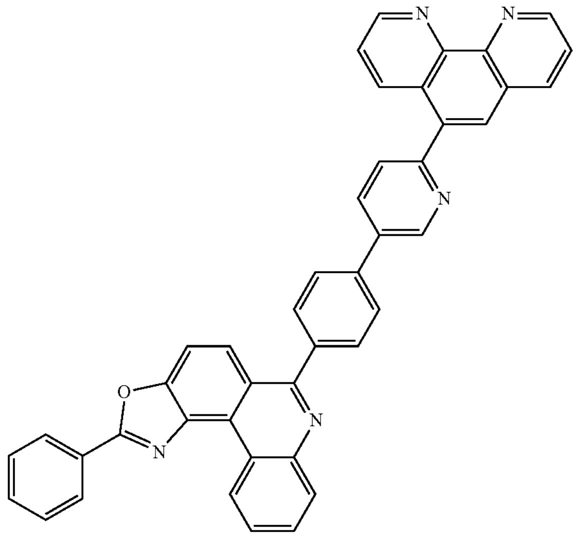
97
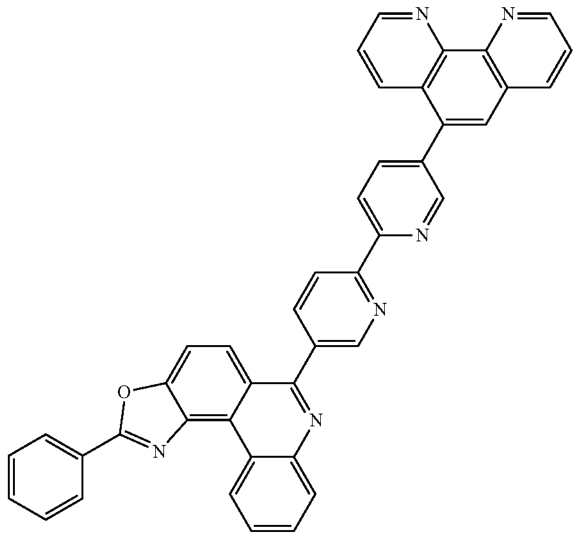

-continued
98
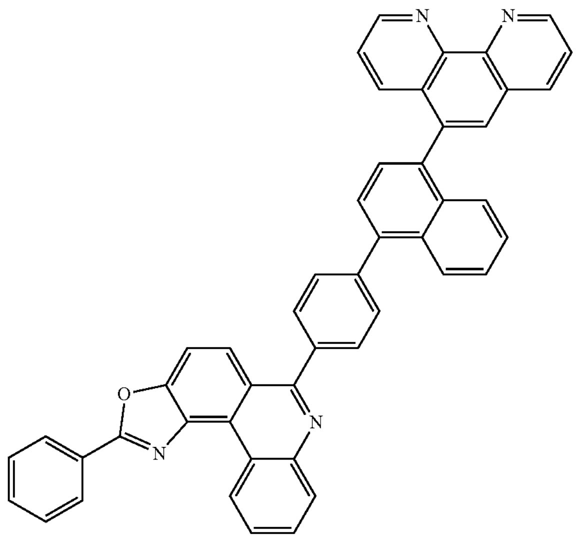
99
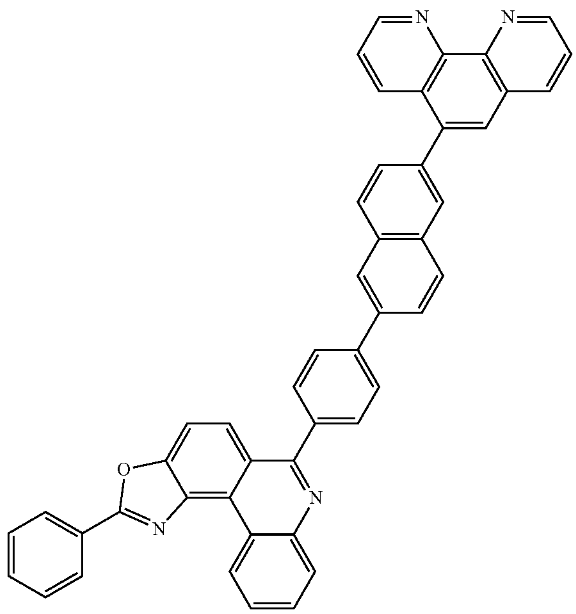

-continued
100
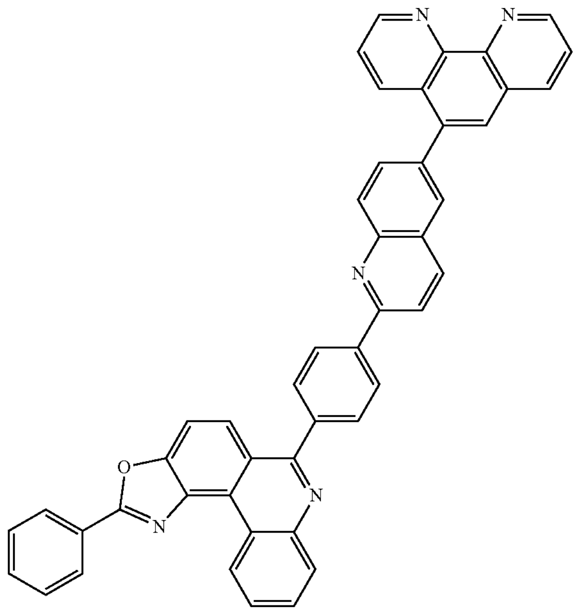
101
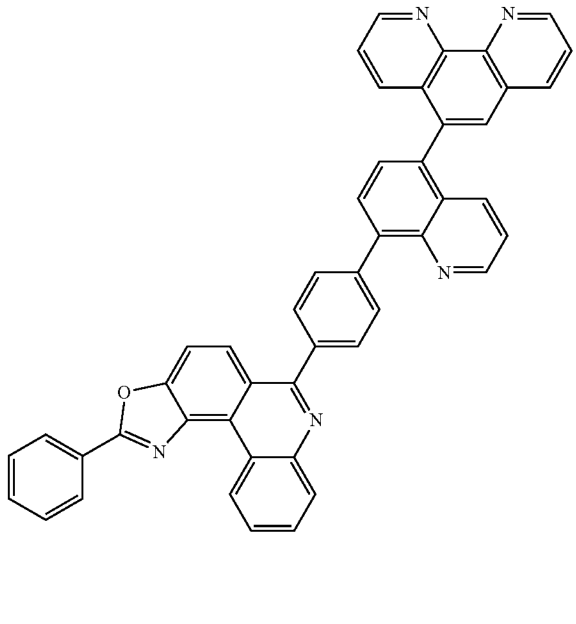

-continued
102
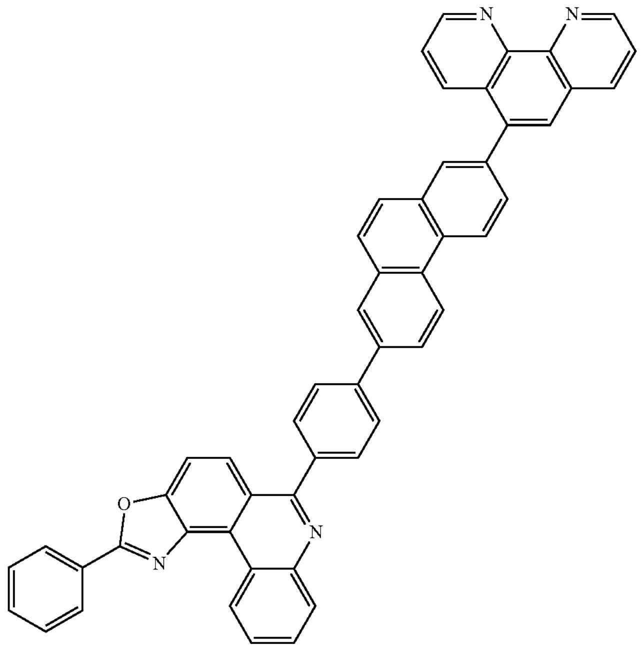
103
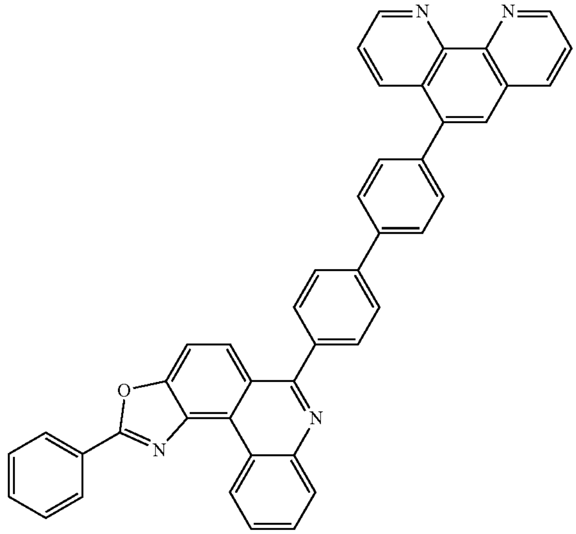

-continued
104
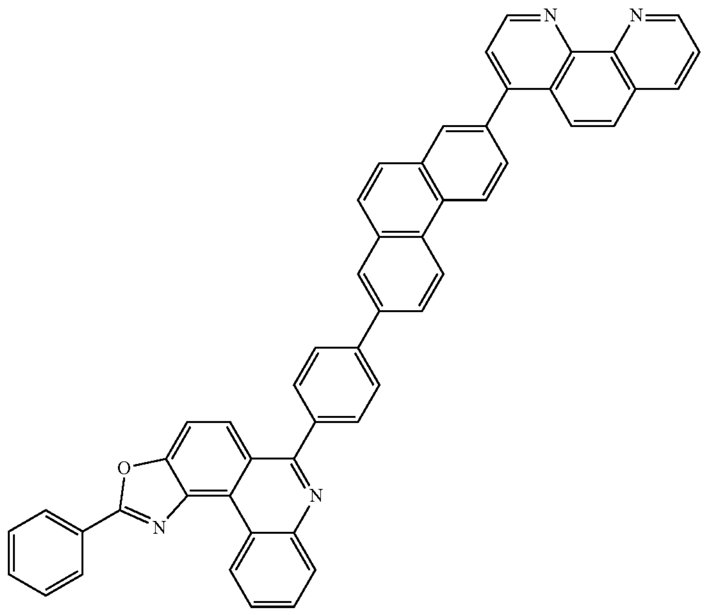
105
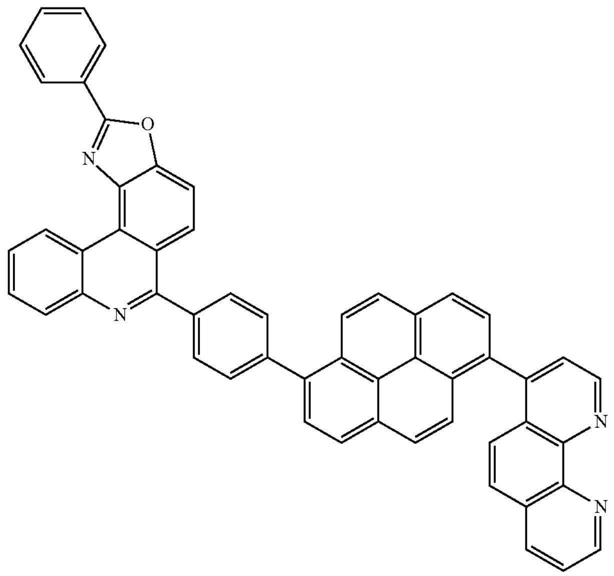

-continued
106
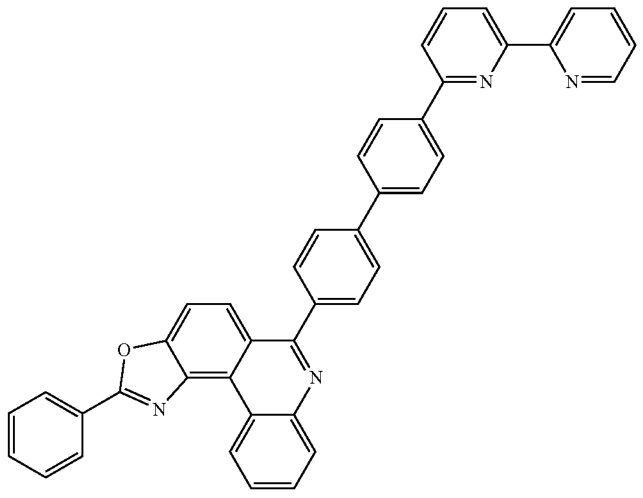
107
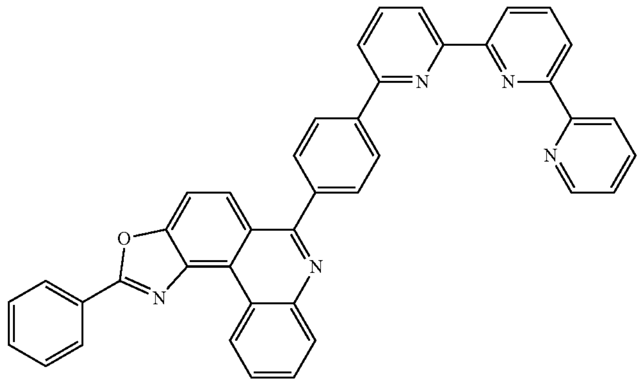
108
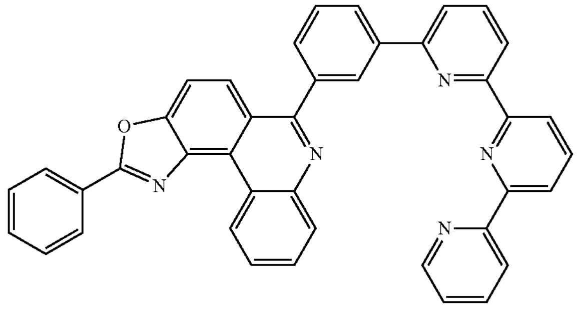

-continued
109
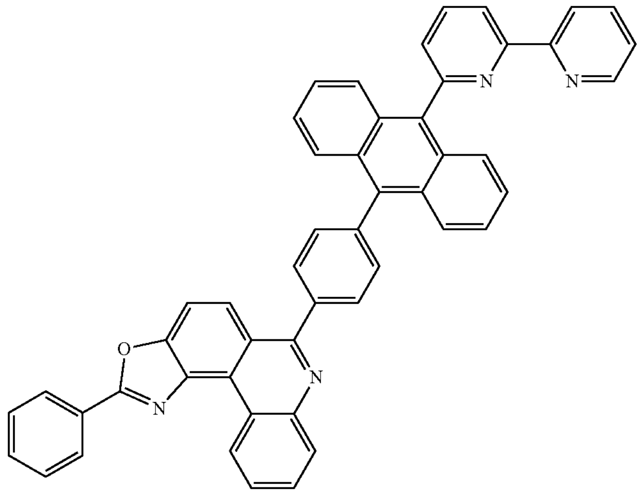
110
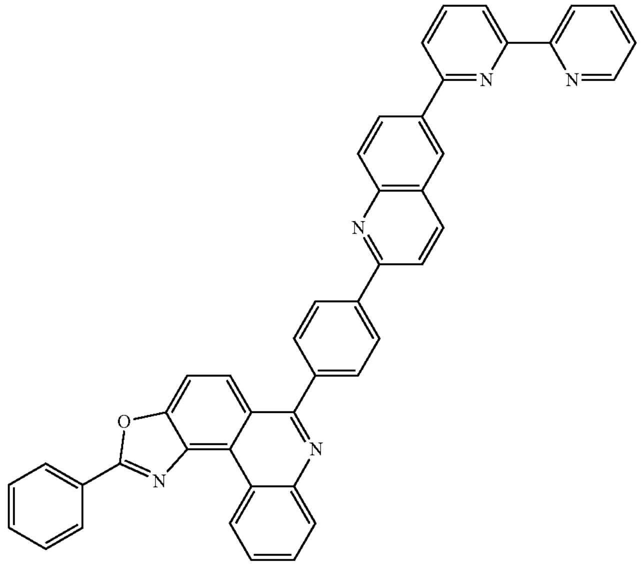
111
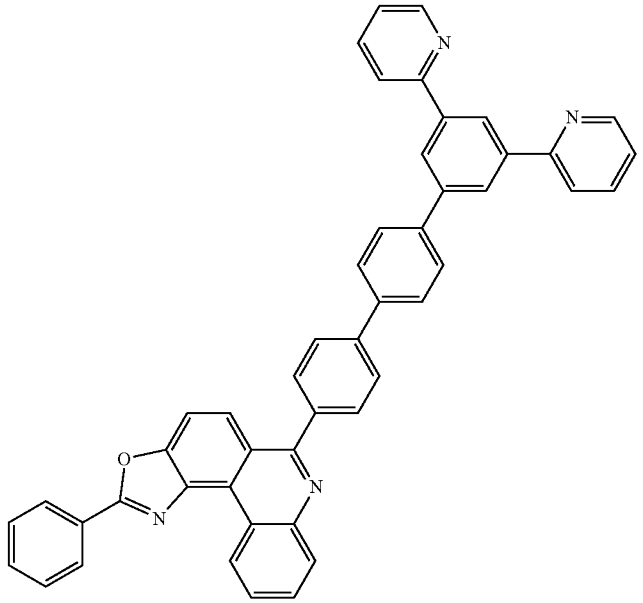

-continued
112
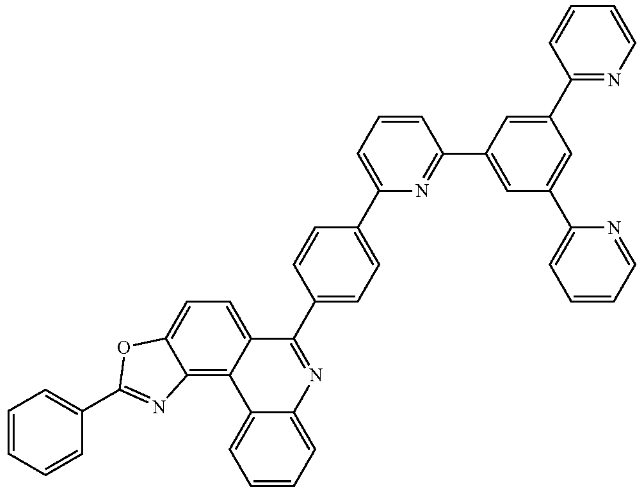
113
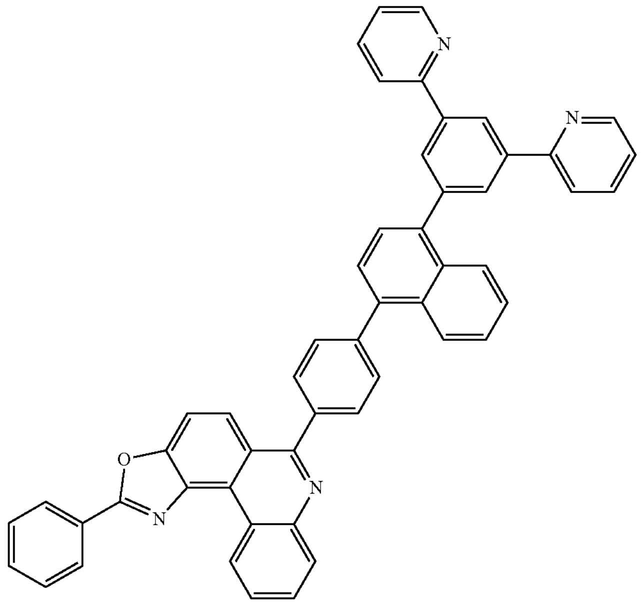
114
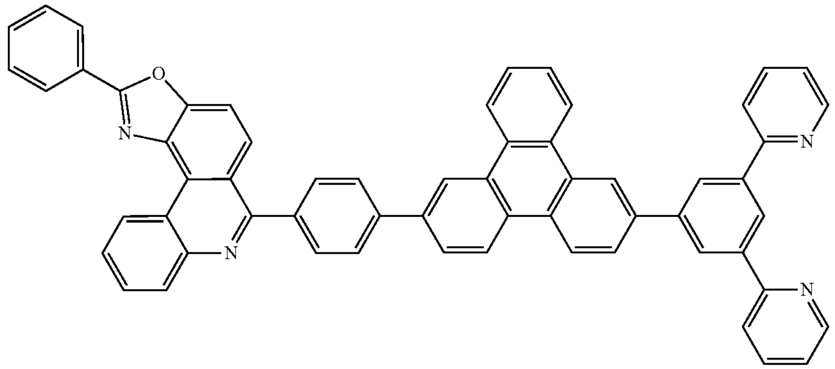

-continued
115
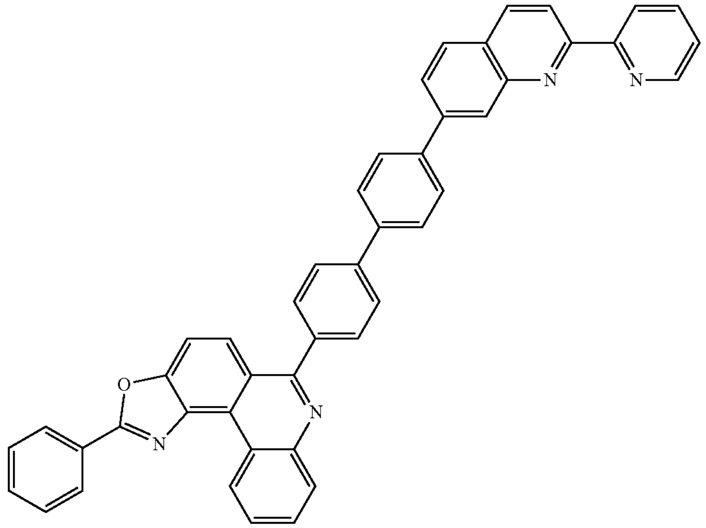
116
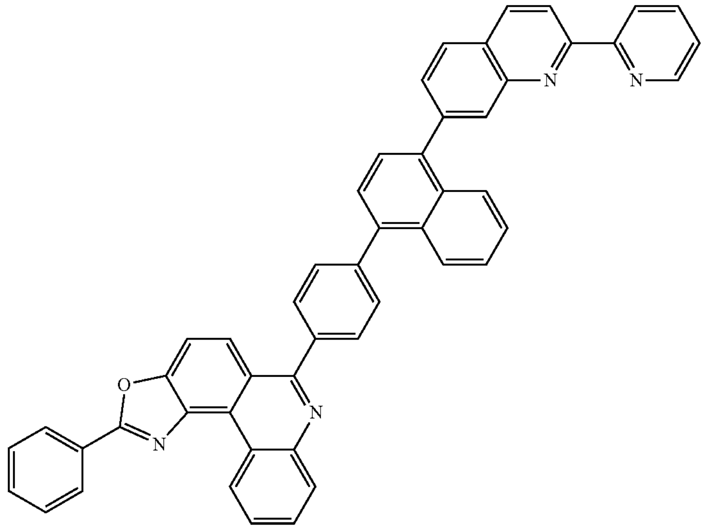

-continued
117
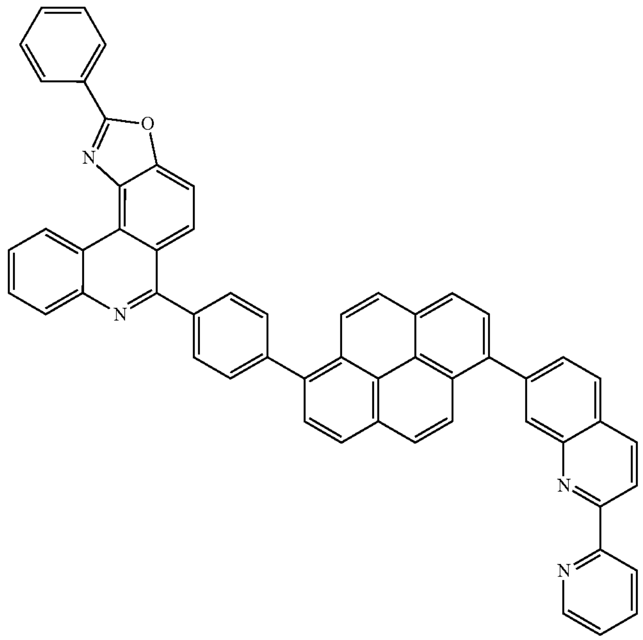
118
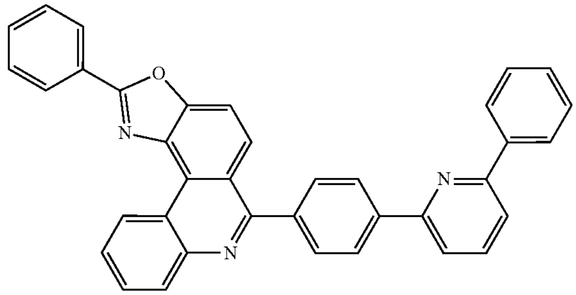
119
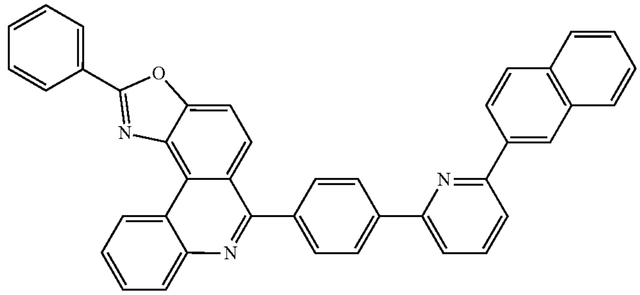
120
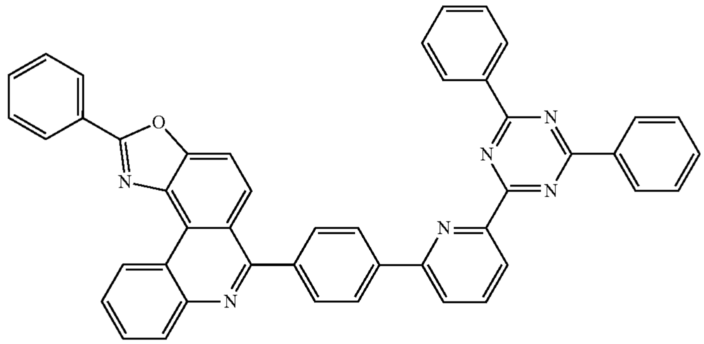

-continued
121
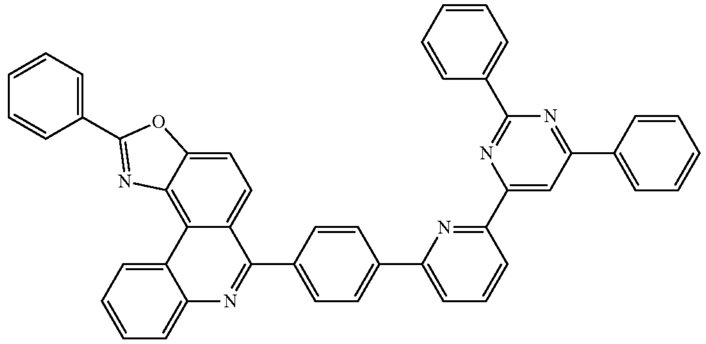
122
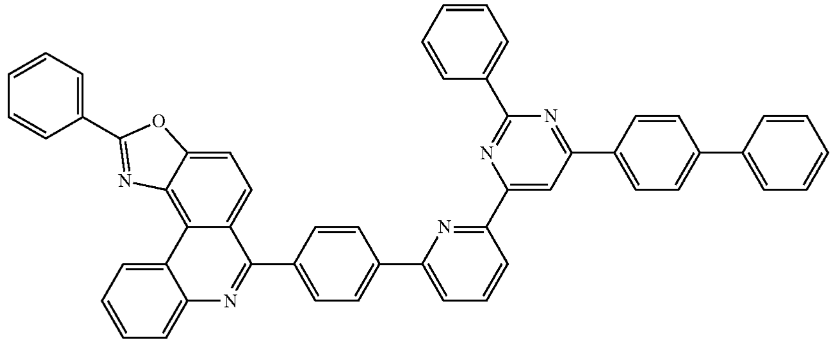
123
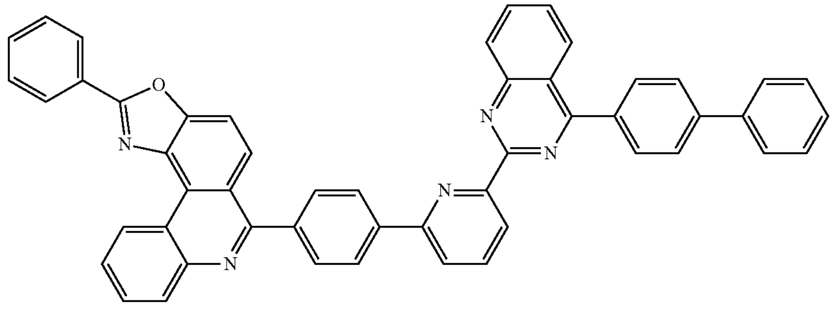
124
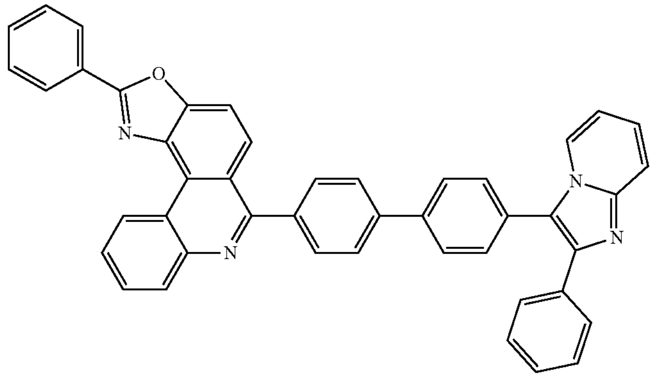

-continued
125
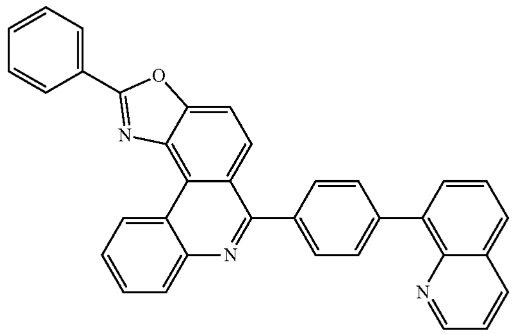
126
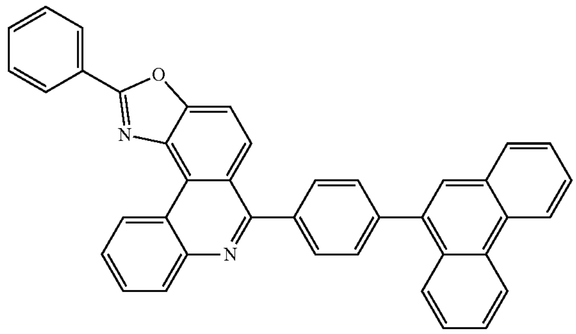
127
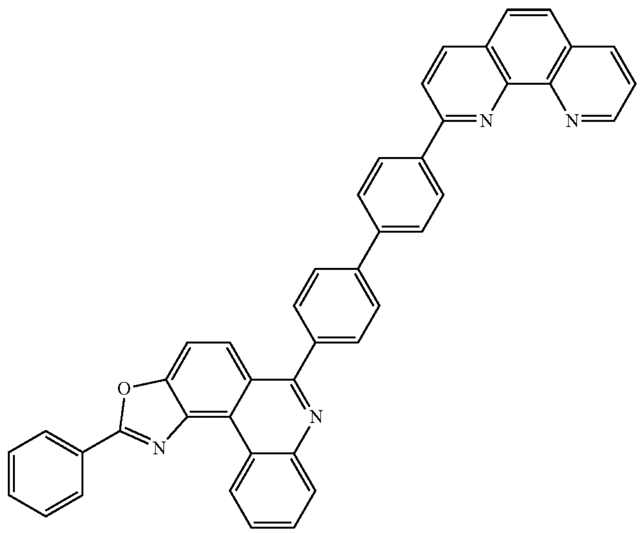

-continued
128
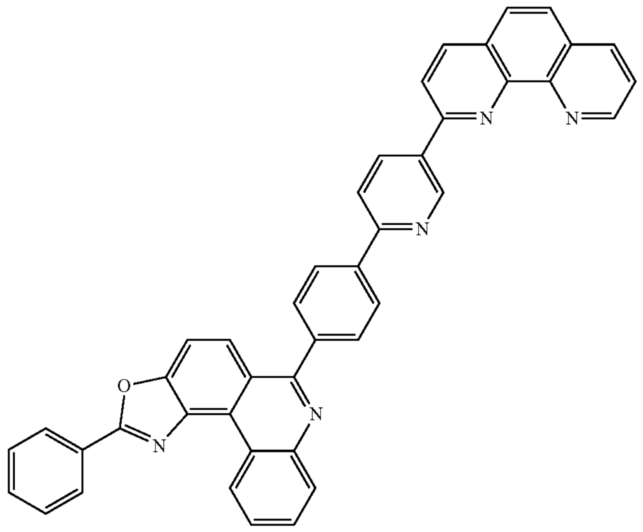
129
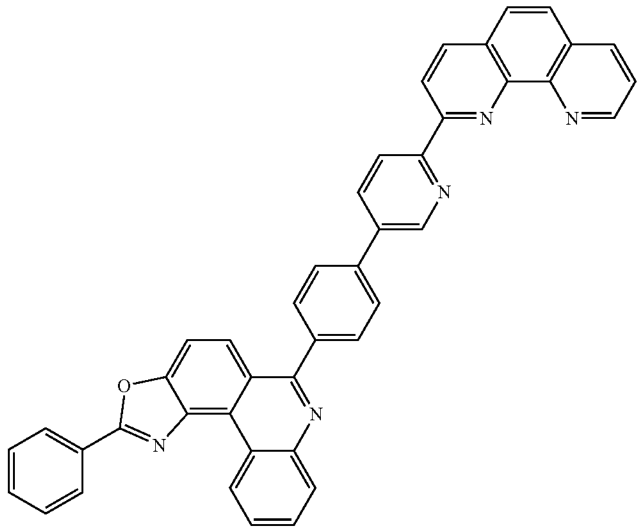
130
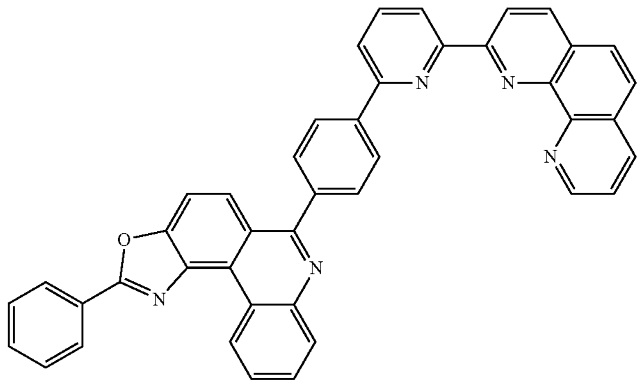

-continued
131
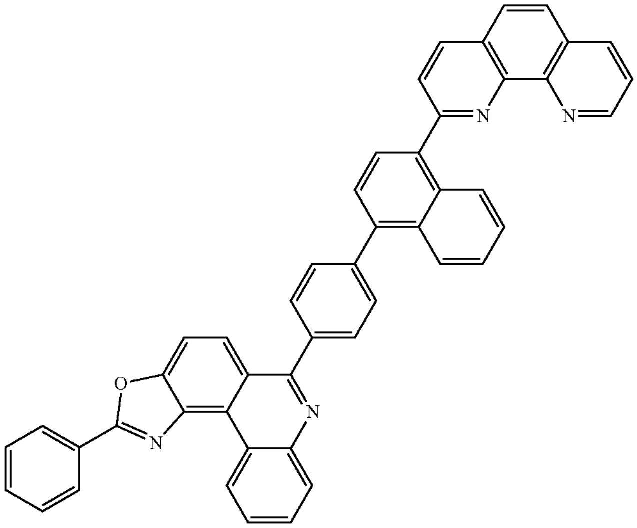
132
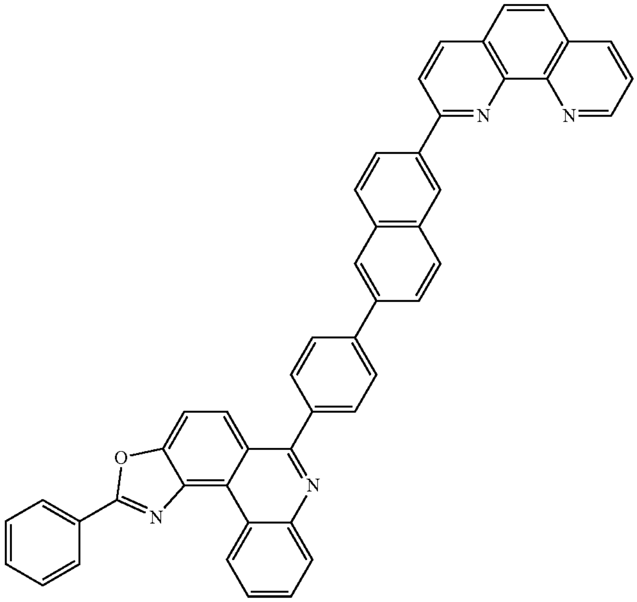
133
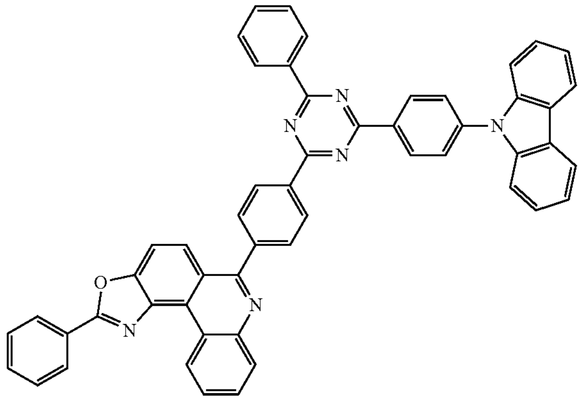

-continued
134
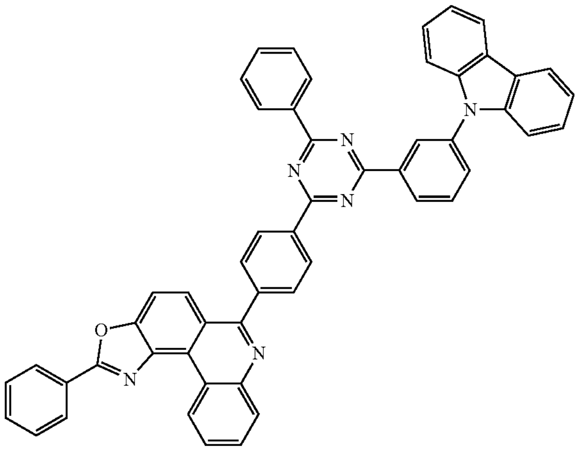
135
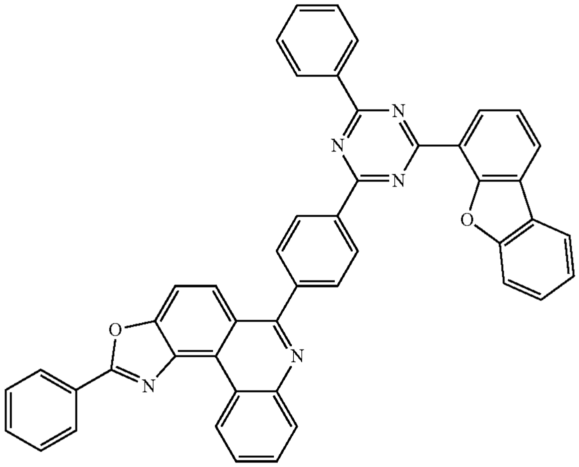
136
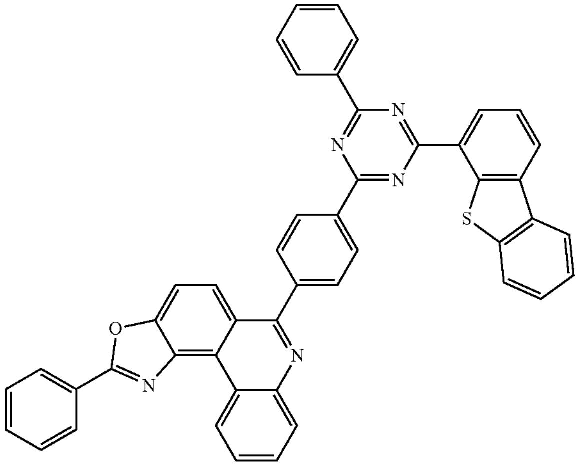
-continued
137
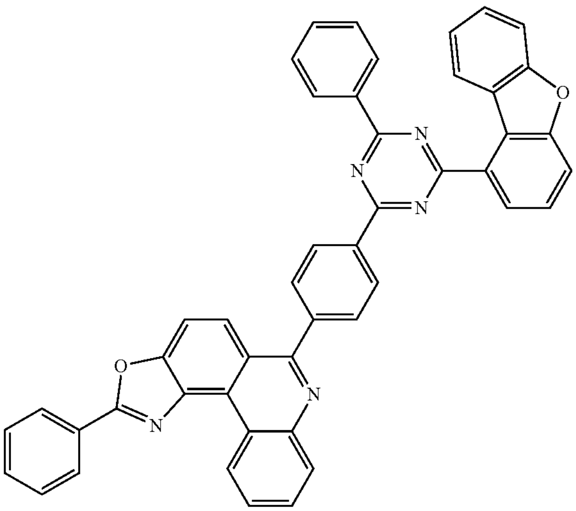
138
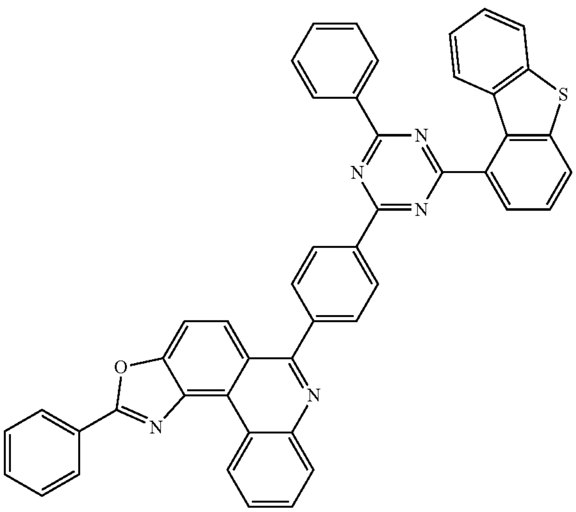
139
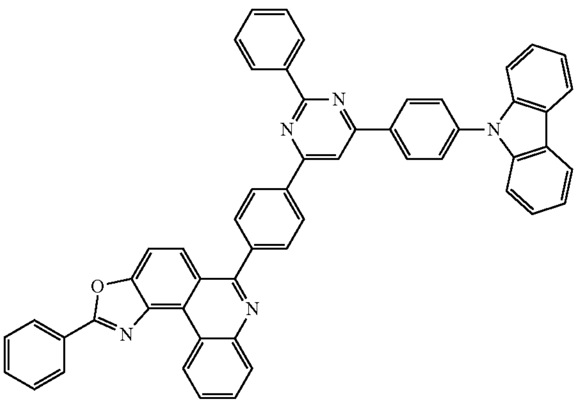

-continued
140
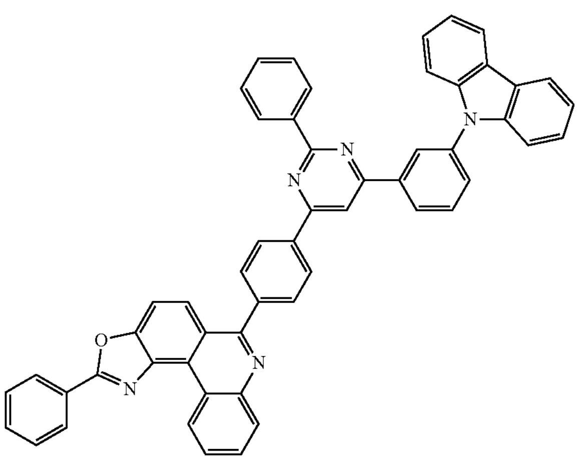
141
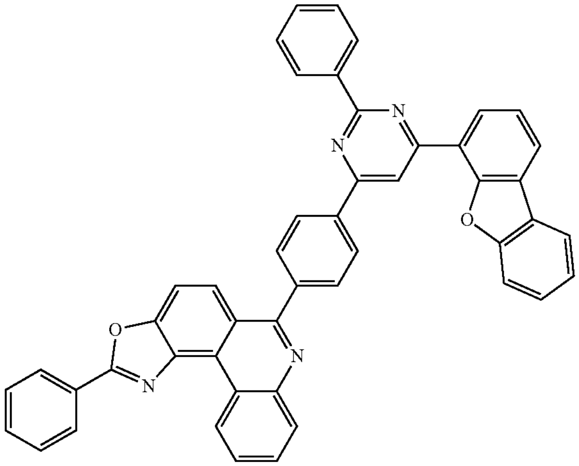
142
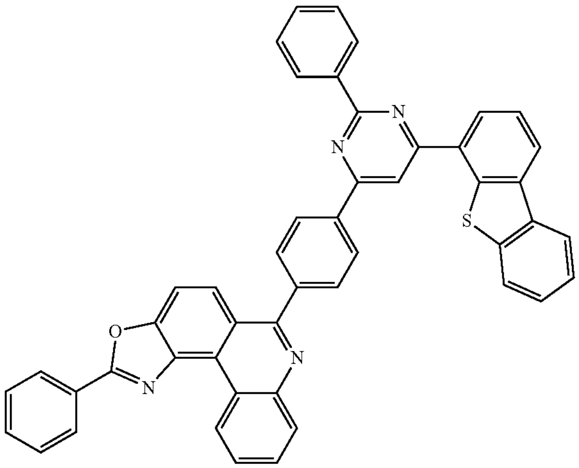
-continued
143
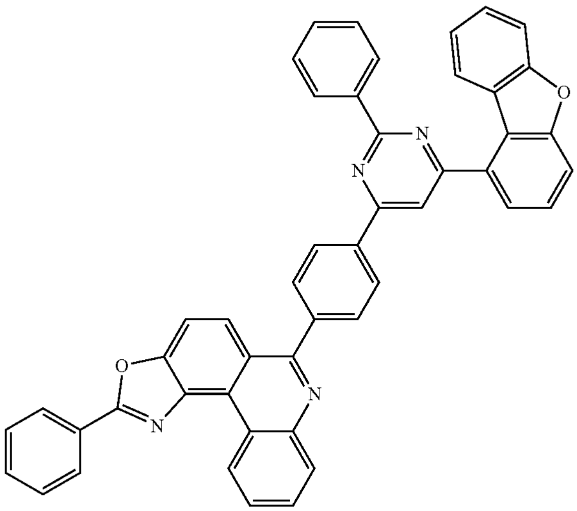
144
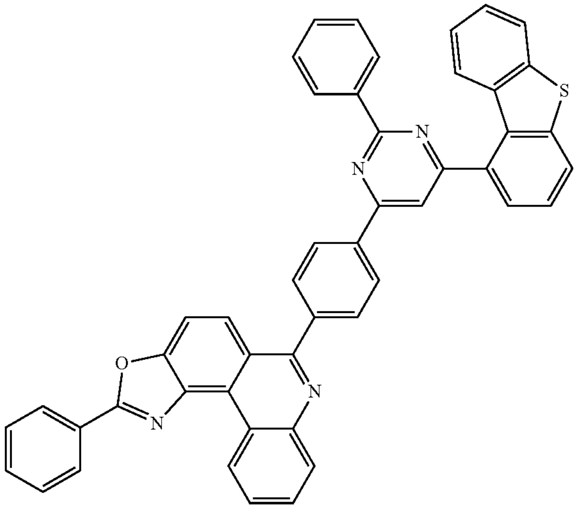
145
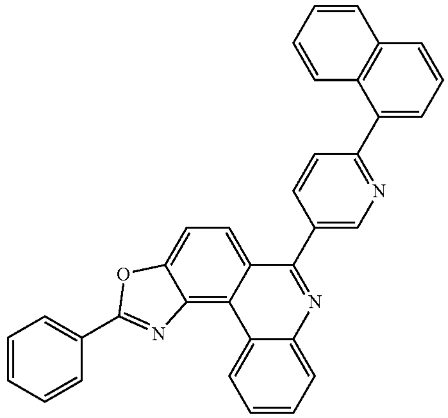

-continued
146
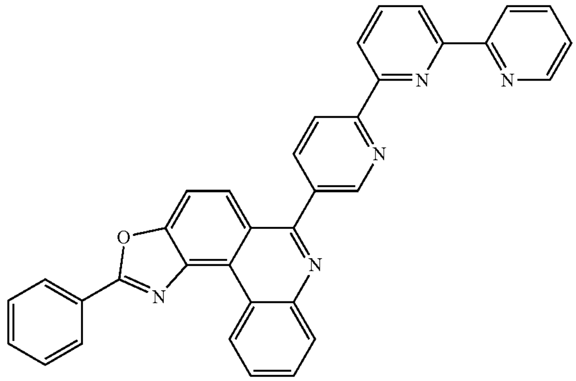
147
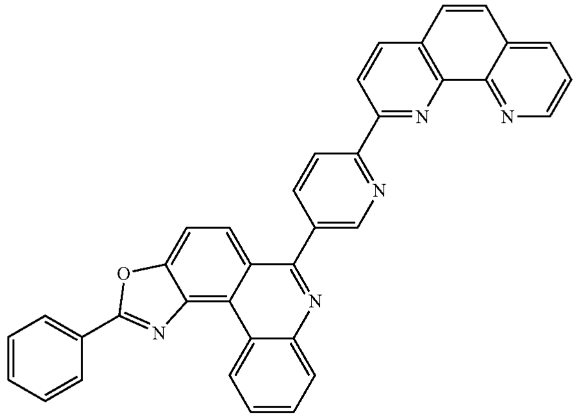
148
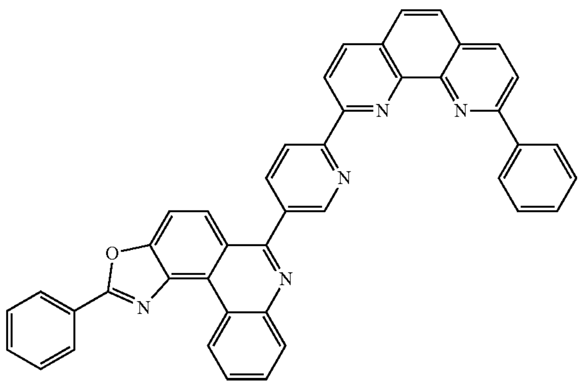
-continued
149
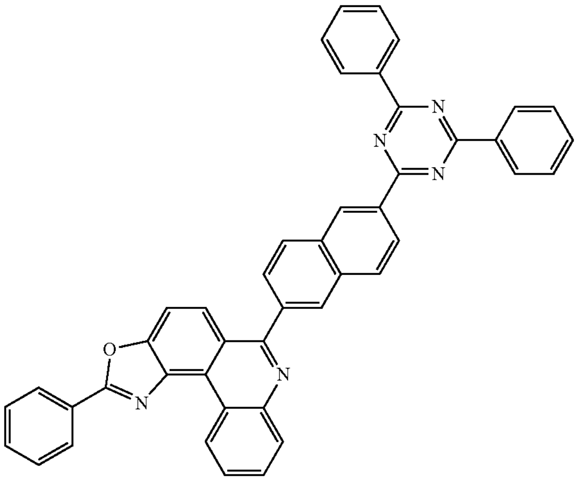
150
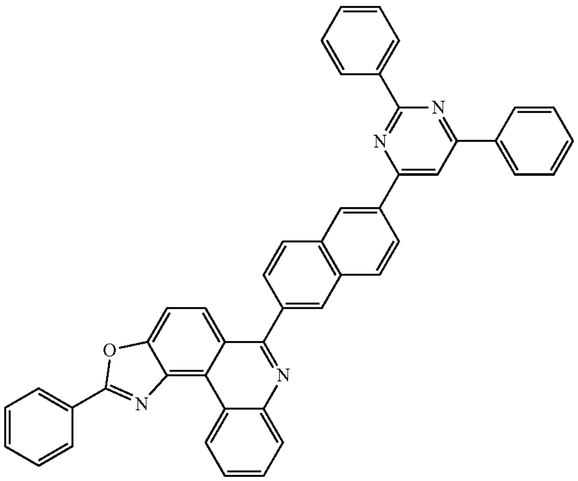
151
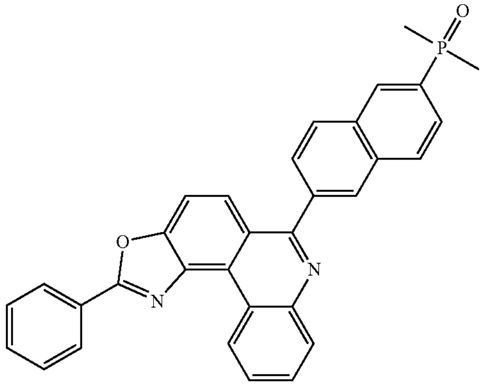

-continued
152
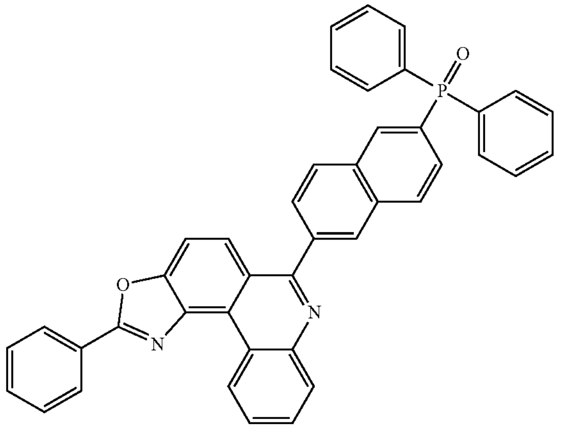
153
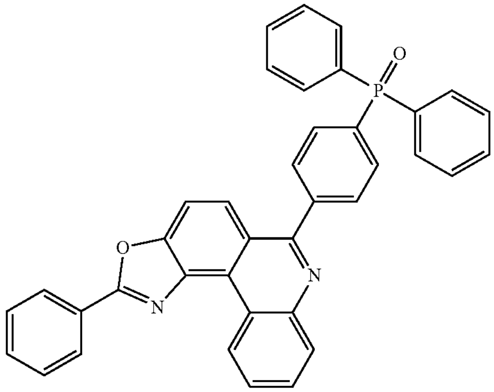
154
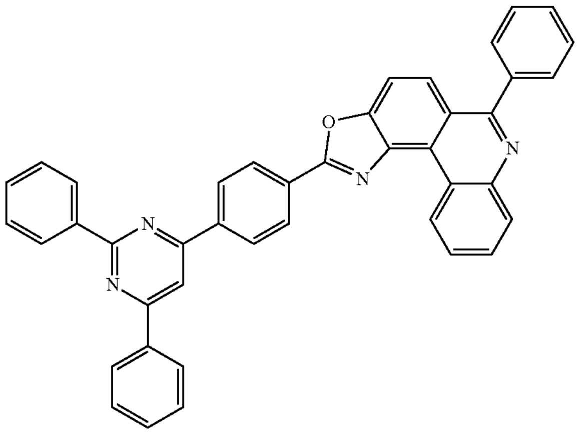
-continued
155
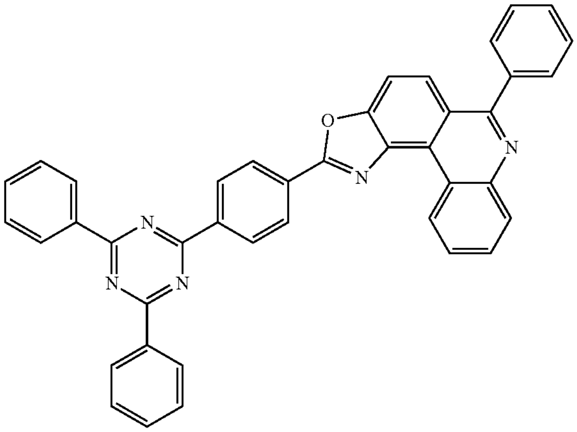
156
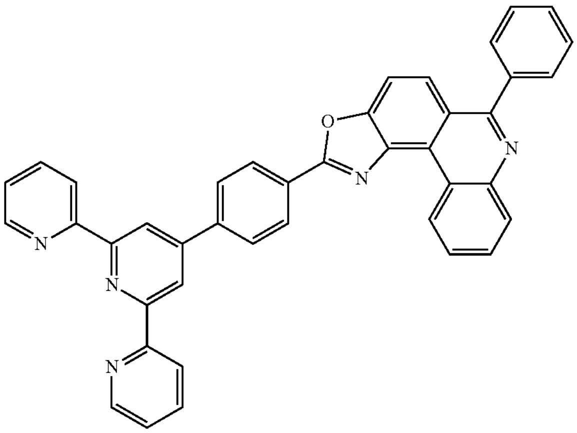
157
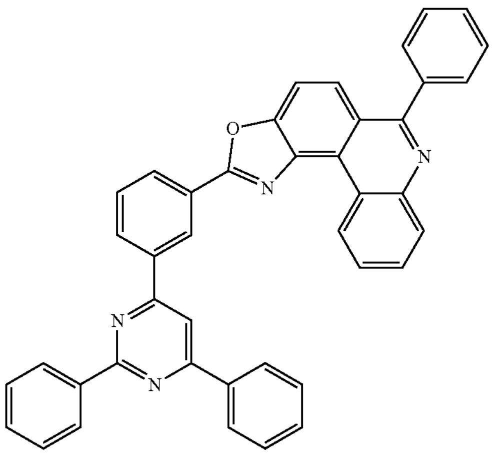

-continued
158
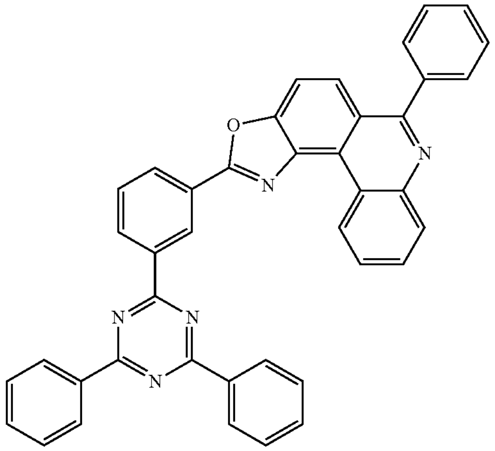
159
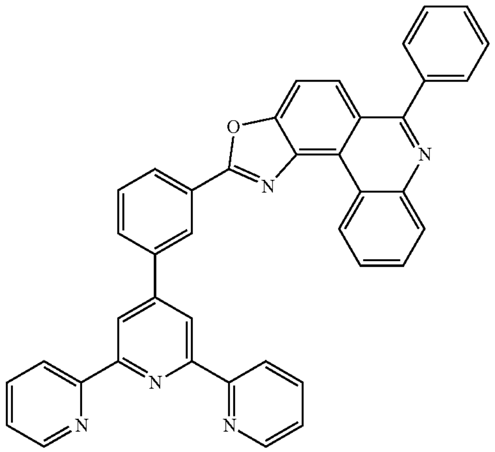
160
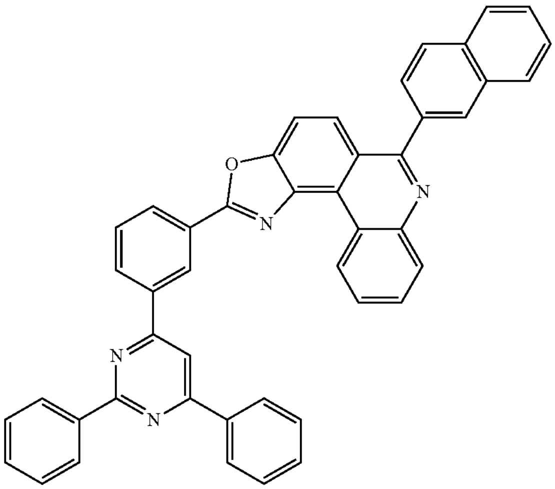
-continued
161
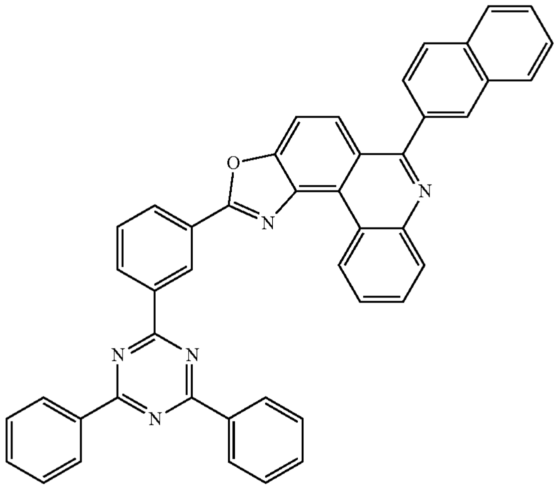
162
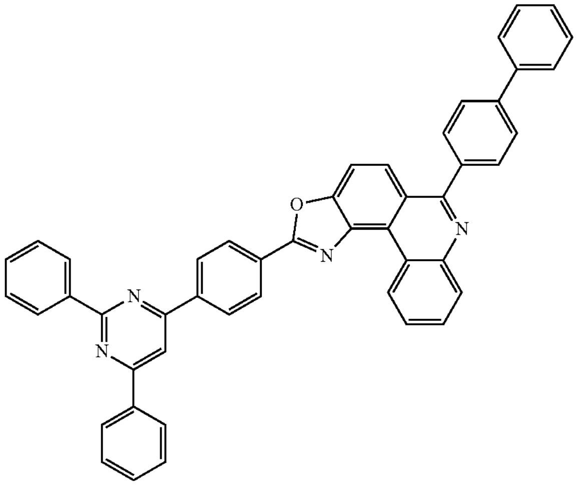
163
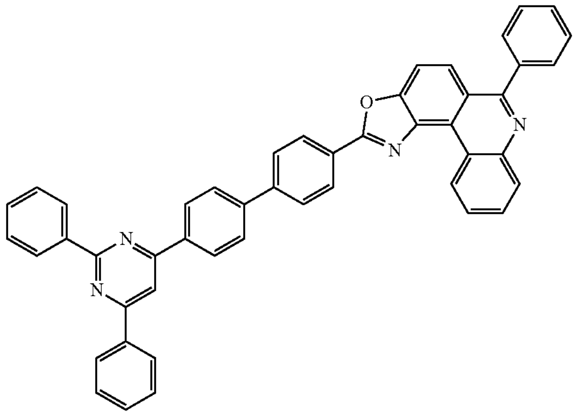

-continued

164

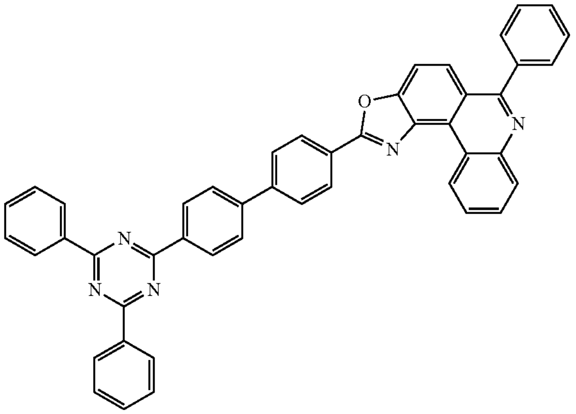

165

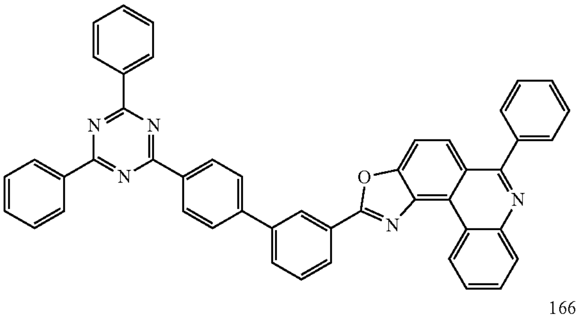

166

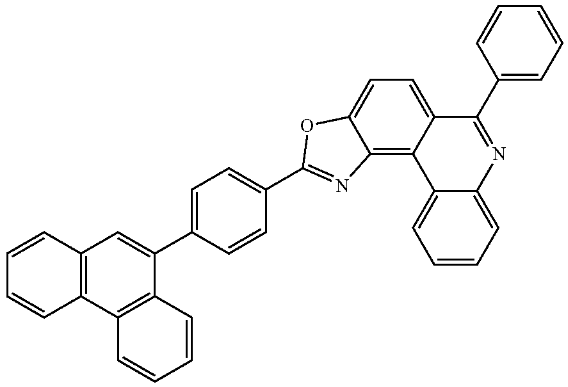

167

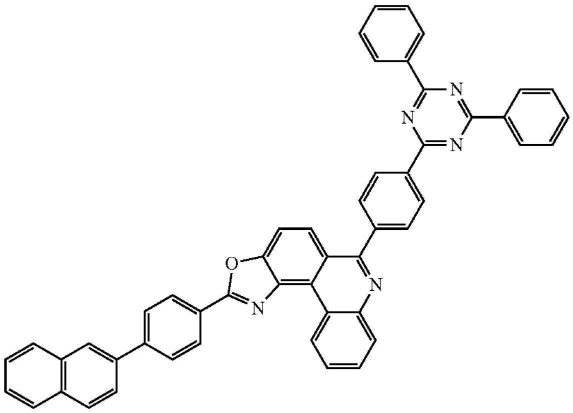

-continued

168

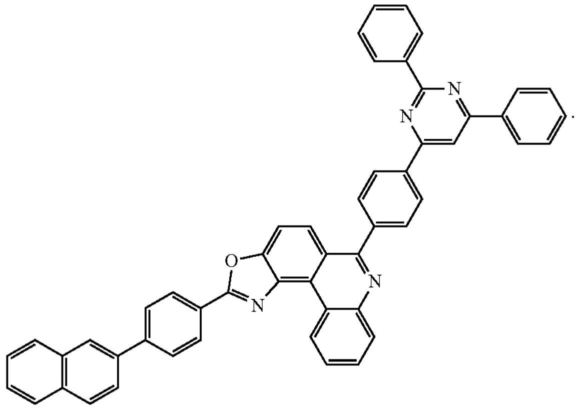

6. An organic light emitting device comprising:

a first electrode;

a second electrode; and one or more organic material layers provided between the first electrode and the second electrode, wherein one or more layers of the organic material layers include the heterocyclic compound of claim 1.

7. The organic light emitting device of claim 6, wherein the organic material layer includes an electron transfer layer, and the electron transfer layer includes the heterocyclic compound.

8. The organic light emitting device of claim 6, wherein the organic material layer includes a hole blocking layer, and the hole blocking layer includes the heterocyclic compound.

9. The organic light emitting device of claim 6, further comprising one, two or more layers selected from the group consisting of a light emitting layer, a hole injection layer, a hole transfer layer, an electron injection layer, an electron transfer layer, an electron blocking layer and a hole blocking layer.

10. The organic light emitting device of claim 6, comprising:

a first electrode;

a first stack provided on the first electrode and including a first light emitting layer;

a charge generation layer provided on the first stack;

a second stack provided on the charge generation layer and including a second light emitting layer; and a second electrode provided on the second stack.

11. The organic light emitting device of claim 10, wherein the charge generation layer includes the heterocyclic compound.

12. The organic light emitting device of claim 10, wherein the charge generation layer is an N-type charge generation layer, and the charge generation layer includes the heterocyclic compound.

* * * * *